(12) United States Patent
Kim et al.

(10) Patent No.: US 11,739,326 B2
(45) Date of Patent: Aug. 29, 2023

(54) RUNX1 INHIBITION FOR TREATMENT OF PROLIFERATIVE VITREORETINOPATHY AND CONDITIONS ASSOCIATED WITH EPITHELIAL TO MESENCHYMAL TRANSITION

(71) Applicants: The Schepens Eye Research Institute, Inc., Boston, MA (US); Massachusetts Eye and Ear Infirmary, Boston, MA (US)

(72) Inventors: Leo A. Kim, Brookline, MA (US); Joseph F. Arboleda-Velasquez, Newtown, MA (US); Dhanesh Amarnani, Allston, MA (US); Dean Eliott, Carlsbad, CA (US)

(73) Assignees: Massachusetts Eye and Ear Infirmary, Boston, MA (US); The Schepens Eye Research Institute, Inc., Boston, MA (US)

( * ) Notice: Subject to any disclaimer, the term of this patent is extended or adjusted under 35 U.S.C. 154(b) by 113 days.

(21) Appl. No.: 16/763,880

(22) PCT Filed: Nov. 14, 2018

(86) PCT No.: PCT/US2018/061110
§ 371 (c)(1),
(2) Date: May 13, 2020

(87) PCT Pub. No.: WO2019/099560
PCT Pub. Date: May 23, 2019

(65) Prior Publication Data
US 2020/0377888 A1 Dec. 3, 2020

Related U.S. Application Data

(60) Provisional application No. 62/586,067, filed on Nov. 14, 2017.

(51) Int. Cl.
| | |
|---|---|
| *C12N 15/113* | (2010.01) |
| *A61P 27/02* | (2006.01) |
| *A61K 9/00* | (2006.01) |
| *A61K 31/4025* | (2006.01) |
| *A61K 31/5513* | (2006.01) |
| *A61K 31/7105* | (2006.01) |
| *A61K 45/06* | (2006.01) |
| *G01N 33/68* | (2006.01) |

(52) U.S. Cl.
CPC .......... *C12N 15/113* (2013.01); *A61K 9/0048* (2013.01); *A61K 31/4025* (2013.01); *A61K 31/5513* (2013.01); *A61K 31/7105* (2013.01); *A61K 45/06* (2013.01); *A61P 27/02* (2018.01); *G01N 33/6893* (2013.01); *C12N 2310/14* (2013.01); *G01N 2333/4706* (2013.01); *G01N 2800/164* (2013.01)

(58) Field of Classification Search
None
See application file for complete search history.

(56) References Cited

U.S. PATENT DOCUMENTS

| | | |
|---|---|---|
| 3,405,122 A | 10/1968 | Berger et al. |
| 4,309,404 A | 1/1982 | Deneale et al. |
| 4,309,406 A | 1/1982 | Guley et al. |
| 4,521,210 A | 6/1985 | Wong |
| 4,556,552 A | 12/1985 | Porter et al. |
| 4,704,295 A | 11/1987 | Porter et al. |
| 4,816,567 A | 3/1989 | Cabilly et al. |
| 4,853,224 A | 8/1989 | Wong |
| 4,997,652 A | 3/1991 | Wong |
| 5,036,101 A | 7/1991 | Hsu et al. |
| 5,041,438 A | 8/1991 | Hsu |
| 5,141,735 A | 8/1992 | Bellemin et al. |
| 5,164,188 A | 11/1992 | Wong |
| 5,164,376 A | 11/1992 | Hsu et al. |
| 5,443,505 A | 8/1995 | Wonq et al. |
| 5,501,856 A | 3/1996 | Ohtori et al. |
| 5,545,806 A | 8/1996 | Lonbera et al. |
| 5,545,807 A | 8/1996 | Surani et al. |
| 5,569,825 A | 10/1996 | Lonbera et al. |
| 5,582,981 A | 12/1996 | Toole et al. |
| 5,625,126 A | 4/1997 | Lonberg et al. |
| 5,633,425 A | 5/1997 | Lonbera et al. |
| 5,641,673 A | 6/1997 | Haseloff et al. |
| 5,641,750 A | 6/1997 | Louis |
| 5,641,773 A | 6/1997 | Pardee et al. |

(Continued)

FOREIGN PATENT DOCUMENTS

| | | |
|---|---|---|
| EP | 1163910 | 12/2001 |
| EP | 1256574 | 11/2002 |

(Continued)

OTHER PUBLICATIONS

Harvard Medical School Dept. of Ophthalmology Home/News, pp. 1-3, retrieved online Dec. 10, 2021, https://eye.hms.harvard.edu/news/researchers-identify-new-target-abnormal-blood-vessel-growth-eyes (Year: 2017).*
Tober et al. Chapter 5: Taking the leap:Runx1 in the formation of blood from endothelium, Current Topics in Developmental Biology vol. 118, pp. 113-162 (Year: 2016).*
Lam et al., "Identification of RUNX1 as a Mediator of Aberrant Retinal Angiogenesis, Diabetes," https://doi.org/10.2337/db16-1035, pp. 1950-1956, Jul. 2017.
Hsu et al., "Combined Tractional and Rhegmatogenous Retinal Detachment in Proliferative Diabetic Retinopathy in the Anti-VEGR Era," Journal of Ophthalmology, vol. 2014, pp. 1-11, Jun. 25, 2014.

(Continued)

*Primary Examiner* — Brian Whiteman
(74) *Attorney, Agent, or Firm* — Fish & Richardson P.C.

(57) ABSTRACT

The present subject matter provides compositions, formulations and methods for preventing or reducing proliferation or migration of retinal cells or epithelial to mesenchymal transition in ocular cells or cells from other tissues.

33 Claims, 35 Drawing Sheets

Specification includes a Sequence Listing.

(56) References Cited

U.S. PATENT DOCUMENTS

| | | | |
|---|---|---|---|
| 5,661,016 A | 8/1997 | Lonbera et al. | |
| 5,731,005 A | 3/1998 | Ottoboni et al. | |
| 5,766,242 A | 6/1998 | Wong et al. | |
| 5,824,072 A | 10/1998 | Wong | |
| 5,837,226 A | 11/1998 | Junaherr et al. | |
| 5,869,079 A | 2/1999 | Wong et al. | |
| 6,074,661 A | 6/2000 | Oleinik et al. | |
| 6,331,313 B1 | 12/2001 | Wong et al. | |
| 6,369,116 B1 | 4/2002 | Wong et al. | |
| 6,699,493 B2 | 3/2004 | Wong | |
| 6,719,971 B1 | 4/2004 | Carter et al. | |
| 7,354,574 B2 | 4/2008 | Peyman | |
| 7,563,906 B2 | 7/2009 | Hagihara et al. | |
| 8,053,454 B2 | 11/2011 | Kearney et al. | |
| 8,293,210 B2 | 10/2012 | Huana et al. | |
| 8,394,826 B2 | 3/2013 | deLong et al. | |
| 8,414,912 B2 | 4/2013 | Ciolino et al. | |
| 8,450,344 B2 | 5/2013 | deLong et al. | |
| 8,484,010 B2 | 7/2013 | Tuszynski et al. | |
| 8,697,359 B1 | 4/2014 | Zhang | |
| 9,023,649 B2 | 5/2015 | Mali et al. | |
| 9,074,199 B1 | 7/2015 | Chavez et al. | |
| 9,133,269 B2 | 9/2015 | Mcconnell et al. | |
| 9,446,048 B2 | 9/2016 | Liu et al. | |
| 10,828,306 B2 | 11/2020 | Eliott et al. | |
| 11,229,662 B2 * | 1/2022 | Arboleda-Velasquez | ............ A61P 35/02 |
| 2004/0229816 A1 | 11/2004 | Paris et al. | |
| 2006/0034834 A1 | 2/2006 | Marasco et al. | |
| 2006/0142193 A1 | 6/2006 | Wei et al. | |
| 2006/0257452 A1 | 11/2006 | Hughes et al. | |
| 2006/0264380 A1 | 11/2006 | Hellstrom et al. | |
| 2007/0141066 A1 | 6/2007 | Phillips et al. | |
| 2008/0014180 A1 | 1/2008 | Lanza et al. | |
| 2008/0131484 A1 | 6/2008 | Robinson et al. | |
| 2009/0203011 A1 | 8/2009 | Liebenberg et al. | |
| 2009/0220488 A1 | 9/2009 | Gardner | |
| 2009/0285786 A1 | 11/2009 | Zon et al. | |
| 2010/0143380 A1 | 6/2010 | Crabb et al. | |
| 2010/0233194 A1 | 9/2010 | Combal et al. | |
| 2010/0330114 A1 | 12/2010 | Verdin et al. | |
| 2011/0305641 A1 | 12/2011 | Kazlauskas et al. | |
| 2012/0202793 A1 | 8/2012 | Sweetnam et al. | |
| 2013/0156795 A1 | 6/2013 | Iavarone et al. | |
| 2014/0004082 A1 | 1/2014 | Liu et al. | |
| 2014/0249135 A1 | 9/2014 | Buraer et al. | |
| 2015/0174138 A1 | 6/2015 | Bernstein et al. | |
| 2017/0049760 A1 | 2/2017 | Schonbrunn et al. | |
| 2017/0296617 A1 | 10/2017 | Schwartz et al. | |
| 2018/0170939 A1 | 6/2018 | Accetta et al. | |
| 2019/0350961 A1 | 11/2019 | Arboleda-Velasquez et al. | |
| 2020/0102384 A1 | 4/2020 | Arboleda-Velasquez et al. | |
| 2020/0103419 A1 | 4/2020 | Arboleda-Velasquez et al. | |
| 2020/0375899 A1 | 12/2020 | Kim et al. | |

FOREIGN PATENT DOCUMENTS

| | | |
|---|---|---|
| EP | 1270570 | 1/2003 |
| WO | WO 1993011161 | 6/1993 |
| WO | WO 1997023222 | 7/1997 |
| WO | WO 1999020620 | 4/1999 |
| WO | WO 1999064011 | 12/1999 |
| WO | WO 2001056988 | 8/2001 |
| WO | WO 2002053143 | 7/2002 |
| WO | WO 2002076976 | 10/2002 |
| WO | WO 2002076977 | 10/2002 |
| WO | WO 2002100833 | 12/2002 |
| WO | WO 2003078662 | 9/2003 |
| WO | WO 2003082808 | 10/2003 |
| WO | WO 2005074643 | 8/2005 |
| WO | WO 2007017065 | 2/2007 |
| WO | WO 2008015001 | 2/2008 |
| WO | WO 2008130315 | 10/2008 |
| WO | WO 2009146456 | 12/2009 |
| WO | WO 2009152901 | 12/2009 |
| WO | WO 2010104851 | 9/2010 |
| WO | WO 2011143484 | 11/2011 |
| WO | WO 2011163669 | 12/2011 |
| WO | WO 2012174419 | 12/2012 |
| WO | WO 2015049356 | 4/2015 |
| WO | WO 2016019165 | 2/2016 |
| WO | WO 2016025744 | 2/2016 |
| WO | WO 2016182904 | 11/2016 |
| WO | WO 2017112823 | 6/2017 |
| WO | WO 2018183216 | 10/2018 |
| WO | WO 2019221959 | 11/2019 |
| WO | WO 2021062412 | 4/2021 |
| WO | WO 2021216378 | 10/2021 |

OTHER PUBLICATIONS

The International Search Report and the Written Opinion from corresponding PCT Application No. PCT/US2018/061110 dated Nov. 14, 2018, 16 pages.

[No Author Listed], "Retinopathy of Prematurity," American Association for Pediatric Ophthalmology and Strabismus, available on or before Apr. 2020, 4 pages.

Antonetti et al., "Vascular Endothelial Growth Factor Induces Rapid Phosphorylation of Tight Junction Proteins Occludin and Zonula Occluden 1," J Biol Chem., Aug. 1999, 274(33):23463-23467.

Arevalo et al., "Tractional Retinal Detachment Following Intravitreal Bevacizumab (Avastin) in Patients With Severe Proliferative Diabetic Retinopathy," Br. J. Ophthalmol., Feb. 2008, 92(2):213-216.

Barberis et al., "Discovery of N-Substituted 7-Azaindoles as Pan-PIM Kinase Inhibitors—Lead Series Identification—Part II," Bioorganic & Medicinal Chemistry Letters, Sep. 2017, 27(20):4735-4740.

Bataille et al., "Thiazolidine Derivatives as Potent and Selective Inhibitors of the PIM Kinase Family," Bioorganic & Medicinal Chemistry, May 2017, 25(9):2657-2665.

Berge et al., "Pharmaceutical Salts", Journal of Pharmaceutical Sciences, Jan. 1977, 66(1):1-19.

Bergers et al., "Tumorigenesis and the Angiogenic Switch," Nature Reviews Cancer, Jun. 2003, 3(6):401-410.

Blackwell et al., "Sequence-specific DNA Binding by the c-Myc Protein," Science, Nov. 1990, 250(4984):1149-1151.

Boerner et al., "Production of Antigen-Specific Human Monoclonal Antibodies from in Vitro-Primed Human Splenocytes," J. Immunol., Jul. 1991, 147(1):86-95.

Boyd, "Diabetic Retinopathy Diagnosis," American Academy of Ophthamology, 2013, retrieved on Sep. 8, 2020, retrieved from URL <https://www.aao.org/eye-health/diseases/diabetic-retinopathX-diagnosis>, 6 pages.

Burns et al., "Hematopoietic Stem Cell Fate Is Established by the Notch-Runx Pathway," Genes & Development, Oct. 2005, 19(19):2331-2342.

Butko et al., "Complex regulation of HSC emergence by the Notch signaling pathway," Dev. Biol., Jan. 2016, 409(1):129-138.

Castilla et al., "Failure of Embryonic Hematopoiesis and Lethal Hemorrhages in Mouse Embryos Heterozygous for a Knocked-In Leukemia Gene CBFB-MYH11," Cell, Nov. 1996, 87(4):687-696.

Chang et al., "PIM Kinase Inhibitors Downregulate STAT3Tyr705 Phosphorylation," Mol Cancer Ther., Sep. 2010, 9(9):2478-2487.

Cheloufi et al., "A Dicer-independent miRNA biogenesis pathway that requires Ago catalysis," Nature, Jun. 2010, 465(7298):584-589.

Chen et al., "Intracellular Antibodies as a New Class of Therapeutic Molecules for Gene Therapy," Human Gene Therapy, 1994, 5(5):595-601.

Chen et al., "Runx1 is required for the endothelial to haematopoietic cell transition but not thereafter," Nature, Feb. 2009, 457(7231):887-891.

Chothia et al., "Canonical Structures for the Hypervariable Regions of Immunoglobulins," J. Mol. Biol., Aug. 1987, 196(4):901-917.

Chothia et al., "Conformations of immunoglobulin hypervariable regions," Nature, Dec. 1989, 342:877-883.

Chung et al., "Developmental and Pathological Angiogenesis," Annu. Rev. Cell Dev. Biol., Nov. 2011, 27:563-584.

(56) References Cited

OTHER PUBLICATIONS

Cole, "Monoclonal Antibodies," Can. Fam. Physician, 1987, 33:369-372.
Colyer et al., "Perforating globe injuries during operation Iraqi Freedom," Ophthalmology, 2008, 115:2087-2093.
Connor et al., "Quantification of oxygen-induced retinopathy in the mouse: a model of vessel loss, vessel regrowth and pathological angiogenesis," Nat Protoc., Oct. 2009, 4(11):1565-1573.
Cunningham et al., "Identification of benzodiazepine Ro5-3335 as an inhibitor of CBF leukemia through quantitative high throughput screen against RUNX1-CBFβ interaction," PNAS, Sep. 2012, 109(36):14592-14597.
Daxer, "The Fractal Geometry of Proliferative Diabetic Retinopathy: Implications for the Diagnosis and the Process of Retinal Vasculogenesis," Current Eye Research, Dec. 1993, 12(12):1103-1109.
Diabetes Control and Complications Trial Research Group, "The Relationship of Glycemic Exposure (HbA1c) to the Risk of Development and Progression of Retinopathy in the Diabetes Control and Complications Trial," Diabetes, Aug. 1995, 44(8):968-983.
Edgar et al., "Gene Expression Omnibus: NCBI gene expression and hybridization array data repository," Nucleic Acids Research, Jan. 2002, 30(1):207-210.
Elbashir et al., "Functional anatomy of siRNAs for mediating efficient RNAi in *Drosophila melanogaster* embryo lysate," The EMBO Journal, Dec. 2001, 20(23):6877-6888.
Eliott et al., "Smoking is a risk factor for proliferative vitreoretinopathy after traumatic retinal detachment," Retina, 2017, 37(7):1229-1235.
Espinoza et al., "Notch Inhibitors for Cancer Treatment," Pharmacol Ther., Aug. 2013, 139(2):95-110.
Extended European Search Report in European Application No. 17871449.9, dated May 25, 2020, 13 pages.
Extended European Search Report in European Appln. No. 18878909.3, dated Jul. 22, 2021, 7 pages.
Fehniger et al., "Single-agent lenalidomide induces complete remission of acute myeloid leukemia in patients with isolated trisomy 13," Blood, 2009, 113(5):1002-1005.
Fire et al., "Potent and Specific Genetic Interference by Double-Stranded RNA in Caenorhabditis Elegans," Nature, 1998, 391:806-810.
Fishwild et al., "High-Avidity Human IgG Kappa Monoclonal Antibodies from a Novel Strain of Minilocus Transgenic Mice," Nature Biotechnology, Aug. 1996, 14(7):845-851.
Friedlander, "Fibrosis and diseases of the eye," J Clin Invest., 2007, 117(3):576-586.
Geback et al., "TScratch: A novel and simple software tool for automated analysis of monolayer wound healing assays," Biotechniques, Apr. 2009, 46(4):265-274.
GenBank Accession No. AA141856.1, "Pim-3 oncogene [*Homo sapiens*]," May 8, 2007, 2 pages.
GenBank Accession No. AB114795.1, "*Homo sapiens* pim-3 mRNA for serine/threonine kinase Pim-3, Complete cds," Nov. 9, 2017, 2 pages.
GenBank Accession No. AK292005.1, "*Homo sapiens* cDNA FLJ75766 complete cds, highly similar to *Homo sapiens* pim-3 oncogene (PIM3), mRNA," Jan. 9, 2008, 2 pages.
GenBank Accession No. BAD42438.1, "Serine/threonine kinase Pim-3 [*Homo sapiens*]," Nov. 9, 2017, 1 page.
GenBank Accession No. BAF84694.1, "Unnamed protein product [*Homo sapiens*]," Jan. 9, 2008, 2 pages.
GenBank Accession No. BC141855.1, "*Homo sapiens* pim-3 oncogene, mRNA (cDNA clone MGC: 167042 Image:8860375), complete cds," May 8, 2007, 2 pages.
GenBank Accession No. NM_000598.4, "*Homo sapiens* insulin like growth factor binding protein 3 (IGFBP3), transcript variant 2, mRNA," May 28, 2019, 4 pages.
GenBank Accession No. NM_001001852, "*Homo sapiens* Pim-3 proto-oncogene, serine/threonine kinase (PIM3), mRNA," May 8, 2020, 3 pages.

GenBank Accession No. NM_001001890.2, "*Homo sapiens* RUNX Family Transcription Factor 1 (RUNX1), Transcript Variant 2, mRNA," May 28, 2019, 7 pages.
GenBank Accession No. NM_001013398.1, "*Homo sapiens* insulin like growth factor binding protein 3 (IGFBP3), transcript variant 1, mRNA," Oct. 13, 2018, 4 pages.
GenBank Accession No. NM_001122607.2, "*Homo sapiens* RUNX Family Transcription Factor 1 (RUNX1), Transcript Variant 3, mRNA", Jun. 7, 2020, 4 pages.
GenBank Accession No. NM_001754.4, "*Homo sapiens* RUNX Family Transcription Factor 1 (RUNX1), Transcript Variant 1, mRNA," Feb. 9, 2020, 5 pages.
GenBank Accession No. NP_000589.2, "Insulin-like growth factor-binding protein 3 isoform b precursor [*Homo sapiens*]," Jun. 14, 2020, 3 pages.
GenBank Accession No. NP_001013416.1, "Insulin-like growth factor-binding protein 3 isoform a precursor [*Homo sapiens*]," Jun. 14, 2020, 3 pages.
GenBank Accession No. XM_005261068.3, "Predicted: *Homo sapiens* RUNX Family Transcription Factor 1 {RUNX1), Transcript Variant X2, mRNA," May 28, 2020, 3 pages.
GenBank Accession No. XM_005261069.4, "Predicted: *Homo sapiens* RUNX family transcription factor 1 (RUNX1), transcript variant X5, mRNA," May 28, 2020, 3 pages.
GenBank Accession No. XM_011529766.2, "Predicted: *Homo sapiens* RUNX family transcription factor 1 (RUNX1), transcript variant XI, mRNA," May 28, 2020, 3 pages.
GenBank Accession No. XM_011529768.2, "Predicted: *Homo sapiens* RUNX family transcription factor 1 (RUNX1), transcript variant X6, mRNA," May 28, 2020, 3 pages.
GenBank Accession No. XM_011529770.2, "Predicted: *Homo sapiens* RUNX Family Transcription Factor 1 (RUNX1), Transcript Variant X8, mRNA", May 28, 2020, 2 pages.
GenBank Accession No. XM_017028487.1, "Predicted: *Homo sapiens* RUNX family transcription factor 1 (RUNX1), transcript variant X4, mRNA," May 28, 2020, 3 pages.
GenBank Accession No. XR_937576.2, "Predicted: *Homo sapiens* RUNX family transcription factor 1 (RUNX1), transcript variant X7, misc_RNA", May 28, 2020, 2 pages.
ghr.nlm.nih.gov [online], "Age-related macular degeneration," Aug. 2016, retrieved from URL <https://ghr.nlm.nih.gov/condition/age-related-macular-degeneration>, 8 pages.
Giani et al., "In Vivo Evaluation of Laser-Induced Choroidal Neovascularization Using Spectral-Domain Optical Coherence Tomography," Investigative Ophthalmology & Visual Science, 2011, 52(6):3880-3887.
Hakeem et al., "Retinopathy of Prematurity: A Study of Prevalence and Risk Factors," Middle East African Journal of Ophthalmology, 2012, 19(3):289-294.
Harris et al., "Glucose Metabolism Impacts the Spatiotemporal Onset and Magnitude of HSC Induction in Vivo," Blood, Mar. 2013, 121(13):2483-2493.
Haubrich et al., "A Randomized Trial of the Activity and Safety of Ro 24-7429 (Tat Antagonist) Versus Nucleoside for Human Immunodeficiency Virus Infection," The Journal of Infectious Diseases, Nov. 1995, 172(5): 1246-1252.
Heckl et al., "Generation of mouse models of myeloid malignancy with combinatorial genetic lesions using CRISPR-Cas9 genome editing," Nat. Biotechnol., 2014, 32(9):941-946.
Holliger et al., "'Diabodies': Small Bivalent and Bispecific Antibody Fragments," Proceedings of the National Academy of Sciences of the United States of America, Jul. 1993, 90(14):6444-6448.
Hong et al., "Runx1 stabilizes the mammary epithelial cell phenotype and prevents epithelial to mesenchymal transition," Oncotarget, Mar. 2017, 8(11):17610-17627.
Hoogenboom et al., "By-Passing immunisation: Human Antibodies from Synthetic Repertoires of Germline VH Gene Segments Rearranged in Vitro," Journal of Molecular Biology, Sep. 1992, 227(2):381-388.
Huang et al., "Bioinformatics Enrichment Tools: Paths Toward the Comprehensive Functional Analysis of Large Gene Lists," Nucleic Acids Research, Jan. 2009, 37(1):1-13.

(56) References Cited

OTHER PUBLICATIONS

Illendula et al., "Small Molecule Inhibitor of CBF~- RUNX Binding for RUNX Transcription Factor Driven Cancers," EBioMedicine, Nov. 2017, 8:117-131.
Imanirad et al., "HIF1a is a Regulator of Hematopoietic Progenitor and Stem Cell Development in Hypoxic Sites of the Mouse Embryo," Stem Cell Res., Jan. 2014, 12(1):24-35.
International Preliminary Report on Patentability in International Appln. No. PCT/US2017/061620, dated May 21, 2019, 17 pages.
International Preliminary Report on Patentability in International Appln. No. PCT/US2018/061110, dated May 28, 2020, 12 pages.
International Search Report in International Appln. No. PCT/US2017/061620, dated Mar. 19, 2018, 24 pages.
Ishikawa et al., "Microarray Analysis of Gene Expression in Fibrovascular Membranes Excised From Patients With Proliferative Diabetic Retinopathy," Investigative Ophthalmology & Visual Science, Feb. 2015, 56(2):932-946.
Ito et al., "RUNX Transcription Factors as Key Targets of TGF-beta Superfamily Signaling," Current Opinion in Genetics and Development, Feb. 2003, 13(1):43-47.
Iwatsuki et al., "Runx1 Promotes Angiogenesis by Downregulation of Insulin-Like Growth Factor-Binding Protein-3", Oncogene, Feb. 2005, 24(7):1129-1137.
Jo et al., "Animal Models of Diabetic Retinopathy: Doors to Investigate Pathogenesis and Potential Therapeutics," Journal of Biomedical Science, 2013, 20:38, 13 pages.
Jones et al., "Replacing the Complementarity-Determining Regions in a Human Antibody with those from a Mouse," Nature, May 1986, 321(6069):522-525.
Joyce, "Amplification, Mutation and Selection of Catalytic RNA," Gene, Oct. 1989, 82(1):83-87.
Kalev-Zylinska et al., "Runx1 is Required for Zebrafish Blood and Vessel Development and Expression of a Human RUNX1-CBF2T1 Transgene Advances a Model for Studies of Leukemogenesis," Development, 2002, 129(8):2015-2030.
Kategaya et al., "USP7 Small-Molecule Inhibitors Interfere With Ubiquitin Binding," Nature, Oct. 2017, 550(7677):534-538.
Kim et al., "A Brief History of Anti-VEGF for the Treatment of Ocular Angiogenesis," The American Journal of Pathology, 2012, 181(2):376-379.
Kim et al., "Characterization of Cells from Patient-Derived Fibrovascular Membranes in Proliferative Diabetic Retinopathy," Molecular Vision, Jun. 2015, 21:673-687.
Kim et al., "Inhibition of Runx1 by the Ro5-3335 benzodiazepine derivative reduces aberrant retinal angiogenesis," Abstract, Presented at Annual Meeting of the Association for Research in Vision and Ophthalmology (ARVO), Baltimore, MD, USA; May 7-11, 2017; IOVS, Jun. 2017, 58(8):4029, 3 pages.
Kim et al., "Pim-1 Kinase Phosphorylates and Stabilizes RUNX3 and Alters Its Subcellular Localization," Journal of Cellular Biochemistry, Nov. 2008, 105(4):1048-1058.
Kohler et al., "Continuous Cultures of Fused Cells Secreting Antibody of Predefined Specificity," Nature, Aug. 1975, 256(5517):495-497.
Kozlowski et al., "A Human Melanoma Line Heterogeneous With Respect to Metastatic Capacity in Athymic Nude Mice," Journal of the National Cancer Institute, Apr. 1984, 72(4):913-917.
Kuiper et al., "The Angio-Fibrotic Switch of VEGF and CTGF in Proliferative Diabetic Retinopathy," PLoS One, Jul. 2008, 3(7):e2675, 7 pages.
Lam et al., "Identification of RUNX1 as a Mediator of Aberrant Retinal Anqioqenesis," Diabetes, 2017, 66:1950-1956.
Liang et al., "In Vitro Scratch Assay: A Convenient and Inexpensive Method for Analysis of Cell Migration in Vitro," Nature Protocols, Mar. 2007, 2(2):329-333.
Lichtinger et al., "Chromatin Regulation by RUNX1," Blood Cells, Molecules and Diseases, Apr. 2010, 44(4):287-290.
Lie-A-Ling et al., "RUNX1 Positively Regulates a Cell Adhesion and Migration Program in Murine Hemogenic Endothelium Prior to Blood Emergence," Blood, Sep. 2014, 124(11):e11-e20.
Lofqvist et al., "IGFBP3 suppresses retinopathy through suppression of oxygen-induced vessel loss and promotion of vascular regrowth," PNAS, 2007, 104(25):10589-10594.
Lonberg et al., "Antigen-Specific Human Antibodies from Mice Comprising Four Distinct Genetic Modifications," Nature, Apr. 1994, 368:856-859.
Lonberg et al., "Human Antibodies from Transgenic Mice," Intern. Rev. Immunol., 1995, 13(1):65-93.
Ludwig, "The Use of Mucoadhesive Polymers in Ocular Drug Delivery," Advanced Drug Delivery Reviews, 2005, 57(11):1595-1639.
Marks et al., "By-Passing Immunization: Human Antibodies from V-Gene Libraries Displayed on Phage," J. Mol. Biol., Dec. 1991, 222(3):581-597.
Martinez-Hoyer et al., "RUNX1 Loss of Function Drives Resistance to Lenalidomide in Del(5Q) Myelodysplastic Syndrome Patients," Leukemia Research, 2017, 1(55):S43-S44.
Masoumpour et al., "Current and Future Techniques in Wound Healing Modulation after Glaucoma Filtering Surgeries," Open Ophthalmol J., 2016, 10:68-85.
mayoclinic.org [online], "Diabetic Retinopathy," Mar. 2015, via Internet archive: Wayback Machine URL<http://web.archive.org/web/20180308085607/https://www.mayoclinic.org/diseases-conditions/diabetic-retinopathy/diagnosis-treatment/drc-20371617>, retrieved on Sep. 30, 2021, URL <https://www.mayoclinic.org/diseases-conditions/diabetic-retinopathy/diagnosis-treatment/drc-20371617>, 7 pages.
mayoclinic.org [online], "Dry Macular Degeneration," 2015, retrieved from URL <https://www.mayoclinic.org/diseasesconditions/drymaculardegeneration/diagnosis-treatment/drc-20350381>, 5 pages.
mayoclinic.org [online], "Wet Macular Degeneration," 2015, retrieved from URL <https://www.mayoclinic.org/diseasesconditions/wet-macular-degeneration/diagnosis-treatment/drc-20351113>, 6 pages.
McAuley et al., "Vitreous Biomarkers in Diabetic Retinopathy: A Systematic Review and Meta-Analysis," Journal of Diabetic Complications, 2014, 28(3):419-425.
McLeod et al., "From Blood Islands to Blood Vessels: Morphologic Observations and Expression of Key Molecules during Hyaloid Vascular System Development," Investigative Ophthalmology & Visual Science, Dec. 2012, 53(13):7912-7927.
Medlineplus.gov [online], "Retinal vein occlusion," Available on or before Mar. 6, 2018, retrieved Feb. 22, 2019, retrieved from URL <https://medlineplus.gov/ency/article/007330.htm>, 4 pages.
Michaud et al., "Integrative Analysis of RUNX1 Downstream Pathways and Target Genes," BMC Genomics, Jul. 2008, 9:363, 17 pages.
Morrison, "Success in Specification," Nature, Apr. 1994, 368:812-813.
Moshfeghi et al., "Retinal Capillary Angioma," American Academy of Ophthamology, Oct. 2013, 7 pages.
my.clevelandclinic.org [online], "Retinal Vein Occlusion (RVO)," 2015, retrieved from URL <https://my.clevelandclinic.org/health/diseases/14206-retinal-vein-occlusion-rvo>, 4 pages.
Nakano et al., "Design and Synthesis of an in Vivo-Efficacious PIM3 Kinase Inhibitor as a Candidate Anti-Pancreatic Cancer Agent," Bioorganic & Medicinal Chemistry Letters, Dec. 2015, 25(24):5687-5693.
Namba et al., "Indispensable Role of the Transcription Factor PEBP2/CBF in Angiogenic Activity of a Murine Endothelial Cell MSS31," Oncogene, Jan. 2000, 19(1):106-114.
nei.nih.gov [online], "Facts About Retinopathy of Prematurity (ROP)," National Eye Institute, available on or before Jun. 2014, retrieved on Feb. 22, 2019, retrieved from URL <https://nei.nih.gov/health/rop/rop>, 3 pages.
Neuberger, "Generating High-Avidity Human Mabs in Mice," Nature Biotechnology, Jul. 1996, 14(7):826, 1 page.
Nicholls et al., "An Improved Method for Generating Single-Chain Antibodies From Hybridomas," Journal of Immunological Methods, Sep. 1993, 165(1):81-91.
Pandya et al., "Neovascular Glaucoma," Medscape, available on or before Oct. 2016, retrieved from URL <https://emedicine.medscape.com/article/1205736-overview#a6>, 15 pages.

(56) References Cited

OTHER PUBLICATIONS

Pettus et al., "Discovery and Optimization of Quinazolinone-pyrrolopyrrolones as Potent and Orally Bioavailable Pan-Pim Kinase Inhibitors," J. Med. Chem., Jun. 2016, 59(13):6407-6430.
Pluckthun, "Antibodies from *Escherichia coli*," The Pharmacology of Monoclonal Antibodies, 1994, 113:269-315.
Presta, "Antibody Engineering," Current Opinion in Structural Biology, 1992, 2(4):593-596.
Rakoczy et al., "Characterization of a Mouse Model of Hyperglycemia and Retinal Neovascularization," The American Journal of Pathology, Nov. 2010, 177(5):2659-2670.
Ran et al., "γ-Secretase Inhibitors in Cancer Clinical Trials are Pharmacologically and Functionally Distinct," EMBO Molecular Medicine, Jul. 2017, 9(7):950-966.
Riechmann et al., "Reshaping Human Antibodies for Therapy," Nature, Mar. 1988, 332:323-327.
Saint-Geniez et al., "Endogenous VEGF Is Required for Visual Function: Evidence for a Survival Role on Muller Cells and Photoreceptors," PLoS One, Nov. 2008, 3(11):e3554, 13 pages.
Sang et al., "Is Blockade of Vascular Endothelial Growth Factor Beneficial for all Types of Diabetic Retinopathy?" Diabetologia, Jul. 2008, 51(9): 1570-1573.
Scholle, "Ocular Ischemic Syndrome," Medscape, 2019, retrieved Sep. 8, 2020, retrieved from URL <https://emedicine.medscape.com/article/1201678-overview>, 3 pages.
Shaki-Loewenstein et al., "A universal strategy for stable intracellular antibodies", Journal of Immunological Methods, Aug. 2005, 303(1-2):19-39.
Shao et al., "Choroid Sprouting Assay: An Ex Vivo Model of Microvascular Angiogenesis," PLoS One, Jul. 2013, 8(7):e69552, 11 pages.
Shazly et al., "Neovascular Glaucoma: Etiology, Diagnosis and Prognosis," Seminars in Ophthalmology, Mar. 2009, 24(2):113-121.
Smith et al., "Oxygen-Induced Retinopathy in the Mouse," Invest Ophthalmol Vis Sci, Jan. 1994, 35(1):101-111.
Sohn et al., "Angiofibrotic Response to Vascular Endothelial Growth Factor Inhibition in Diabetic Retinal Detachment," Arch Ophthalmol, Sep. 2012, 130(9):1127-1134.
Sui et al., "oPOSSUM: Identification of Over-represented Transcription Factor Binding Sites in Co-Expressed Genes," Nucleic Acids Research, 2005, 33(10):3154-3164.
Terelak-Borys et al., "Ocular Ischemic Syndrome—A Systematic Review," Med Sci Monit, Aug. 2012, 18(8):RA138-RA144.
Trapnell et al., "TopHat: Discovering Splice Junctions with RNA-Seq," Bioinformatics, Apr. 2009, 25(9):1105-1111.
Tuerk et al., "Systematic Evolution of Ligands by Exponential Enrichment: RNA Ligands to Bacteriophage T4 DNA Polymerase," Science, Aug. 1990, 249(4968):505-510.
Turell et al., "Vascular Tumors of the Retina and Choroid: Diagnosis and Treatment," Middle East Afr J Ophthalmol., 2010, 17(3):191-200.
UniProt Accession No. P17936, "Insulin-like growth factor-binding protein 3," Nov. 1, 1990, 8 pages.
UniProt Accession No. Q01196-10, "Runt-related transcription factor 1," Apr. 1, 1993, 1 page.
UniProt Accession No. Q01196-11, "RUNX1_Human Isoform AML-IL of Runt-related transcription factor 1," Apr. 1, 1993, 1 page.
UniProt Accession No. Q01196-2, "RUNX1_Human Isoform AML-1A of Runt-related transcription factor 1," Apr. 1, 1993, 1 page.
UniProt Accession No. Q01196-3, "RUNX1_Human Isoform AML-1C of Runt-related transcription factor 1," Apr. 1, 1993, 1 page.
UniProt Accession No. Q01196-4, "RUNX1_Human Isoform AML-IE of Runt-related transcription factor 1," Apr. 1, 1993, 1 page.
UniProt Accession No. Q01196-5, "RUNX1_Human Isoform AML-1FA of Runt-related transcription factor 1," Apr. 1, 1993, 1 page.
UniProt Accession No. Q01196-6, "RUNX1_Human Isoform AML-1FB of Runt-related transcription factor 1," Apr 1, 1993, 1 page.
UniProt Accession No. Q01196-7, "RUNX1_Human Isoform AML-1FC of Runt-related transcription factor 1," Apr. 1, 1993, 1 page.
UniProt Accession No. Q01196-8, "RUNX1_Human Isoform AML-IG of Runt-related transcription factor 1," Apr. 1, 1993, 1 page.
UniProt Accession No. Q01196-9, "RUNX1_Human Isoform AML-IH of Runt-related transcription factor 1," Apr. 1, 1993, 1 page.
UniProt Accession No. Q86V86, "Serine/threonine-protein kinase pim-3," Nov. 21, 2003, 6 pages.
Van Geest et al., "A Shift in the Balance of Vascular Endothelial Growth Factor and Connective Tissue Growth Factor by Bevacizumab Causes the Angiofibrotic Switch in Proliferative Diabetic Retinopathy," Br J Ophthalmol, Jan. 2012, 96(4):587-590.
Verhoeyen et al., "Reshaping Human Antibodies: Grafting an Antilysozyme Activity," Science, Mar. 1988, 239(4847):1534-1536.
Wang et al. "Discovery of 5-Azaindazole (GNE-955) as a Potent Pan-Pim Inhibitor With Optimized Bioavailability," J. Med. Chem., Apr. 2017, 60(10):4458-4473.
Yadav et al., "Tumour Angiogenesis and Angiogenic Inhibitors: A Review," J Clin Diagn Res., Jun. 2015, 9(6):XE01-XE05.
Yoshida et al., "Gene expression profile of fibrovascular membranes from patients with proliferative diabetic retinopathy," Br J Ophthalmol., 2010, 94(6):795-801.
Yuan et al., "Notch Signaling: An Emerging Therapeutic Target for Cancer Treatment," Cancer Letters, Dec. 2015, 369(1):20-27.
Zapata et al., "Engineering Linear F(ab')2 Fragments for Efficient Production in *Escherichia coli* and Enhanced Anti-Proliferative Activity," Protein Engineering, Oct. 1995, 8(10): 1057-1062.
Zhou et al., "RUNX proteins desensitize multiple myeloma to lenalidomide via protecting IKZFs from degradation," Leukemia, 2019, 33:2006-2021.
International Search Report and Written Opinion in International Appln. No. PCT/US2021/049322, dated Feb. 8, 2022, 12 pages.
International Search Report and Written Opinion in International Appln. No. PCT/US2021/027798, dated Sep. 28, 2021, 13 pages.
Kita et al., "Role of TGF-beta in proliferative vitreoretinal diseases and ROCK as a therapeutic target," Proceedings of the National Academy of Science, Nov. 2008, 105(45):17504-17509.
Office Action in European Appln. No. 17871449.9, dated Jul. 5, 2022, 15 pages.
Ulrich et al. "CD147 as a Target for COVID-19 Treatment: Suggested Effects 2, 4-6, 19, 21-23 of Azithromycin and Stem Cell Engagement," Stem Cell Reviews and Reports, Apr. 2020, 16:434-440, 7 pages.
Office Action in Australian Appln. No. 2018369784, dated Nov. 8, 2022, 4 pages.
Office Action in Japanese Appln. No. 2020-544393, dated Nov. 14, 2022, 8 pages (with English translation).
Pratt et al., "Abstract 1010: Identification of evolutionarily conserved transcription response elements associated with regulation of cadherin expression in retinal pigment epithelial cells," Molecular Biology of the Cell, 2004, 15(Suppl. S):182A, 1 page.
Yang et al., "Mechanisms of epithelial—mesenchymal transition in proliferative vitreoretinopathy," Discov Med., Oct. 2015, 20(110):207-217, 21 pages.
Ackermann et al., "Pulmonary Vascular Endothelialitis, Thrombosis, and Angiogenesis in Covid-19," New England Journal of Medicine, Jul. 2020, 383(2):120-8.
Alder et al., "Diagnostic utility of telomere length testing in a hospital-based setting," Proceedings of the National Academy of Sciences of the United States of America, Mar. 2018, 115(10):E2358-E2365.
Amarnani et al., "Effect of Methotrexate on an In Vitro Patient-Derived Model of Proliferative Vitreoretinopathy," Invest Ophthalmol Vis Sci., Aug. 2017, 58(10):3940-3949.
Asato et al., "Comparison of gene expression profile of epiretinal membranes obtained from eyes with proliferative vitreoretinopathy to that of secondary epiretinal membranes," PLoS One, 2013, 8(1):e54191, 8 pages.
Bataller and Brenner, "Liver fibrosis," J Clin Invest, Feb. 2005, 15(2):209-18.
Beigel et al., "Remdesivir for the Treatment of Covid-19—Final Report," New England Journal of Medicine, Nov. 2020, 383(19):1813-26, 14 pages.

(56) References Cited

OTHER PUBLICATIONS

Bellissimo et al., "Runx1 negatively regulates inflammatory cytokine production by neutrophils in response to Toll-like receptor signaling," Blood Advances, Mar. 2020, 4(6):1145-58.

Belser et al., "Ocular tropism of respiratory viruses," Microbiol Mol Biol Rev., Mar. 2013, 77(1):144-56.

Bonniaud et al., "Smad3 Null Mice Develop Airspace Enlargement and Are Resistant to TGF-β-Mediated Pulmonary Fibrosis," The Journal of Immunology, Aug. 2004, 173(3):2099, 11 pages.

Bravo et al., "The leukemia-associated AML1 (Runx1)-CBFbeta complex functions as a DNA-induced molecular clamp," Nature Structural Biology, Apr. 2001, 8(4):371-8.

Castoreno et al., "Small molecules discovered in a pathway screen target the Rho pathway in cytokinesis," Nat Chem Biol., Jun. 2010, 6(6):457-463, 21 pages.

Cheema et al., "Keratoconjunctivitis as the initial medical presentation of the novel coronavirus disease 2019 (COVID-19)," Can J Ophthalmol., Aug. 2020, 55(4):e125-e129.

Chen et al., "Ocular manifestations of a hospitalised patient with confirmed 2019 novel coronavirus disease," Br J Ophthalmol., Jun. 2020, 104(6):748-751.

Ciolino et al., "A drug-eluting contact lens," Invest Ophthalmol Vis Sci., Jul. 2009, 50(7):3346-3352.

Delgado-Tirado et al., "Topical delivery of a small molecule RUNX1 transcription factor inhibitor for the treatment of proliferative vitreoretinopathy," Scientific Reports, Nov. 2020, 10(1):20554, 15 pages.

Dua et al., "The ocular surface as part of the mucosal immune system: conjunctival mucosa-specific lymphocytes in ocular surface pathology," Eye (Lond.), 1995, 9(Pt 3):261-7.

Dubois et al., "Evidence that furin is an authentic transforming growth factor-beta1-converting enzyme," Am J Pathol., Jan. 2001, 158(1):305-16.

Eapen et al., "Endothelial to mesenchymal transition: a precursor to post-COVID-19 interstitial pulmonary fibrosis and vascular obliteration?," European Respiratory Journal, Oct. 2020, 56(4):2003167, 3 pages.

Frangogiannis, "Fibroblast-Extracellular Matrix Interactions in Tissue Fibrosis," HHS Public Access Author Manuscript, doi:10.1007/s40139-016-0099-1, published online Feb. 5, 2016, 14 pages; Published in final edited form as: Curr Pathobiol Rep., Mar. 2016, 4(1):11-18.

Fràter-Schröder et al., "Tumor necrosis factor type alpha, a potent inhibitor of endothelial cell growth in vitro, is angiogenic in vivo," Proc Natl Acad Sci USA, Aug. 1987, 84(15):5277-81.

Fu et al., "The effects of the Rho-kinase inhibitor Y-27632 on arachidonic acid-, GTPγS-, and phorbol ester-induced $Ca^{2+}$-sensitization of smooth muscle," FEBS Lett, Nov. 1998, 440(1-2):183-187.

George et al., "Pulmonary fibrosis and COVID-19: the potential role for antifibrotic therapy," The Lancet Respiratory Medicine, Aug. 2020, 8(8):807-15.

Glinsky, "Tripartite Combination of Candidate Pandemic Mitigation Agents: Vitamin D, Quercetin, and Estradiol Manifest Properties of Medicinal Agents for Targeted Mitigation of the COVID-19 Pandemic Defined by Genomics-Guided Tracing of SARS-CoV-2 Targets in Human Cells," Biomedicines, May 2020, 8(5):129, 26 pages.

Graney and Lee, "Impact of novel antifibrotic therapy on patient outcomes in idiopathic pulmonary fibrosis: patient selection and perspectives," Patient Relat Outcome Meas., 2018, 9:321-8.

Haghjou et al., "Sustained release intraocular drug delivery devices for treatment of uveitis," J Ophthalmic Vis Res., Oct. 2011, 6(4):317-329.

Hendren et al., "Description and Proposed Management of the Acute COVID-19 Cardiovascular Syndrome," Circulation, Apr. 2020, 141(23):1903-1914, 19 pages.

Hiscott et al., "Pathobiology of epiretinal and subretinal membranes: possible roles for the matricellular proteins thrombospondin 1 and osteonectin (SPARC)," Eye (Lond)., Jul. 2002, 16(4):393-403.

Hiscott et al., "Retinal pigment epithelial cells in epiretinal membranes: an immunohistochemical study," Br J Ophthalmol., Oct. 1984, 68(10):708-15.

Hoyt et al., "Alterations in pulmonary mRNA encoding procollagens, fibronectin and transforming growth factor-beta precede bleomycin-induced pulmonary fibrosis in mice," J Pharmacol Exp Ther., Aug. 1988, 246(2):765-71.

Hsu et al., "Inhibition of type 1 human immunodeficiency virus replication by a tat antagonist to which the virus remains sensitive after prolonged exposure in vitro," Proc Natl Acad Sci USA, Jun. 1993, 90(14):6395-9.

Huertas et al., "Endothelial cell dysfunction: a major player in SARS-CoV-2 infection (COVID-19)?," European Respiratory Journal, Jul. 2020, 56(1):2001634, 5 pages.

Hutchinson et al., "Global incidence and mortality of idiopathic pulmonary fibrosis: a systematic review," European Respiratory Journal, Sep. 2015, 46(3):795-806.

Ikenoya et al., "Inhibition of rho-kinase-induced myristoylated alanine-rich C kinase substrate (MARCKS) phosphorylation in human neuronal cells by H-1152, a novel and specific Rho-kinase inhibitor," J. Neurochem., Apr. 2002, 81(1):9-16.

Ishizaki et al., "Pharmacological properties of Y-27632, a specific inhibitor of rho-associated kinases," Mol Pharmacol., May 2000, 57(5):976-83.

Ji et al., "Inflammatory regulatory network mediated by the joint action of NF-kB, STAT3, and AP-1 factors is involved in many human cancers," Proceedings of the National Academy of Sciences, May 2019, 116(19):9453-9462.

Kim et al., "Controlled drug release from an ocular implant: an evaluation using dynamic three-dimensional magnetic resonance imaging," Invest. Ophthalmol. Vis. Sci., Aug. 2004, 45(8):2722-2731.

Kim et al., "RUNX1 is essential for mesenchymal stem cell proliferation and myofibroblast differentiation," Proc Natl Acad Sci USA, Nov. 2014, 111(46):16389-94.

Knipe et al., "The Rho Kinases: Critical Mediators of Multiple Profibrotic Processes and Rational Targets for New Therapies for Pulmonary Fibrosis," Pharmacol Rev., Jan. 2015, 67(1):103-117.

Korol et al., "RhoA/ROCK signaling regulates TGFβ-induced epithelial-mesenchymal transition of lens epithelial cells through MRTF-A," Mol Med., Dec. 2016, 22:713-723.

Lederer et al., "Idiopathic Pulmonary Fibrosis," New England Journal of Medicine, May 2018, 378(19):1811-23.

Lee et al., "TGF-β regulates cell fate during epithelial-mesenchymal transition by upregulating survivin," Cell Death & Disease, Jul. 2013, 4(7):e714, 10 pages.

Li et al., "RUNX1 promotes tumour metastasis by activating the WNT/beta-catenin signalling pathway and EMT in colorectal cancer," J Exp Clin Cancer Res, Aug. 2019, 38(1):334, 13 pages.

Liao et al., "Rho kinase (ROCK) inhibitors," J Cardiovasc Pharmacol, Jul. 2007, 50(1):17-24.

Liberati et al., "Smads bind directly to the Jun family of AP-1 transcription factors," Proc Natl Acad Sci USA, Apr. 1999, 96(9):4844-9.

Lin et al., "Discovery and Prectinical Development of Netarsudil, a Novel Ocular Hypotensive Agent for the Treatment of Glaucoma," J Ocul Pharmacol Ther., 2018, 34(1-2):40-51.

Lin et al., "LncRNA Hoxaas3 promotes lung fibroblast activation and fibrosis by targeting miR-450b-5p to regulate Runx1," Cell Death & Disease, Aug. 2020, 11(8):706, 14 pages.

Liu et al., "Conjunctiva is not a preferred gateway of entry for SARS-CoV-2 to infect respiratory tract," Med Virol., Sep. 2020, 92(9):1410-1412.

Lucas et al., "Abstract: Formation of abdominal adhesions is inhibited by antibodies to transforming growth factor-beta 1," J Surg Res., Oct. 1996, 65(2):135-8, 4 pages.

Maher, "PROFILEing idiopathic pulmonary fibrosis: rethinking biomarker discovery," European Respiratory Review, Jun. 2013, 22(128):148-52.

(56) References Cited

OTHER PUBLICATIONS

Malaviya et al., "Anti-TNFα therapy in inflammatory lung diseases," HHS Public Access Author Manuscript, doi: 10.1016/j.pharmthera.2017.06.008, published online Nov. 4, 2017, 23 pages; Published in final edited form as: Pharmacol Ther., Dec. 2017, 180:90-8.

Malaviya et al., "Attenuation of Nitrogen Mustard-Induced Pulmonary Injury and Fibrosis by Anti-Tumor Necrosis Factor-a Antibody," Toxicological Sciences, Nov. 2015, 148(1):71-88.

Martin et al., "TGF-β1 and radiation fibrosis: a master switch and a specific therapeutic target?," Int J Radiat Oncol Biol Phys., May 2000, 47(2):277-90.

Martines et al., "Pathology and Pathogenesis of SARS-CoV-2 Associated with Fatal Corona virus Disease, United States," Emerg Infect Dis., Sep. 2020, 26(9):2005-15.

Moshirfar et al., "Use of Rho kinase Inhibitors in Ophthalmology: A Review of the Literature," Med Hypothesis Discov Innov Ophthalmol., Fall 2018, 7(3):101-111.

Mukhopadhyay et al., "Role of TNFα in pulmonary pathophysiology," Respiratory Research, 2006, 7(1):125, 9 pages.

O'Hare et al., "Targeting Runt-Related Transcription Factor 1 Prevents Pulmonary Fibrosis and Reduces Expression of Severe Acute Respiratory Syndrome Coronavirus 2 Host Mediators," The American Journal of Pathology, Jul. 2021, 191(7):1193-1208.

Ojo et al., "Pulmonary Fibrosis in COVID-19 Survivors: Predictive Factors and Risk Reduction Strategies," Pulmonary Medicine, Aug. 2020, 2020:6175964, 10 pages.

Palakurthi et al., "Investigation of kinetics of methotrexate for therapeutic treatment of intraocular lymphoma," Current Eye Research, Oct. 2010, 35(12):1105-1115.

Pashaei et al., "Immunotherapy for SARS-CoV-2: potential opportunities," Expert Opin Biol Ther., Oct. 2020, 20(10):1111-5.

Polak et al., "A systematic review of pathological findings in COVID-19: a pathophysiological timeline and possible mechanisms of disease progression," Mod Pathol., Nov. 2020, 33(11):2128-38.

Riddell et al., "RUNX1: an emerging therapeutic target for cardiovascular disease," Cardiovasc Res., Mar. 2020, 116(8):1410-1423.

Robert et al., "A Drug Delivery System for Administration of Anti-TNF-α Antibody," Transl Vis Sci Technol., Mar. 2016, 5(2):11, 11 pages.

Sainson et al., "TNF primes endothelial cells for angiogenic sprouting by inducing a tip cell phenotype," Blood, May 2008, 111(10):4997-5007.

Schaefer et al., "In situ detection of SARS-CoV-2 in lungs and airways of patients with COVID-19," Modern Pathology, Jun. 2020, 33(11):2104-14.

Selman et al., "Idiopathic pulmonary fibrosis: an epithelial fibroblastic cross-talk disorder," Respir Res., 2002, 3(1):3, 8 pages.

Shah et al., "Alk5/Runx1 signaling mediated by extracellular vesicles promotes vascular repair in acute respiratory distress syndrome," Clin Transl Med, Jun. 2018, 7(1):19, 18 pages.

Shaw et al., "Topical administration of a Rock/Net inhibitor promotes retinal ganglion cell survival and axon regeneration after optic nerve injury," Exp Eye Res., May 2017, 158:33-42, 19 pages.

Shen et al., "Discovery of Novel ROCK1 Inhibitors via Integrated Virtual Screening Strategy and Bioassays," Scientific Reports, Nov. 2015, 5:16749, 14 pages.

Shen et al., "Isolation and Culture of Primary Mouse Retinal Pigment Epithelial (RPE) Cells with Rho-Kinase and TGFβR-1/ALK5 Inhibitor," Med Sci Monit., Dec. 2017, 23:6132-6136.

Sinha and Ware, "Selective tumour necrosis factor receptor-1 inhibition in acute lung injury: a new hope or a false dawn?," Thorax, Aug. 2018, 73(8):699-701.

Strongman et al., "Incidence, Prevalence, and Survival of Patients with Idiopathic Pulmonary Fibrosis in the UK," Adv Ther., May 2018, 35(5):724-36.

Taheri et al., "Nanoparticles of conjugated methotrexate-human serum albumin: preparation and cytotoxicity evaluations" J Nanomaterials, Jan. 2011, 2011:768201, 7 pages.

Tang et al., "Runt-Related Transcription Factor 1 Regulates LPS-Induced Acute Lung Injury via NF-κB Signaling," Am J Respir Cell Mol Biol., 2017, 57(2):174-83.

Tashiro et al., "Exploring Animal Models That Resemble Idiopathic Pulmonary Fibrosis," Frontiers in Medicine, Jul. 2017, 4:118, 11 pages.

The Recovery Collaborative Group, "Dexamethasone in Hospitalized Patients with Covid-19—Preliminary Report," New England Journal of Medicine, Feb. 2021, 384(8):693-704, 11 pages.

Thomas, "Furin at the cutting edge: from protein traffic to embryogenesis and disease," HHS Public Access Author Manuscript, doi: 10.1038/nrm934, published online 2002, 32 pages; Published in final edited form as Nat Rev Mol Cell Biol., Oct. 2002, 3(10):753-66.

Vancheri et al., "Nintedanib with Add-on Pirfenidone in Idiopathic Pulmonary Fibrosis. Results of the INJOURNEY Trial," Am J Respir Crit Care Med., Feb. 2018, 197(3):356-63.

Velez and Whitcup, "New developments in sustained release drug delivery for the treatment of intraocular disease," Br J Ophthalmol, 1999, 83:1225-1229.

Vijayaragavan et al., "Controlled Release of Methotrexate Using Alpha-Lactalbumin Microparticles," Int J Pharm Res, 2011, 3(1):39-44.

Whitmore et al., "TNF-α signaling regulates RUNX1 function in endothelial cells," The FASEB Journal, Feb. 2021, 35(2):e21155, 17 pages.

Wikipedia.org [online], "Rho kinase inhibitor," last updated Feb. 20, 2023, retrieved on Mar. 14, 2023, retrieved from URL<https://en.wikipedia.org/wiki/Rho_kinase_inhibitor>, 5 pages.

Wu et al., "Characteristics of Ocular Findings of Patients With Coronavirus Disease 2019 (COVID-19) in Hubei Province, China," JAMA Ophthalmol., May 2020, 138(5):575-578.

Wu et al., "The ROCK inhibitor, thiazovivin, inhibits human corneal endothelial-to-mesenchymal transition/epithelial-to-mesenchymal transition and increases ionic transporter expression," Int J Mol Med., Oct. 2017, 40(4):1009-1018.

Xie et al., "Single-Cell Deconvolution of Fibroblast Heterogeneity in Mouse Pulmonary Fibrosis," Cell Rep., Mar. 2018, 22(13):3625-40.

Yamaguchi et al., "Rho-Kinase/ROCK as a Potential Drug Target for Vitreoretinal Diseases," J Ophthalmol., 2017, 2017:8543592, 8 pages.

Yan et al., "Feedback regulation of TGF-β signaling," Acta Biochimica et Biophysica Sinica, Jan. 2018, 50(1):37-50.

Yarrow et al., "Screening for cell migration inhibitors via automated microscopy reveals a Rho-kinase inhibitor," Chem. Biol., Mar. 2005, 12(3):385-395.

Yue et al., "TGF-β: Titan of Lung Fibrogenesis," HHS Public Access Author Manuscript, doi: 10.2174/10067, Oct. 2013, 20 pages; Published in final edited form as: Curr Enzym Inhib., Jul. 2010, 6(2):10.2174/10067.

Yzaguirre et al., "The Role of Runx1 in Embryonic Blood Cell Formation," RUNX Proteins in Development and Cancer, Singapore: Springer Singapore, Groner et al. (eds.), 2017, pp. 47-64.

Zhou et al., "Runt-Related Transcription Factor 1 (RUNX1) Promotes TGF-f3-Induced Renal Tubular Epithelial-to-Mesenchymal Transition (EMT) and Renal Fibrosis through the P13K Subunit p110δ," EBioMedicine, May 2018, 31:217-25.

Zhou et al., "Sustained subconjunctival delivery of infliximab protects the cornea and retina following alkali burn to the eye," Invest Ophthalmol Vis Sci., Jan. 2017, 58(1):96-105.

\* cited by examiner

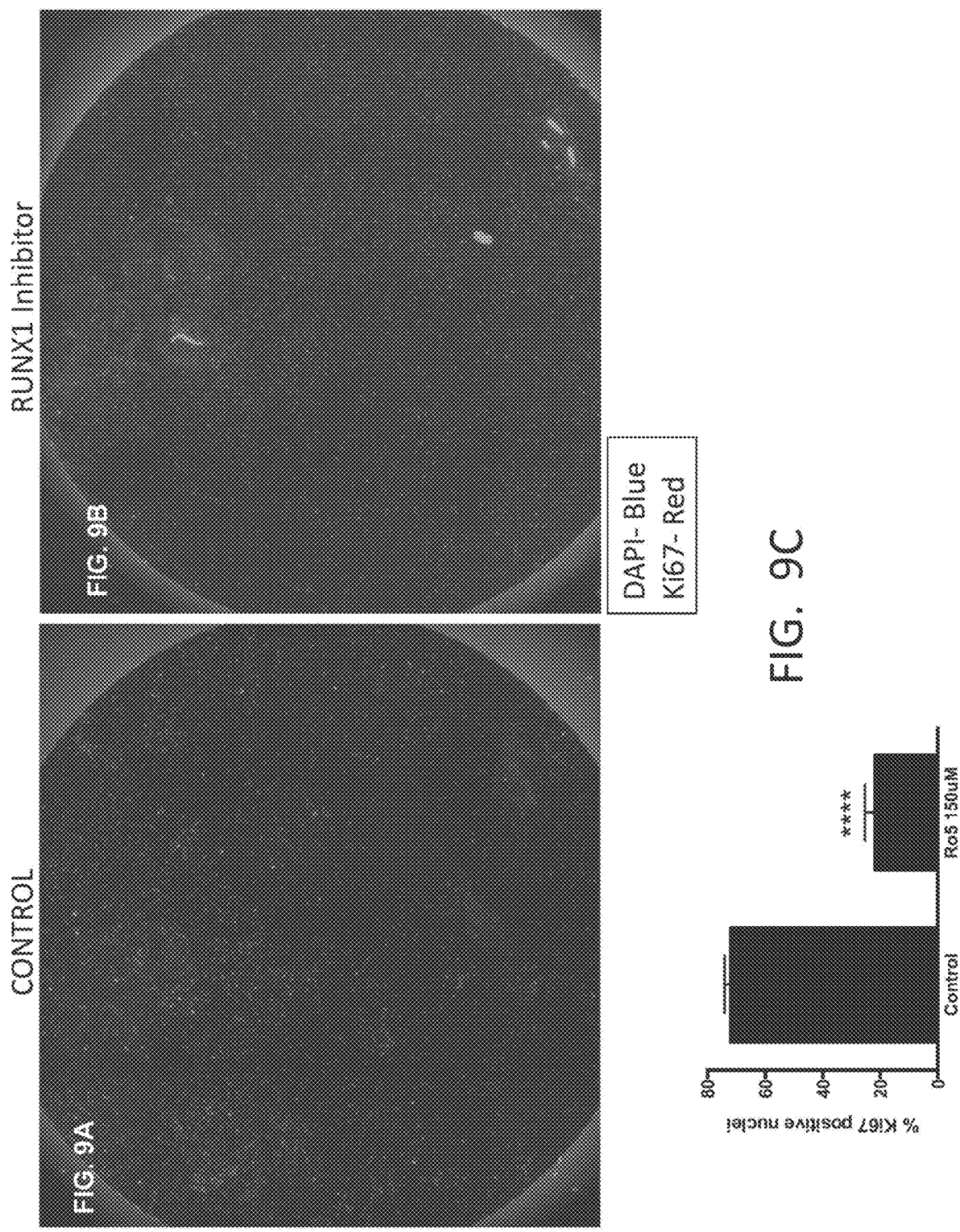

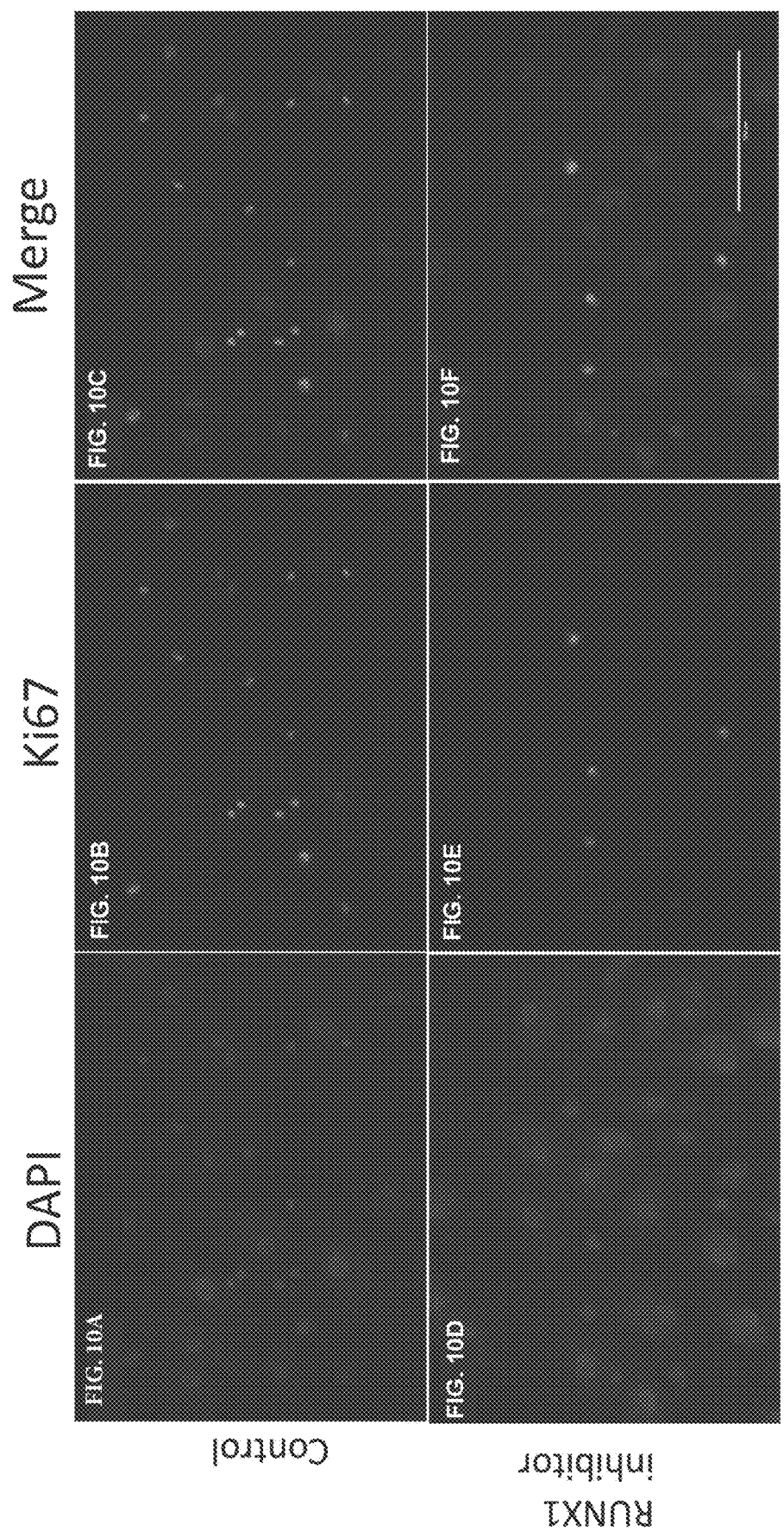

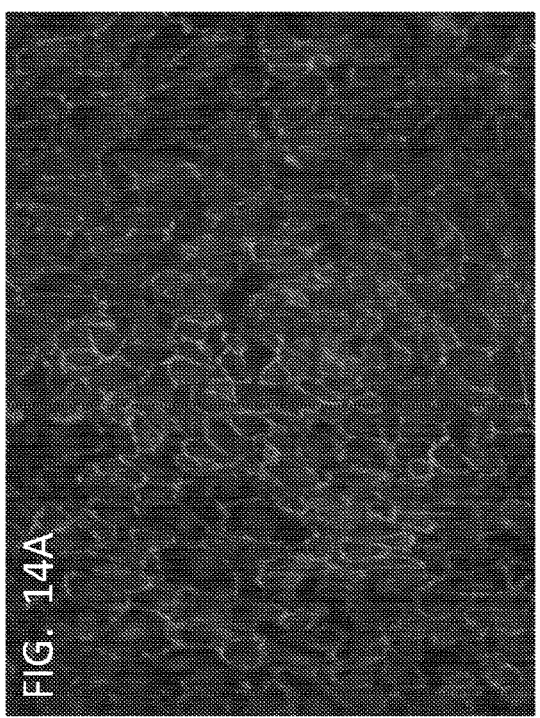
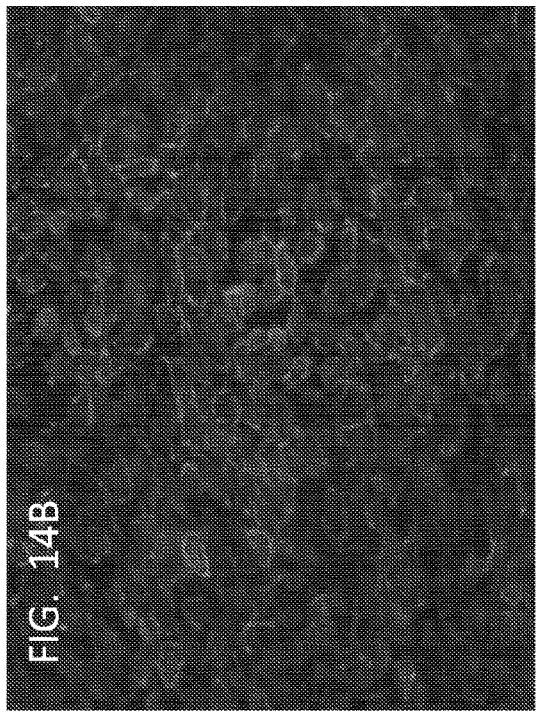
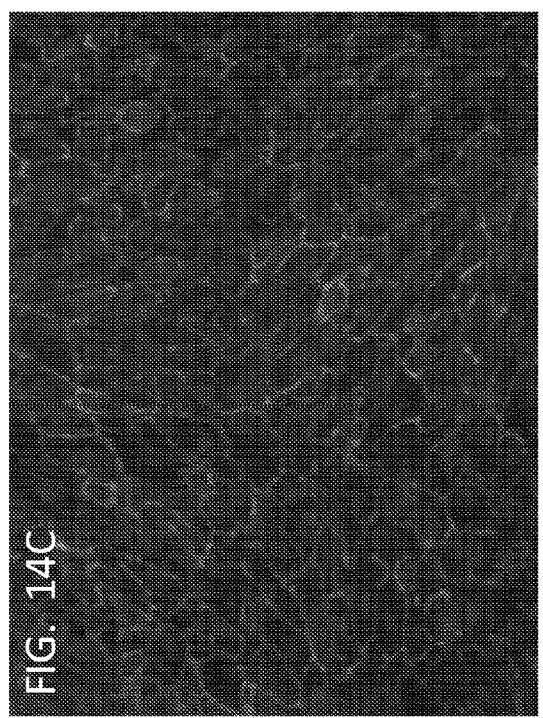
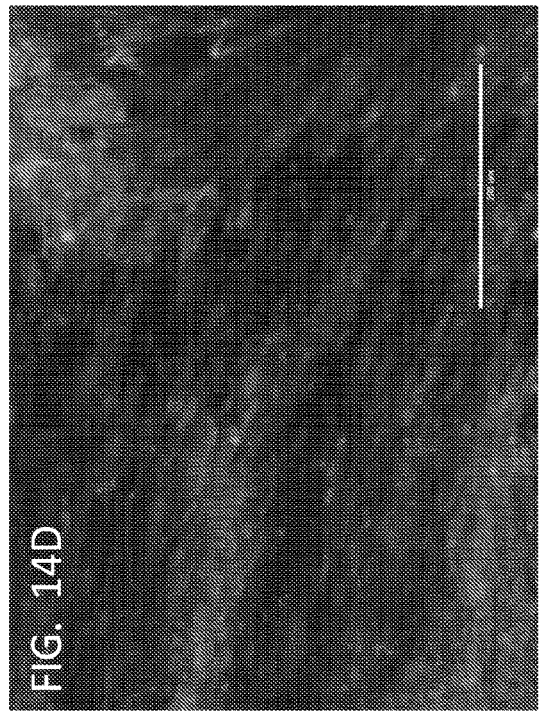

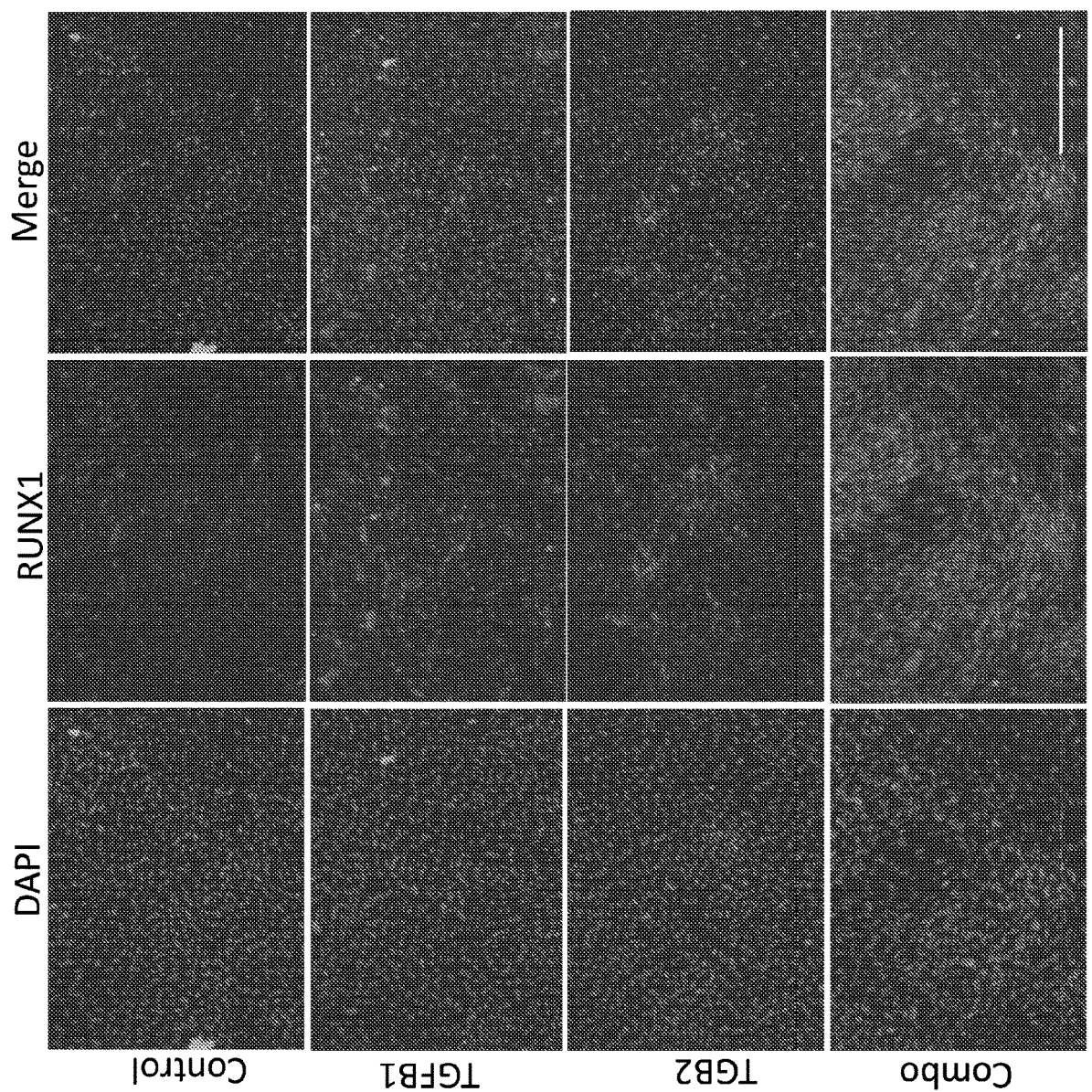

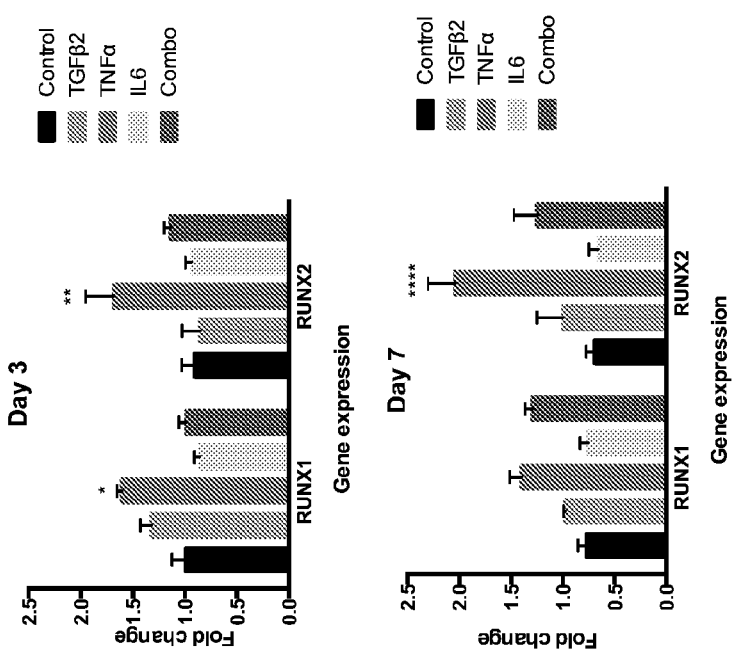
FIG. 21B
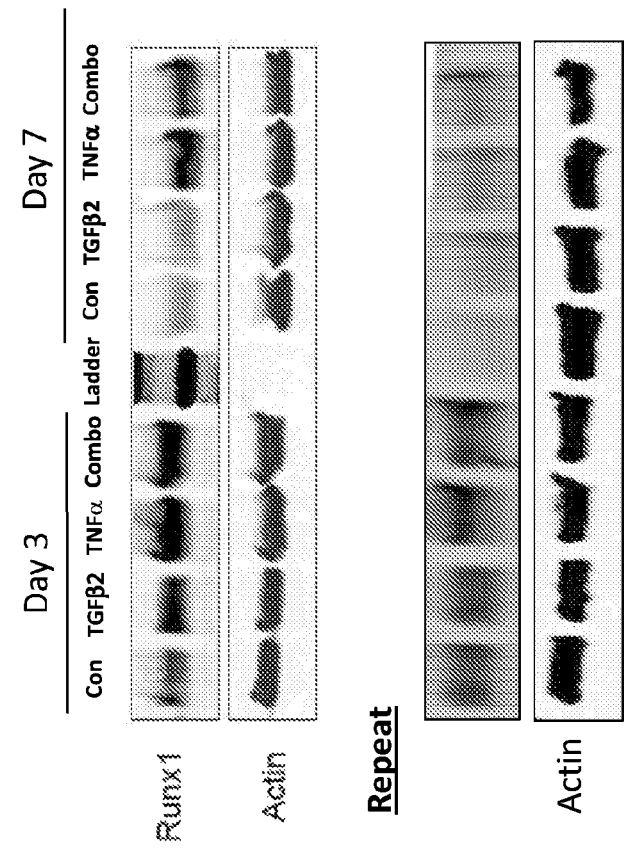
FIG: 21A

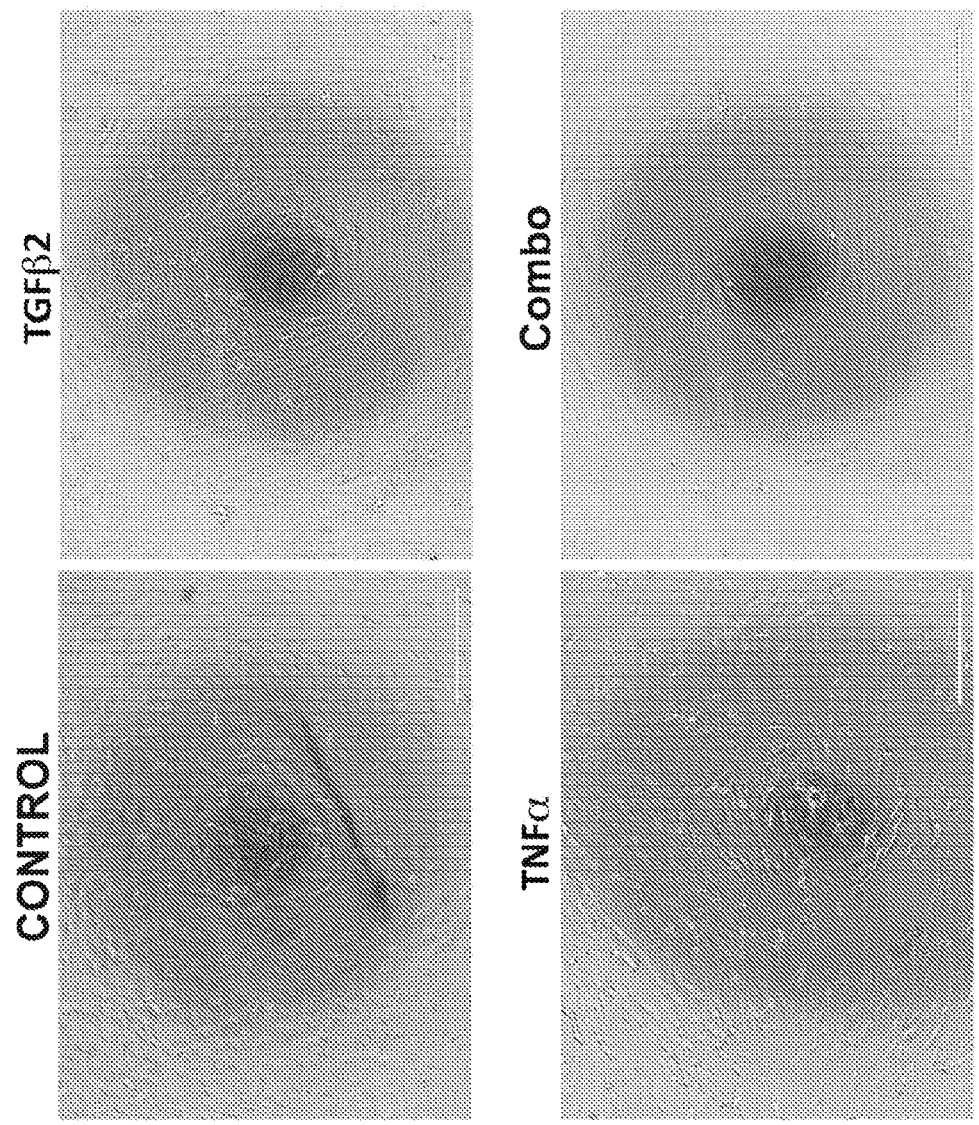
FIG: 24

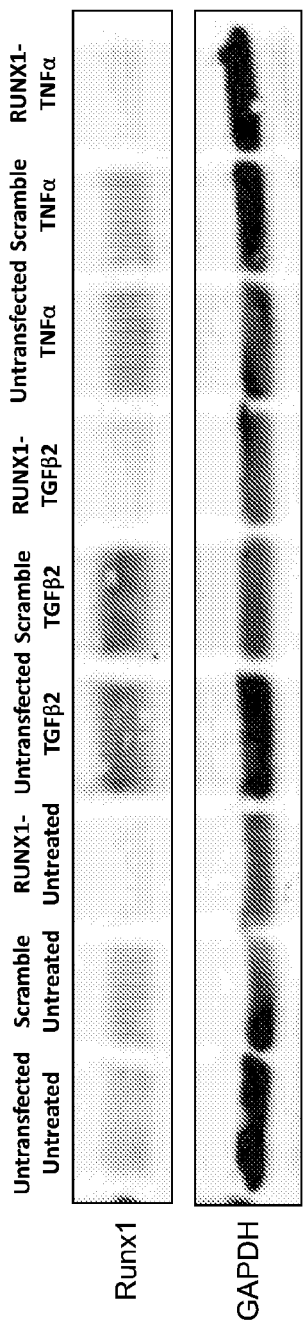
FIG: 30A
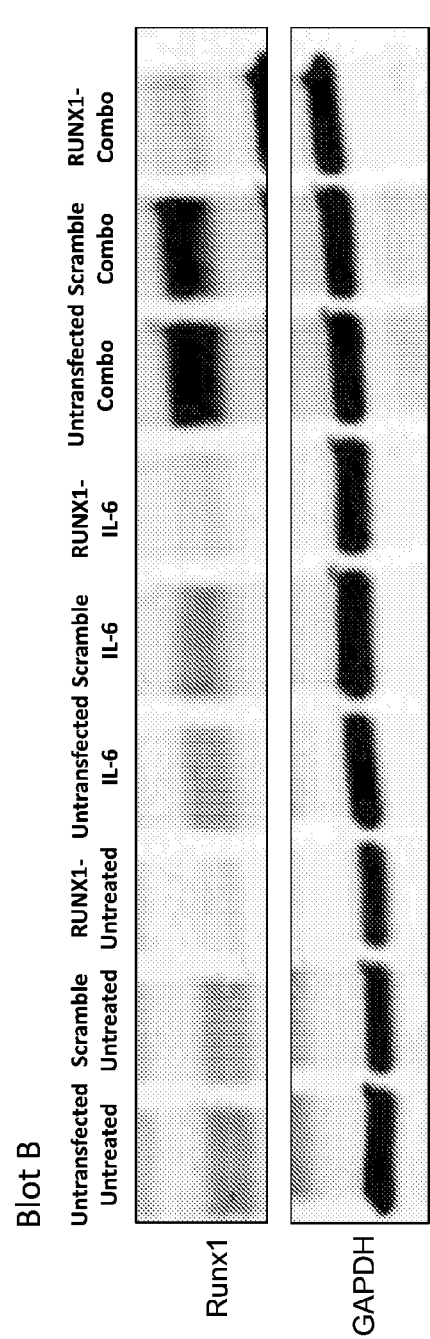
FIG. 30B

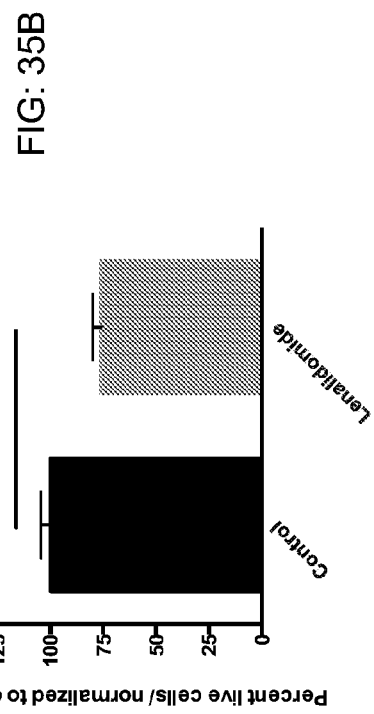
FIG. 35A
FIG. 35B
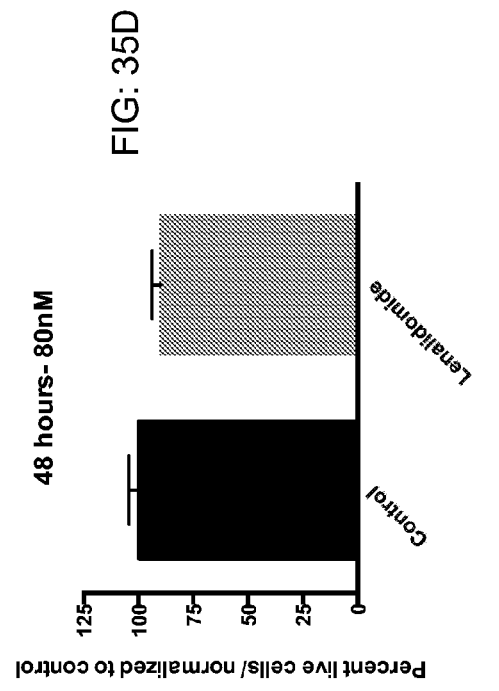
FIG. 35C
FIG. 35D

RUNX1 INHIBITION FOR TREATMENT OF PROLIFERATIVE VITREORETINOPATHY AND CONDITIONS ASSOCIATED WITH EPITHELIAL TO MESENCHYMAL TRANSITION

RELATED APPLICATIONS

This application claims benefit of priority to U.S. Provisional Application No. 62/586,067, filed Nov. 14, 2017, the entire contents of which is incorporated herein by reference.

STATEMENT AS TO FEDERALLY SPONSORED RESEARCH

This invention was made with government support under EY021624 awarded by the National Institutes of Health and under W81XWH-17-2-0006 award by the Department of Defense. The Government has certain rights in the invention.

CROSS-REFERENCES TO RELATED APPLICATIONS

This application is a national stage application filed under 35 U.S.C. § 371, of International Patent Application No PCT/US2018/061110, filed on Nov. 14, 2018, which claims the benefit of and priority to U.S. Provisional Application No. 62/586,067, filed on Nov. 14, 2017, the entire contents of which are incorporated herein by reference in their entirety.

INCORPORATION BY REFERENCE OF SEQUENCE LISTING

The contents of the sequence listing text file named "036770-567001WO_Sequence_Listing_txt", which was created on Nov. 15, 2018 and is 209,506 bytes in size, are incorporated herein by reference in its entirety.

FIELD OF THE INVENTION

The present invention relates to preventing or reducing proliferation, migration, or mesenchymal transition of retinal pigment epithelial cells.

BACKGROUND

Retinal detachment (RD) is an important cause of sudden visual loss in the United States, with approximately 40,000 cases occurring annually. Permanent visual loss will result if treatment is delayed. A retinal detachment is the separation of the neurosensory retina from the retinal pigment epithelium (RPE). In the nonpathologic state, the retinal pigment epithelium is a continuous epithelial monolayer occluded by tight junctions, which maintain a strict separation of the underlying choroidal capillary beds from the photoreceptors of the sensory retina, thus forming the outer blood-retina barrier. Its functions include the nourishment of photoreceptors, elimination of waste products, and reabsorption of subretinal fluid.

The definitive treatment of retinal detachment is surgical repair. Multiple operative techniques are available to the treating retinologist, but the principles underlying treatment of retinal detachment remain the same: removal of fluid from the subretinal space, relief of any existing traction, and treatment and prophylaxis against the underlying cause for the ingression of fluid, whether it be due to a retinal break or an exudative process.

Proliferative vitreoretinopathy (PVR) is the most common cause for failure of retinal detachment surgery, a complication which occurs in 5-10% of all retinal detachment surgeries. PVR can also occur spontaneously in the absence of surgery. PVR is most likely to develop following repeated surgical procedures of the eye, following significant physiologic insult to the eye such as in trauma, as well as in retinal detachments complicated by multiple tears, giant tears, vitreous hemorrhage, or in eyes with uveitis. PVR is especially prevalent after retinal detachment associated with open globe injury, where it occurs in approximately 50% of cases (Colyer M., et al. Perforating globe injuries during operation Iraqi Freedom. *Ophthalmology.* 2008; 115:2087-2093, and Eliott D. et al., Smoking is a risk factor for proliferative vitreoretinopathy after traumatic retinal detachment. *Retina.* 2017; 37:1229-1235).

PVR is also a common complication of post-traumatic eye surgery. In this case, cells also grow uncontrollably beneath or on top of the retina triggering pre/sub-retinal membrane formation, tractional retinal detachment, and permanent vision loss. PVR occurs in 40-60% of patients with open globe injury. Hence PVR is highly relevant for the military and military-related eye trauma. Colyer, M. H., et al., Perforating globe injuries during operation Iraqi Freedom. Ophthalmology, 2008.115(11): p. 2087-93.

Currently, there are no medical treatments for PVR. Current standard of care for PVR includes invasive and complex surgery that often yields disappointing results.

SUMMARY OF THE INVENTION

Provided herein are solutions to the clinical problems described above. The present subject matter provides methods for preventing or reducing proliferation or migration or mesenchymal transition of retinal pigment epithelial (RPE) cells or other cells including retinal glial cells, macrophages, and fibroblasts in a subject who comprises a retinal hole or a retinal tear, the method comprising administering to the subject a Runt-Related Transcription Factor 1 (RUNX1) inhibitor. For example, the methods are useful for preventing or reducing proliferation, migration, or mesenchymal transition of retinal pigment epithelial cells, corneal epithelial cells, conjunctival epithelial cells, and other cells within the eye. PVR is diagnosed by the observation of cell outgrowths, membranes and bands in the vitreous during an ophthalmological exam, fundus or optical coherence tomography (OCT). The methods and compositions described herein are also useful for RUNX1 inhibition for treatment of proliferative vitreoretinopathy and other conditions associated with epithelial to mesenchymal transition (EMT). Thus, the invention encompasses a composition for preventing or reducing proliferation or migration of retinal pigment epithelial (RPE) cells in a subject who comprises a retinal hole or retinal tear, the composition comprising a RUNX1, inhibitor, e.g., a pharmaceutical composition comprising the inhibitor and a pharmaceutically-acceptable carrier or excipient. An excipient is an inactive substance that serves as the vehicle or medium for a drug or other active substance.

In embodiments, the subject comprises proliferative vitreoretinopathy (PVR). In other aspects, the subject comprises retinal detachment, wherein the retinal detachment comprises rhegmatogenous retinal detachment, exudative detachment, or tractional retinal detachment.

In embodiments, the RUNX1 inhibitor decreases the expression and/or activity of RUNX1. The RUNX1 inhibitor, may comprise a small molecule or an inhibitory nucleic acid. In aspects, the inhibitory nucleic acid comprises an RNA interfering agent (RNAi) or an RNA expressing/encoding an inhibitory protein. In particular aspects, the RNAi comprises siRNA. In other aspects, the RUNX1 inhibitor is a small molecule. In embodiments, the small molecule comprises the structure of Formula I:

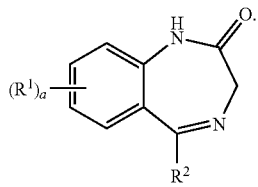

In other embodiments, the RUNXI small molecule of Formula I comprises Ro5-3335. In embodiments, the small molecule inhibitor comprises the structure of Formula III:

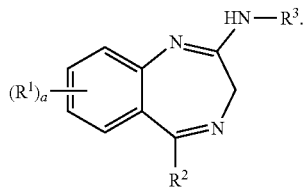

In other embodiments, the RUNX1 small molecule of Formula III comprises Ro 24-7429. In other embodiments, the RUNX1 small molecule inhibitor comprises the structure of Formula V:

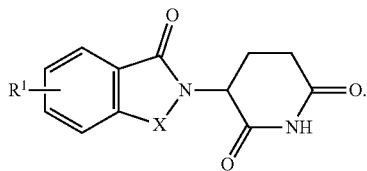

In embodiments, the small molecule of Formula V comprises lenalidomide. In other examples, the method further comprises administering methotrexate.

In embodiments, the RUNX1 inhibitor may be formulated into a composition. In other embodiments, the composition may be formulated as a solution, suspension, semi-liquid, emulsion, ointment, cream, foam gel, powder or a controlled-release/sustain-release formulation.

In aspects, the composition is administered topically or by intravitreal injection.

In other aspects, the composition may be administered to the eye in a concentration of about 0.001 mg to about 10 mg of the inhibitor per eye.

In embodiments, the composition may be administered to the eye of a subject in an amount from about 50 µL to about 100 µL per eye.

In further embodiments, the composition may further comprise an anti-inflammatory agent, e.g., a combination therapy treatment approach such as one in which a RUNX1 inhibitor is administered and an anti-inflammatory agent is administered before, after, or concurrently with the anti-inflammatory agent. In embodiments, the anti-inflammatory agent comprises a steroid or a nonsteroidal anti-inflammatory drug (NSAID). For example, the anti-inflammatory agent comprises prednisolone acetate, diclofenac sodium, or a combination thereof.

In further aspects, the inhibitor may be at a concentration of about 0.001% w/v to about 100% w/v.

The subject to be treated is preferably a mammal in need of such treatment, e.g., has been diagnosed with, is suffering from/has, or is at risk of developing one or more disorders or diseases described herein. The mammal can be, e.g., any mammal, e.g., a human, a primate, a mouse, a rat, a dog, a cat, a cow, a horse, or a pig. In a preferred embodiment, the mammal is a human.

In other aspects, the subject has not been diagnosed with aberrant angiogenesis. In other aspects, the subject has not been diagnosed with small vessel disease.

In aspects, the subject has not undergone surgery. In additional aspects, the inhibitor may be administered prior to a surgery, during a surgery or after a surgery. The surgery may comprise of retinal detachment surgery, glaucoma surgery, corneal surgery, cataract surgery, or any penetrating surgery of the eye. In other aspects, the subject has suffered a trauma to the eye.

Also provided herein are methods for diagnosing aberrant epithelial to mesenchymal transition (EMT) of retinal and ocular cells in a subject, the methods comprising: providing a test sample from said subject (e.g., via ocular surgery), assaying the level of runt-related transcription factor 1 (RUNX1) protein or mRNA in the test sample; and, and thereby diagnosing the subject as having aberrant EMT of retinal cells if the level of RUNX1 protein or mRNA is elevated in the test sample compared to a normal control. In embodiments, diagnosis of aberrant epithelial to mesenchymal transition of retinal cells may be performed by clinical exam or imaging. Such methods may also be used to measure RUNX1 levels, e.g., level of expression, as a biomarker for PVR and/or an indication of the severity of the disorder. The methods are also useful to monitor the effect/efficacy of treatment.

In embodiments, levels of RUNX1 may be measured using ELISA, Q-RT-PCR, Western blot analysis, immunohistochemistry, or immunofluorescence. In other embodiments, the test sample from the subject may be obtained during ocular surgery.

Also provided herein are methods for treating or reducing the severity of proliferative vitreoretinopathy (PVR) in a subject, the method comprising: identifying a subject comprising PVR, and administering to said subject a runt-related transcription factor 1 (RUNX1) inhibitor.

Each embodiment disclosed herein is contemplated as being applicable to each of the other disclosed embodiments. Thus, all combinations of the various elements described herein are within the scope of the invention.

Also described herein are methods for monitoring whether a disease (e.g., that comprises proliferative vitreoretinopathy (PVR) as well as a number of other disorders described herein, e.g., pathologic ocular fibrosis, or pathologic ocular proliferation, is progressing in a subject who has been diagnosed with the disease. The method comprises periodically determining the level of RUNX1 protein or mRNA in said subject, and identifying the disease as worsening if the level of RUNX1 protein or mRNA increases over time; identifying the disease as improving if the level of RUNX1 protein or mRNA decreases over time; identifying the disease as neither worsening or improving if the level of RUNX1 protein or mRNA remains the same or about the same over time, wherein determining the level of RUNX1 protein or mRNA comprises providing a test sample from said subject; and assaying the level of RUNX1 protein or mRNA in the test sample.

Described herein is a method for diagnosing a proliferative vitreoretinopathy (PVR) in a subject, the method comprising providing a test sample from said subject, assaying the level of runt-related transcription factor 1 (RUNX1) protein or mRNA in the test sample; and diagnosing the subject as having aberrant PVR if the level of RUNX1 protein or mRNA is elevated in the test sample compared to a normal control.

Also provided herein are methods for identifying whether a therapy has reduced or ameliorated a disease that comprises proliferative vitreoretinopathy (PVR) in a subject, the method comprising providing a pre-therapy test sample from said subject, assaying the pre-therapy level of RUNX1 protein or mRNA in the pre-therapy test sample; administering the therapy to the subject; providing a post-therapy test sample from said subject; assaying the post-therapy level of RUNX1 protein or mRNA in the post-therapy test sample; and identifying the therapy as having reduced or ameliorated said disease if the level of RUNX1 protein or mRNA in the post-therapy test sample is lower than the level of RUNX1 protein or mRNA in the pre-therapy sample.

In other examples, described herein are methods of reducing proliferation and migration of cells undergoing epithelial to mesenchymal transition (EMT) within an eye of a subject, the method comprising administering a runt-related transcription factor 1 (RUNX1) inhibitor to the subject. In embodiments, the EMT related disease comprises pathologic ocular fibrosis, proliferation, conjunctival fibrosis, ocular cicatricial pemphigoid, corneal scarring, corneal epithelial down growth, or aberrant post-surgical fibrosis. In some examples, the inhibitor is administered during or after glaucoma surgery, cataract surgery, or Laser-Assisted in situ keratomileusis (LASIK). In other examples, the inhibitor is administered during or after intraocular surgery.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

FIG. 2A-2I indicated that RUNX1 was present in Cells from human PVR (C-PVR) from several patient donors.

FIG. 4A is an image depicting the immunofluorescence staining of membranes from patients with PVR counterstained with DAPI. FIB. 4B is an image depicting the immunofluorescence staining of membranes from patients with PVR stained with RUNX1. FIG. 4C is a merged image of FIGS. 4A and 4B. FIG. 4D is an image depicting the immunofluorescence staining of membranes from patients with PVR counterstained with DAPI. FIG. 4E is an image depicting the immunofluorescence staining of membranes from patients with PVR stained with RUNX1. FIG. 4F is a merged image of FIGS. 4D and 4E. FIG. 4A-4F showed additional images of staining of RUNX1 in PVR.

FIG. 3B is an image depicting the immunohistochemical staining of human PVR membranes of RUNX1, counterstained with hematoxylin in membranes obtained from patients with PVR.

FIG. 9A is an image depicting a control (vehicle treated) Ki67 staining 48 hours post treatment. FIG. 9B is an image depicting Ki67 staining 48 hours post treatment with RUNX1 inhibitor, Ro5-3335 at 150 µM. A significant reduction in cell number and proliferative capacity of C-PVR cells was observed. FIG. 9C is a bar graph depicting the quantitation of images from FIGS. 9A and 9B.

FIG. 10A is an image depicting DAPI staining of untreated controls. FIG. 10B is an image depicting Ki67 staining of untreated controls. FIG. 10C is a merged image of FIGS. 10A and 10B. FIG. 10D is an image depicting DAPI staining of cells treated with RUNX1 inhibitor, Ro5-3335. FIG. 10E is an image depicting Ki67 staining of cells treated with RUNX1 inhibitor, Ro5-3335. FIG. 10F is a merged image of FIGS. 10D and 10E. FIG. 10A-10E are a higher magnification than FIGS. 9A and 9B; and depict a significant reduction in the cell number and proliferative capacity of C-PVR cells.

FIGS. 11A and 11B showed epithelial-mesenchymal transition (FIG. 11B) compared to control (FIG. 11A).

FIG. 14A is an immunofluorescence image depicting mature ARPE-19 cells 7 days post treatment of untreated control. FIG. 14B is an immunofluorescence image depicting mature ARPE-19 cells 7 days post treatment with TGFβ1. FIG. 14C is an immunofluorescence image depicting mature ARPE-19 cells 7 days post treatment with TGFβ2. FIG. 14D is an immunofluorescence image depicting mature ARPE-19 cells 7 days post treatment with a combination of TGFβ2, TNFα, and IL-6 (10 ng/ml each). A reduction in the epithelial markers Zonula occludens-1 in the treatments was observed as compared to controls.

FIG. 15 are immunofluorescence staining images of ARPE-19 cells 7 days post treatment with TGFβ1, TGFβ2, and combination of TGFβ2, TNFα and IL-6 (10 ng/ml each). A significant increase in the RUNX1 expression in the treatments was observed as compared to controls. This indicated that RUNX1 expression increased with EMT.

FIG. 16 is magnified data from FIG. 13.

FIG. 21A are images depicting immunoblots indicating that RUNX1 protein expression levels were increased in growth factor induced Epithelial to Mesenchymal Transition (EMT). The increase in RUNX1 protein was observed upon treatment with growth factors: transforming growth factor beta 2 (TGFβ2), tumor necrosis factor alpha (TNFα) and combination treatment, including TGFβ2, TNFα, and interleukin-6 (IL-6), at 3 and 7 days post treatment.

FIG. 21B are bar graphs indicating that an increase in RUNX1 and runt related transcription factor 2 (RUNX2) RNA expression was observed upon treatment with growth factors (TGFβ2, TNFα, and IL-6, each at 10 ng/mL) at 3 and 7 days post treatment. ("Con" depicts control). *P<0.05, P<0.01, **P<0.0001.

FIG. 24 are bright field images of C-PVR cells 7 days post treatment with TGFβ2, TNFα, and a combination of TGFβ2, TNFα and IL-6, which showed EMT compared to control (top, left picture). EMT was assessed as morphological changes including cell shape with more elongated, fibroblast-like shaped cells in the combination treatment. This experiment showed that TNFα, TGFβ2 and IL-6 induced EMT in C-PVR cells derived from human proliferative vitreoretinopathy membranes. Scale bars—400 microns.

FIG. 30A is an image of an immunoblot showing RUNX1 protein levels in ARPE-19 cells treated with TGFβ2 and TNFα. These data showed that each of these growth factors induced protein expression of RUNX1. The data also showed that siRNA treatment efficiently reduced the induction of RUNX1 triggered by each of these growth factors alone. These data demonstrated that RUNX1 inhibition can be used to limit the effect of these growth factors as it relates to PVR.

FIG. 30B is an image of an immunoblot showing RUNX1 protein levels in ARPE-19 cells treated with IL-6 or with a combination of these growth factors (combination comprises TGFβ2, TNFα, and IL-6). These data showed that each of these growth factors induced protein expression of RUNX1 and that such induction was stronger when the growth factors were combined. It also showed that siRNA treatment efficient reduced the induction of RUNX1 triggered by each of these growth factors alone or in combination. These data demonstrated that RUNX1 inhibition can be used to limit the effect of these growths factors as it relates to PVR.

FIG. 35A is a bar graph indicating that at 40 nM and 72 hours lenalidomide inhibited proliferation in C-PVR cells. The data were compared to vehicle treated, and showed a significant reduction in percent live cells at 72 hours. *P<0.05.

FIG. 35B is a bar graph indicating that at 80 nM and 72 hours, lenalidomide inhibited proliferation in C-PVR cells. The data were compared to vehicle treated, and showed a significant reduction in percent live cells at 72 hours. *P<0.05.

FIG. 35C is a bar graph indicating that at 40 nM and 48 hours, lenalidomide inhibited proliferation in C-PVR cells. *P<0.05.

FIG. 35D is a bar graph indicating that at 80 nM and 48 hours, lenalidomide inhibited proliferation in C-PVR cells. *P<0.05.

DETAILED DESCRIPTION

Figure 1:
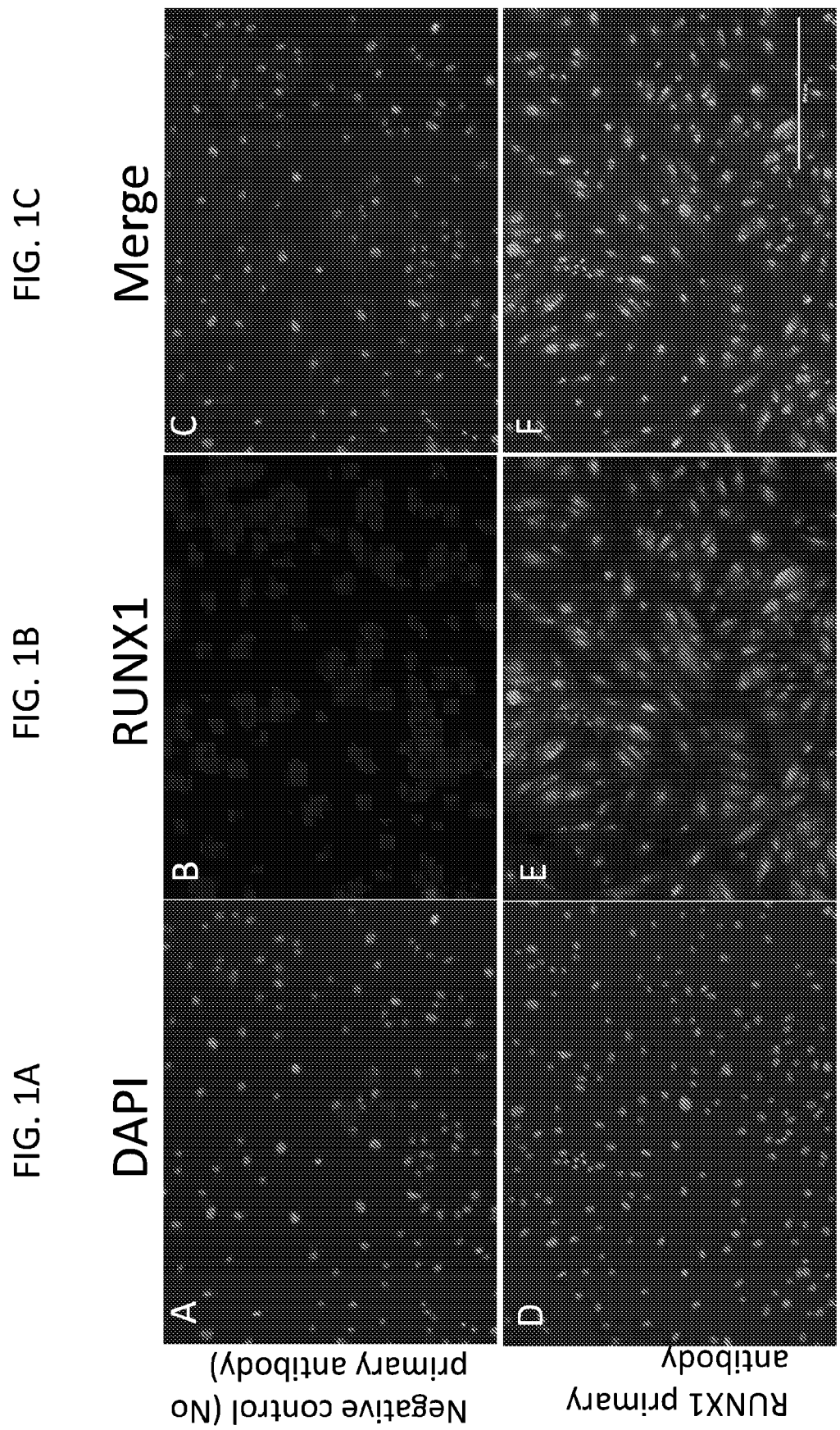
FIG. 1A is an image depicting the immunofluorescence staining of a negative control counterstained with DAPI.
FIG. 1B is an image depicting the immunofluorescence staining of a negative control of staining of RUNX1.
FIG. 1C is a merged image depicting the immunofluorescence staining of FIG. 1A and FIG. 1B.
FIG. 1D is an image depicting the immunofluorescence staining of the RUNX1 primary antibody counterstained with DAPI.
FIG. 1E is an image depicting the immunofluorescence staining of the RUNX1.
FIG. 1F is a merged image depicting the immunofluorescence staining of FIGS. 1D and 1E.
Figure 2:
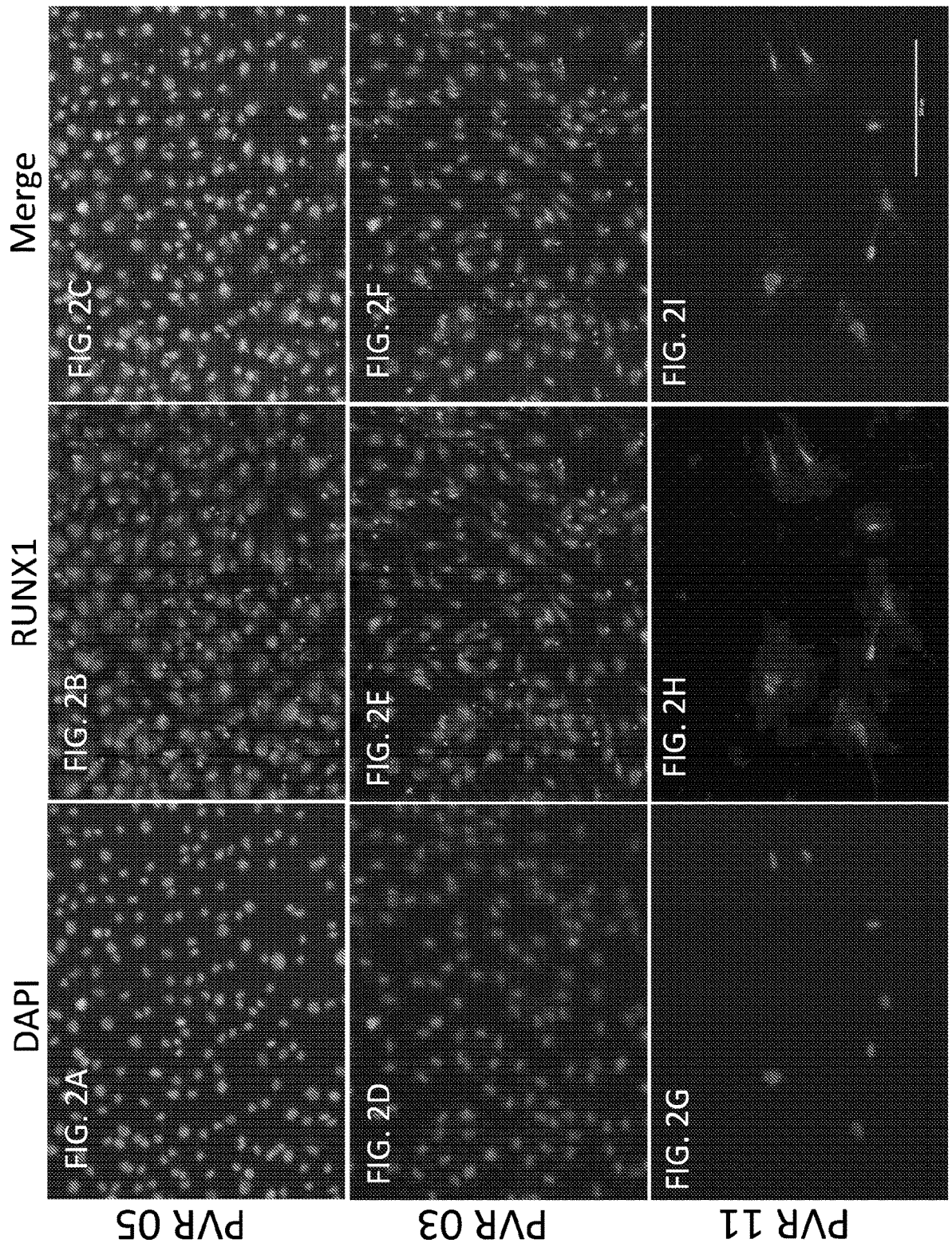
FIG. 2A is an image depicting the immunofluorescence staining of patient sample 5 (membranes obtained from patient with PVR), counterstained with DAPI.
FIG. 2B is an image depicting the immunofluorescence staining of RUNX1 in patient sample 5.
FIG. 2C is a merged image of FIGS. 2A and 2B.
FIG. 2D is an image depicting the immunofluorescence staining of patient sample 3, counterstained with DAPI.
FIG. 2E is an image depicting the immunofluorescence staining of RUNX1 in patient sample 3.
FIG. 2F is a merged image of FIGS. 2D and 2E.
FIG. 2G is an image depicting the immunofluorescence staining of patient sample 11 (membranes obtained from patient with PVR) counterstained with DAPI.
FIG. 2H is an image depicting the immunofluorescence staining of RUNX1 in patient sample 11.
FIG. 2I is a merged image of FIGS. 2G and 2H.
Figure 3:
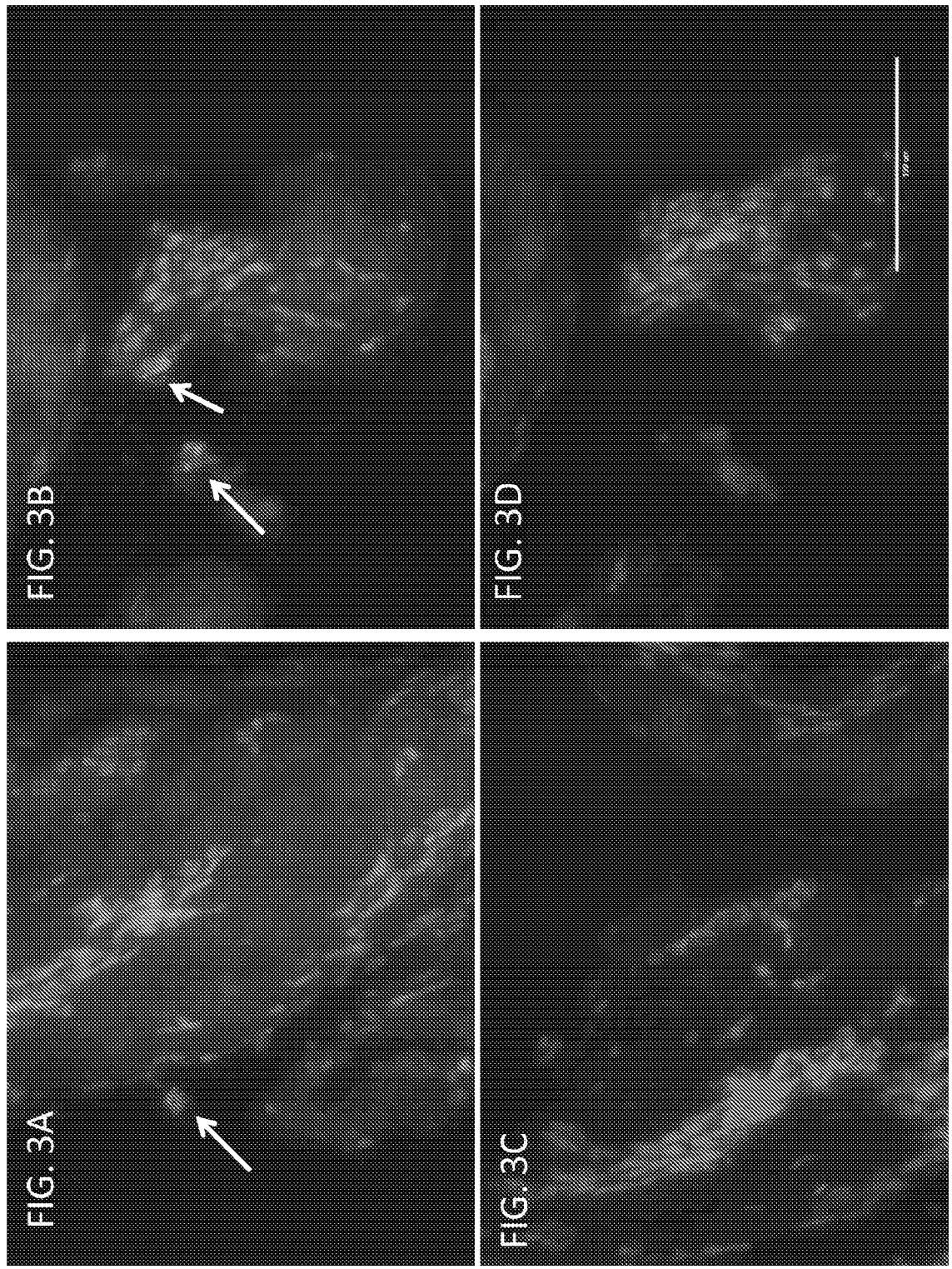
FIG. 3A is an image depicting the immunofluorescence staining of RUNX1 in human PVR membranes (e.g., patients with PVR).
FIG. 3B is an image depicting the immunofluorescence staining of RUNX1 in human PVR membranes counterstained with DAPI.
FIG. 3C is an image depicting the immunofluorescence staining of a negative control counterstained with DAPI.
FIG. 3D is an image depicting the immunofluorescence staining of a negative control counterstained with DAPI.
Figure 4:
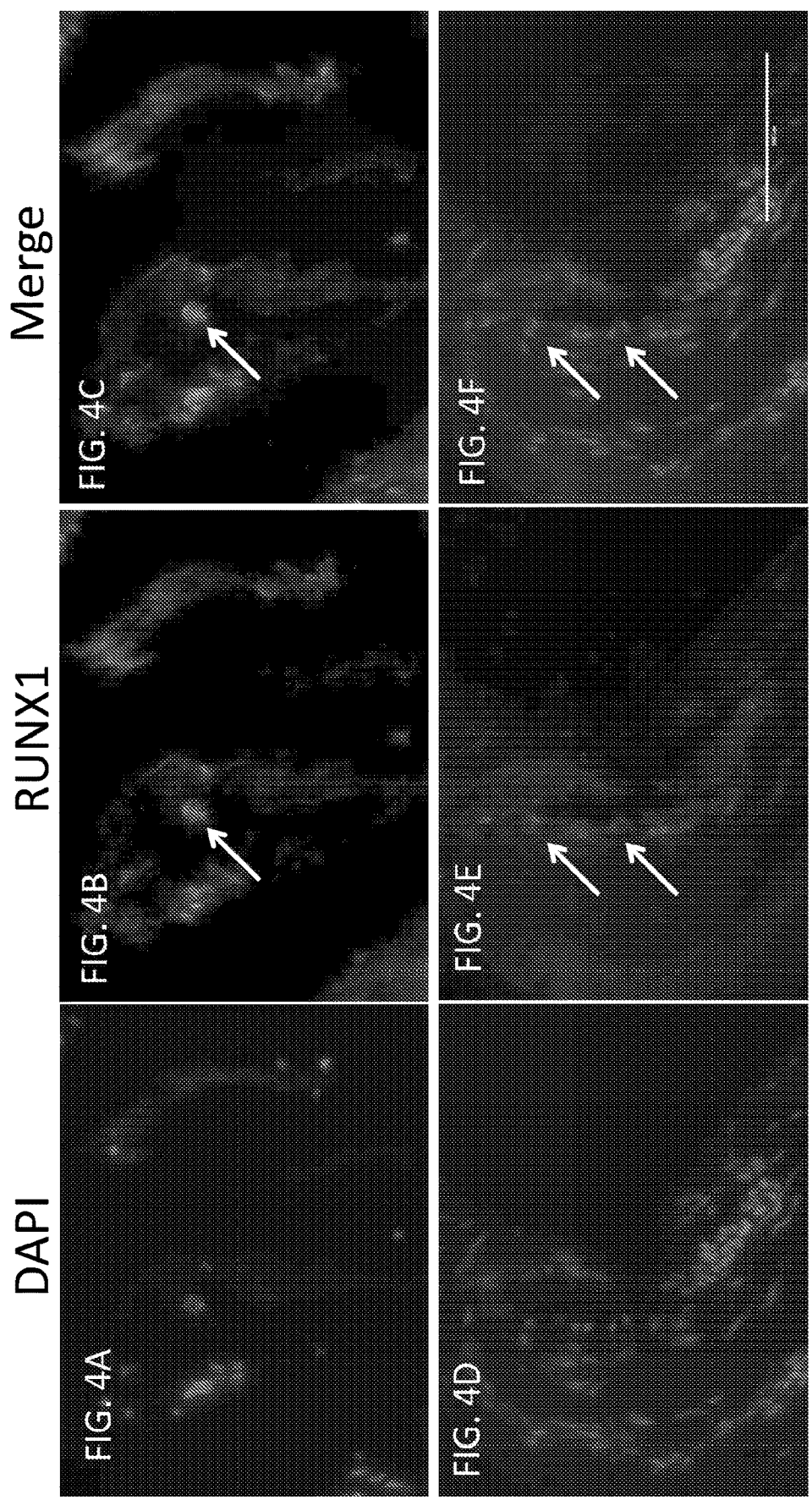

The present disclosure relates to methods for treating retinal detachment disorders, (e.g., proliferative vitreoretinopathy, PVR). Currently there are no medical (e.g., no non-surgical) treatments or management for PVR, which is a severe complication of retinal detachment, and commonly associated with eye trauma. Current management of PVR includes a potentially risky and invasive surgical method to remove the membrane directly from the eye. The compositions and methods are useful for the treatment of diseases afflicted with proliferation or migration of retinal pigment epithelial cells, glial, inflammatory cells, and mesenchymal cells as found in PVR.

The disclosure described herein is based on the surprising discovery that the Runt-Related Transcription Factor 1 (RUNX1) is highly expressed in surgically removed human PVR membranes, and cells derived from them (C-PVR). RUNX1 has been implicated in other biological processes including endothelial-cell derived blood vessel formation during embryonic development and normal angiogenesis. However, a role for RUNX1 in PVR (or EMT in retinal cells) has not previously been described. The disclosure herein describes actual patient-derived PVR membranes as a resource to highlight the specific expression of RUNX1 and to study its effect on RUNX1 inhibition. Current methods rely on surrogate cell types thought to be involved in the pathogenesis of PVR.

Additionally, RUNX1 expression is enhanced in an in vitro model of retinal pigment epithelial (RPE) cells undergoing epithelial to mesenchymal transition (EMT). The inhibition or RUNX1 via siRNA or a small molecule inhibitor significantly reduced the growth and migration of C-PVR culture. RUNX1 inhibition also significantly reduced the growth of human PVR membrane explants in culture.

Additionally, RUNX1 inhibition significantly reduced EMT in two in vitro models using ARPE-19 and C-PVR cultures. Reduction of EMT was characterized by morphological changes, increased expression in epithelial markers, and decreased expression of mesenchymal markers.

Accordingly, provided herein, are methods for preventing and treating PVR and other conditions associated with EMT by targeting RUNX1. This will allow for specific medical management of membranes, and caused their regression and impeded their growth and thus potentially avoiding the need for surgery.

Retinal Detachment Disorder

Retinal detachment is a disorder of the eye in which the neurosensory retina separates from the retinal pigment epithelial layer underneath. The mechanism most commonly involves a break in the retina that then allows the fluid in the eye to get behind the retina. A break in the retina can occur from a posterior vitreous detachment, injury to the eye, or inflammation of the eye. Other risk factors include being short sighted and previous cataract surgery. Typically, diagnosis is accomplished by either looking at the back of the eye with an ophthalmoscope or by ultrasound.

Symptoms include an increase in the number of floaters, flashes of light, and worsening of the outer part of the visual field, which may be described as a curtain over part of the field of vision. In about 7% of cases both eyes are affected. Without treatment permanent loss of vision may occur. In patients with a retinal tear, efforts to prevent it becoming a detachment include cryotherapy using a cold probe or photocoagulation using a laser. Treatment of retinal detachment should be carried out in a timely manner.

Retinal detachment can be examined by fundus photography or ophthalmoscopy. Ultrasound has diagnostic accuracy similar to that of examination by an ophthalmologist. Recent meta-analysis shows the diagnostic accuracy of emergency department (ED) ocular ultrasonography is high. The sensitivity and specificity ranged from 97% to 100% and 83% to 100%. The typical feature of retinal detachment when viewed on ultrasound is "flying angel sign," it shows the detached retina moving with a fixed point under the B mode, linear probe 10 MHz. In embodiments, retinal detachment may be visualized by a fundus exam. Alternatively, a B-scan or wide-field fundus photography may be used to visualize retinal detachment.

Retinal detachments affect between 0.6 and 1.8 people per 10,000 per year. About 0.3% of people are affected at some point in their life. It is most common in people who are in their 60s or 70s, and males are more often affected than females. The long term outcomes depend on the duration of the detachment and whether the macula was detached. If treated before the macula detaches outcomes are generally good. Optionally, the subject has not been diagnosed or characterized with some other ocular disorder comprising age-related macular degeneration or an ocular angiogenesis disease or disorder.

When the retina is pulled away from the back of the eye, it is a retinal detachment. Typically, the vitreous moves away from the retina without causing problems. But sometimes the vitreous pulls hard enough to tear the retina in one or more places, and thus causing a retinal tear. Fluid may pass through a retinal tear, lifting the retina off the back of the eye. The symptoms of vitreous separation, retinal tear, and retinal detachment are similar and sometimes can overlap. On occasion, the patient may notice the floaters and flashing lights (photopsia) more commonly associated with isolated vitreous separation. An ophthalmologist, optometrist, or primary care physician may be suspicious about a more serious problem if symptoms are of very recent or sudden onset and are accompanied by a shower of spots or "cobwebs." Of even greater concern is the loss of peripheral vision, which may present as a shadow moving toward the center of one's field of vision.

Additionally, in retinal detachment, a retinal hole may develop. Because the vitreous is attached to the retina with tiny strands of collagen, it can pull on the retina as it shrinks. Sometimes, this shrinkage can tear off a small piece of the retina in the periphery, causing a hole or tear of the periphery retina. If this missing piece of retina is in the macula, it's called a macular hole. Additionally, another direct cause of macular holes due to vitreous shrinkage is when the collagen strands stay attached to the retina forming an epiretinal membrane. These membranes can contract around the macula, causing the macula to develop a hole from the traction. Retinal detachments commonly occur secondary to peripheral retinal tears/holes, and rarely form macular holes.

In other aspects, a minority of retinal detachments result from trauma, including blunt blows to the orbit, penetrating trauma, and concussions to the head.

There are three types of retinal detachment:

(1) Rhegmatogenous retinal detachment—A rhegmatogenous retinal detachment occurs due to a break in the retina (e.g., a retinal tear) that allows fluid to pass from the vitreous space into the subretinal space between the sensory retina and the retinal pigment epithelium. Retinal breaks are divided into three types—holes, tears and dialyses. Holes form due to retinal atrophy especially within an area of lattice degeneration. Tears are due to vitreoretinal traction. Dialyses are very peripheral and circumferential, and may be either tractional or atrophic. The atrophic form most often occurs as idiopathic dialysis of the young.

(2) Exudative, serous, or secondary retinal detachment—An exudative retinal detachment occurs due to inflammation, injury or vascular abnormalities that results in fluid accumulating underneath the retina without the presence of a hole, tear, or break. In evaluation of retinal detachment it is critical to exclude exudative detachment as surgery will make the situation worse, not better. Although rare, exudative detachment can be caused by the growth of a tumor on the layers of tissue beneath the retina, namely the choroid. This cancer is called a choroidal melanoma.

(3) Tractional retinal detachment—A tractional retinal detachment occurs when fibrous (from PVR membrane) or fibrovascular (from neovascular disorders such as proliferative diabetic retinopathy) tissue, caused by an injury, inflammation or neovascularization, pulls the sensory retina from the retinal pigment epithelium Proliferative Vitreoretinopathy Proliferative vitreoretinopathy (PVR) is a clinical syndrome that develops as a complication of rhegmatogenous retinal detachment and is also commonly associated with eye trauma. PVR is the most common cause of failure in retinal detachment surgery, however, it can also occur with untreated eyes with retinal detachment. In particular, PVR can occur with vitreous hemorrhage, after cryotherapy, after laser retinopexy, pneumatic retinopexy, scleral buckling, or vitrectomy, and after a variety of surgical complications. PVR is also common after eye traumas (e.g., penetrating injuries) and other conditions associated with prolonged inflammation.

PVR occurs in about 8-10% of patients undergoing primary retinal detachment surgery and prevents the successful surgical repair of rhegmatogenous retinal detachment. PVR can be treated with surgery to reattach the retina, however, the visual outcome of the surgery is very poor. If PVR is progressive, then despite complex surgery, low vision in the eye results.

Pathophysiology

PVR is characterized by proliferation or migration of cells derived from retinal pigment epithelium (RPE), glia, or inflammatory recruitment on the retinal surface and within the vitreous gel. These cells transdifferentiate and take on contractile properties. The process of PVR can start when there is an interruption to the surface lining (e.g., through posterior vitreous detachment and local preretinal membrane formation or retinal tears in the periphery). The PVR process is self-propagating and is often considered an inappropriate excess wound-healing response. The cellular proliferation can increase the influx of inflammatory cytokines and inflammatory cells.

In embodiments, as described herein proliferation or migration of RPE cells describes their transdifferentiation to assume contractile properties through internal cellular contractile proteins and by laying down extracellular collagen. The cells can multiply and grow along any available scaffolding (e.g., the retinal surfaces or elements of the residual vitreous gel). The mass contraction can lead to retinal wrinkles, folds, tears, and traction retinal detachment.

During rhegmatogenous retinal detachment, fluid from the vitreous humor enters a retinal hole. The accumulation of fluid in the subretinal space and the tractional force of the vitreous on the retina result in rhegmatogenous retinal detachment. During this process the retinal cell layers come in contact with vitreous cytokines. These cytokines trigger the ability of the retinal pigmented epithelium (RPE) to proliferate and migrate. The process involved resembles fibrotic wound healing by the RPE cells. The RPE cells undergo epithelial-mesenchymal transition (EMT) and develop the ability to migrate out into the vitreous. During this process the RPE cell layer-neural retinal adhesion and RPE-ECM (extracellular matrix) adhesions are lost. The RPE cells lay down fibrotic membranes while they migrate and these membranes contract and pull at the retina. Thus, this leads to secondary retinal detachment after primary retinal detachment surgery.

During RPE disruption, inflammation may play an important role in the development of PVR. Cytokines IL-6, IL-1, TNF-α and IFN-γ have been identified in high concentrations in the vitreous in the early, proliferative stages of PVR, but they decrease to normal levels in the scarring phase. Other molecules involved in PVR include TGFβ and IL-6.

Risk Factors and Clinical Signs

As described above, the most common development of PVR is after a retinal detachment surgery and/or repair, although patients can develop PVR spontaneously with retinal detachment prior to surgery or with longstanding primary detachments. Multiple factors have been associated with the formation of PVR. In general, processes that increase vascular permeability are more likely to increase the probability of PVR formation. Specific risk factors that have been identified include: uveitis; large, giant, or multiple tears; vitreous hemorrhage, preoperative or postoperative choroidal detachments; aphakia; multiple previous surgeries; and large detachments involving greater than 2 quadrants of the eye.

Early signs of PVR are often subtle and can include cellular dispersion in the vitreous and on the retinal surface, which can appear as a white opacification of the retinal surface and small wrinkles or folds. More developed PVR is characteristic with fixed folds and retinal detachment. Diagnosis is typically done by indirect ophthalmoscopy and slit-lamp biomicroscopy. Additionally, an ultrasound can help visualize immobile retinal folds of detachment and prominent vitreous membranes. Also, wide-field fundus photography can be used to visualize retinal detachments. However, the clinical history and exam is often enough to make the diagnosis of a retinal detachment.

Development Stages

Ocular wound healing typically occurs in 3 stages: (1) an inflammatory stage, (2) a proliferative stage, and (3) a modulatory stage. PVR can be viewed in a similar fashion, with the wound being the retinal detachment. This healing response often takes place over many weeks. Early on, preretinal PVR adopts an immature appearance and consistency. During this phase, the retina may still remain compliant, and the PVR membrane may be difficult to remove due to its amorphous form. By 6 to 8 weeks, however, the PVR membrane becomes more mature, taking on a white, fibrotic appearance. In this stage, the PVR is more easily identifiable, causes rigidity of the retina, and can be more identifiably removed.

Classification

The extent of PVR in patients is often classified (or graded) depending on the severity. The most commonly used classification system was published by the Retina Society Terminology Committee. It classifies the appearance of PVR based on clinical signs and its geographic location (Grade A, B, C, or D). Grade A is characterized by the appearance of vitreous haze and RPE cells in the vitreous, or by pigment clumping. Grade B is characterized by wrinkling of the edges of the retinal tear or the inner retinal surface. Grade C is characterized by posterior or anterior full thickness retinal folds with the presence of epi/subretinal membranes/bands. Grade D is characterized by fixed retinal folds in all four quadrants. Diagnosis via clinical examination and imaging for PVR is known in the art, e.g., as described in the classification of retinal detachment with proliferative vitreoretinopathy. Ophthalmology, 1983; 90(2): p. 121-5. Clinical examination and classification schemes are further described in Di Lauro et al., J Ophthalmol. 2016; Volume 2016, Article ID 7807596, 6 pages 2016: 7807596. (PMCID: PMC4939352); hereby incorporated by reference.

PVR is Distinct from Proliferative Diabetic Retinopathy

PVR is a condition distinct from proliferative diabetic retinopathy (PDR). PVR is a condition distinct from a small blood vessel disease. The fundamental process involved in PDR is aberrant angiogenesis, and therefore impacting vascular endothelial cells. To the contrary, in PVR, the fundamental processes is the aberrant epithelial to mesenchymal transition (EMT) of retinal pigment epithelial derived cells, and other cells within the eye. Accordingly, the disclosure herein provides the surprising discovery that targeting RUNX1 may be used as a therapeutic target for the management of PVR.

Retinal Pigment Epithelium

The retinal pigment epithelium (RPE) is the pigmented cell layer just outside the neurosensory retina that nourishes retinal visual cells, and is firmly attached to the underlying choroid and overlying retinal visual cells. The RPE forms a monolayer of cells beneath the sensory retina that is normally mitotically inactive except when it is participating in retinal wound repair, where it plays a central role. When wound repair is complete, the RPE usually stops proliferating; failure to do so can result in blinding disorders such as proliferative vitreoretinopathy (PVR) and disciform scarring. For instance, after detachment of the sensory retina, the RPE changes in morphology and begins to proliferate. Multilayered colonies of dedifferentiated RPE cells are formed. Cells then begin to migrate into the subretinal space where they engulf rod outer segments. In some instances, cells migrate onto the surface of the retina and form epiretinal membranes. These events have been implicated in the pathogenesis of proliferative vitreoretinopathy, severe scarring occurring in association with macular degeneration, and poor or delayed recovery of vision after retinal reattachment. Despite these important consequences, little is known about the stimuli involved in RPE dedifferentiation and loss of density-dependent growth control.

Other conditions associated with EMT including cancer, e.g., mesothelioma, Ocular Chronic Graft-Versus-Host Disease, corneal scarring, corneal epithelial downgrowth, conjunctival scarring, eye tumors like melanoma, ocular fibrosis, fibrosis, and complication of glaucoma surgery such as fibrosis (post surgical fibrosis as described in, e.g., Current and Future Techniques in Wound Healing Modulation after Glaucoma Filtering Surgeries. Masoumpour M B, et al. Open Ophthalmol J. 2016. Open Ophthalmol J. 2016 Feb. 29; 10:68-85. doi: 10.2174/1874364101610010068. eCollection 2016) as well as fibrosis and glaucoma (Friedlander et al., J Clin Invest. 2007, Mar. 1; 117(3): 576-586. Published online 2007 Mar. 1. doi: [10.1172/JCI31030] PMCID: MC1804382 PMID). RUNX1 inhibition is useful for reduction, treatment, or prevention of aberrant or pathological EMT occurring in the eye. For example, the methods described herein are used for reducing proliferation and migration of cells within the eye undergoing epithelial to mesenchymal transition, e.g., inhibitors are administered to subjects diagnosed with, suffering from, or having EMT-associated diseases of pathologic ocular fibrosis and proliferation. Diseases include but are not limited to: conjunctival fibrosis (e.g. ocular cicatricial pemphigoid), corneal scarring, corneal epithelial down growth, and/or aberrant post-surgical fibrosis (e.g. after glaucoma surgery, cataract surgery, LASIK, or any intraocular surgery).

Runt-Related Transcription Factor 1

Runt-related transcription factor 1 (RUNX1), also known as acute myeloid leukemia 1 protein (AML1) or core-binding factor subunit alpha-2 (CBFA2), is a protein that in humans is encoded by the RUNX1 gene.

RUNX1 is a transcription factor that regulates the differentiation of hematopoietic stem cells into mature blood cells. RUNX1 also plays a role in the development of the neurons that transmit pain. It belongs to the Runt-related transcription factor (RUNX) family of genes which are also called core binding factor-α (CBFα). RUNX proteins form a heterodimeric complex with core binding factor β (CBFβ) which confers increased deoxyribonucleic acid (DNA) binding and stability to the complex.

In humans, the RUNX1 gene is 260 kilobases (kb) in length, and is located on chromosome 21 (21q22.12). The gene can be transcribed from 2 alternative promoters, promoter 1 (distal) or promoter 2 (proximal). As a result, various isoforms of RUNX1 can be synthesized, facilitated by alternative splicing. The full-length RUNX1 protein is encoded by 12 exons. Among the exons are two defined domains, namely the runt homology domain (RHD) or the runt domain (exons 2, 3 and 4), and the transactivation domain (TAD) (exon 6). These domains are necessary for RUNX1 to mediate DNA binding and protein-protein interactions respectively. The transcription of RUNX1 is regulated by 2 enhancers (regulatory element 1 and regulatory element 2), and these tissue specific enhancers enable the binding of lymphoid or erythroid regulatory proteins, therefore the gene activity of RUNX1 is highly active in the hematopoietic system.

An exemplary isoform of RUNX1 (Q01196-1; SEQ ID NO: 1) has 453 amino acids. As a transcription factor (TF), its DNA binding ability is encoded by the runt domain (residues 50-177 of SEQ ID NO: 1), which is homologous to the p53 family Without wishing to be bound by any scientific theory, the runt domain of RUNX1 is believed to bind to the core consensus sequence TGTGGNNN of SEQ ID NO: 1 (where NNN can represent either TTT or TCA). DNA recognition is achieved by loops of the 12-stranded β-barrel and the C-terminus "tail" (residues 170-177 of SEQ ID NO: 1), which clamp around the sugar phosphate backbone and fits into the major and minor grooves of DNA. Specificity is achieved by making direct or water-mediated contacts with the bases. RUNX1 can bind DNA as a monomer, but its DNA binding affinity is enhanced by 10 fold if it heterodimerizes with the CBFβ, also via the runt domain. The RUNX family is often referred to as α-subunits, together with binding of a common β-subunit CBFβ, RUNX can behave as heterodimeric transcription factors collectively called the core binding factors (CBFs).

An amino acid sequence for human RUNX1 is publically available in the UniProt database under accession number Q01196-1 (SEQ ID NO: 1) and is as follows:

MRIPVDASTSRRFTPPSTALSPGKMSEALPLGAPDAGAALAGKLRSGDRS

MVEVLADHPGELVRTDSPNFLCSVLPTHWRCNKTLPIAFKVVALGDVPDG

TLVTVMAGNDENYSAELRNATAAMKNQVARFNDLRFVGRSGRGKSFTLTI

TVFTNPPQVATYHRAIKITVDGPREPRRHRQKLDDQTKPGSLSFSERLSE

LEQLRRTAMRVSPHHPAPTPNPRASLNHSTAFNPQPQSQMQDTRQIQPSP

PWSYDQSYQYLGSIASPSVHPATPISPGRASGMTTLSAELSSRLSTAPDL

TAFSDPRQFPALPSISDPRMHYPGAFTYSPTPVTSGIGIGMSAMGSATRY

HTYLPPPYPGSSQAQGGPFQASSPSYHLYYGASAGSYQFSMVGGERSPPR

ILPPCTNASTGSALLNPSLPNQSDVVEAEGSHSNSPTNMAPSARLEEAVW

RPY

Amino acid sequences of additional isoforms are publically available in the UniProt database under accession numbers Q01196-2 (SEQ ID NO: 2); Q01196-3 (SEQ ID NO: 3); Q01196-4 (SEQ ID NO: 4); Q01196-5 (SEQ ID NO: 5); Q01196-6 (SEQ ID NO: 6); Q01196-7 (SEQ ID NO: 7); Q01196-8 (SEQ ID NO: 8); Q01196-9 (SEQ ID NO: 9); Q01196-10 (SEQ ID NO: 10); and Q01196-11 (SEQ ID NO: 11).

Exemplary landmark sequences and domains include, residues 80-84 (DNA binding domain), residues 135-143 (DNA binding domain), residues 168-177 (DNA binding domain), residues 291-371 (interaction with K(lysine) acetyltransferase 6A (KATA6A)), residues 307-400 (interaction with K(lysine) acetyltransferase 6B (KATA6B)), and residues 362-402 (interaction with forkhead box P3 (FOXP3)).

A nucleotide sequence that encodes human RUNX1 is publically available in the GenBank database under accession number NM_001001890.2 (SEQ ID NO: 12) and is as follows (start and stop codon are bolded and underlined):

CATAGAGCCAGCGGGCGCGGGCGGGACGGGCGCCCCGCGGCCGGACCCAG

CCAGGGCACCACGCTGCCCGGCCCTGCGCCGCCAGGCACTTCTTTCCGGG

GCTCCTAGGGACGCCAGAAGGAAGTCAACCTCTGCTGCTTCTCCTTGGCC

TGCGTTGGACCTTCCTTTTTTTGTTGTTTTTTTTGTTTTTCCCCTTTCT

TCCTTTTGAATTAACTGGCTTCTTGGCTGGATGTTTTCAACTTCTTTCCT

GGCTGCGAACTTTTCCCCAATTGTTTTCCTTTTACAACAGGGGGAGAAAG

TGCTCTGTGGTCCGAGGCGAGCCGTGAAGTTGCGTGTGCGTGGCAGTGTG

CGTGGCAGGATGTGCGTGCGTGTGTAACCCGAGCCGCCCGATCTGTTTCG

ATCTGCGCCGCGGAGCCCTCCCTCAAGGCCCGCTCCACCTGCTGCGGTTA

CGCGGCGCTCGTGGGTGTTCGTGCCTCGGAGCAGCTAACCGGCGGGTGCT

GGGCGACGGTGGAGGAGTATCGTCTCGCTGCTGCCCGAGTCAGGGCTGAG

TCACCCAGCTGATGTAGACAGTGGCTGCCTTCCGAAGAGTGCGTGTTTGC

ATGTGTGTGACTCTGCGGCTGCTCAACTCCCAACAAACCAGAGGACCAGC

CACAAACTTAACCAACATCCCCAAACCCGAGTTCACAGATGTGGGAGAGC

TGTAGAACCCTGAGTGTCATCGACTGGGCCTTCTTATGATTGTTGTTTTA

AGATTAGCTGAAGATCTCTGAAACGCTGAATTTTCTGCACTGAGCGTTTT
GACAGAATTCATTGAGAACAGAGAACATGACAAGTACTTCTAGCTCAG
CACTGCTCCAACTACTGAAGCTGATTTTCAAGGCTACTTAAAAAAATCTG
CAGCGTACATTAATGGATTTCTGTTGTGTTTAAATTCTCCACAGATTGTA
TTGTAAATATTTTATGAAGTAGAGCATATGTATATATTTATATATACGTG
CACATACATTAGTAGCACTACCTTTGGAAGTCTCAGCTCTTGCTTTTCGG
GACTGAAGCCAGTTTTGCATGATAAAAGTGGCCTTGTTACGGGAGATAAT
TGTGTTCTGTTGGGACTTTAGACAAAACTCACCTGCAAAAAACTGACAGG
CATTAACTACTGGAACTTCCAAATAATGTGTTTGCTGATCGTTTTACTCT
TCGCATAAATATTTTAGGAAGTGTATGAGAATTTTGCCTTCAGGAACTTT
TCTAACAGCCAAAGACAGAACTTAACCTCTGCAAGCAAGATTCGTGGAAG
ATAGTCTCCACTTTTTAATGCACTAAGCAATCGGTTGCTAGGAGCCCATC
CTGGGTCAGAGGCCGATCCGCAGAACCAGAACGTTTTCCCCTCCTGGACT
GTTAGTAACTTAGTCTCCCTCCTCCCCTAACCACCCCGCCCCCCCCAC
CCCCCGCAGTAATAAAGGCCCCTGAACGTGTATGTTGGTCTCCCGGGAGC
TGCTTGCTGAAGATCCGCGCCCCTGTCGCCGTCTGGTAGGAGCTGTTTGC
AGGGTCCTAACTCAATCGGCTTGTTGTGATGCGTATCCCCGTAGATGCCA
GCACGAGCCGCCGCTTCACGCCGCCTTCCACCGCGCTGAGCCCAGGCAAG
ATGAGCGAGGCGTTGCCGCTGGGCGCCCCGGACGCCGGCGCTGCCCTGGC
CGGCAAGCTGAGGAGCGGCGACCGCAGCATGGTGGAGGTGCTGGCCGACC
ACCCGGGCGAGCTGGTGCGCACCGACAGCCCCAACTTCCTCTGCTCCGTG
CTGCCTACGCACTGGCGCTGCAACAAGACCCTGCCCATCGCTTTCAAGGT
GGTGGCCCTAGGGGATGTTCCAGATGGCACTCTGGTCACTGTGATGGCTG
GCAATGATGAAAACTACTCGGCTGAGCTGAGAAATGCTACCGCAGCCATG
AAGAACCAGGTTGCAAGATTTAATGACCTCAGGTTTGTCGGTCGAAGTGG
AAGAGGGAAAAGCTTCACTCTGACCATCACTGTCTTCACAAACCCACCGC
AAGTCGCCACCTACCACAGAGCCATCAAAATCACAGTGGATGGGCCCGA
GAACCTCGAAGACATCGGCAGAAACTAGATGATCAGACCAAGCCCGGGAG
CTTGTCCTTTTCCGAGCGGCTCAGTGAACTGGAGCAGCTGCGGCGCACAG
CCATGAGGGTCAGCCCACACCACCCAGCCCCCACGCCCAACCCTCGTGCC
TCCCTGAACCACTCCACTGCCTTTAACCCTCAGCCTCAGAGTCAGATGCA
GGATACAAGGCAGATCCAACCATCCCCACCGTGGTCCTACGATCAGTCCT
ACCAATACCTGGGATCCATTGCCTCTCCTTCTGTGCACCCAGCAACGCCC
ATTTCACCTGGACGTGCCAGCGGCATGACAACCCTCTCTGCAGAACTTTC
CAGTCGACTCTCAACGGCACCCGACCTGACAGCGTTCAGCGACCCGCGCC
AGTTCCCCGCGCTGCCCTCCATCTCCGACCCCGCATGCACTATCCAGGC
GCCTTCACCTACTCCCGACGCCGGTCACCTCGGGCATCGGCATCGGCAT
GTCGGCCATGGGCTCGGCCACGCGCTACCACACCTACCTGCCGCCGCCCT
ACCCCGGCTCGTCGCAAGCGCAGGGAGGCCCGTTCCAAGCCAGCTCGCCC
TCCTACCACCTGTACTACGGCGCCTCGGCCGGCTCCTACCAGTTCTCCAT

GGTGGGCGGCGAGCGCTCGCCGCCGCGCATCCTGCCGCCCTGCACCAACG
CCTCCACCGGCTCCGCGCTGCTCAACCCCAGCCTCCCGAACCAGAGCGAC
GTGGTGGAGGCCGAGGGCAGCCACAGCAACTCCCCCACCAACATGGCGCC
CTCCGCGCGCCTGGAGGAGGCCGTGTGGAGGCCCTACTGAGGCGCCAGGC
CTGGCCCGGCTGGGCCCCGCGGGCCGCCGCCTTCGCCTCCGGGCGCGCGG
GCCTCCTGTTCGCGACAAGCCCGCCGGGATCCCGGGCCCTGGGCCCGGCC
ACCGTCCTGGGGCCGAGGGCGCCCGACGGCCAGGATCTCGCTGTAGGTCA
GGCCCGCGCAGCCTCCTGCGCCCAGAAGCCCACGCCGCCGCCGTCTGCTG
GCGCCCCGGCCCTCGCGGAGGTGTCCGAGGCGACGCACCTCGAGGGTGTC
CGCCGGCCCCAGCACCCAGGGGACGCGCTGGAAAGCAAACAGGAAGATTC
CCGGAGGGAAACTGTGAATGCTTCTGATTTAGCAATGCTGTGAATAAAAA
GAAAGATTTTATACCCTTGACTTAACTTTTTAACCAAGTTGTTTATTCCA
AAGAGTGTGGAATTTTGGTTGGGGTGGGGGGAGAGGAGGGATGCAACTCG
CCCTGTTTGGCATCTAATTCTTATTTTTAATTTTTCCGCACCTTATCAAT
TGCAAAATGCGTATTTGCATTTGGGTGGTTTTTATTTTTATATACGTTTA
TATAAATATATATAAATTGAGCTTGCTTCTTTCTTGCTTTGACCATGGAA
AGAAATATGATTCCCTTTTCTTTAAGTTTTATTTAACTTTTCTTTTGGAC
TTTTGGGTAGTTGTTTTTTTTTGTTTTGTTTTGTTTTTTGAGAAACAGC
TACAGCTTTGGGTCATTTTTAACTACTGTATTCCCACAAGGAATCCCCAG
ATATTTATGTATCTTGATGTTCAGACATTTATGTGTTGATAATTTTTTAA
TTATTTAAATGTACTTATATTAAGAAAAAATATCAAGTACTACATTTTCTT
TTGTTCTTGATAGTAGCCAAAGTTAAATGTATCACATTGAAGAAGGCTAG
AAAAAAAGAATGAGTAATGTGATCGCTTGGTTATCCAGAAGTATTGTTTA
CATTAAACTCCCTTTCATGTTAATCAAACAAGTGAGTAGCTCACGCAGCA
ACGTTTTTAATAGGATTTTTAGCACTGAGGGTCACTCCAAGGATCAGAA
GTATGGAATTTTCTGCCAGGCTCAACAAGGGTCTCATATCTAACTTCCTC
CTTAAAACAGAGAAGGTCAATCTAGTTCCAGAGGGTTGAGGCAGGTGCCA
ATAATTACATCTTTGGAGAGGATTTGATTTCTGCCCAGGGATTTGCTCAC
CCCAAGGTCATCTGATAATTTCACAGATGCTGTGTAACAGAACACAGCCA
AAGTAAACTGTGTAGGGGAGCCACATTTACATAGGAACCAAATCAATGAA
TTTAGGGGTTACGATTATAGCAATTTAAGGGCCCACCAGAAGCAGGCCTC
GAGGAGTCAATTTGCCTCTGTGTGCCTCAGTGGAGACAAGTGGGAAAACA
TGGTCCCACCTGTGCGAGACCCCTGTCCTGTGCTGCTCACTCAACAACA
TCTTTGTGTTGCTTTCACCAGGCTGAGACCCTACCCTATGGGGTATATGG
GCTTTTACCTGTGCACCAGTGTGACAGGAAAGATTCATGTCACTACTGTC
CGTGGCTACAATTCAAAGGTATCCAATGTCGCTGTAAATTTTATGGCACT
ATTTTTATTGGAGGATTTGGTCAGAATGCAGTTGTTGTACAACTCATAAA
TACTAACTGCTGATTTTGACACATGTGTGCTCCAAATGATCTGGTGGTTA
TTTAACGTACCTCTTAAAATTCGTTGAAACGATTTCAGGTCAACTCTGAA
GAGTATTTGAAAGCAGGACTTCAGAACAGTGTTTGATTTTTATTTTATAA
ATTTAAGCATTCAAATTAGGCAAATCTTTGGCTGCAGGCAGCAAAAACAG

-continued

CTGGACTTATTTAAAACAACTTGTTTTTGAGTTTTCTTATATATATATTG

ATTATTTGTTTTACACACATGCAGTAGCACTTTGGTAAGAGTTAAAGAGT

AAAGCAGCTTATGTTGTCAGGTCGTTCTTATCTAGAGAAGAGCTATAGCA

GATCTCGGACAAACTCAGAATATATTCACTTTCATTTTTGACAGGATTCC

CTCCACAACTCAGTTTCATATATTATTCCGTATTACATTTTTGCAGCTAA

ATTACCATAAAATGTCAGCAAATGTAAAAATTTAATTTCTGAAAAGCACC

ATTAGCCCATTTCCCCCAAATTAAACGTAAATGTTTTTTTTCAGCACATG

TTACCATGTCTGACCTGCAAAAATGCTGGAGAAAAATGAAGGAAAAAATT

ATGTTTTTCAGTTTAATTCTGTTAACTGAAGATATTCCAACTCAAAACCA

GCCTCATGCTCTGATTAGATAATCTTTTACATTGAACCTTTACTCTCAAA

GCCATGTGTGGAGGGGCTTGTCACTATTGTAGGCTCACTGGATTGGTCA

TTTAGAGTTTCACAGACTCTTACCAGCATATATAGTATTTAATTGTTTCA

AAAAAAATCAAACTGTAGTTGTTTTGGCGATAGGTCTCACGCAACACATT

TTTGTATGTGTGTGTGTGTGCGTGTGTGTGTGTGTGTGAAAAATTGCA

TTCATTGACTTCAGGTAGATTAAGGTATCTTTTTATTCATTGCCCTCAGG

AAAGTTAAGGTATCAATGAGACCCTTAAGCCAATCATGTAATAACTGCAT

GTGTCTGGTCCAGGAGAAGTATTGAATAAGCCATTTCTACTGCTTACTCA

TGTCCCTATTTATGATTTCAACATGGATACATATTTCAGTTCTTTCTTTT

TCTCACTATCTGAAAATACATTTCCCTCCCTCTCTTCCCCCCAATATCTC

CCTTTTTTTCTCTCTTCCTCTATCTTCCAAACCCCACTTTCTCCCTCCTC

CTTTTCCTGTGTTCTCTTAAGCAGATAGCACATACCCCCACCCAGTACCA

AATTTCAGAACACAAGAAGGTCCAGTTCTTCCCCCTTCACATAAAGGAAC

ATGGTTTGTCAGCCTTTCTCCTGTTTATGGGTTTCTTCCAGCAGAACAGA

GACATTGCCAACCATATTGGATCTGCTTGCTGTCCAAACCAGCAAACTTT

CCTGGGCAAATCACAATCAGTGAGTAAATAGACAGCCTTTCTGCTGCCTT

GGGTTTCTGTGCAGATAAACAGAAATGCTCTGATTAGAAAGGAAATGAAT

GGTTCCACTCAAATGTCCTGCAATTTAGGATTGCAGATTTCTGCCTTGAA

ATACCTGTTTCTTTGGGACATTCCGTCCTGATGATTTTTATTTTTGTTGG

TTTTTATTTTTGGGGGAATGACATGTTTGGGTCTTTTATACATGAAAAT

TTGTTTGACAATAATCTCACAAAACATATTTTACATCTGAACAAAATGCC

TTTTTGTTTACCGTAGCGTATACATTTGTTTTGGGATTTTTGTGTGTTTG

TTGGGAATTTTGTTTTAGCCAGGTCAGTATTGATGAGGCTGATCATTTG

GCTCTTTTTTCCTTCCAGAAGAGTTGCATCAACAAAGTTAATTGTATTT

ATGTATGTAAATAGATTTTAAGCTTCATTATAAAATATTGTTAATGCCTA

TAACTTTTTTTCAATTTTTTGTGTGTGTTTCTAAGGACTTTTTCTTAGG

TTTGCTAAATACTGTAGGGAAAAAAATGCTTCTTTCTACTTTGTTTATTT

TAGACTTTAAAATGAGCTACTTCTTATTCACTTTTGTAAACAGCTAATAG

CATGGTTCCAATTTTTTTAAGTTCACTTTTTTGTTCTAGGGGAAATGA

ATGTGCAAAAAAGAAAAGAACTGTTGGTTATTTGTGTTATTCTGGATG

TATAAAAATCAATGGAAAAAAATAAACTTTCAAATTGAAATGACGGTATA

ACACATCTACTGAAAAAGCAACGGGAAATGTGGTCCTATTTAAGCCAGCC

CCCACCTAGGGTCTATTTGTGTGGCAGTTATTGGGTTTGGTCACAAAACA

TCCTGAAAATTCGTGCGTGGGCTTCTTTCTCCCTGGTACAAACGTATGGA

ATGCTTCTTAAAGGGGAACTGTCAAGCTGGTGTCTTCAGCCAGATGACAT

GAGAGAATATCCCAGAACCCTCTCTCCAAGGTGTTTCTAGATAGCACAGG

AGAGCAGGCACTGCACTGTCCACAGTCCACGGTACACAGTCGGGTGGGCC

GCCTCCCCTCTCCTGGGAGCATTCGTCGTGCCCAGCCTGAGCAGGGCAGC

TGGACTGCTGCTGTTCAGGAGCCACCAGAGCCTTCCTCTCTTTGTACCAC

AGTTTCTTCTGTAAATCCAGTGTTACAATCAGTGTGAATGGCAAATAAAC

AGTTTGACAAGTACATACACCATA

Additional RUNX1-encoding nucleotide sequences are publically available in the GenBank database under accession numbers NM_001754.4 (*Homo sapiens*, SEQ ID NO: 13); NM_001122607.1 (*Homo sapiens*, SEQ ID NO: 14); XM_005261068.3 (*Homo sapiens*, SEQ ID NO: 15); XM_011529770.2 (*Homo sapiens*, SEQ ID NO: 16); XR_937576.2 (*Homo sapiens*, SEQ ID NO: 17); XM_011529768.2 (*Homo sapiens*, SEQ ID NO: 18); XM_005261069.4 (*Homo sapiens*, SEQ ID NO: 19); XM_017028487.1 (*Homo sapiens*, SEQ ID NO: 20); XM_011529767.2 (*Homo sapiens*, SEQ ID NO: 21); and XM_011529766.2 (*Homo sapiens*, SEQ ID NO: 22).

Runt-Related Transcription Factor 2

Runt-related transcription factor 2 (RUNX2), also known as core-binding factor subunit alpha-1, is a protein that in humans is encoded by the RUNX2 gene. RUNX2 has been is a transcription factor that has been associated with osteoblast differentiation.

An amino acid sequence for human RUNX2 is publically available in the GenBank Database under accession number NP_001019801.3 (SEQ ID NO: 23), and is as follows:

```
  1  masnslfstv  tpcqqnffwd  pstsrrfspp  ssslqpgkms
     dvspvvaaqq  qqqqqqqqqq
 61  qqqqqqqqqq  qeaaaaaaaa  aaaaaaaaav  prlrpphdnr
     tmveiiadhp  aelvrtdspn
121  flcsvlpshw  rcnktlpvaf  kvvalgevpd  gtvvtvmagn
     denysaelrn  asavmknqva
181  rfndlrfvgr  sgrgksftlt  itvftnppqv  atyhraikvt
     vdgpreprrh  rqklddskps
241  lfsdrlsdlg  riphpsmrvg  vppqnprpsl  nsapspfnpq
     gqsqitdprq  aqssppwsyd
301  qsypsylsqm  tspsihsttp  lsstrgtglp  aitdvprris
     dddtatsdfc  lwpstlskks
361  qagaselgpf  sdprqfpsis  sltesrfsnp  rmhypatfty
     tppvtsgmsl  gmsatthyht
```

```
421 ylpppypgss qsqsgpfqts stpylyygts sgsyqfpmvp ggdrspsrml ppctttsngs 481 tllnpnlpnq ndgvdadgsh sssptvlnss grmdesvwrp y
```

Exemplary landmark sequences and domains include, residues 49-71 (polyglutamine repeat), residues 73-89 (polyalanine repeat), residues 109-230 (runt domain), residues 242-258 (domain for interaction with forkhead Box 01 (FOXO1)), residues 336-439 (domain for interaction with K(lysine) acetyltransferase 6A (KATA6A)), residues 374-488 (domain for interaction with K(lysine) acetyltransferase 6B (KATA6B)), and residues 430-521 (RUNX1 inhibition domain).

Additional amino acid sequences of human RUNX2 isoforms are publically available in the GenBank database under accession numbers: NP_001015051.3 (*Homo sapiens*, SEQ ID NO: 24), Q13950.2 (*Homo sapiens*, SEQ ID NO: 25), and NP_001265407.1 (*Homo sapiens* SEQ ID NO: 26) Amino acid sequences of additional RUNX2 isoforms are publically available in the GenBank database under accession numbers NP_001139392.1 (*Mus musculus*, SEQ ID NO: 27) NP_001139510.1 (*Mus musculus*, SEQ ID NO: 28), NP_001258556.1 (*Mus musculus*, SEQ ID NO: 29), NP_001258559.1 (*Mus musculus*, SEQ ID NO: 30), and NP_001258560.1 (*Mus musculus*, SEQ ID NO: 31).

Nucleic acids of additional RUNX2 human isoforms are publically available in the GenBank database under accession numbers: NM_001015051.3 (*Homo sapiens*, SEQ ID NO: 32), NM_001024630.3 (*Homo sapiens*, SEQ ID NO: 33), and NM_001278478.1 (*Homo sapiens*, SEQ ID NO: 34). Nucleic acid sequences of additional RUNX2 isoforms are publically available in the GenBank database under accession numbers NM_001145920.2 (*Mus musculus*, SEQ ID NO: 35), NM_001146038.2 (*Mus musculus*, SEQ ID NO: 36), NM_001271627.1 (*Mus musculus*, SEQ ID NO: 37), NM_001271630.1 (*Mus musculus*, SEQ ID NO: 38), and NM_001271631.1 (*Mus musculus*, SEQ ID NO: 39).

Exemplary Inhibitors

Aspects of the present subject matter relate to the administration of an RUNX1 inhibitor. In various embodiments, an inhibitor may be, e.g., an aptamer, an oligonucleotide (e.g., an antisense oligonucleotide, a ribozyme, or an RNA interfering molecule), a peptide, an antibody or a fragment thereof, or a small molecule, that specifically binds to RUNX1 or a polynucleotide that encodes RUNX1.

Small Molecule CBFβ-RUNX1 Inhibitors

In various embodiments, the RUNX1 inhibitor is a small molecule inhibitor. Non-limiting examples include:

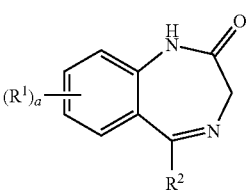
(Formula I)

or pharmaceutically acceptable salts or esters thereof, wherein each $R^1$ is individually selected from halogen, alkyl, aryl, heteroaryl, or alkoxy; $R^2$ is selected from aryl or heteroaryl; and a is 0 to 4;

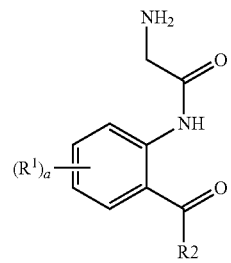
(Formula II)

or a pharmaceutically acceptable salt or ester thereof, wherein each $R^1$ is individually selected from halogen, alkyl, aryl, heteroaryl, or alkoxy; $R^2$ is selected from aryl or heteroaryl; and a is 0 to 4; or

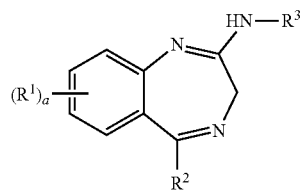
(Formula III)

or a pharmaceutically acceptable salt or ester thereof, wherein each $R^1$ is individually selected from halogen, alkyl, aryl, heteroaryl, or alkoxy; R2 is selected from aryl or heteroaryl; $R^3$ is alkyl or aryl; and a is 0 to 4.

In certain embodiments of formulae I-III, $R^2$ is a heteroaryl, particularly pyrrolyl, and especially pyrrol-2-yl. In certain embodiments of formulae I-III, $R^1$ is a halogen, particularly Cl or F. In certain embodiments of formula III, $R^3$ is a lower alkyl. In certain embodiments of formulae I-III, $R^2$ is a heteroaryl, particularly pyrrolyl, and especially pyrrol-2-yl; and $R^1$ is a halogen, particularly Cl or F. In certain embodiments of formula III, R2 is a heteroaryl, particularly pyrrolyl, and especially pyrrol-2-yl; $R^1$ is a halogen, particularly Cl or F; and $R^3$ is a lower alkyl.

The term "alkoxy" refers to a group of the formula —OR, wherein R is an organic group such as an alkyl group, optionally substituted with an alkenyl, alkynyl, aryl, aralkyl, cycloalkyl, halogenated alkyl, or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Alkyl groups may be substituted alkyls wherein one or more hydrogen atoms are substituted with a substituent such as halogen, cycloalkyl, alkoxy, amino, hydroxyl, aryl, or carboxyl. For example, an "alkoxyalkyl" has the structure—ROR, wherein R is an alkyl group.

The term "aryl" refers to any carbon-based aromatic group including, but not limited to, benzyl, naphthyl, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be optionally substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "heteroaryl" refers to a mono- or poly-cyclic (e.g., bi-, or tri-cyclic or more) fused or non-fused, radical or ring system having at least one aromatic ring, having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "derivative" refers to a compound or portion of a compound that is derived from or is theoretically derivable from a parent compound.

The term "pharmaceutically acceptable salt or ester" refers to salts or esters prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., J. Pharm. Sci. 66:1 (1977). "Pharmaceutically acceptable esters" includes those derived from compounds described herein that are modified to include a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$ alkoxymethyl esters for example methoxy-methyl, $C_{1-6}$ alkanoyloxymethyl esters for example pivaloyloxymethyl, phthalidyl esters, $C_{3-8}$ cycloalkoxycarbonyloxy C1-6 alkyl esters for example 1-cyclohexylcarbonyl-oxyethyl; 1,3-dioxolen-2-onylmethyl esters for example 5-methyl-1,3-dioxolen-2-onylmethyl; and $C_{1-6}$ alkoxycarbonyloxyethyl esters for example 1-methoxycarbonyl-oxyethyl which may be formed at any carboxy group in the compounds.

In some embodiments relating to a small molecule inhibitor that binds RUNX1, the small molecule inhibitor comprises Ro5-3335, Ro24-7429, NSC140873, MLS000548294, MLS001048862, or NSC156594. See, e.g., Cunningham et al. (2012) Proc Natl Acad Sci USA, 109(36): 14592-14597, Haubrich, R. et al., J Infect Dis 172(5): 1246-52, and U.S. Patent Application Publication No. 2014/0004082, the entire contents of each of which are incorporated herein by reference. Additional examples of RUNX1 inhibitors are described in U.S. Pat. Nos. 5,641,773; 5,164,376; 5,141,735; 5,041,438; 5,036,101; and 3,405,122, as well as U.S. Patent Application Publication No. 2014/0004082, the entire contents of each of which are hereby incorporated herein by reference.

Ro5-3335 has the following structure:

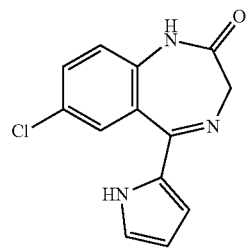 [SMILES: O=C1CN=C(c2ccc[nH]2)c2cc(Cl)ccc2N1]

The CAS Registry Number for Ro5-3335 is 30195-30-3.

Ro24-7429 has the following structure:

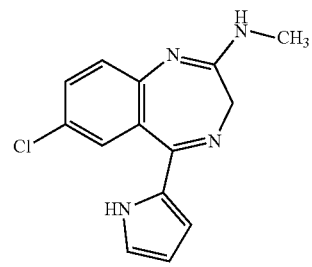 [SMILES: CNC1=Nc2ccc(Cl)cc2C(c2ccc[nH]2)=NC1]

The CAS Registry Number for Ro24-7429 is 139339-45-0.

NSC140873 has the following structure:

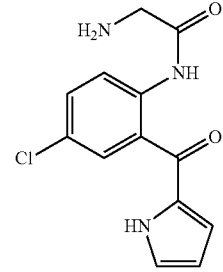 [SMILES: NCC(=O)Nc1ccc(Cl)cc1C(=O)c1ccc[nH]1]

The CAS Registry Number for NSC140873 is 106410-13-3.

MLS000548294 has the following structure:

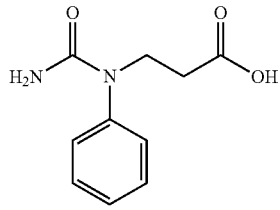 [SMILES: NC(=O)N(CCC(=O)O)c1ccccc1]

The PubChem ID for MLS000548294 is 768985.

MLS001048862 has the following structure:

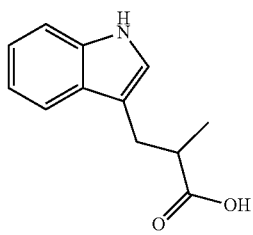

The PubChem ID for MLS001048862 is 2772042.

NSC156594 has the following structure:

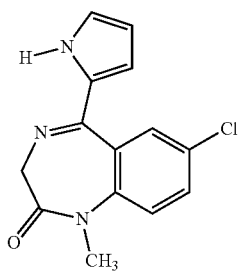 [SMILES: CN1C(=O)CN=C(c2ccc[nH]2)c2cc(Cl)ccc21]

The PubChem ID for NSC156594 is 457993.

The synthesis of several of the compounds disclosed above and analogs thereof have been previously described, for example, in U.S. Pat. Nos. 5,641,773; 5,164,376; 5,141,735; 5,041,438; 5,036,101; and 3,405,122, the entire contents of each of which are incorporated herein by reference.

In some embodiments, the RUNX1 inhibitor inhibits RUNX1 via inhibition of CBFß, which is the transcriptional partner of RUNX1.

Non-limiting examples of CBMß inhibitors include:

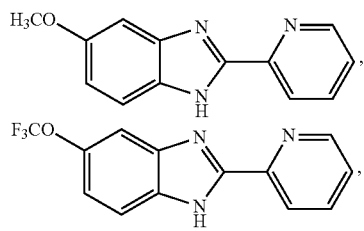

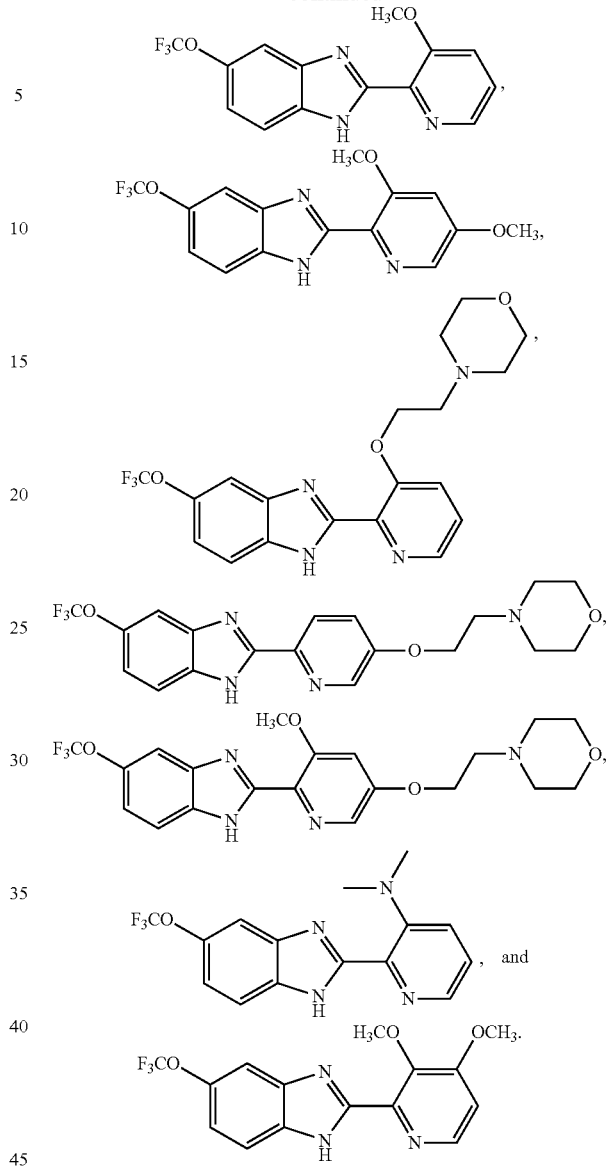

Non-limiting descriptions of CBFβ inhibitors and aspects thereof are described in Illendula et al. (2016) *EBioMedicine* 8: 117-131, the entire content of which is incorporated herein by reference. In some examples, the inhibitor comprises a pyridyl benzimidazole.

Proteins and Peptides

In some embodiments, a protein, peptide, or a fragment thereof is used to inhibit RUNX1. A non-limiting example of such an inhibitor for RUNX1 is a dominant negative CBF-Beta protein (CBFB-MYH11). See, e.g., Castilla et al. (1996) *Cell.* 1996; 87:687-696, the entire content of which is hereby incorporated herein by reference.

RNA

In some embodiments, a RNA is used to encode a protein that inhibits RUNX1 or the RNA itself has inhibitory properties.

Aptamers

Aptamers are small, single stranded biomolecules, typically oligonucleotides (either DNA or RNA) or peptides, that bind to a specific target molecule (e.g. a protein or small molecule such as a steroid). They can be considered analogous to antibodies in their specificity but, unlike antibodies, aptamers are have a relatively low molecular weight. Peptide-based aptamers are generally less than thirty residues long while nucleotide-based aptamers are typically less than one hundred residues long.

Non-limiting examples of methods that are useful for designing aptamers that target a particular protein, such as RUNX1, are described in U.S. Pat. Nos. 8,484,010; 5,582,981; PCT International Patent Application No. WO 2015/049356; Blackwell et al., (1993) Science 250:1104-1110; Blackwell, et al., (1990) Science 250:1149-1152; Tuerk and Gold (1990) Science 249:505-510; and Joyce (1989) Gene 82:83-87, the entire contents of each of which are incorporated herein by reference.

Antisense Oligonucleotides

As used herein, an "antisense oligonucleotide" is an oligonucleotide that inhibits gene expression by a mechanism other than RNAi. Non-limiting examples of antisense oligonucleotides which decrease the amount of RUNX1 produced by cells that can be employed in the methods described herein include antisense oligonucleotides that are complementary (e.g., at least about 90, 95, 96, 97, 98, 99, or 100% complementary) to a stretch of at least about 10, 11, 12, 13, 14, 15, 16, 17, 18, 19, 20, 21, 22, 23, 24, 25, 26, 27, 28, 29 or 30 consecutive nucleotides having a sequence found within a nucleotide sequence that encodes RUNX1, such as any of the RUNX1-encoding nucleotide sequences disclosed herein.

Antisense oligonucleotides comprise nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of RUNX1 gene products in the cell.

Antisense oligonucleotides can comprise deoxyribonucleotides, ribonucleotides, or a combination of both. Antisense oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters.

Modifications of gene expression can be obtained by designing antisense oligonucleotides which will form duplexes to the control, 5', or regulatory regions of the gene. Antisense oligonucleotides that target the transcription initiation site, e.g., between positions −10 and +10 from the start site, are used in some embodiments. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (Nicholls et al., 1993, J Immunol Meth 165:81-91). Antisense oligonucleotides that are complementary to a sequence that includes the translational start site, and/or that are complementary to a portion of a target mRNA within 10 nucleotides of the translational start site, are used in various embodiments. An antisense oligonucleotide also can be designed to block translation of mRNA by preventing the transcript from binding to ribosomes.

Precise complementarity is not required for successful complex formation between an antisense oligonucleotide and the complementary sequence of a RUNX1 polynucleotide. Antisense oligonucleotides which comprise, for example, 2, 3, 4, or 5 or more stretches of contiguous nucleotides which are precisely complementary to a RUNX1, each separated by a stretch of contiguous nucleotides which are not complementary to adjacent RUNX1 nucleotides, can provide sufficient targeting specificity for RUNX1 mRNA. In some embodiments, each stretch of complementary contiguous nucleotides is at least 4, 5, 6, 7, or 8 or more nucleotides in length. Noncomplementary intervening sequences may be, e.g., 1, 2, 3, or 4 nucleotides in length. One skilled in the art can easily use the calculated melting point of an antisense-sense pair to determine the degree of mismatching which will be tolerated between a particular antisense oligonucleotide and a particular RUNX1 polynucleotide sequence. Antisense oligonucleotides can be modified without affecting their ability to hybridize to a RUNX1 polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3' or 5'-substituted oligonucleotide in which the 3' hydroxyl group and/or the 5' phosphate group is substituted, also can be employed in a modified antisense oligonucleotide. These modified antisense oligonucleotides can be prepared by methods well known in the art.

Ribozymes

Ribozymes are RNA molecules with catalytic activity (Uhlmann et al., 1987, Tetrahedron. Lett. 215, 3539-3542). Ribozymes can be used to inhibit gene function by cleaving an RNA sequence, as is known in the art. The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences. The coding sequence of a polynucleotide can be used to generate ribozymes which will specifically bind to mRNA transcribed from the polynucleotide. Methods of designing and constructing ribozymes which can cleave other RNA molecules in trans in a highly sequence specific manner have been developed and described in the art. For example, the cleavage activity of ribozymes can be targeted to specific RNAs by engineering a discrete "hybridization" region into the ribozyme. The hybridization region contains a sequence complementary to the target RNA and thus specifically hybridizes with the target RNA.

Specific ribozyme cleavage sites within an RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate RNA targets also can be evaluated by testing accessibility to hybridization with complementary oligonucleotides using ribonuclease protection assays. The nucleotide sequences shown in SEQ ID NOs: 1-26 and their complements provide sources of suitable hybridization region sequences. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease RUNX1 expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer element, and a transcriptional terminator signal, for controlling transcription of ribozymes in the cells (U.S. Pat. No. 5,641,673). Ribozymes also can be engineered to provide an additional level of regulation, so that destruction of mRNA occurs only when both a ribozyme and a target gene are induced in the cells.

RNA Interference

As used herein, an "RNA interference" inducing compound refers to a compound capable of inducing RNA interference or "RNAi" of target gene (e.g., RUNX1) expression, depending on the context. RNAi involves mRNA degradation. The use of RNAi has been described in Fire et al. (1998) Nature 19; 391(6669):806-11, Elbashir et al. (2001) EMBO J. 20(23): 6877-6888, and Cheloufi et al. (2010) Nature 465, 584-589, the entire contents of each of which are incorporated herein by reference.

Isolated RNA molecules can mediate RNAi. That is, the isolated RNA molecules of the present subject matter mediate degradation or block expression of mRNA that is the transcriptional product of the gene, which is also referred to as a target gene. For convenience, such mRNA may also be referred to herein as mRNA to be degraded. RNAi molecules may be, e.g., double-stranded RNA, small interfering RNA (siRNA), hairpin RNA, microRNA molecules which may be altered compared to naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the RNA molecules of the present invention can also comprise nonstandard nucleotides, including non-naturally occurring nucleotides or deoxyribonucleotides. Collectively, all such altered RNAi molecules may be referred to as analogs or analogs of naturally-occurring RNA. RNA of the present invention need only be sufficiently similar to natural RNA that it has the ability to mediate RNAi.

As used herein the phrase "mediate RNAi" refers to and indicates the ability to distinguish which mRNA molecules are to be afflicted with the RNAi machinery or process. RNA that mediates RNAi interacts with the RNAi machinery such that it directs the machinery to degrade particular mRNAs or to otherwise reduce the expression of the target protein. In some embodiments, the present invention relates to RNA molecules that direct cleavage of specific mRNA to which their sequence corresponds. It is not necessary that there be perfect correspondence of the sequences, but the correspondence must be sufficient to enable the RNA to direct RNAi inhibition by cleavage or blocking expression of the target mRNA. In some embodiments, an RNAi molecule comprises a stretch of about 16 to 29, 18 to 23, 21-23, or at least 12, 13, 14, 15, 16, 17, 18, 19, 20, 21, 22, 23, 24, or 25 nucleotides having a sequence that is at least about 90, 95, 96, 97, 98, 99, or 100% complementary to a target sequence. As noted above, the RNA molecules of the present invention may comprise an RNA portion and some additional portion, for example a deoxyribonucleotide portion.

Antibodies

In some embodiments, the RUNX1 inhibitor is an antibody or a fragment thereof.

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, an $F_{ab}$ expression library, single-chain antibody molecules (e.g., scFv), and multispecific antibodies formed from antibody fragments. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

An "antibody fragment" refers to a molecule other than an intact antibody that comprises a portion of an intact antibody that binds the antigen to which the intact antibody binds. The terms "full length antibody," "intact antibody," and "whole antibody" are used herein interchangeably to refer to an antibody having a structure substantially similar to a native antibody structure or having heavy chains that contain an Fc region.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs." Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three hypervariable regions (HVRs) of each variable domain interact to define an antigen binding site on the surface of the VH-VL dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

A "Fab" fragment contains a variable and constant domain of the light chain and a variable domain and the first constant domain (CHI) of the heavy chain. F(ab') 2 antibody fragments comprise a pair of Fab fragments which are generally covalently linked near their carboxy termini by hinge cysteines between them. Other chemical couplings of antibody fragments are also known in the art, "Single-chain Fv" or "scFv" antibody fragments comprise the VH and VL domains of an antibody, wherein these domains are present in a single polypeptide chain. Generally the Fv polypeptide further comprises a polypeptide linker between the VH and L domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-31S (1994).

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, BP 404,097; WO 93/11161; and Hollinger et al., Proc. Natl. Acad. Sci. USA, 90:6444-6448 (1993).

The expression "linear antibodies" refers to the antibodies described in Zapata et al., Protein Eng., 8 (10): 1057-1062 (1995). Briefly, these antibodies comprise a pair of tandem segments which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

As used herein, the term "epitope" includes any protein determinant capable of specific binding to an antibody, an antibody fragment, or a T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; preferably ≤100 nM and most preferably ≤10 nM.

Antibodies can be produced according to any method known in the art.

Methods of preparing monoclonal antibodies are known in the art. For example, monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a full length protein or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) Monoclonal Antibodies: Principles and Practice Academic Press) Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some examples, the antibodies to an epitope for an interested protein as described herein or a fragment thereof are humanized antibodies. Humanized forms of non-human (e.g., murine) antibodies are chimeric molecules of immunoglobulins, immunoglobulin chains or fragments thereof (such as Fv, $F_{ab}$, $F_{ab'}$, $F_{(ab')2}$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al. 1986. Nature 321:522-525; Riechmann et al. 1988. Nature 332:323-329; Presta. 1992. Curr. Op. Struct. Biol. 2:593-596). Humanization can be essentially performed following methods of Winter and co-workers (see, e.g., Jones et al. 1986. Nature 321:522-525; Riechmann et al. 1988. Nature 332:323-327; and Verhoeyen et al. 1988. Science 239:1534-1536), by substituting rodent CDRs or CDR sequences for the corresponding sequences of a human antibody. Accordingly, such humanized antibodies are chimeric antibodies (e.g., U.S. Pat. No. 4,816,567), wherein substantially less than an intact human variable domain has been substituted by the corresponding sequence from a non-human species.

In various examples the antibodies to an epitope of an interested protein as described herein or a fragment thereof are human antibodies. Human antibodies can also be produced using various techniques known in the art, including phage display libraries (Hoogenboom and Winter. 1991. J. Mol. Biol. 227:381-388; Marks et al. 1991. J. Mol. Biol. 222:581-597) or the preparation of human monoclonal antibodies [e.g., Cole et al. 1985. Monoclonal Antibodies and Cancer Therapy Liss; Boerner et al. 1991. J. Immunol. 147(1):86-95]. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al. 1992. Bio/Technology 10:779-783; Lonberg et al. 1994. Nature 368:856-859; Morrison. 1994. Nature 368: 812-13; Fishwild et al. 1996. Nature Biotechnology 14:845-51; Neuberger. 1996. Nature Biotechnology 14:826; Lonberg and Huszar. 1995. Intern. Rev. Immunol. 13:65-93. U.S. Pat. No. 6,719,971 also provides guidance to methods of generating humanized antibodies.

In some embodiments, an intrabody is used to inhibit RUNX1. An "intrabody" (from intracellular and antibody) is an antibody that works within the cell to bind to an intracellular antigen. Intrabodies typically lack disulfide bonds and are capable of modulating the expression or activity of target genes through their specific binding activity. Intrabodies include single domain fragments such as isolated VH and VL domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions. In various embodiments, the intrabody is expressed within a target cell, e.g., by a viral or plasmid expression vector that has been introduced into the target cell. An intrabody may remain in the cytoplasm, or it may have a nuclear localization signal, or it may undergo cotranslational translocation across the membrane into the lumen of the endoplasmic reticulum, provided that it is retained in that compartment through a KDEL sequence. Because antibodies ordinarily are designed to be secreted from the cell, intrabodies require special alterations, including the use of single-chain antibodies (scFvs), modification of immunoglobulin VL domains for hyperstability, selection of antibodies resistant to the more reducing intracellular environment, or expression as a fusion protein with maltose binding protein or other stable intracellular proteins. Non-limiting aspects of intrabodies are described, e.g., in U.S. Pat. No. 9,133,269; U.S. Patent Application Publication No. 2006/0034834; Chen et al. (1994) Human gene therapy 5 (5): 595-601; and Shaki-Loewenstein et al. (2005) Journal of immunological methods 303 (1-2): 19-39, the entire contents of each of which are incorporated herein by reference.

Exemplary antibodies against RUNX1 include, but are not limited to, antibodies obtained from Abcam (Cambridge, Mass., USA) (e.g., Cat. Nos. ab23980, ab35962, ab189172, ab189153, and ab91002), antibodies obtained from Novus Biologicals (Littleton, Colo., USA) (e.g., Cat. Nos. NBP1-89105, H00000861-M05, H00000861-M06, MAB2399, and H00000861-M02), and antibodies obtained from ThermoFisher Scientific (Cambridge, Mass., USA) (e.g., 710233, MA5-15814, PA1-41078, OSR00271W, PAS-17434, PAS-19638, PAS-12409, PAS-40076, and PAS-17351).

Gene Therapy

In some embodiments, a gene editing method is used to modulate (e.g., reduce) RUNX1 expression and/or activity. Non-limiting examples of gene editing systems useful in such embodiments include the clustered regularly interspaced short palindromic repeat (CRISPR)-Cas system; zinc finger nuclease (ZFN) systems, and transcription activator-like effector-based nuclease (TALEN) systems.

Exemplary aspects of the CRISPR-Cas system are described in, e.g., U.S. Pat. No. 9,023,649, issued May 5, 2015; U.S. Pat. No. 9,074,199, issued Jul. 7, 2015; and U.S. Pat. No. 8,697,359, issued Apr. 15, 2014 the entire contents of each of which are incorporated herein by reference.

With their highly flexible but specific targeting, CRISPR-Cas systems can be manipulated and redirected to become powerful tools for genome editing. CRISPR-Cas technology permits targeted gene cleavage and gene editing in a variety of eukaryotic cells, and editing can be directed to virtually any genomic locus. Exemplary CRISPR Cas genes include Cas1, Cas2, Cas3', Cas3", Cas4, Cas5, Cas6, Cas6e (formerly referred to as CasE, Cse3), Cas6f (i.e., Csy4), Cas7, Cas8a1, Cas8a2, Cas8b, Cas8c, Cas9, Cas10, Cas10d, Csy1, Csy2, CPf1, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. These enzymes are known; for example, the amino acid sequence of *Streptococcus pyogenes* Cas9 protein may be found in the SwissProt database under accession number Q99ZW2.

Other non-limiting examples of approaches for gene editing include the use of zinc finger nucleases, which are artificial restriction enzymes generated by fusing a zinc finger DNA-binding domain to a DNA-cleavage domain. A zinc finger nuclease is a site-specific endonuclease designed to bind and cleave DNA at specific positions. There are two protein domains. The first domain is the DNA binding domain, which consists of eukaryotic transcription factors and contain the zinc finger. The second domain is the nuclease domain, which consists of the Fold restriction enzyme and is responsible for the catalytic cleavage of DNA. The DNA-binding domains of individual ZFNs typically contain between three and six individual zinc finger repeats and can each recognize between 9 and 18 basepairs. If the zinc finger domains are perfectly specific for their intended target site then even a pair of 3-finger ZFNs that recognize a total of 18 basepairs can, in theory, target a single locus in a mammalian genome. Various strategies have been developed to engineer Cys2His2 zinc fingers to bind desired sequences. These include both "modular assembly" and selection strategies that employ either phage display or cellular selection systems. The most straightforward method to generate new zinc-finger arrays is to combine smaller zinc-finger "modules" of known specificity. The most common modular assembly process involves combining three separate zinc fingers that can each recognize a 3 basepair DNA sequence to generate a 3-finger array that can recognize a 9 basepair target site. Other procedures can utilize either 1-finger or 2-finger modules to generate zinc-finger arrays with six or more individual zinc fingers. Numerous selection methods have been used to generate zinc-finger arrays capable of targeting desired sequences. Initial selection efforts utilized phage display to select proteins that bound a given DNA target from a large pool of partially randomized zinc-finger arrays. More recent efforts have utilized yeast one-hybrid systems, bacterial one-hybrid and two-hybrid systems, and mammalian cells. The non-specific cleavage domain from the type IIs restriction endonuclease FokI is typically used as the cleavage domain in ZFNs. This cleavage domain must dimerize in order to cleave DNA and thus a pair of ZFNs are required to target non-palindromic DNA sites. Standard ZFNs fuse the cleavage domain to the C-terminus of each zinc finger domain. In order to allow the two cleavage domains to dimerize and cleave DNA, the two individual ZFNs must bind opposite strands of DNA with their C-termini a certain distance apart. The most commonly used linker sequences between the zinc finger domain and the cleavage domain requires the 5' edge of each binding site to be separated by 5 to 7 bp.

TALENs are restriction enzymes that can be engineered to cut specific sequences of DNA. They are made by fusing a TAL effector DNA-binding domain to a DNA cleavage domain. Transcription activator-like effectors (TALEs) can be engineered to bind practically any desired DNA sequence, so when combined with a nuclease, DNA can be cut at specific locations. The restriction enzymes can be introduced into cells, for use in gene editing or for genome editing in situ. Alongside zinc finger nucleases and CRISPR/Cas9, TALEN is a prominent tool in the field of genome editing.

NOTCH Signaling Inhibition

Notch signaling is an upstream regulator of the expression of Runx genes (Burns C E, et al., Genes and Development, 2005, 19:2331-2342). Modalities for preventing or reducing proliferation or migration of RPE cells is based on inhibition of the Notch receptors (Notch 1, Notch 2, Notch 3, Notch 4) and its ligands (Delta like 1, Delta like 2, Delta like 5, Jagged 1 and Jagged 2) or other modulators of the Notch pathway operate via regulation of RUNX1. These modalities of treatment include inhibition of gamma-secretase, modulating antibodies against the receptors and the ligands, and other small molecules, biologicals and genetic approaches that inhibit RUNX1 expression via modulation of Notch signaling activity.

In some embodiments, NOTCH signaling is modulated to reduce RUNX1 function. For example, a NOTCH inhibitor is used to reduce RUNX1 expression or activity. Non-limiting examples of NOTCH inhibitors include aptamers, oligonucleotides (e.g., antisense oligonucleotides, ribozymes, and RNAi molecules), peptides (e.g., a portion of or the entire extracellular domain of a NOTCH protein), antibodies, antibody fragments, and small molecules that specifically bind to a NOTCH protein or a polynucleotide that encodes a NOTCH protein. Non-limiting examples of small molecule inhibitors for NOTCH proteins include compounds having the following structures:

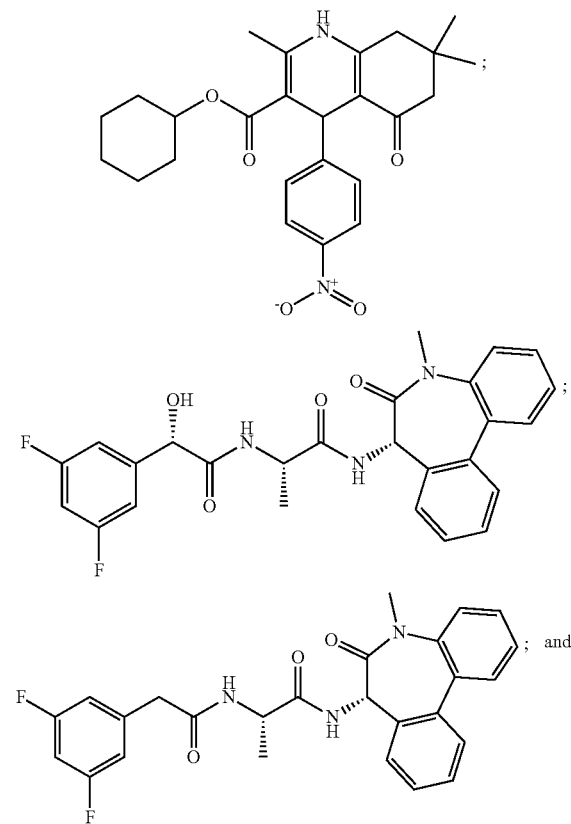

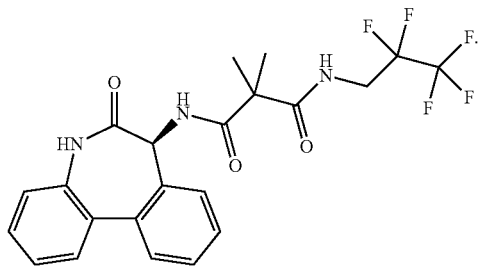

Additional non-limiting examples of NOTCH inhibitors (as well as aspects of NOTCH signaling) are described in Espinoza and Miele, *Pharmacol Ther.* 2013, 139(2): 95-110; and Yuan et al., *Cancer Letters* 2015, 369(1) 20-27, the entire contents of each of which are incorporated herein in their entireties.

Immunomodulatory Imide Drug (IMiD) Inhibitors

In some examples, the RUNX1 inhibitor comprises an immunomodulatory imide drug (IMiD). IMiDs are a class of immunomodulatory drugs containing an imide group. In non-limiting examples, the IMiD includes thalidomide and its analogs, e.g., lenalidomide, pomalidomide, and apremilast.

In various embodiments, the IMiD comprises:

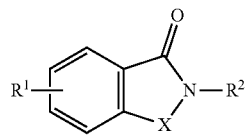

(Formula IV)

or pharmaceutically acceptable salts or esters thereof, wherein:

$R^1$=H, $NH_2$, $NHC(O)CH_3$

X=$CH_2$, C(O)

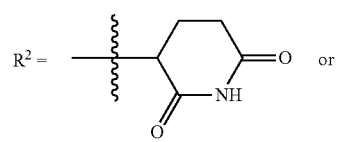

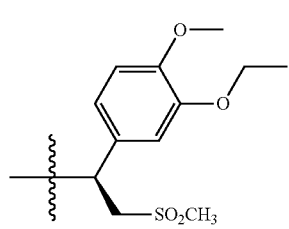

For example, Formula IV encompasses lenalidomide, pomalidomide, thalidomide, and/or apremilast.

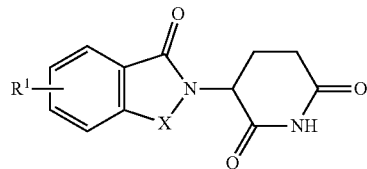

(Formula V)

or pharmaceutically acceptable salts or esters thereof, wherein:

$R^1$=H, $NH_2$, $NHC(O)CH_3$

X=$CH_2$, C(O)

For example, Formula V encompasses lenalidomide, pomalidomide, and/or anthalidomide.

In some examples, the IMiD is lenalidomide. The IUPAC name for lenalidomide is 3-(7-amino-3-oxo-1H-isoindol-2-yl)piperidine-2,6-dione. The CAS Registry Number for lenalidomide is 191732-72-6.

Lenalidomide has the following structure:

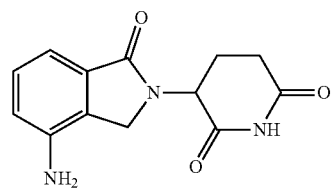 [SMILES: Nc1cccc2c1CN(C1CCC(=O)NC1=O)C2=O]

In some examples, the IMiD is thalidomide. The IUPAC name for thalidomide is 2-(2,6-dioxopiperidin-3-yl)isoindole-1,3-dione. The CAS Registry Number for thalidomide is 50-35-1.

Thalidomide has the following structure:

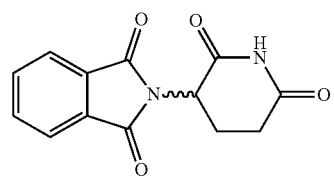 [SMILES: O=C1CCC(N2C(=O)c3ccccc3C2=O)C(=O)N1]

In some examples, the IMiD is pomalidomide. The IUPAC name for pomalidomide is 4-amino-2-(2,6-dioxopiperidin-3-yl)isoindole-1,3-dione. The CAS Registry Number for pomalidomide is 19171-19-8.

Pomalidomide has the following structure:

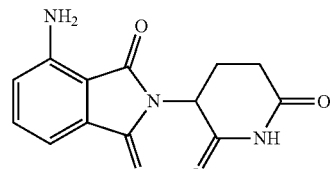

In some examples, the IMiD is apremilast. The IUPAC name for apremilast is N-[2-[(1S)-1-(3-ethoxy-4-methoxyphenyl)-2-methylsulfonylethyl]-1,3-dioxoisoindol-4-yl]acetamide. The CAS Registry Number for apremilast is 608141-41-9.

Apremilast has the following structure:

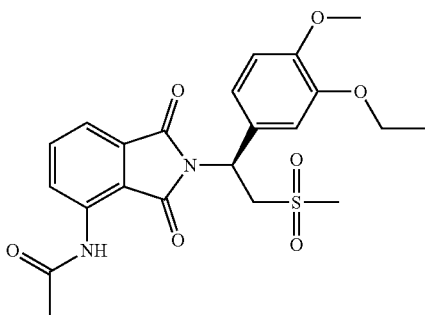 [SMILES: CCOc1cc([C@@H](CS(C)(=O)=O)N2C(=O)c3cccc(NC(C)=O)c3C2=O)ccc1OC]

In other examples, the IMiD comprises phosphodiesterase type 4 (PDE4) inhibitor, e.g., rolipram The IUPAC name for rolipram is 4-(3-cyclopentyloxy-4-methoxyphenyl)pyrrolidin-2-one. The CAS Registry Number for rolipram is 61413-54-5.

Rolipram has the following structure:

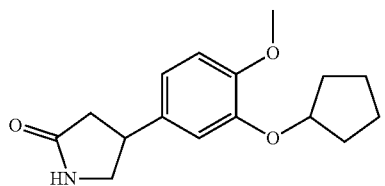 [SMILES: COc1ccc(C2CNC(=O)C2)cc1OC1CCCC1]

The RUNX1 inhibitors may have one or more chiral centers, and thus can exist as one or more stereoisomers. Such stereoisomers can exist as a single enantiomer, a mixture of enantiomers, a mixture of diastereomers, or a racemic mixture.

As used herein, the term "stereoisomers" refers to compounds made up of the same atoms having the same bond order but having different three-dimensional arrangements of atoms that are not interchangeable. The three-dimensional structures are called configurations. As used herein, the term "enantiomers" refers to two stereoisomers that are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

Pharmaceutical Formulations and Delivery

Dosages, formulations, dosage volumes, regimens, and methods for administering a RUNX1 inhibitor may vary. Thus, minimum and maximum effective dosages vary depending on the method of administration.

"Administering" an inhibitor described herein can be effected or performed using any of the various methods and delivery systems known to those skilled in the art. The administering can be, for example, intravenous, oral, ocular (e.g., subconjunctival, intravitreal, retrobulbar, or intracameral), intramuscular, intravascular, intra-arterial, intracoronary, intramyocardial, intraperitoneal, subcutaneous, inhaled, or intrathecal. Other non-limiting examples include topical administration, or coating of a device to be placed within the subject. Topical administration also includes administration of the inhibitor(s) by eye drop, e.g., contacting the surface of the eye with a liquid (aqueous, lipid, or combination thereof) or gel formulation. In other embodiments, administration is carried by injection, e.g., using a needle, or via a catheter.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

As used herein, a "monotherapy" is therapy that is administered to inhibit, treat, or prevent a disorder, such as proliferation or migration of retinal pigment epithelial (RPE) in a subject who comprise a retinal hole or a retinal tear, such as found in PVR), without any other therapy that is used to treat the disorder. A monotherapy for treating a disorder may optionally be combined with another treatment that is used to ameliorate a symptom of the disorder while not being directed against the disorder, for example an analgesic compound, an antipyretic compound, and/or an anti-inflammatory compound (e.g., aspirin, ibuprofen, naproxen, or acetaminophen) may be administered concurrently with the monotherapy.

In various embodiments of the invention, a composition comprising a RUNX1 inhibitor may be administered only once or multiple times. For example, a RUNX1 inhibitor may be administered using a method disclosed herein at least about once, twice, three times, four times, five times, six times, or seven times per day, week, month, or year. In some embodiments, a composition comprising a RUNX1 inhibitor is administered once per month. In certain embodiments, the composition is administered once per week, once every two weeks, once a month via intravitreal injection. In various embodiments, such as embodiments involving eye drops, a composition is self-administered.

For the treatment of an ocular disorder, a RUNX1 inhibitor (e.g., a pharmaceutical composition comprising a RUNX1 inhibitor) may be administered locally, e.g., as a topical eye drop, peri-ocular injection (e.g., sub-tenon), intraocular injection, intravitreal injection, retrobulbar injection, intraretinal injection, subretinal injection, suprachoroidal, subconjunctival injection, or using iontophoresis, or peri-ocular devices which can actively or passively deliver drug.

Sustained release of drug may be achieved by the use of technologies such as implants (e.g., solid implants) (which may or may not be bio-degradable) or bio-degradable polymeric matrices (e.g., micro-particles). These may be administered, e.g., peri-ocularly or intravitreally.

Pharmaceutical formulations adapted for topical administration may be formulated as aqueous solutions, ointments, creams, suspensions, lotions, powders, solutions, pastes, gels, sprays, aerosols, liposomes, microcapsules, microspheres, or oils.

For treatments of the eye or other external tissues, such as the mouth or skin, the formulations (e.g., a pharmaceutical composition comprising a RUNX1 inhibitor) may be applied as a topical ointment or cream. When formulated in an ointment, a RUNX1 inhibitor may be employed with either a paraffinic or a water-miscible ointment base. Alternatively, a RUNX1 inhibitor may be formulated in a cream with an oil-in-water cream base or a water-in-oil base.

The present subject matter provides compositions comprising a RUNX1 inhibitor and a carrier or excipient suitable for administration to ocular tissue. Such carriers and excipients are suitable for administration to ocular tissue (e.g., sclera, lens, iris, cornea, uvea, retina, macula, or vitreous tissue) without undue adverse side effects (such as toxicity, irritation, and allergic response) commensurate with a reasonable benefit/risk ratio.

Pharmaceutical formulations adapted for topical administrations to the eye include eye drops wherein a RUNX1 inhibitor is dissolved or suspended in a suitable carrier, especially an aqueous solvent. Formulations to be administered to the eye will have ophthalmically compatible pH and osmolality. The term "ophthalmically acceptable vehicle" means a pharmaceutical composition having physical properties (e.g., pH and/or osmolality) that are physiologically compatible with ophthalmic tissues.

In some embodiments, an ophthalmic composition of the present invention is formulated as sterile aqueous solutions having an osmolality of from about 200 to about 400 milliosmoles/kilogram water ("mOsm/kg") and a physiologically compatible pH. The osmolality of the solutions may be adjusted by means of conventional agents, such as inorganic salts (e.g., NaCl), organic salts (e.g., sodium citrate), polyhydric alcohols (e.g., propylene glycol or sorbitol) or combinations thereof.

In various embodiments, the ophthalmic formulations of the present invention may be in the form of liquid, solid or semisolid dosage form. The ophthalmic formulations of the present invention may comprise, depending on the final dosage form, suitable ophthalmically acceptable excipients. In some embodiments, the ophthalmic formulations are formulated to maintain a physiologically tolerable pH range. In certain embodiments, the pH range of the ophthalmic formulation is in the range of from about 5 to about 9. In some embodiments, pH range of the ophthalmic formulation is in the range of from about 6 to about 8, or is about 6.5, about 7, or about 7.5.

In some embodiments, the composition is in the form of an aqueous solution, such as one that can be presented in the form of eye drops. By means of a suitable dispenser, a desired dosage of the active agent can be metered by administration of a known number of drops into the eye, such as by one, two, three, four, or five drops.

One or more ophthalmically acceptable pH adjusting agents and/or buffering agents can be included in a composition of the invention, including acids such as acetic, boric, citric, lactic, phosphoric, and hydrochloric acids; bases such as sodium hydroxide, sodium phosphate, sodium borate, sodium citrate, sodium acetate, and sodium lactate; and buffers such as citrate/dextrose, sodium bicarbonate, and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium, or ammonium cations and chloride, citrate, ascorbate, borate, phosphate, bicarbonate, sulfate, thiosulfate, or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g., poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition, and polymeric coatings that will enhance drug diffusion, erosion, dissolution, and osmosis.

Formulations for drug delivery using ocular devices may combine one or more active agents and adjuvants appropriate for the indicated route of administration. For example, a RUNX1 inhibitor (optionally with another agent) may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers, and a carrier or diluent that has a time delay property. Representative examples of biodegradable compositions can include albumin, gelatin, starch, cellulose, dextrans, polysaccharides, poly (D,L-lactide), poly (D,L-lactide-co-glycolide), poly (glycolide), poly (hydroxybutyrate), poly (alkylcarbonate) and poly (orthoesters), and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig, Adv. Drug Deliv. Rev. 3; 57:1595-639 (2005), the entire content of which is incorporated herein by reference.

Biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; 6,699,493; and 8,293,210, the entire contents of each of which are incorporated herein by reference.

The implants may be monolithic, i.e. having the active agent (e.g., a RUNX1 inhibitor) or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including a RUNX1 inhibitor, may be distributed in a non-homogenous pattern in the matrix. For example, the implant may include a portion that has a greater concentration of a RUNX1 inhibitor relative to a second portion of the implant.

The intraocular implants disclosed herein may have a size of between about 5 um and about 2 mm, or between about 10 um and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 μg, more preferably about 500-1000 ug. For example, an implant may be about 500 ug, or about 1000 ug. For non-human subject, the dimensions and total weight of the implant(s) may be larger or smaller, depending on the type of subject. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques, and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm Spheres may be in the range of 0.5 um to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Microspheres for ocular delivery are described, for example, in U.S. Pat. Nos. 5,837,226; 5,731,005; 5,641,750; 7,354,574; and U.S. Pub. No. 2008-0131484, the entire contents of each of which are incorporated herein by reference.

For oral or enteral formulations for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. Nos. 4,704,295; 4,556,552; 4,309,404; and 4,309,406, the entire contents of each of which are incorporated herein by reference.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds, e.g., nucleic acid molecules, polynucleotides, polypeptides, proteins, or small molecules are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (RNA or DNA) is free of the genes or sequences that flank it in its naturally-occurring state. Similarly, a purified peptide or protein (e.g., identified by a specific amino acid sequence) is free of the amino acids that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. An individual described as a "subject," "patient," "individual," and the like does not necessarily have a given disease, but may be merely seeking medical advice. The terms "subject," "patient," "individual," and the like as used herein include all members of the animal kingdom that may suffer from the indicated disorder. In some aspects, the subject is a mammal, and in some aspects, the subject is a human.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. Treating also encompasses the prevention or amelioration of any symptom or symptoms of the disorder. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A the "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

In various embodiments, an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

A "control" sample or value refers to a sample that serves as a reference, usually a known reference, for comparison to a test sample. For example, a test sample can be taken from a test subject, e.g., a subject in need of diagnosis for a disease, and compared to samples from known conditions, e.g., a subject (or subjects) that does not have the disease (a negative or normal control), or a subject (or subjects) who does have the disease (positive control). A control can also represent an average value gathered from a number of tests or results. One of skill in the art will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are variable in controls, variation in test samples will not be considered as significant.

The term, "normal amount" with respect to a compound (e.g., a protein) refers to a normal amount of the protein in an individual known not to be diagnosed with a disease that comprises increased proliferation or migration of RPE cells in a subject who comprises a retinal hole or retinal tear. The amount of a protein can be measured in a test sample and compared to the "normal control" level, utilizing techniques such as reference limits, discrimination limits, or risk defining thresholds to define cutoff points and abnormal values (e.g., for a particular retinal detachment complication or a symptom thereof). The normal control level means the level of one or more proteins or combined protein indices typically found in a subject known not suffering from a disease that comprises increased proliferation or migration of RPE cells in a subject who comprises a retinal hole or retinal tear. Such normal control levels and cutoff points may vary based on whether a protein is used alone or in a formula combining with other proteins into an index. Alternatively, the normal control level can be a database of protein patterns from previously tested subjects who did not develop increased proliferation or migration of RPE cells (in a subject also comprising a retinal hole or retinal tear) or a particular symptom thereof (e.g., in the event the disease develops or a subject already having the disease is tested) over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease (or a symptom thereof) in question or is not at risk for the disease.

Relative to a control level, the level that is determined may an increased level. As used herein, the term "increased" with respect to level (e.g., protein level) refers to any % increase above a control level. In various embodiments, the increased level may be at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level.

Relative to a control level, the level that is determined may a decreased level. As used herein, the term "decreased" with respect to level (e.g., protein level) refers to any % decrease below a control level. In various embodiments, the decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

"Risk" in the context of the present disclosure, relates to the probability that an event will occur over a specific time period, as in the development of a neovascularization disorder or a symptom thereof, and can mean a subject's "absolute" risk or "relative" risk. In various embodiments, a "high risk" subject is a subject who is likely to develop a disease that comprises increased proliferation or migration of RPE cells in a subject who comprises a retinal hole or retinal tear or a symptom thereof within, e.g., about 1, 2, 3, 4, or 5 years. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used [odds are according to the formula p/(1−p) where p is the probability of event and (1−p) is the probability of no event] to no-conversion.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

EMT

Epithelial-mesenchymal transition (EMT) is characterized by a loss of cell adhesion, which leads to constriction and extrusion of new mesenchymal cells. EMT is a process by which epithelial cells lose their cell polarity and cell-cell adhesion, and gain migratory and invasive properties to become mesenchymal stem cells (which are multipotent stromal cells that can differentiate into a variety of cell types. EMT is essential for numerous developmental processes including mesoderm formation and neural tube formation. EMT has also been shown to occur in wound healing, in organ fibrosis and in the initiation of metastasis in cancer progression. EMT, and its reverse process, MET (mesenchymal-epithelial transition) are critical for development of many tissues and organs in the developing embryo, and numerous embryonic events such as gastrulation, neural crest formation, heart valve formation, palatogenesis and myogenesis. Epithelial cells are closely connected to each other by tight junctions, gap junctions and adherens junctions, have an apico-basal polarity, polarization of the actin cytoskeleton and are bound by a basal lamina at their basal surface. Mesenchymal cells, on the other hand, lack this polarization, have a spindle-shaped morphology and interact with each other only through focal points. Epithelial cells express high levels of E-cadherin, whereas mesenchymal cells express those of N-cadherin, fibronectin and vimentin. Thus, EMT entails profound morphological and phenotypic changes to a cell. Based on the biological context, EMT has been categorized into 3 types: developmental (Type I), fibrosis and wound healing (Type II), and cancer (Type III).

Loss of E-cadherin is a fundamental event in EMT. Many transcription factors (TFs) that can repress E-cadherin directly or indirectly are considered as EMT-TF (EMT inducing TFs). SNAI1/Snail 1, SNAI2/Snail 2 (also known as Slug or Zinc finger protein), Zinc finger E-box binding homeobox 1 and 2 (ZEB1 and ZEB2), transcription factor 3 (TCF3) and krueppel-like factor 8 (KLF8) can bind to the E-cadherin promoter and repress its transcription, whereas factors such as Twist (also referred to as class A basic helix-loop-helix protein 38; bHLHa38), Goosecoid, transcription factor 4 (TCF4), homeobox protein Sineoculis homeobox homolog 1 (SIX1) and fork-head box protein C2 (FOXC2) repress E-cadherin indirectly.

Several signaling pathways (transforming growth factor beta (TGF-β), fibroblast growth factor (FGF), epidermal growth factor (EGF), hepatocyte growth factor (HGF), Wnt/beta-catenin and Notch) and hypoxia may induce EMT. In particular, Ras-MAPK (mitogen-activated protein kinases) activates Snail and Slug. Slug triggers the steps of desmosomal disruption, cell spreading, and partial separation at cell-cell borders, which comprise the first and necessary phase of the EMT process.

Wnt signaling pathway regulates EMT in gastrulation, cardiac valve formation and cancer. Activation of Wnt pathway in breast cancer cells induces the EMT regulator SNAIL and upregulates the mesenchymal marker, vimentin. Also, active Wnt/beta-catenin pathway correlates with poor prognosis in breast cancer patients in the clinic. Similarly, TGF-β activates the expression of SNAIL and ZEB to regulate EMT in heart development, palatogenesis, and cancer. The breast cancer bone metastasis has activated TGF-β signaling, which contributes to the formation of these lesions. However, on the other hand, tumor protein 53 (p53), a well-known tumor suppressor, represses EMT by activating the expression of various microRNAs—miR-200 and miR-34 that inhibit the production of protein ZEB and SNAIL, and thus maintain the epithelial phenotype.

After the initial stage of embryogenesis, the implantation of the embryo and the initiation of placenta formation are associated with EMT. The trophoectoderm cells undergo EMT to facilitate the invasion of endometrium and appropriate placenta placement, thus enabling nutrient and gas exchange to the embryo. Later in embryogenesis, during gastrulation, EMT allows the cells to ingress in a specific area of the embryo—the primitive streak in amniotes, and the ventral furrow in *Drosophila*. The cells in this tissue express E-cadherin and apical-basal polarity.

During wound healing, keratinocytes at the border of the wound undergo EMT and undergo re-epithelialization or MET when the wound is closed. Snail2 expression at the migratory front influences this state, as its overexpression accelerates wound healing. Similarly, in each menstrual cycle, the ovarian surface epithelium undergoes EMT during post-ovulatory wound healing.

Initiation of metastasis requires invasion, which is enabled by EMT. Carcinoma cells in a primary tumor lose cell-cell adhesion mediated by E-cadherin repression and break through the basement membrane with increased invasive properties, and enter the bloodstream through intravasation. Later, when these circulating tumor cells (CTCs) exit the bloodstream to form micro-metastases, they undergo MET for clonal outgrowth at these metastatic sites. Thus, EMT and MET form the initiation and completion of the invasion-metastasis cascade. At this new metastatic site, the tumor may undergo other processes to optimize growth. For example, EMT has been associated with programmed death ligand 1 (PD-L1) expression, particularly in lung cancer. Increased levels of PD-L1 suppresses the immune system which allows the cancer to spread more easily.

EMT has been shown to be induced by androgen deprivation therapy in metastatic prostate cancer. Activation of EMT programs via inhibition of the androgen axis provides a mechanism by which tumor cells can adapt to promote disease recurrence and progression. Brachyury, Axl (tyrosine protein kinase receptor UFO), MEK, and Aurora kinase A are molecular drivers of these programs, and inhibitors are currently in clinical trials to determine therapeutic applications. Oncogenic protein kinase C iota type (PKC-iota) can promote melanoma cell invasion by activating Vimentin during EMT. PKC-iota inhibition or knockdown resulted an increase E-cadherin and ras homolog gene family, member A (RhoA) levels while decreasing total Vimentin, phophorylated Vimentin (S39) and partitioning defective 6 homolog alpha (Par6) in metastatic melanoma cells. Cells that undergo EMT gain stem cell-like properties, thus giving rise to Cancer Stem Cells (CSCs).

In addition to the treatment of PVR, the compositions and methods described herein can be used for the treatment and prevention of Epithelial-mesenchymal transition (EMT)-associated diseases. For example, EMT-associated diseases comprise pathological ocular fibrosis and pathological ocular proliferation. Additional diseases and conditions are described by Masoumpour, M. et al., in a journal article entitled, "Current and Future Techniques in Wound Healing Modulation after Glaucoma Filtering Surgeries" *The Open Ophthalmology Journal*, 2016 (10); 68-85, incorporated herein by reference in its entirety. Other exemplary EMT-associated diseases are described in an article by Friedlander, M., entitled, "Fibrosis and diseases of the eye" *The Journal of Clinical Investigation* 117(3); 576-586 (2007), incorporated herein by reference in its entirety. For example, the article describes diseases in the anterior segment of the eye (e.g., corneal opacification and glaucoma), dystrophies, herpetic keratitis, inflammation (e.g., pterygium), macula edema, retinal and vitreous hemorrhage, fibrovascular scarring, neovascular glaucoma, age-related macular degeneration (ARMD), diabetic retinopathy (DR), retinopathy of prematurity (ROP), subretinal fibrosis, epiretinal fibrosis, and gliosis.

Example 1: Expression of RUNX1 in Cells Derived from Human PVR Membranes (C-PVR)

Figure 5:
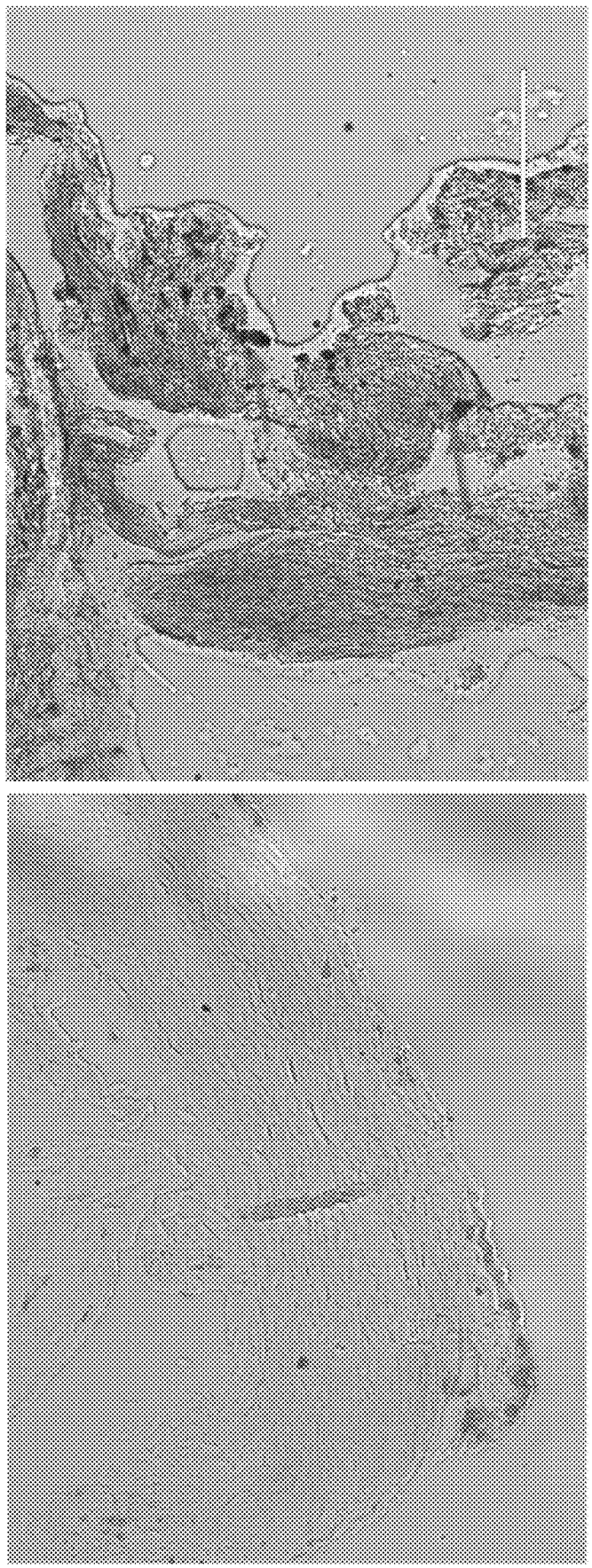
FIG. 5A is an image depicting the immunohistochemical staining of human PVR membranes of a control, counterstained with hematoxylin in membranes obtained from patients with PVR.

Immunofluorescence staining of RUNX1 in C-PVR cells showed expression of RUNX1 in C-PVR cells (FIG. 1) Immunofluorescence staining of RUNX1 in human PVR membranes (from patients with PVR) showed expression of RUNX1 (FIG. 3A-3D). Additionally, human PVR membrane from a patient (e.g., case 5) showed expression of RUNX1 (FIG. 3A-3D and FIG. 4A-4F). Additionally, immunohistochemistry of human PVR membranes showed RUNX1 expression (FIGS. 5A and 5B).

Methods

C-PVR cells were grown in a 48 well plate for 24-72 hours, fixed in 4% paraformaldehyde overnight at 4° C. and stained with rabbit anti-RUNX1 primary antibody (1:100; LifeSpan Biosciences). Cells were incubated with goat anti-rabbit 594 secondary antibody (1:300; Life Technologies) and DAPI for 2 hours, then washed and imaged.

Human PVR membrane tissue (e.g., case 5) was freshly obtained and was fixed in 10% formalin overnight and sectioned (6 µm). Serial sections were deparaffinized in 100% xylene, rehydrated in a series of ethanol steps and washed in PBS. Heat-induced epitope retrieval was performed in boiling citrate buffer (pH 6). The slides were blocked and incubated with primary antibody rabbit anti-RUNX1 (1:100; LifeSpan Biosciences) overnight at 4° C. followed by incubation with secondary goat anti-rabbit Alexa Fluor 594 (1:300 Life Technologies) and DAPI for two hours at room temperature. Slides were then washed and imaged (FIGS. 3A-3D and 4A-4F).

Immunohistochemistry

Human PVR membrane (e.g., case 5) freshly obtained was fixed in 10% formalin overnight and sectioned (6 µm). Serial sections were deparaffinized in 100% xylene, rehydrated in a series of ethanol steps and washed in PBS. Heat-induced epitope retrieval was performed in boiling citrate buffer (pH 6). The slides were blocked and incubated with primary antibody mouse anti-RUNX1 (1:100; Santa Cruz Biotechnologies) overnight at 4° C. The following day, sections were incubated in a biotinylated secondary antibody (1:300; Life Technologies) followed by tyramide amplification system and 3,3' Diaminobenzidine chromogen staining. Slides were then washed and imaged (FIGS. 5A and 5B).

Example 2: Inhibition of RUNX1 in Cells Derived from Human PVR Membrane

Figure 6:
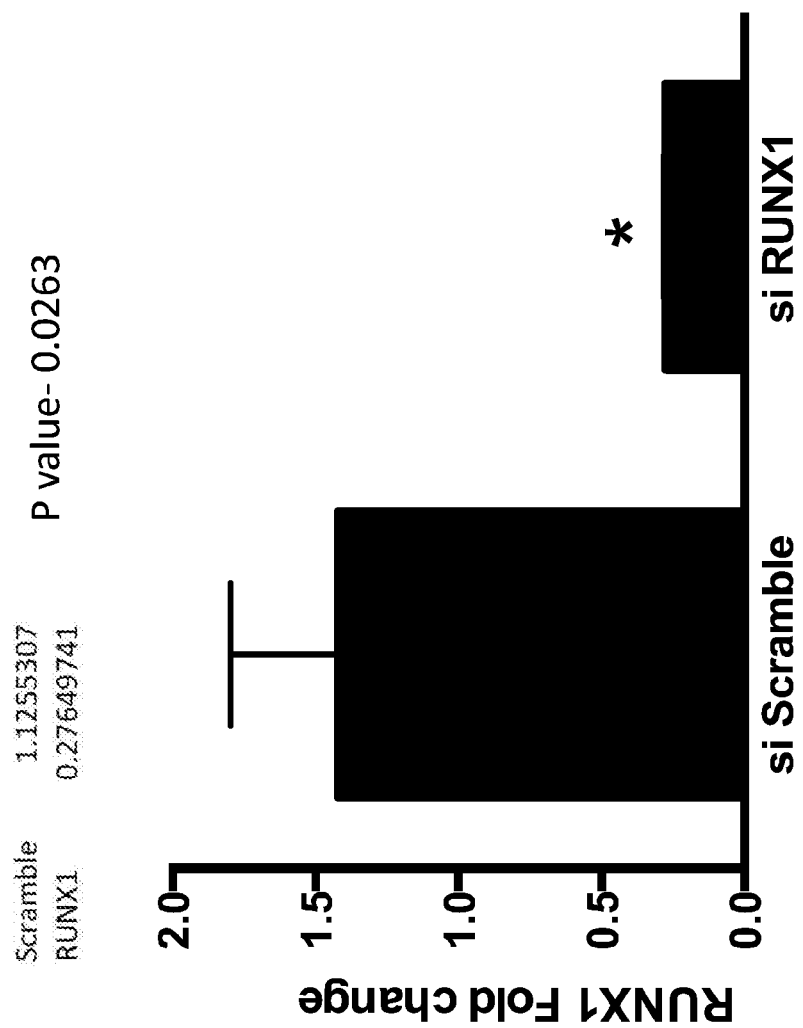
FIG. 6 is a bar graph depicting that siRNA effectively knocked down expression of RUNX1 in C-PVR cells. A significant reduction was observed in the gene expression of RUNX1 in C-PVR cells 48 hours after transfection with siRUNX1 compared to siScramble.
Figure 7:
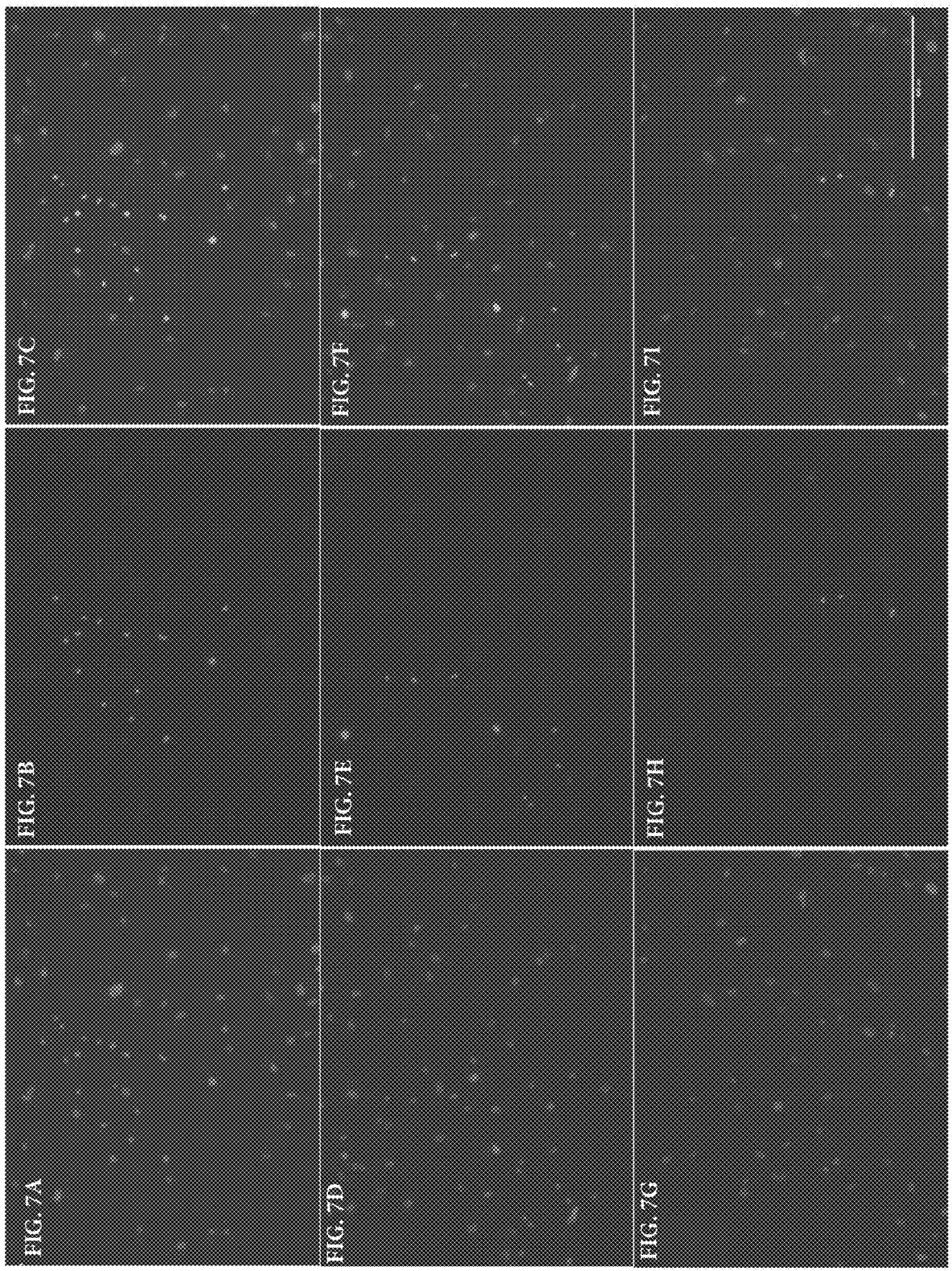
FIG. 7A is an image depicting DAPI staining of untreated controls.
FIG. 7B is an image depicting RUNX1 staining of untreated controls.
FIG. 7C is a merged image of FIGS. 7A and 7B.
FIG. 7D is an image depicting DAPI staining of siScramble.
FIG. 7E is an image depicting RUNX1 staining of siScramble.
FIG. 7F is a merged image of FIGS. 7E and 7F.
FIG. 7G is an image depicting DAPI staining of siRUNX1.
FIG. 7H is an image depicting RUNX1 staining of siRUNX1.
FIG. 7I is a merged image of FIGS. 7G and 7H. Ki67 staining 48 hours post siRNA knockdown of RUNX1 (FIG. 7G-7I) compared to scramble (FIG. 7D-7F) and untreated controls (FIG. 7A-7C) showed a significant reduction in cell number and proliferative capacity of C-PVR cells.
Figure 8:
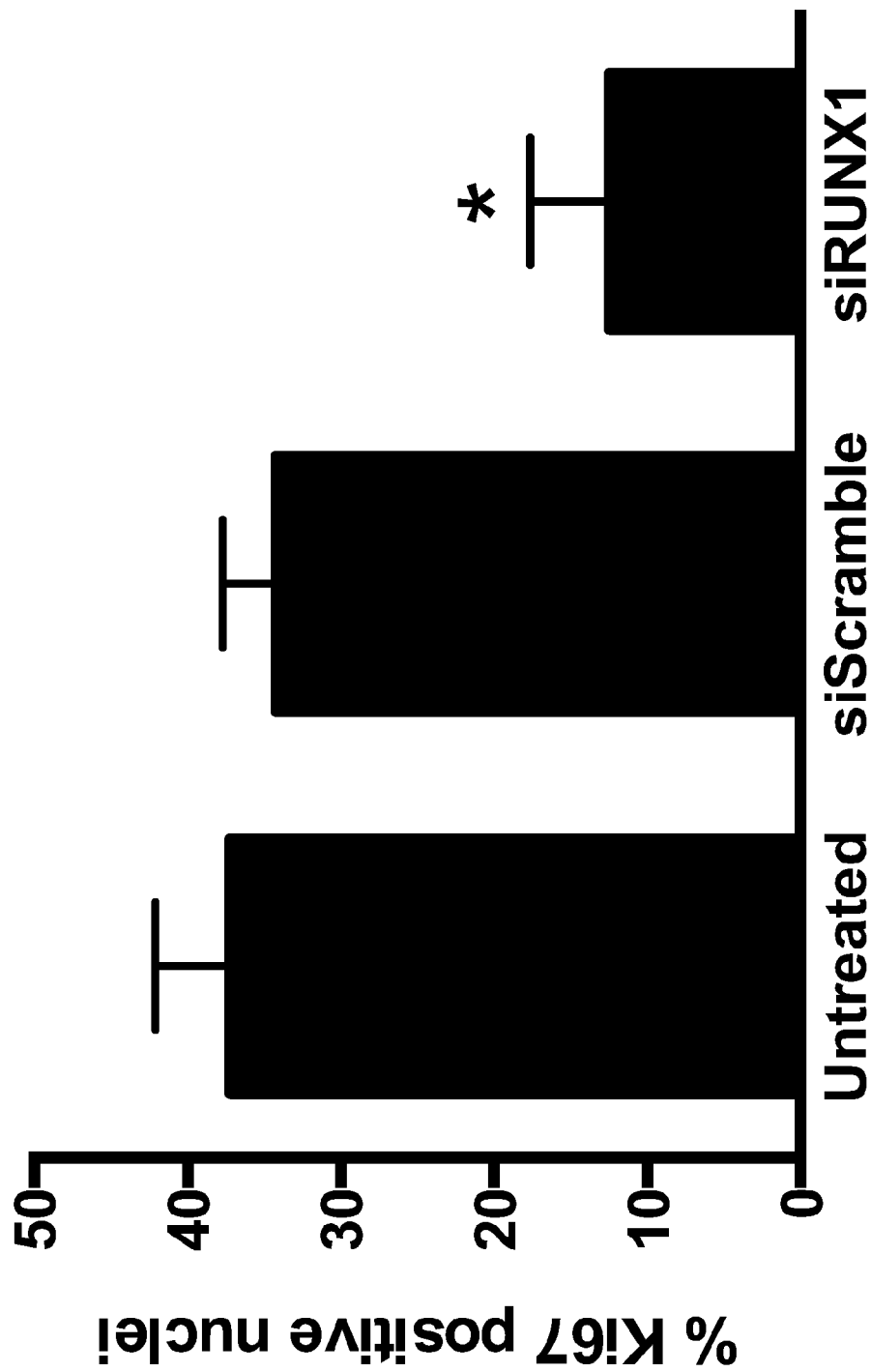
FIG. 8 is a bar graph depicting the quantification of proliferation from siRUNX1, siScramble and untreated cells. A significant reduction was observed in the number of Ki67 positive proliferating cells 48 hours after transfection with siRUNX1 compared to siScramble and untreated cells. The graph depicts quantification of images from FIG. 7A-7F.

Proliferation of cells derived from human PVR membrane (C-PVR) was inhibited by the RUNX1 inhibitor, Ro5-335 (FIG. 9A-9C). A significant reduction in the cell number and proliferative capacity of C-PVR cells was observed (FIG. 9A-9C). The RUNX1 inhibitor, Ro5-335 reduced the growth of human PVR membranes in an explant model (FIG. 18A-18D). Growth was observed from control explants (FIGS. 18A and 18C) as compared to the explants treated with RUNX1 inhibitor, Ro5-335 (FIGS. 18B and 18D), which showed now growth after four days.

siRNA knocked down RUNX1 expression in C-PVR cells (FIG. 6). A significant reduction in gene expression of RUNX1 in C-PVR was observed 48 hours after transfection with siRNUNX1 compared to siScramble. Ki67 staining 48 hours post siRNA knockdown of RUNX1 (FIG. 7G) compared to scramble (FIGS. 7D and 7F) and untreated controls (FIG. 7A-7C) showed a significant reduction in cell number and proliferative capacity of C-PVR cells.

siRNA

C-PVR cells (e.g., case 5) were grown in a 48 well plate for 24 hours and transfected with siRNUNX1 or siScramble using Darmafect (Dharmacon). 48 hours post-transfection, cells were washed and RNA was collected and PCR was performed (FIG. 6).

Ki67 Staining of siRNA

C-PVR (e.g., case 5) cells were transfected with the siRUNX1 or siScramble for 48 hours and washed and fixed with 4% paraformaldehyde for 10 minutes at room temperature. The cells were washed with PBS and blocked for an hour in (10% goat serum in PBS) incubated with rabbit anti-Ki67 antibody (1:50; Novus Biologicals) overnight at 4 degrees. Cells were incubated with secondary antibody goat anti-rabbit 594 (1:300; Life Technologies) for 2 hours along with DAPI, then were washed and imaged (FIG. 7A-7I; quantitation depicted in FIG. 8).

Treatment with RUNX1 Inhibitor

C-PVR cells (e.g., case 5) were cultured in 48 well plates for 24, followed by treatment with 150 μM RUNX1 inhibitor (Ro5-3335, Calbiochem), or vehicle only for a period of 48 hours. The cells were washed and fixed with 4% paraformaldehyde for 10 minutes at room temperature. The cells were washed with PBS and blocked for an hour in (10% goat serum in PBS) incubated with rabbit anti-Ki67 antibody (1:50; Novus Biologicals) overnight at 4 degrees. Cells were incubated with secondary antibody goat anti-rabbit 594 (1:300; Life Technologies) for 2 hours along with DAPI, washed, imaged and quantified using Image J (FIGS. 9A and 9B).

Ki67 Staining of Treatment with RUNX1 Inhibitor

C-PVR cells (e.g., case 5) were cultured in 48 well plates for 24, followed by treatment with 150 μM RUNX1 inhibitor (Ro5-3335, Calbiochem), or vehicle only for a period of 48 hours. The cells were washed and fixed with 4% paraformaldehyde for 10 minutes at room temperature. The cells were washed with PBS and blocked for an hour in (10% goat serum in PBS) incubated with rabbit anti-Ki67 antibody (1:50; Novus Biologicals) overnight at 4 degrees. Cells were incubated with secondary antibody goat anti-rabbit 594 (1:300; Life Technologies) for 2 hours along with DAPI, washed and imaged.

Example 3: Effect of TGFβ, TNFα and IL-6 on ARPE-19 Cells

Figures 11A, 11B:
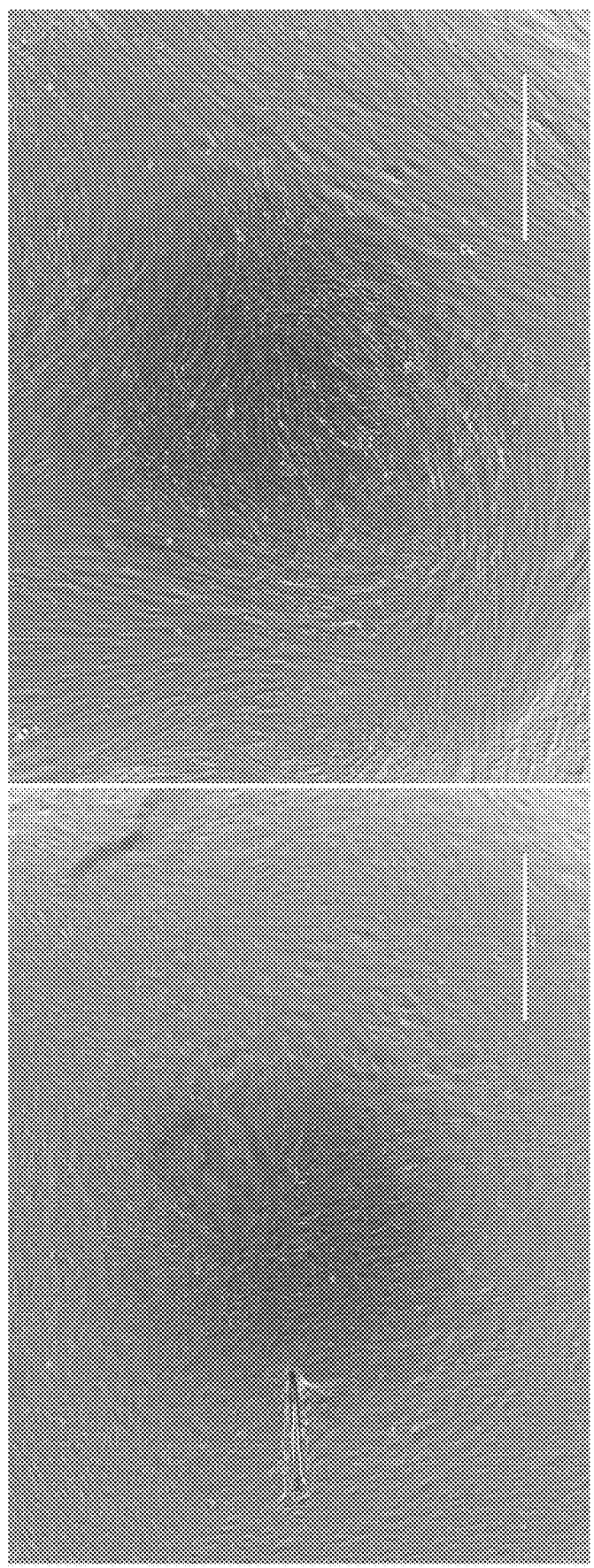
FIG. 11A is a bright-field image depicting ARPE-19 cells 7 days post-treatment of control cells.
FIG. 11B is a bright-field image depicting ARPE-19 cells 7 days post-treatment with TGFβ2, TNFα, and IL-6 (from Preprotec).

ARPE-19 cells at 7 days post treatment with TGFβ2, TNFα, and IL-6 (all from Preprotec) showed Epithelial-Mesenchymal transition (FIG. 11B) as compared to control (FIG. 11A). ARPE-19 cells underwent EMT with combination treatment (e.g., combination of TGFβ2, TNFα, and IL-16), FIG. 12.

Figure 13:
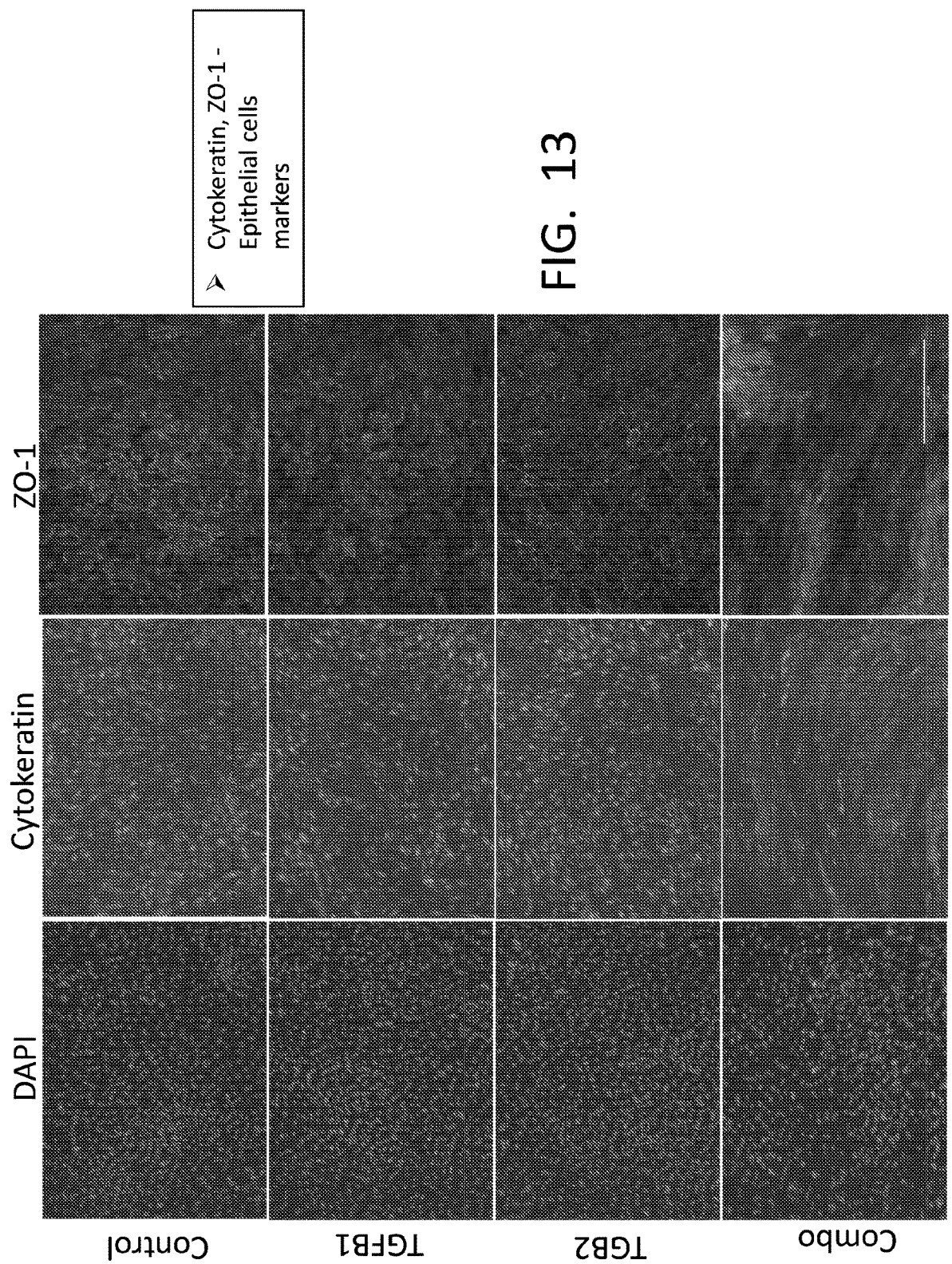
FIG. 13 are immunofluorescence staining images of mature ARPE-19 cells 7 days post treatment with TGFβ1, TGFβ2, and combination of TGFβ2, TNFα and IL-6 (10 ng/ml). A reduction in the epithelial markers, cytokeratin (middle panel) and Zonula occludens-1 (ZO-1) (right panel) in the treatments was observed as compared to controls. Losing ZO-1 organization is a marker of EMT. Therefore data showed that combination treatment also impacted ZO-1 distribution.

ARPE-19 cells 7 days post treatment with TGFβ1, TGFβ2, and combination of TGFβ2, TNFα and IL-6 (10 ng/ml each) showed a reduction in the epithelial markers, cytokeratin (FIG. 13, middle panel) and Zonula occludens-1 (ZO-1) (FIG. 13, right panel) in the treatments compared to controls. Losing ZO-1 organization is a marker of EMT, and therefore the data showed that the combination treatment also impacted ZO-1 distribution (FIG. 13). Additionally, ARPE-19 cells 7 days post treatment with TGFβ1, TGFβ2, and combination of TGFβ2, TNFα and IL-6 (10 ng/ml) showed a reduction in the epithelial markers Zonula occludens-1 in the treatments compared to controls (FIG. 14A-14D).

RUNX1 Expression Increases with EMT

ARPE-19 cells 7 days post treatment with TGFβ1, TGFβ2, and combination of TGFβ2, TNFα and IL-6 (10 ng/ml each) showed a significant increase in the RUNX1 expression in the treatments compared to controls (FIG. 15). This indicated that RUNX1 expression increased with EMT. ARPE-19 cells 7 days post treatment with a combination of TGFβ2, TNFα and IL-6 (10 ng/ml) showed a significant increase in the RUNX1 expression in the treatments compared to controls (FIG. 16, which depicts magnified data from FIG. 13).

ARPE-19 cells 7 days post treatment with a combination of TGFβ2, TNFα and IL-6 (10 ng/ml each) showed a significant increase in the RUNX1 expression (FIG. 17, middle panel) and a reduction in the epithelial marker cytokeratin (FIG. 17, right panel) in the treatments compared to controls. This showed that RUNX1 increased expression and was also present at the 3-week time point when ZO-1 changes of distribution were present.

Cell Culture

ARPE-19 cells (ATCC) were grown to confluence and maintained in 1% for 7-10 days. Cells were treated with a combination of TGFβ2, TNFα and IL-6 (each at 10 ng/ml) for 7 days and images were taken.

Immunofluorescence

Figure 12:
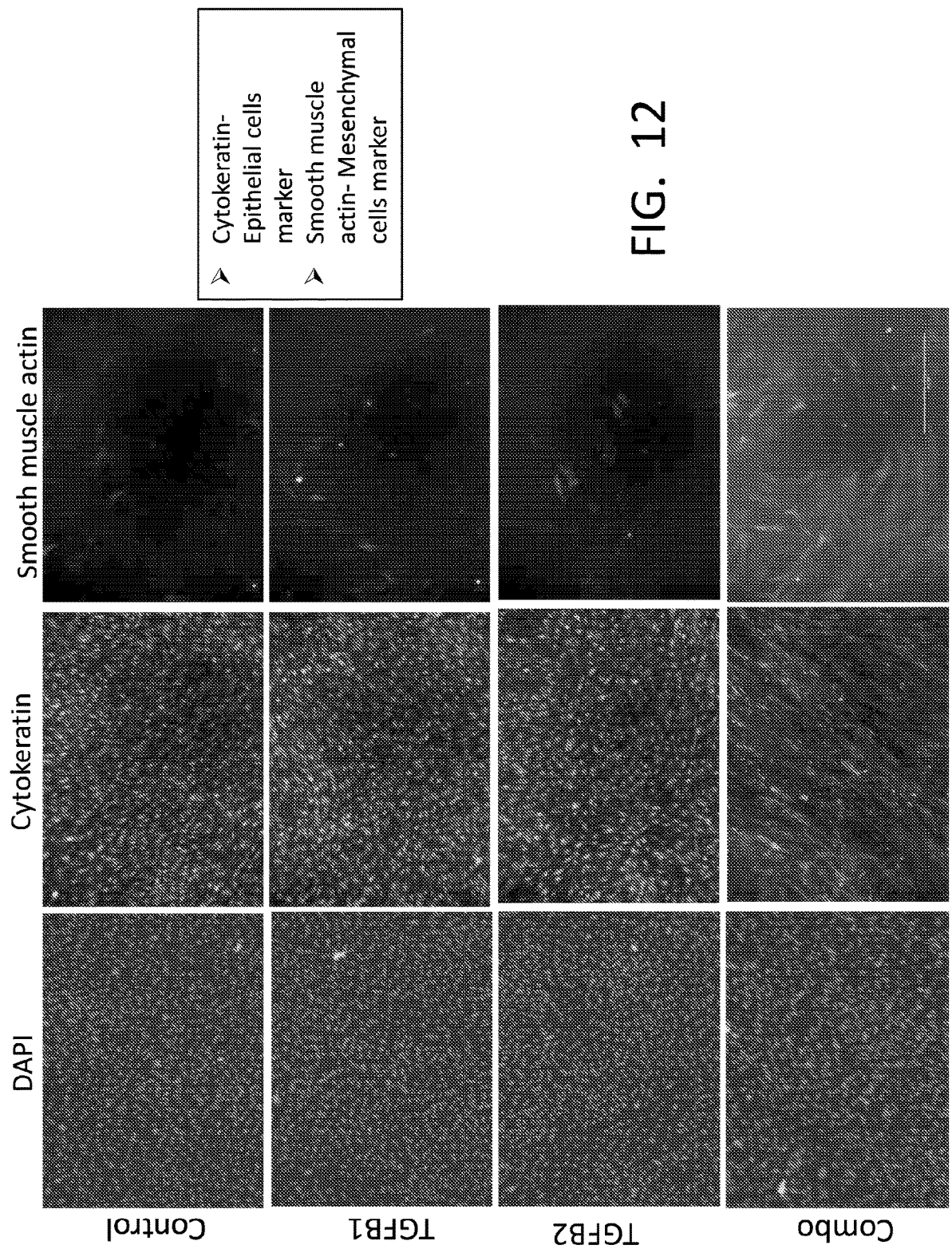
FIG. 12 are immunofluorescence staining images of ARPE-19 cells 7 days post treatment with TGFβ1, TGFβ2, and combination of TGFβ2, TNFα and IL-6 (10 ng/ml each). A reduction in the epithelial marker (cytokeratin—middle panel) was observed, and increase in the mesenchymal marker (smooth muscle actin—right panel) in the treatments was compared as compared to controls. This showed that ARPE-19 cells underwent EMT with combination treatment.

ARPE-19 cells were grown to confluence and maintained in 1% for 7-10 days. Cells were treated with TGβ1, TGFβ2, and a combination of TGFβ2, TNFα and IL-6 (10 ng/ml) for 7 days (combo). Cells were washed and fixed with 4% paraformaldehyde for 10 minutes at room temperature. Cells were incubated with primary antibodies, mouse anti-cytokeratin (1:250; Abcam) or smooth muscle actin (1:50; DAKO) overnight at 4° C. The following day, cells were incubated with secondary antibody goat anti-mouse 488 (1:300; Life Technologies) for 2 hours at room temperature and DAPI. Cells were washed with PBS and imaged (FIG. 12).

ARPE-19 cells were grown to confluence and maintained in 1% for 3 weeks. Cells were treated with TGβ1, TGFβ2, and a combination of TGFβ2, TNFα and IL-6 (10 ng/ml) for 7 days. Cells were washed and fixed with 4% paraformaldehyde for 10 minutes at room temperature. Cells were incubated with primary antibodies, mouse anti-cytokeratin (1:250; Abcam) or rabbit anti ZO1 (1:250; Life Technologies) overnight at 4° C. The following day, cells were incubated with secondary antibody goat anti-mouse 488 and goat anti-rabbit 594 (1:300; Life Technologies) for 2 hours at room temperature and DAPI. Cells were washed with PBS and imaged.

ARPE-19 cells were grown to confluence and maintained in 1% for 3 weeks. Cells were treated with TGβ1, TGFβ2, and a combination of TGFβ2, TNFα and IL-6 (10 ng/ml) for 7 days. Cells were washed and fixed with 4% paraformaldehyde for 10 minutes at room temperature. Cells were incubated with primary antibody rabbit anti ZO1 (1:250; Life Technologies) overnight at 4° C. The following day, cells were incubated with secondary antibody goat anti-rabbit 594 (1:300; Life Technologies) for 2 hours at room temperature and DAPI. Cells were washed with PBS and imaged (FIG. 14A-14D).

ARPE-19 cells were grown to confluence and maintained in 1% for 7-10 days. Cells were treated with TGβ1, TGFβ2, and a combination of TGFβ2, TNFα and IL-6 (10 ng/ml) for 7 days. Cells were washed and fixed with 4% paraformaldehyde for 10 minutes at room temperature. Cells were incubated with primary antibody rabbit anti-RUNX1 (1:100; LifeSpan Biosciences) overnight at 4° C. The following day, cells were incubated with secondary antibody goat anti-mouse 594 (1:300; Life Technologies) for 2 hours at room temperature and DAPI. Cells were washed with PBS and imaged (FIG. 15).

Figure 16:
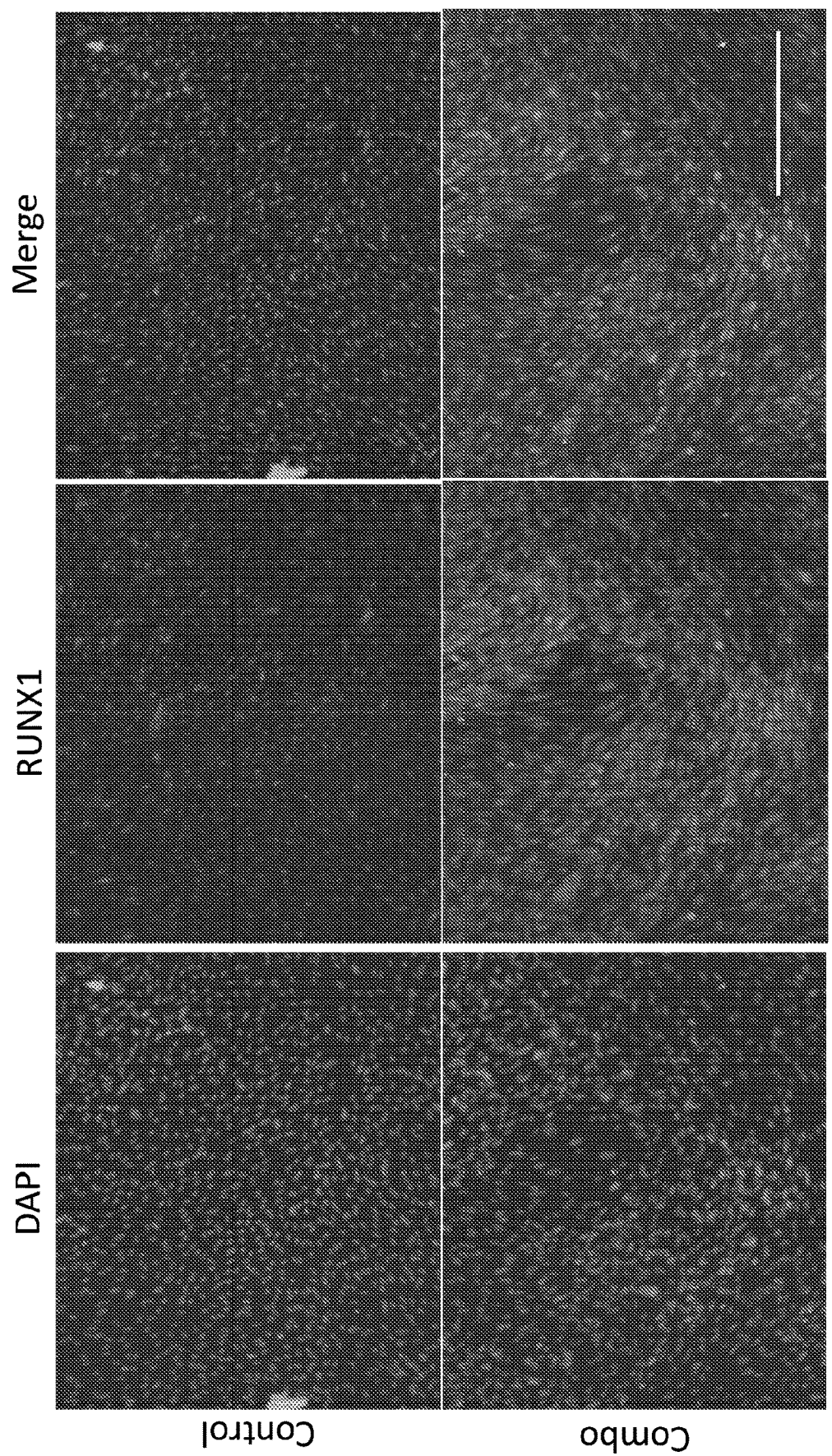
FIG. 16 are immunofluorescence staining of ARPE-19 cells 7 days post treatment with a combination of TGFβ2, TNFα and IL-6 (10 ng/ml each). A significant increase in the RUNX1 expression in the treatments compared to controls was observed.

ARPE-19 cells were grown to confluence and maintained in 1% for 7-10 days. Cells were treated with TGβ1, TGFβ2, and a combination of TGFβ2, TNFα and IL-6 (10 ng/ml) for 7 days. Cells were washed and fixed with 4% paraformaldehyde for 10 minutes at room temperature. Cells were incubated with primary antibody rabbit anti-RUNX1 (1:100; LifeSpan Biosciences) overnight at 4° C. The following day, cells were incubated with secondary antibody goat anti-rabbit 594 (1:300; Life Technologies) for 2 hours at room temperature and DAPI. Cells were washed with PBS and imaged (FIG. 16).

Figure 17:
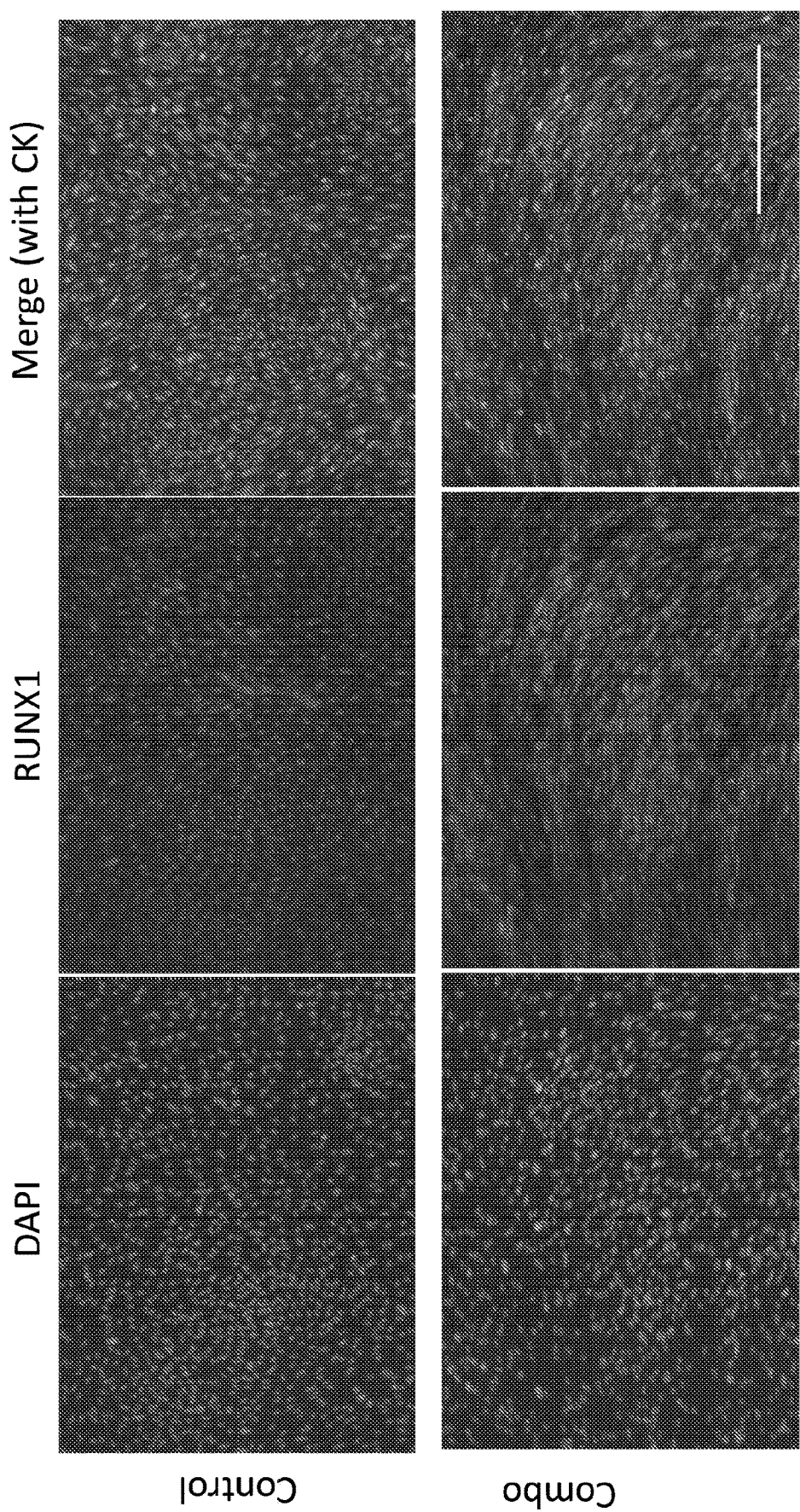
FIG. 17 are immunofluorescence staining images of ARPE-19 cells 7 days post treatment with a combination of TGFβ2, TNFα and IL-6 (10 ng/ml each). A significant increase in the RUNX1 expression (middle panel) and a reduction in the epithelial marker cytokeratin (merge—right panel) in the treatments was observed compared to controls. This showed that RUNX1 increased expression was also present at the 3-week time point when ZO-1 changes of distribution were present.
Figure 18A:
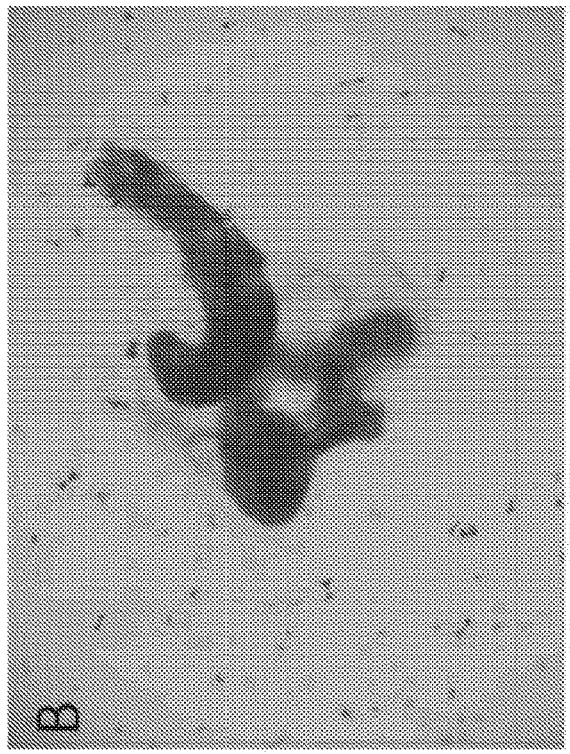
FIG. 18A is an image depicting a primary explant culture treated with a control (4× magnification).
Figure 18B:
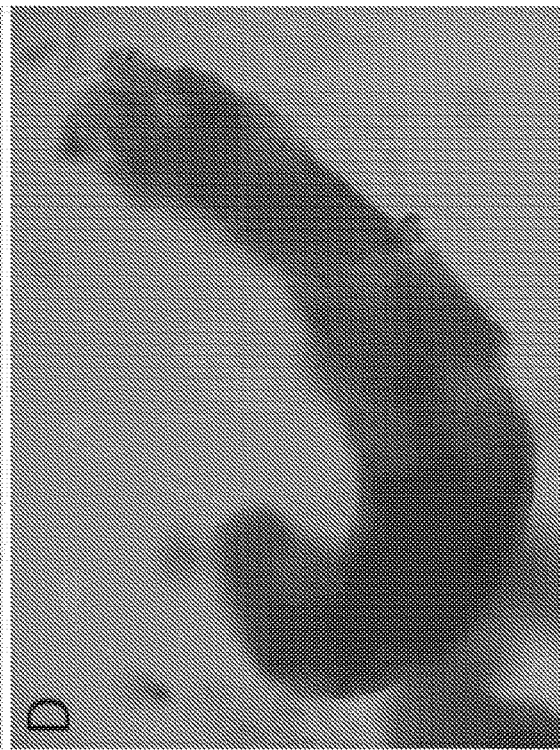
FIG. 18B is an image depicting a primary explant culture treated with RUNX1 inhibitor, Ro5-3335 at 150 µM (4× magnification).
Figure 18C:
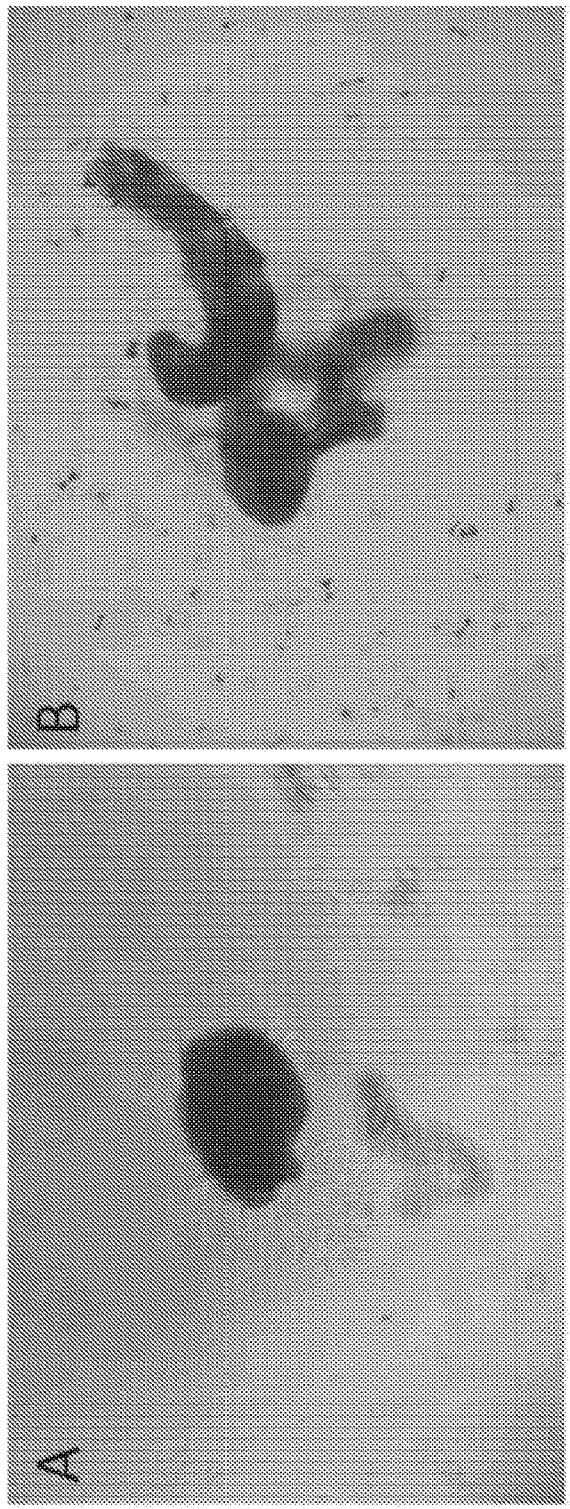
FIG. 18C is an image depicting a primary explant culture treated with a control (10× magnification).
Figure 18D:
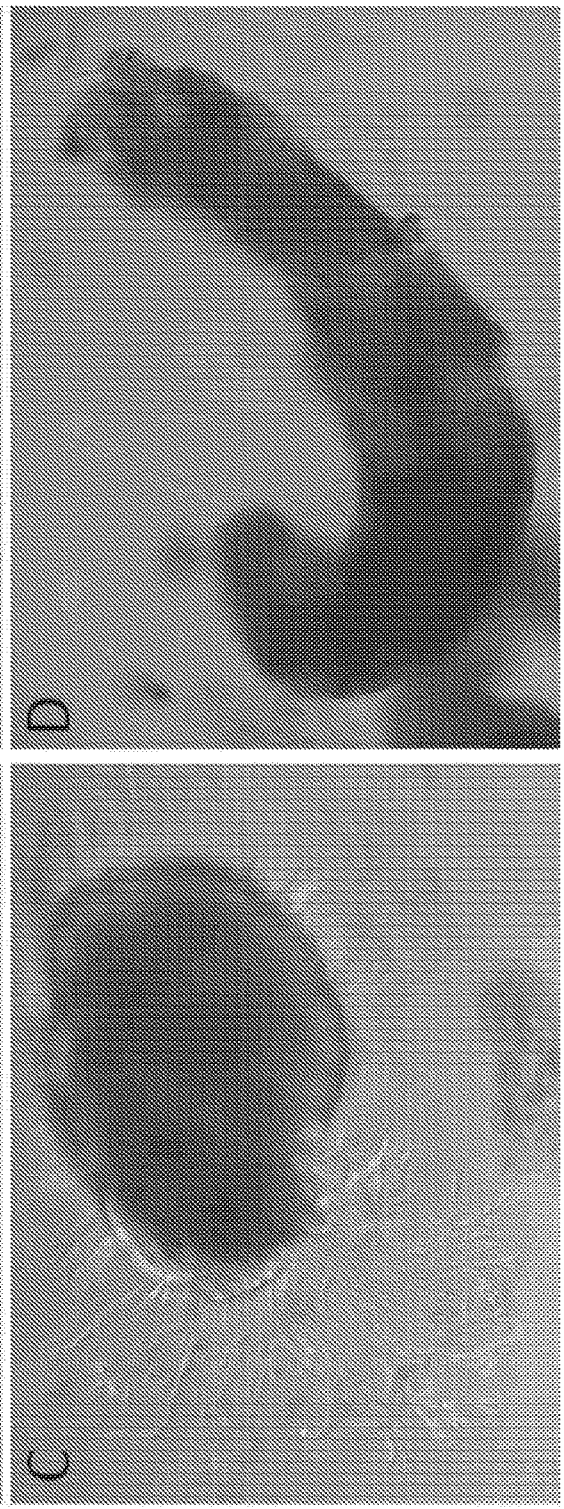
FIG. 18D is an image depicting a primary explant culture treated with RUNX1 inhibitor, Ro5-3335 (10× magnification). Growth was observed from control explants compared to the explants treated with RUNX1 inhibitor, which showed no growth after 4 days.

ARPE-19 cells were grown to confluence and maintained in 1% for 7-10 days. Cells were treated with a combination of TGFβ2, TNFα and IL-6 (10 ng/ml) for 7 days. Cells were washed and fixed with 4% paraformaldehyde for 10 minutes at room temperature. Cells were incubated with primary antibodies rabbit anti-RUNX1 (1:100; LifeSpan Biosciences) and mouse anti-cytokeratin (1:250; Abcam) overnight at 4° C. The following day, cells were incubated with secondary antibodies goat anti-mouse 488 and goat anti-rabbit 594 (1:300; Life Technologies) for 2 hours at room temperature and DAPI. Cells were washed with PBS and imaged (FIG. 17).

Example 4: RUNX1 Expression and Effect of RUNX1 Inhibitor

RUNX1 Expression is Common in Membranes from Different Donors with PVR

Figures 19A, 19B:
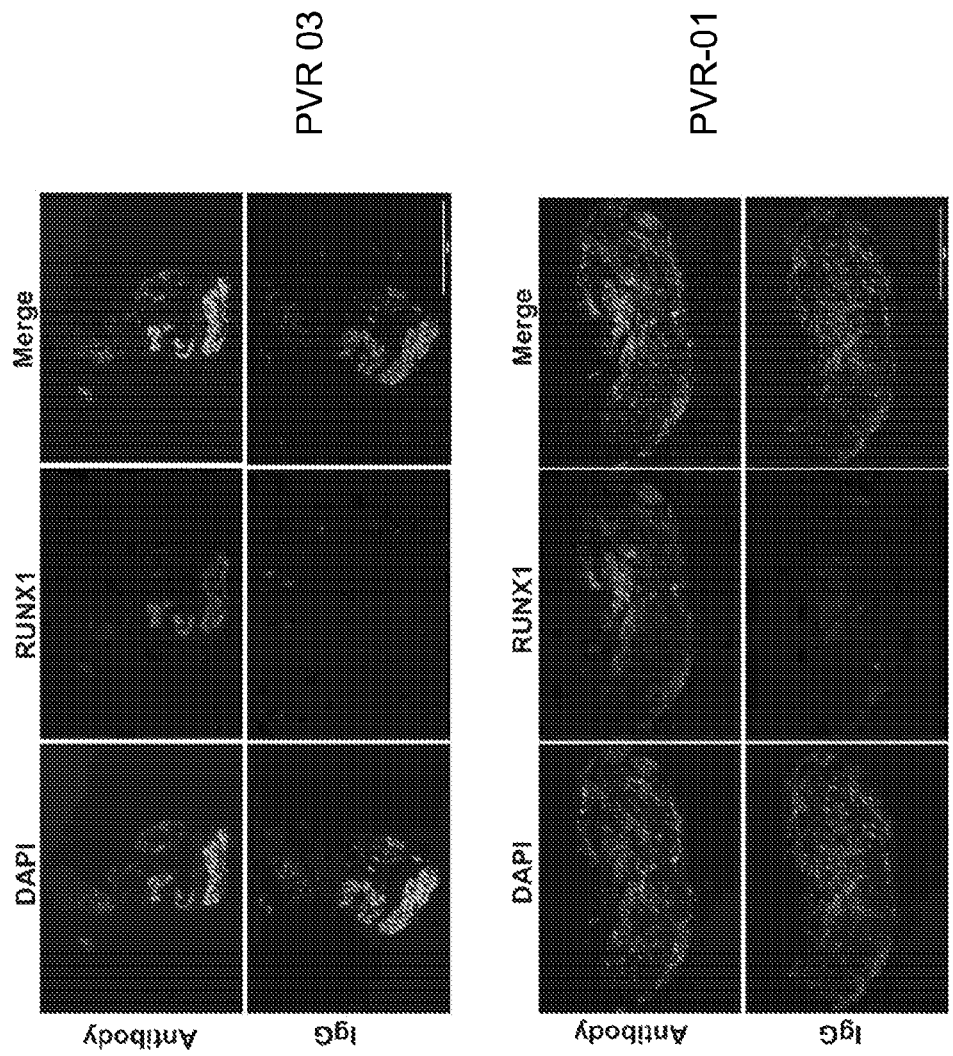
FIG. 19A are immunofluorescence staining images of RUNX1 and counterstained with DAPI in membranes obtained from patients with PVR (Case 1 "PVR 01" and Case 3 "PVR 03"). These images showed that RUNX1 expression was a common feature in membranes from different donors with PVR. Scale bars—400 microns.
FIG. 19B are immunofluorescence staining images of RUNX1 and counterstained with DAPI in membranes obtained from patients with PVR (Case 1 and Case 3). These images showed that RUNX1 expression was a common feature in membranes from different donors with PVR. Scale bars—400 microns.

RUNX1 expression was a common feature in membranes from different donors with PVR (FIGS. 19A and 19B). Freshly obtained donor human PVR membrane (Case 1 "PVR 01" and 3 "PVR 03") were fixed in 10% formalin overnight and sectioned (6 μm). Serial sections were deparaffinized in 100% xylene, rehydrated in a series of ethanol steps and washed in phosphate buffered saline (PBS). Heat-induced epitope retrieval was performed in boiling citrate buffer (pH 6). The slides were blocked and incubated with primary antibody rabbit anti-RUNX1 (1:100; LifeSpan Biosciences) overnight at 4° C., followed by incubation with secondary goat anti rabbit Alexa Fluor 594 (1:300 Life Technologies) and DAPI. The slides were then washed and imaged. These data indicate common RUNX1 expression (e.g., level of RUNX1) among different donors with PVR.

The Proliferation Marker, Ki67, has a Similar Pattern for RUNX1

Figures 20A, 20B:
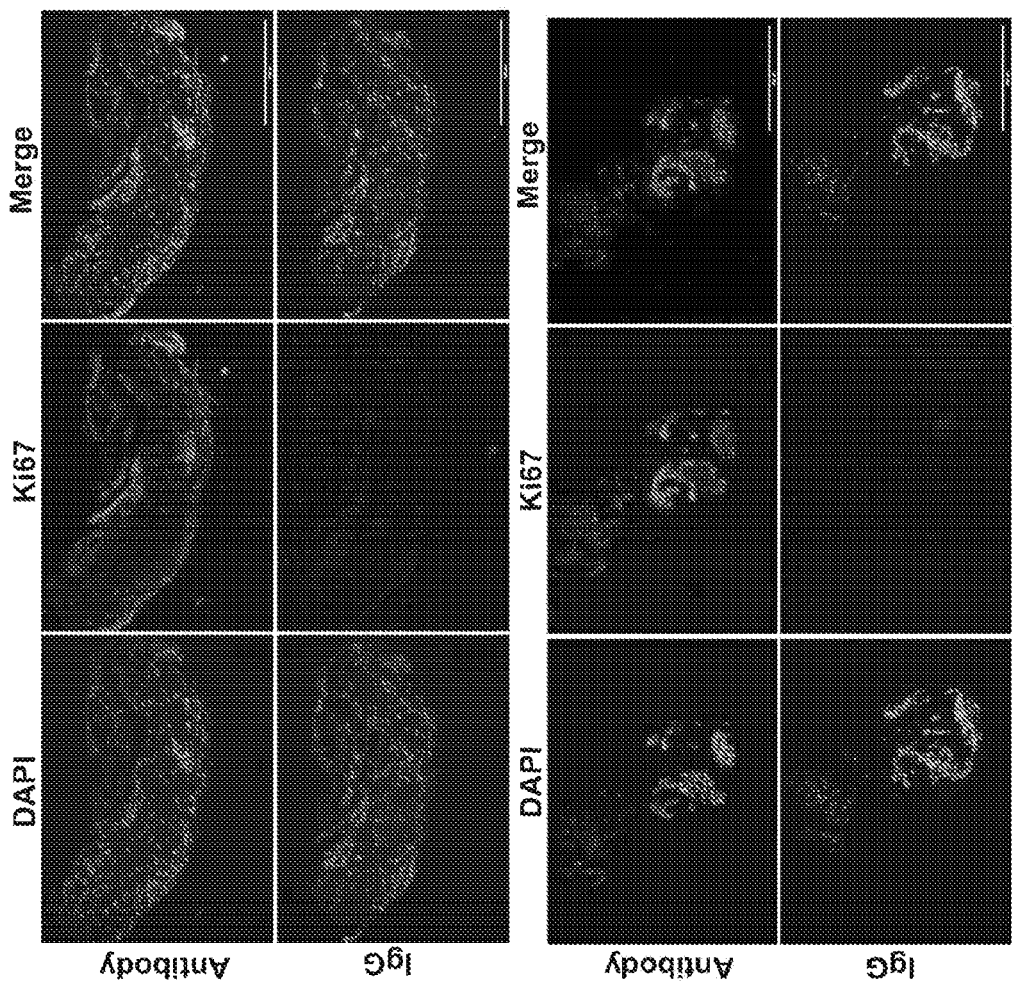
FIG. 20A are immunofluorescence staining images of Ki67 (also known ask antigen Ki-67 or Ki-67 or MKI67) (bottom, middle, FIG. 20B), RUNX1 (top, middle, FIG. 20A) and counterstained with DAPI in contiguous sections of membranes obtained from patients with PVR. These images showed that the population of cells expressing RUNX1 within PVR membranes actively proliferated, as demonstrated by their expression of Ki67. Scale bars-400 microns.
FIG. 20B are immunofluorescence staining images of Ki67 (bottom, middle, FIG. 20B), RUNX1 (top, middle, FIG. 20A) and counterstained with DAPI in contiguous sections of membranes obtained from patients with PVR. These images showed that the population of cells expressing RUNX1 within PVR membranes actively proliferated, as demonstrated by their expression of Ki67. Scale bars—400 microns.

The population of cells expressing RUNX1 within PVR membranes actively proliferated, as demonstrated by their expression of Ki67 (FIGS. 20A and 20B). Freshly obtained donor human PVR membrane was fixed in 10% formalin overnight and sectioned (6 μm). Serial sections were deparaffinized in 100% xylene, rehydrated in a series of ethanol steps and washed in PBS. Heat-induced epitope retrieval was performed in boiling citrate buffer (pH 6). The slides were blocked and incubated with primary antibody rabbit anti-Ki67 (1:100; Novus Biologicals) overnight at 4° C. followed by incubation with secondary goat anti rabbit Alexa Fluor 594 (1:300 Life Technologies) and DAPI. Slides were washed and imaged. For RUNX1, the slides were blocked and incubated with primary antibody rabbit anti-RUNX1 (1:100; LifeSpan Biosciences) overnight at 4° C. followed by incubation with secondary goat anti rabbit Alexa Fluor 594 (1:300 Life Technologies) and DAPI. Slides were washed and imaged. These data demonstrate that cells expressing RUNX1 within the PVR membrane were actively proliferating. This was demonstrated by the expression of Ki67.

RUNX1 Protein Expression Levels are Increased in Growth Factor-Induced EMT

RUNX1 protein expression levels were increased in growth factor induced EMT (FIGS. 21A and 21B). Increased levels of RUNX1 protein was observed upon treatment with growth factors TGFβ2, TNFα and combination treatment, including TGFβ2, TNFα and IL-6 at 3 and 7 days post treatment. Increase in RUNX1 and RUNX2 RNA expression was also observed upon treatment with growth factors at 3 and 7 days post treatment. ARPE-19 cells were seeded into 6-well pates at a density of 100,000 cells in complete media. At confluence cells were treated with growth factors TGFβ2, TNFα and a combination treatment of TGFβ2, TNFα and IL-6. Cells were washed with ice-cold PBS, lysed and collected at 3 and 7 day time points, and immunoblotted for RUNX1 (1:200, SantaCruz Biotechnology, Dallas, Tex.) and β-Actin (1:1000, Cell Signaling Technology, Danvers, Mass.) as a loading control. ARPE-19 cells were also seeded into 6-well pates at a density of 100,000 cells, in complete media. At confluence, cells were treated with growth factors TGFβ2, TNFα and a combination treatment of TGFβ2, TNFα and IL-6. Cells were washed with PBS, lysed and collected. Quantitative RT-PCR of mRNA expression was performed and values were reported as relative fold change in expression level. These data indicate that an increase in RUNX1 protein level, and RUNX1 RNA was observed with growth factor treatment.

RUNX1 Inhibition Resulted in Inhibition of EMT

Figure 22:
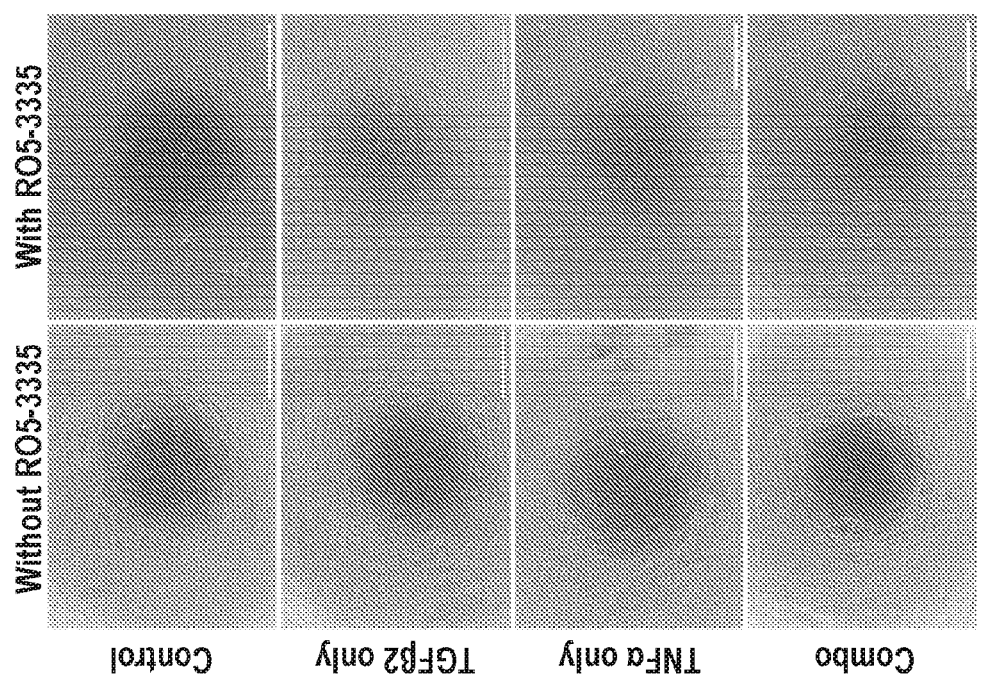
FIG. 22 are bright field images depicting ARPE-19 cells 3 days post treatment with TGFβ2, TNFα, and a combination of TGFβ2, TNFα and IL-6 with RUNX1 inhibitor (Ro5-3335). 150 µM of Ro5-3335 showed either no or reduced EMT (right panels), compared to vehicle treatment (left panels). EMT was determined by morphological changes including cell shape. This data demonstrated that RUNX1 inhibition using Ro5-3335 resulted in inhibition of EMT. Scale bars—400 microns.

RUNX1 inhibition, using Ro5-3335, resulted in inhibition of EMT. ARPE-19 cells were grown to confluence and maintained in 1% serum for 7-10 days (FIG. 22). Cells were treated with growth factors TGFβ2, TNFα and IL-6 (10 ng/ml each) for 3 days, with 150 μM RUNX1 inhibitor (Ro5-3335, Calbiochem) or without (e.g., vehicle). The results demonstrated no (or reduced) EMT compared to vehicle treated cells. EMT was determined by morphological changes including cell shape.

Figure 23A:
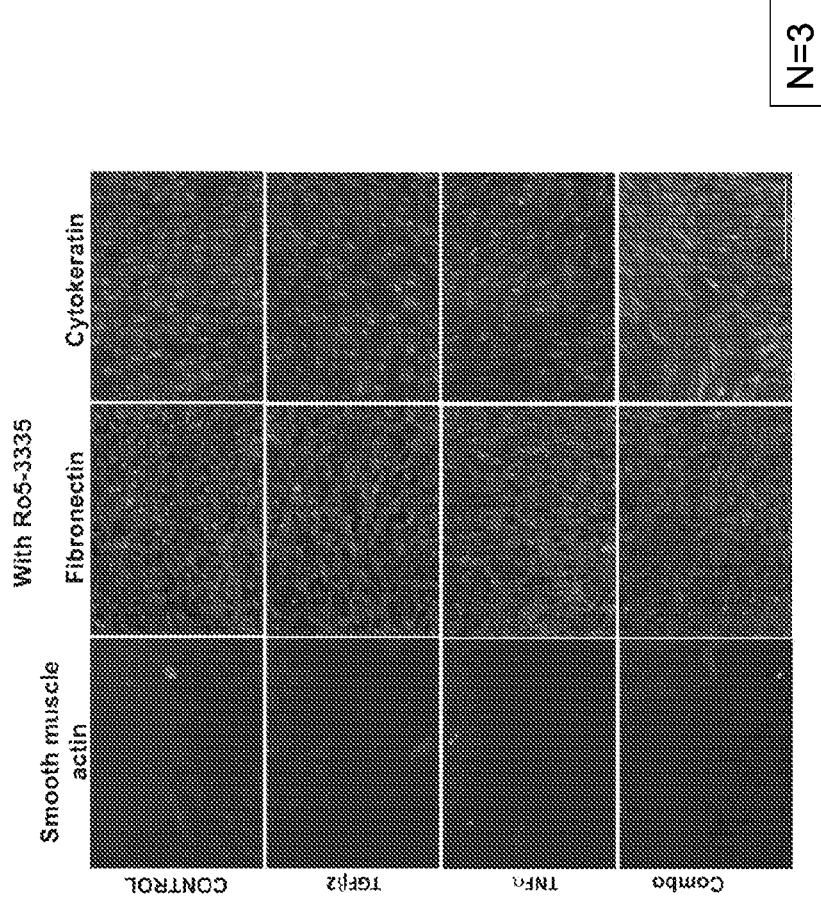
FIG. 23A are immunofluorescence staining images of ARPE-19 cells 3 days post treatment with TGFβ2, TNFα, and combination of TGFβ2, TNFα and IL-6 (10 ng/mL each). Also shown is treatment without a RUNX1 small molecule inhibitor (Ro5-3335), assessed as a reduction in the epithelial marker (cytokeratin—right panel) and an increase in the mesenchymal markers such as fibronectin (middle panel) and smooth muscle actin (left panel). Scale bars—200 microns.
Figure 23B:
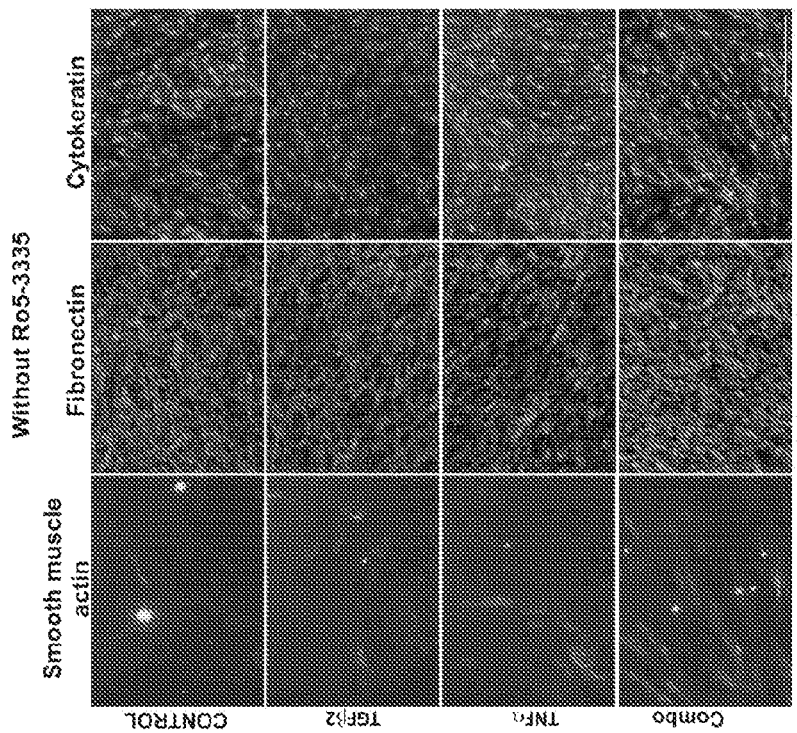
FIG. 23B are immunofluorescence staining images of ARPE-19 cells 3 days post treatment with TGFβ2, TNFα, and combination of TGFβ2, TNFα and IL-6 (10 ng/mL each). The data showed that treatment with a RUNX1 small molecule inhibitor (Ro5-3335) prevented EMT, which was assessed as a reduction in the epithelial marker (cytokeratin—right panel) and an increase in the mesenchymal markers such as fibronectin (middle panel) and smooth muscle actin (left panel). Scale bars—200 microns.

Furthermore, treatment with RUNX1 small molecule inhibitor, Ro5-335, in ARPE-19 cells prevented EMT. This was assessed by the reduction in the epithelial marker, cytokeratin, and an increase in the mesenchymal markers such as fibronectin, and smooth muscle actin (FIGS. 23A and 23B). ARPE-19 cells were grown to confluence and maintained in 1% for 7-10 days. Cells were treated with TGFβ2, TNFα, and a combination of TGFβ2, TNFα and IL-6 (10 ng/ml each) for 3 days with or without 150 uM RUNX1 inhibitor (Ro5-3335, Calbiochem) or vehicle. Cells were washed and fixed with 4% paraformaldehyde for 10 minutes at room temperature. Cells were incubated with primary antibodies, mouse anti-cytokeratin (1:250; Abcam), or rabbit anti-fibronectin (1:500, Sigma) or smooth muscle actin (1:50; DAKO) overnight at 4° C. The following day, cells were incubated with secondary antibody goat anti-mouse 488 or goat anti-rabbit 594 (1:300; Life Technologies) respectively for 2 hours at room temperature and DAPI. Cells were washed with PBS and imaged. These data showed that inhibition of RUNX1 (e.g., with a small molecule), prevented EMT.

Growth Factors Induced EMT in C-PVR Cells Derived from Human Proliferative Vitreoretinopathy Membranes Growth factors, e.g., TNFα, TGFβ2 and IL-6 induced EMT in C-PVR cells derived from human proliferative vitreoretinopathy membranes (FIG. 24). EMT was assessed by morphological changes including cell shape, such as elongated, fibroblast-like shaped cells in the combination treatment (e.g., TNFα, TGFβ2 and IL-6). C-PVR cells were grown to confluence. Cells were treated with a combination of TGFβ2, TNFα and a combination of TGFβ2, TNFα and IL-6 (10 ng/ml each) for 7 days. These data demonstrate that growth factors induced EMT in C-PVR cells.

Figure 25:
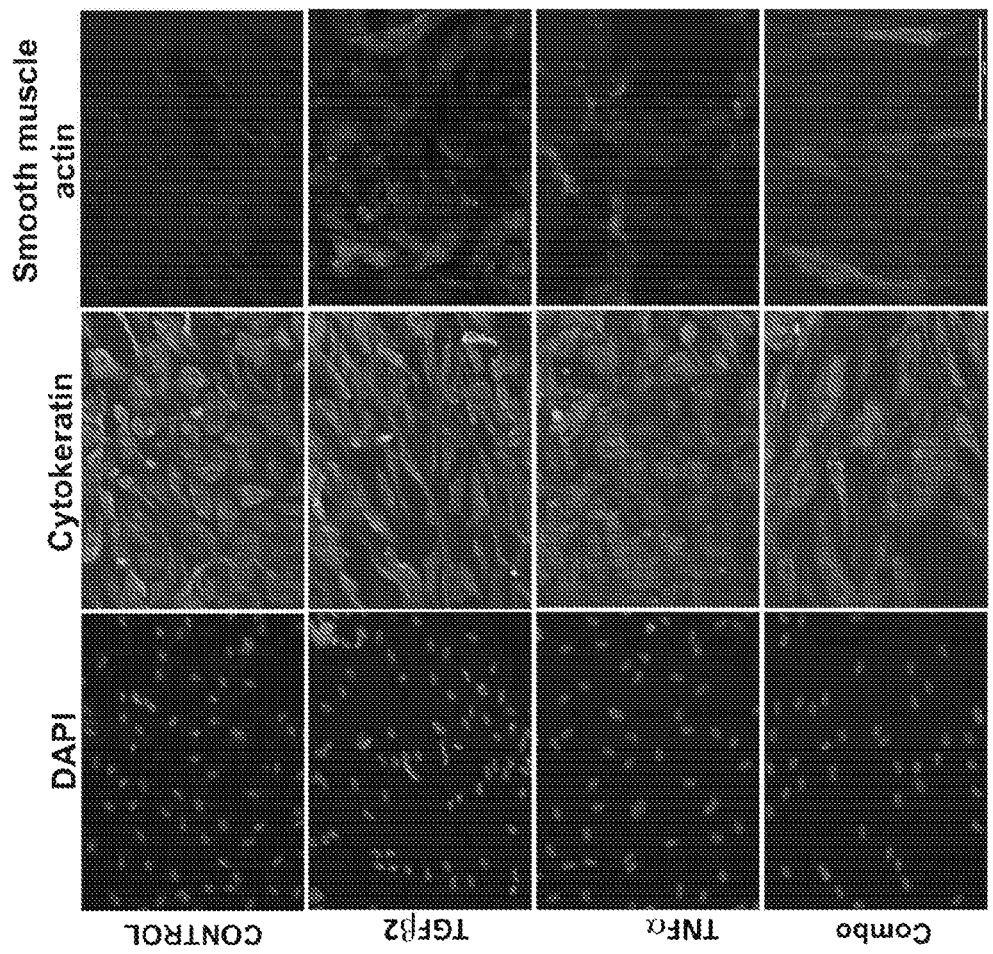
FIG. 25 are immunofluorescence staining images of C-PVR cells 7 days post treatment with TGFβ2, TNFα and a combination of TGFβ2, TNFα and IL-6 (10 ng/ml each), which showed a reduction in the epithelial marker (cytokeratin—middle panel) and increase in the mesenchymal marker (smooth muscle actin—right panel) in the treatments compared to controls (top row). This experiment demonstrated that these growth factors induced EMT in C-PVR cells from human proliferative vitreoretinopathy. Scale bar—200 microns.

Furthermore, growth factors (e.g., TGFβ2, TNFα, and combination with TGFβ2, TNFα, and IL-6) induced EMT in C-PVR cells from human proliferative vitreoretinopathy (FIG. 25). C-PVR cells were grown to confluence. Cells were treated with TGFβ2, TNFα and a combination of TGFβ2, TNFα and IL-6 (10 ng/ml each) for 7 days. Cells were washed and fixed with 4% paraformaldehyde for 10 minutes at room temperature. Cells were incubated with primary antibodies, mouse anti-cytokeratin (1:250; Abcam) or smooth muscle actin (1:50; DAKO) overnight at 4° C. The following day, cells were incubated with secondary antibody goat anti-mouse 488 (1:300; Life Technologies) for 2 hours at room temperature and DAPI. Cells were washed with PBS and imaged. These data demonstrated that growth factors (e.g., TGFβ2, TNFα, and combination with TGFβ2, TNFα, and IL-6) induced EMT in C-PVR cells from human proliferative vitreoretinopathy (e.g., caused changes in cytokeratin and α-smooth muscle actin).

RUNX1 Expression Levels were Increased in Growth Factor-Induced EMT

Figure 26B:
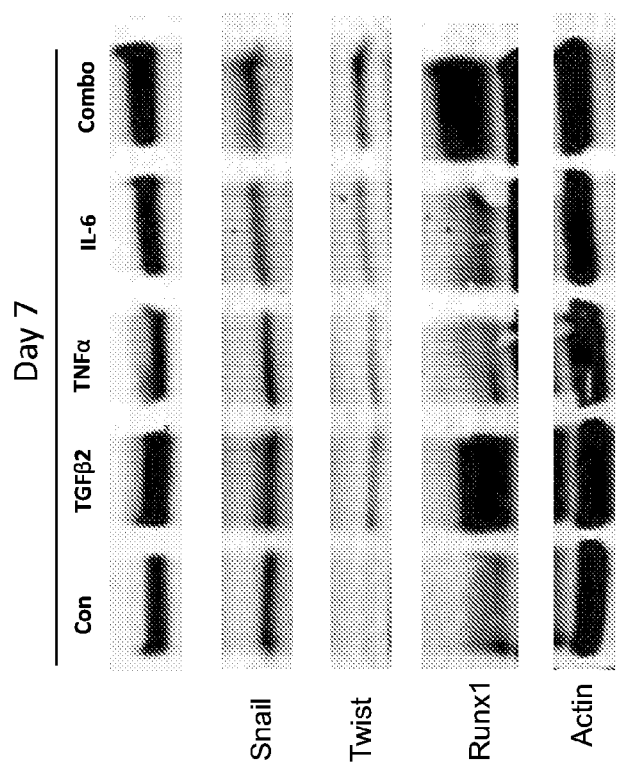
FIG. 26B are images of immunoblots showing that an increase in the protein for RUNX1, N-Cadherin (Mesenchymal marker), Snail, and Twist (Snail and Twist are EMT transition markers) was observed compared to β-actin, which was used as a loading control on treatment with growth factors at 7 days post treatment. ****P<0.0001.
Figure 26A:
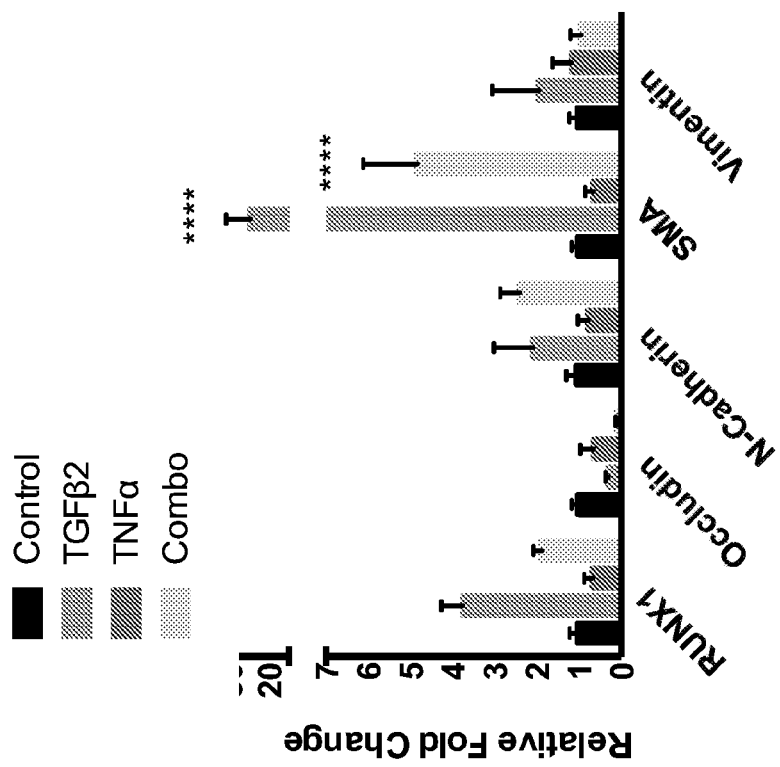
FIG. 26A is a bar graph depicting that RUNX1 expression levels were increased in growth factor-induced EMT. An increase in RUNX1 RNA was observed along with an increase in mesenchymal markers, N-Cadherin, Smooth muscle actin and vimentin and a decrease in Epithelial marker, occludin was on treatment with growth factors TGFβ2, TNFα and combination treatment of TGFβ2, TNFα and IL-6 at 7 days post treatment.

An increase in RUNX1 expression (e.g., RNA) and RUNX1 protein was observed in growth-factor induced EMT ((FIGS. 26A and 26B). C-PVR cells were seeded into 12-well pates. At confluence, cells were treated with growth factors TGFβ2, TNFα and a combination treatment of TGFβ2, TNFα and IL-6. Cells were washed with PBS, lysed and collected. Quantitative RT-PCR of mRNA expression was performed and values were reported as relative fold change in expression level. C-PVR cells were also seeded into 6-well pates. At confluence, cells were treated with growth factors TGFβ2, TNFα and a combination treatment of TGFβ2, TNFα and IL-6. Cells were washed with ice-cold PBS, lysed and collected at 7 day time point and immunoblotted for RUNX1 (1:200, SantaCruz Biotechnology, Dallas, Tex.), N-Cadherin (1:500, Santa Cruz Biotechnology), Snail (1:500, Abcam), Twist (Abcam) and Beta-Actin (1:1000, Cell Signaling Technology, Danvers, Mass.) as a loading control. These data demonstrate that growth factors (e.g., TGFβ2 and combination—TGFβ2, TNFα, and IL-6) caused changes in EMT markers in C-PVR cells.

Figure 27B:
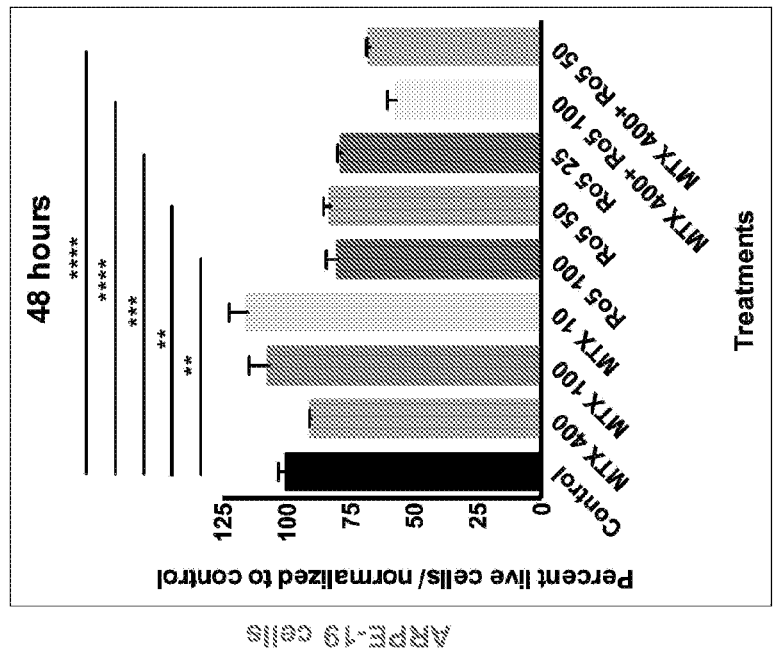
FIG. 27B is a bar graph showing results of a CyQuant cell proliferation assay 48 hours post treatment with a RUNX1 inhibitor (Ro5-3335) at 100 μM, 50 μM and 25 μM, and methotrexate at 400 μM, 100 μM and 10 μM, alone or in combination compared to vehicle treated. The data showed a significant reduction in percent live cells at 48 hours. This experiment showed that RUNX1 inhibition was more efficacious than treatment with methotrexate at inhibiting growth of ARPE-19 cells. The data also showed that RUNX1 inhibition can be used as an adjuvant in combination to treatments like methotrexate. *P<0.05, P<0.01, *P<0.001, ****P<0.0001.
Figure 27A:
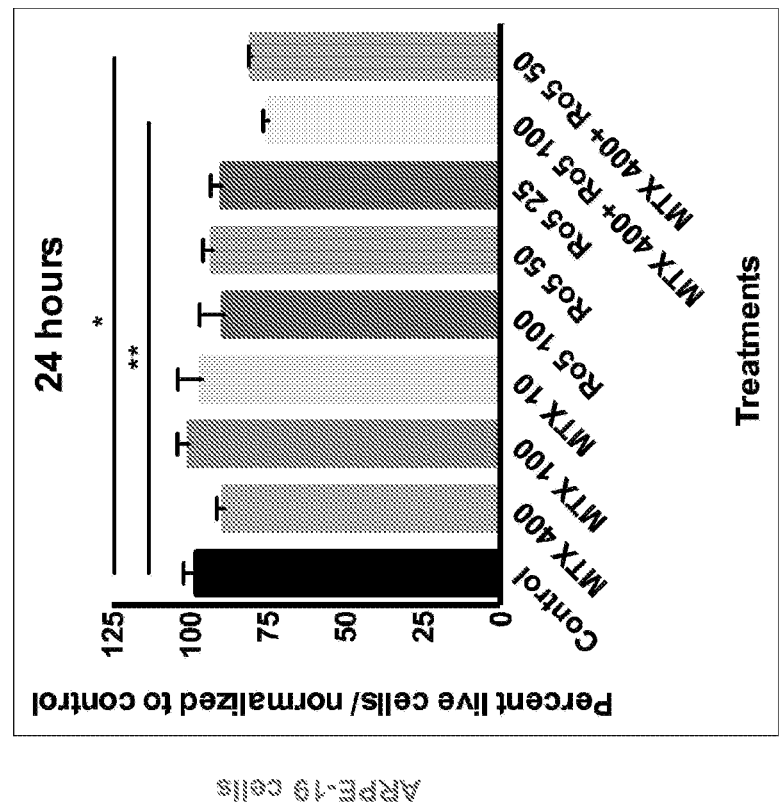
FIG. 27A is a bar graph showing results of a CyQuant cell proliferation assay 24 hours post treatment with a RUNX1 inhibitor (Ro5-3335) at 100 μM, 50 μM and 25 μM, and methotrexate at 400 μM, 100 μM and 10 μM, alone or in combination compared to vehicle treated. The data showed a significant reduction in percent live cells at 24 hours. This experiment showed that RUNX1 inhibition was more efficacious than treatment with methotrexate at inhibiting growth of ARPE-19 cells. The data also showed that RUNX1 inhibition can be used as an adjuvant in combination to treatments like methotrexate.*P<0.05, P<0.01, *P<0.001, ****P<0.0001.
Figure 28A:
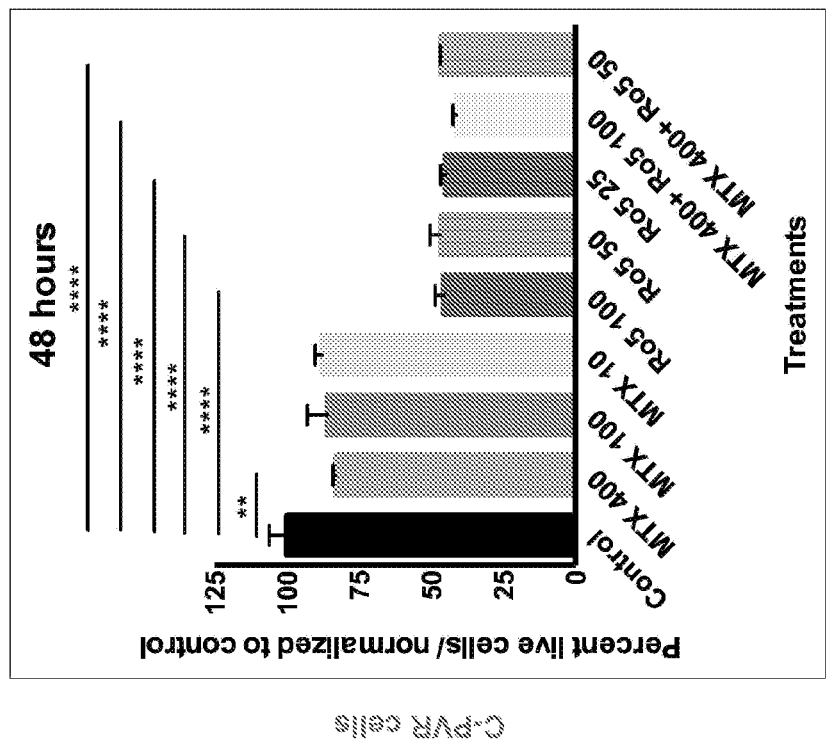
FIG. 28A is a bar graph showing results of a cell proliferation assay at 24 hours post treatment with a RUNX1 inhibitor (Ro5-3335) at 100 μM, 50 μM and 25 μM, and methotrexate at 400 μM, 100 μM and 10 μM, alone or in combination compared to vehicle treated. The data showed a significant reduction in percent live cells at 24 hours. This experiment showed that RUNX1 inhibition was more efficacious than treatment with methotrexate at inhibiting growth of C-PVR cells. The data also showed that RUNX1 inhibition can be used as an adjuvant in combination to treatments like methotrexate. *P<0.05, P<0.01, *P<0.001, ****P<0.0001.
Figure 28B:
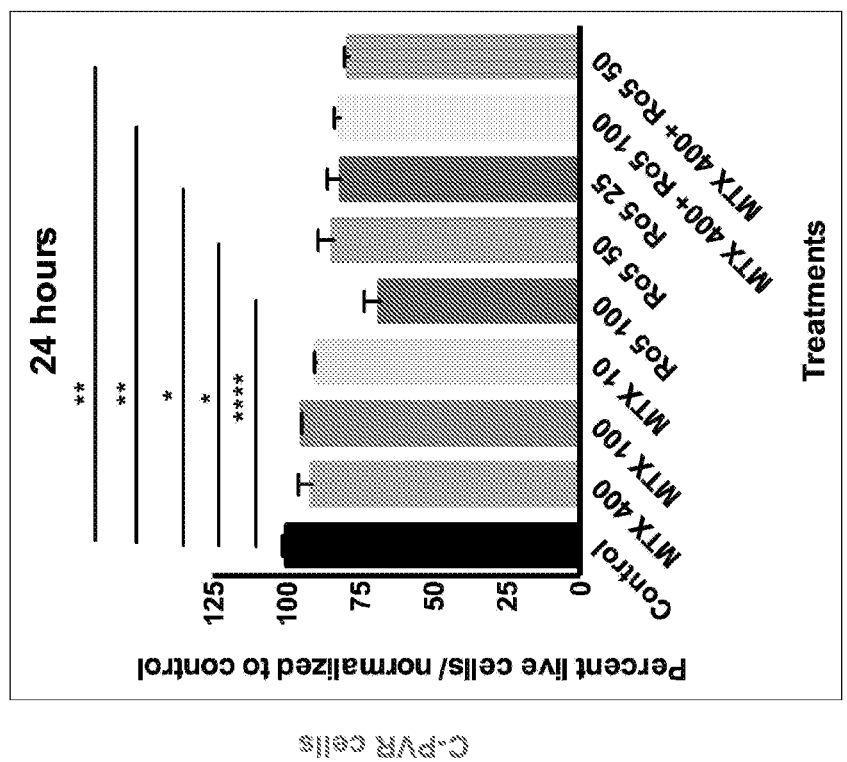
FIG. 28B is a bar graph showing results of a cell proliferation assay at 48 hours post treatment with a RUNX1 inhibitor (Ro5-3335) at 100 μM, 50 μM and 25 μM, and methotrexate at 400 μM, 100 μM and 10 μM, alone or in combination compared to vehicle treated. The data showed a significant reduction in percent live cells at 48 hours. This experiment showed that RUNX1 inhibition was more efficacious than treatment with methotrexate at inhibiting growth of C-PVR cells. The data also showed that RUNX1 inhibition can be used as an adjuvant in combination to treatments like methotrexate. *P<0.05, P<0.01, *P<0.001, ****P<0.0001.

RUNX1 Inhibition was More Effective at Inhibiting Growth of ARPE-19 Cells and C-PVR Cells, as Compared to Methotrexate RUNX1 inhibition was more efficacious at inhibiting growth of ARPE-19 cells, as compared to treatment with methotrexate (FIGS. 27A and 27B). Furthermore, the data reported that RUNX1 inhibition could be used as an adjuvant in combination to treatments (e.g., such as methotrexate). ARPE 19 cells were cultured in 96 well plates for 8 hours, followed by treatment with RUNX1 inhibitor (Ro5-3335, Calbiochem) or Methotrexate (Sigma) in growth media or vehicle only for a period of 24 or 48 hours. The cells were washed and the CyQuant Direct nucleic acid stain was added and incubated at 37° C. in the incubator. Fluorescence read outs were measured at wavelengths as instructed in the protocol. These data demonstrated the comparison of efficacy of methotrexate and RUNX1 inhibitor, and indicated that RUNX1 inhibition was more effective. Similar results were also observed in C-PVR cells. For example, it was shown that RUNX1 inhibition was more efficacious than treatment with methotrexate at inhibiting growth of C-PVR cells (FIG. 28A and FIG. 28B).

Figure 29:
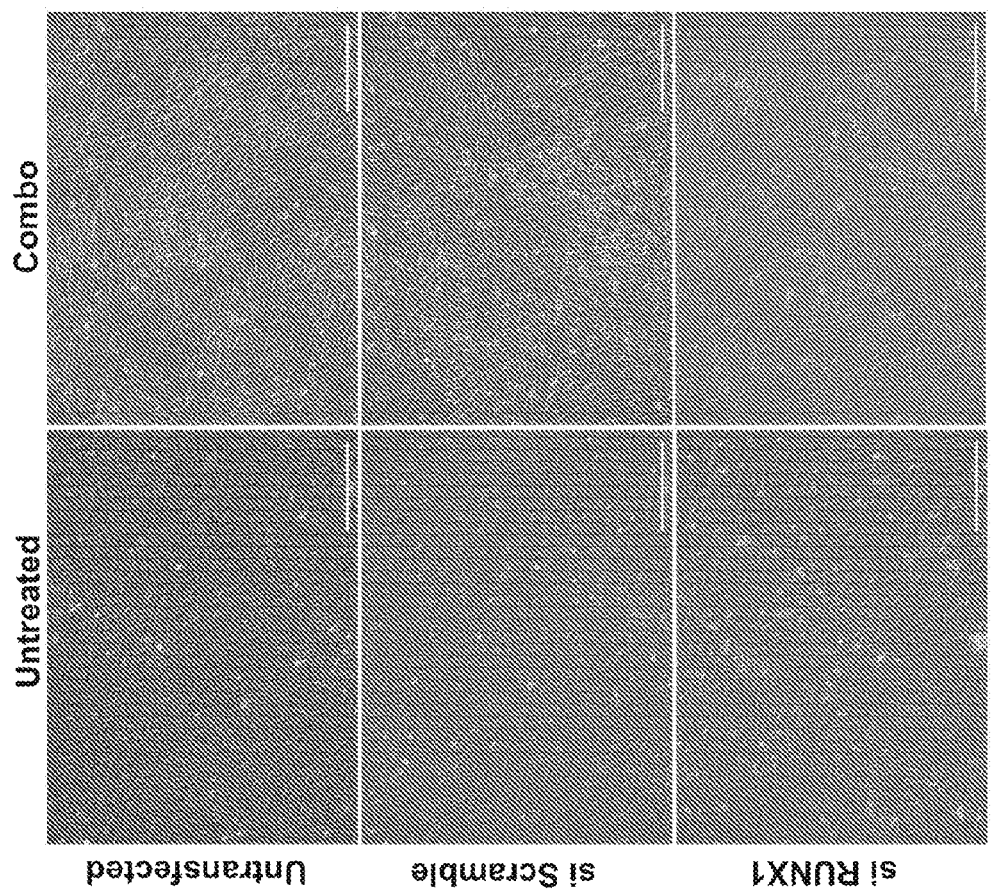
FIG. 29 are bright field images of ARPE-19 cells. RUNX1 knockdown using siRNA was effective at inhibiting EMT in cells treated with a growth factor cocktail including TGFβ2, TNFα and IL-6, compared to untransfected (right top) and si-scramble (right middle). EMT was determined by morphological changes including cell shape. This data demonstrated that RUNX1 inhibition using siRNA resulted in inhibition of EMT. Scale bars—400 microns.
Figure 31:
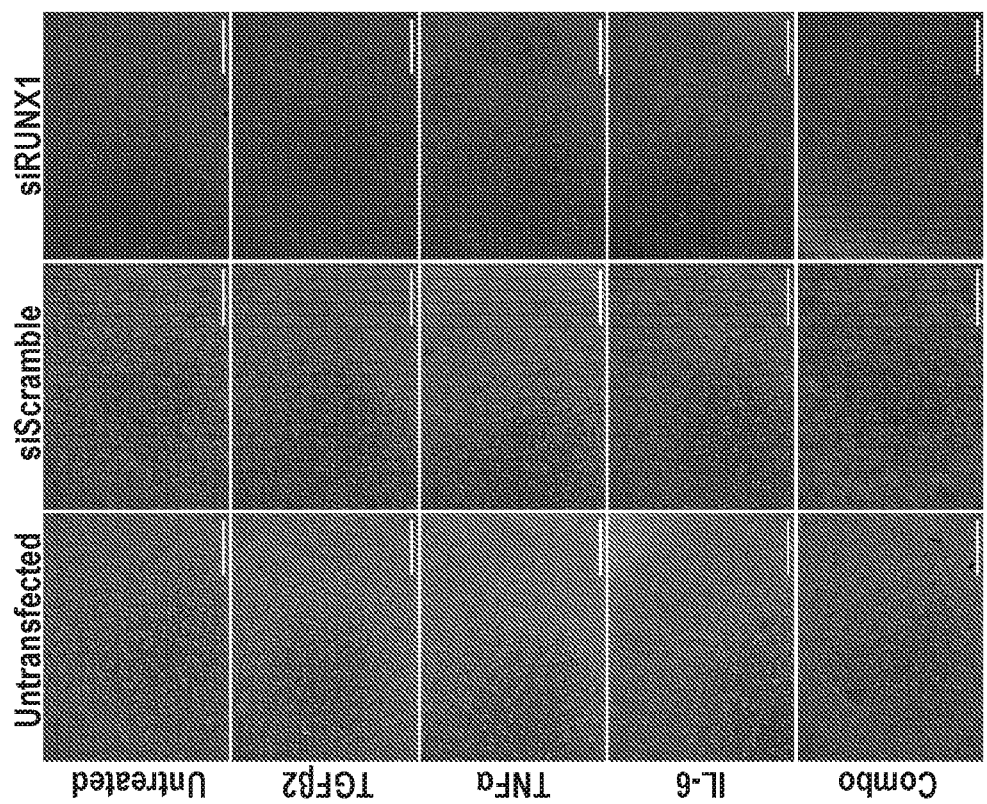
FIG. 31 is a series of bright field images of C-PVR cells, 72 hours after RUNX1 knockdown and 48 hours post treatment with a combination of TGFβ2, TNFα and IL-6, and which showed no or reduced EMT (right bottom picture) compared to un-transfected (right top) and Scramble (right middle). EMT was determined by morphological changes including cell shape. These data demonstrate that RUNX1 inhibition using siRNA resulted in inhibition of EMT. Scale bars—1000 microns.
Figure 32B:
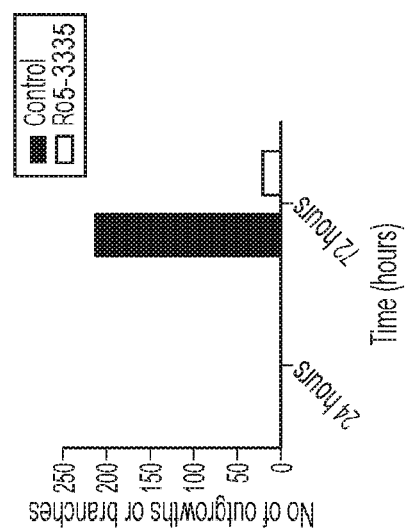
FIG. 32B is a bar graph indicating the number of outgrowths (or branches) after 24 hours and 72 hours with the control (DMSO) and with Ro5-3335.
Figure 32A:
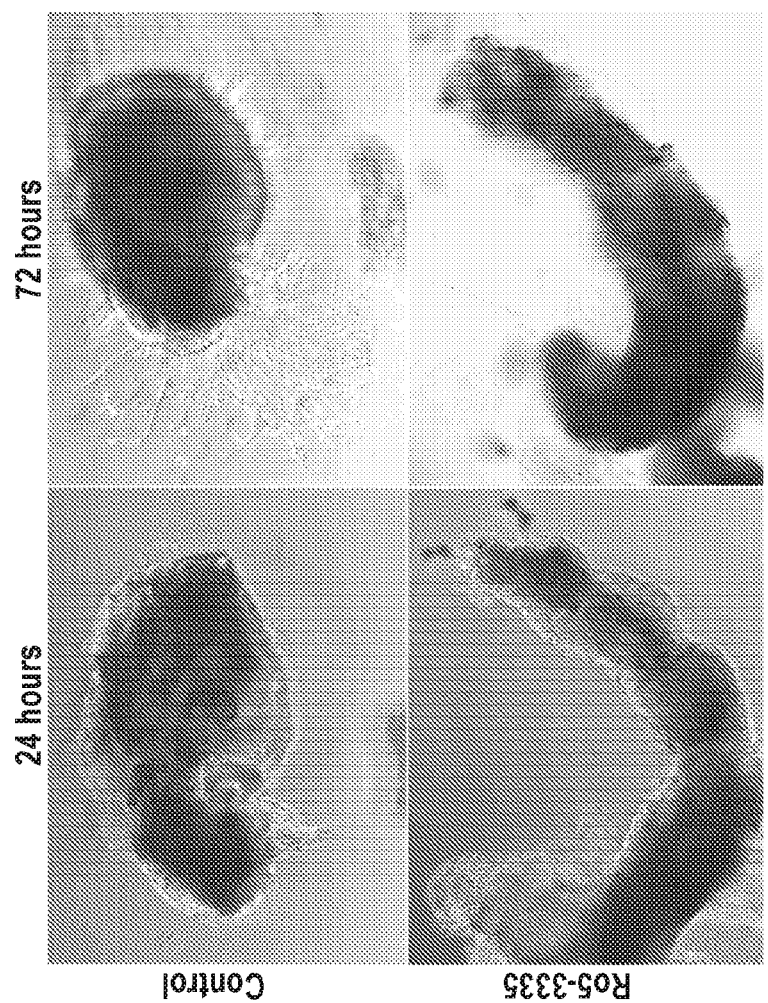
FIG. 32A is a series of images indicating that apoptosis, less branching and a faster regression of the branches was observed in human PVR explants treated with RUNX1 inhibitor, Ro5-3335 at 150 μm. Detachment of the branches from the primary tissue was also observed. Top panels showed explant treated with DMSO (vehicle) and bottom panels showed explant after treatment with Ro5-3335.
Figure 33B:
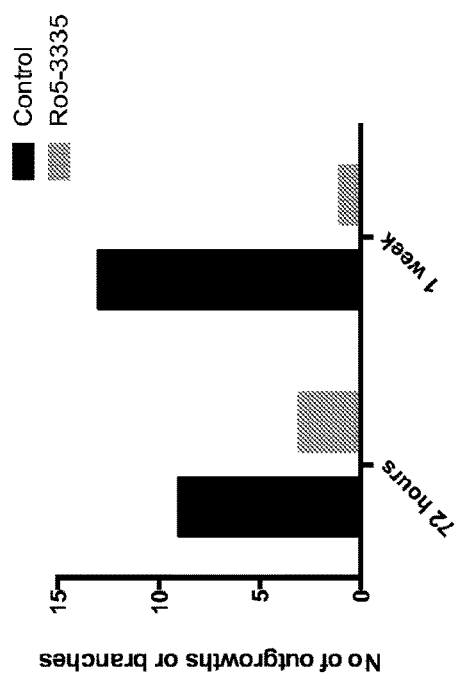
FIG. 33B is a bar graph indicating the number of outgrowths (or branches) after 24 hours and 72 hours with the control (DMSO) and with Ro5-3335.
Figure 33A:
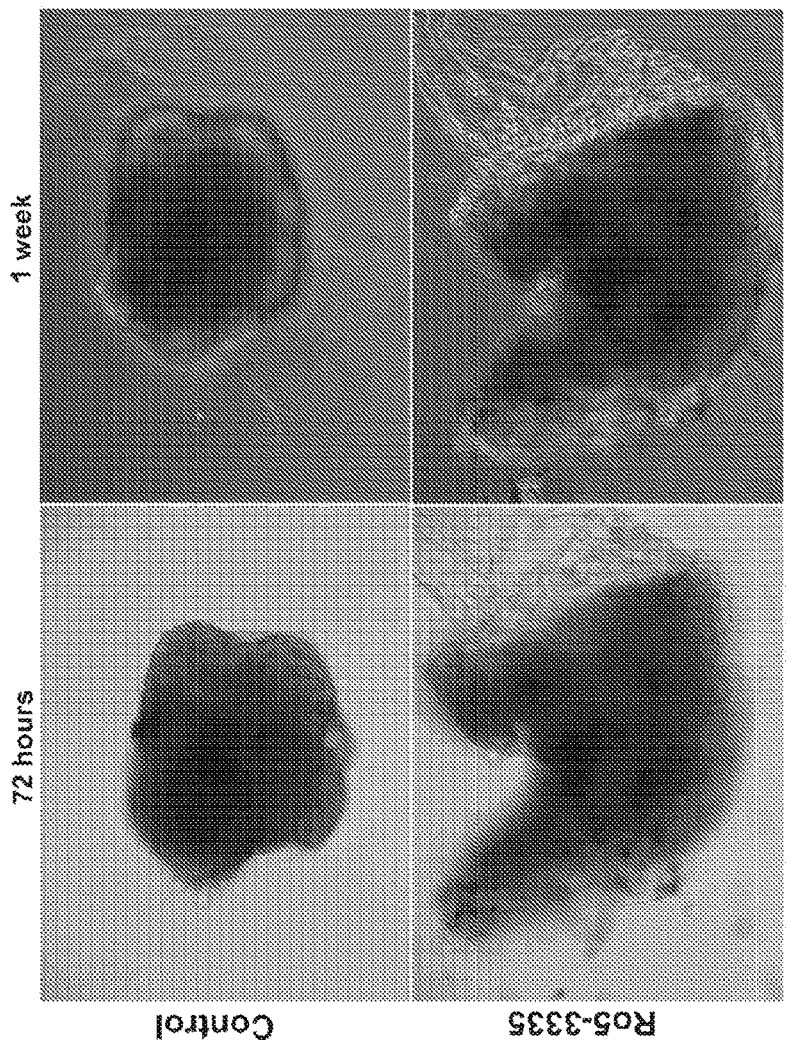
FIG. 33A is a series of images indicating that apoptosis, less branching and a faster regression of the branches was observed in another human PVR explant treated with RUNX1 inhibitor, Ro5-3335 at 150 μm. Detachment of the branches from the primary tissue was also observed. Top panels showed explant treated with DMSO (vehicle) and bottom panels showed explant after treatment with Ro5-3335.

RUNX1 Knockdown Inhibited EMT in ARPE-19 Cells, and Partially Inhibited EMT in C-PVR Cells RUNX1 inhibition using siRNA resulted in the inhibition of EMT (FIG. 29). ARPE-19 cells were grown to 60-70% confluence. Cells were transfected with siScramble or siRUNX1 overnight in and treated with growth factors TGFβ2, TNFα and IL-6 (10 ng/ml) for 2 days. Bright field images were taken using the EVOS microscope. The data demonstrated that RUNX1 knockdown inhibited EMT in ARPE-19 cells. Similarly, RUNX1 inhibition using siRNA resulted in inhibition of EMT in C-PVR cells (FIG. 31). C-PVR cells were grown to 60-70% confluence. Cells were transfected with siScramble or siRUNX1 overnight in and treated with growth factors TGFβ2, TNFα and IL-6 (10 ng/mL each) for 2 days. Bright field images were taken using the EVOS microscope, and showed inhibition of EMT. EMT was determined by morphological changes (e.g., cell shape).

Growth Factor Triggered RUNX1 Induction was Inhibited Using siRNA

Growth factor triggered RUNX1 induction was inhibited using siRNA. ARPE-19 cells were grown to 60-70% confluence. Cells were transfected with siScramble or siRUNX1 overnight in and treated with growth factors TGFβ2, TNFα and IL-6 (10 ng/ml) for 2 days. Cells were washed with ice-cold PBS, lysed and collected and immunoblotted for RUNX1 (1:200, SantaCruz Biotechnology, Dallas, Tex.), and glyceraldehyde 3-phosphate dehydrogenase (GAPDH) (1:1000, SantaCruz Biotechnology) as a loading control. These data show that each of these growth factors (e.g., TGFβ2, TNFα and IL-6) induced protein expression of RUNX1 and that such induction was stronger when the growth factors were combined. Furthermore, the data also showed that siRNA treatment efficient reduced the induction of RUNX1 triggered by each of these growth factors alone or in combination. This data demonstrated that RUNX1 inhibition can be used to limit the effect of these growths factors as it relates to PVR.

Significant Reduction of Human PVR was Observed in an Explant Model after Treatment with RUNX1 Inhibitor After treatment with a RUNX1 inhibitor, Ro5-3335, a significant reduction of human PVR in an explant model was observed (FIG. 32A-32B and FIG. 33A-33B). This result was observed from two different donors. PVR membranes were freshly obtained from patients and placed in growth factor-reduced Matrigel (BD Biosciences) seeded in 24 well plates. 30 μl of matrigel were used to coat the bottom of 24 well plates without touching the edges of the well. After seeding the PVR membrane, explant plates were incubated in a 37° C. cell incubator without medium for 10 minutes in order for the Matrigel to solidify. 500 μl of medium was added to each well and incubated at 37° C. with 5% $CO_2$. The explants were treated with RUNX1 inhibitor (Ro5-3335). Phase contrast photos of individual explants were taken daily.

Figure 34B:
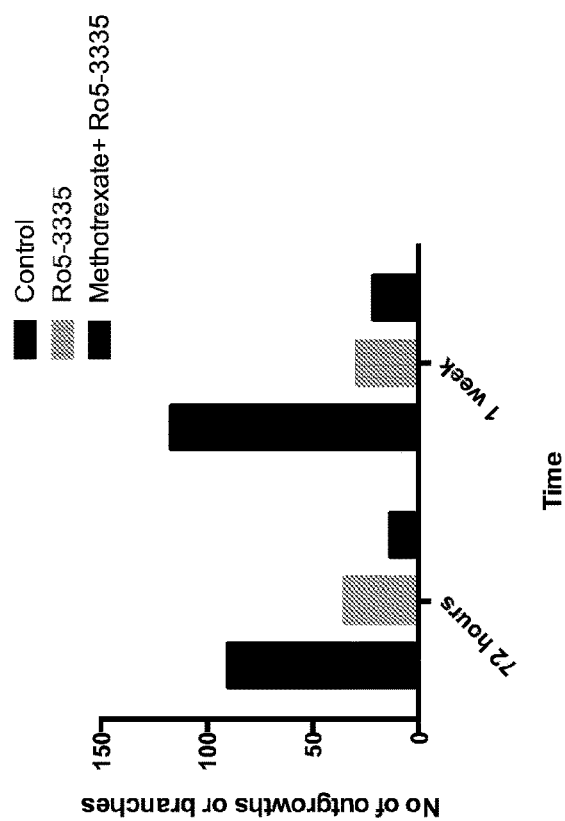
FIG. 34B is a bar graph indicating the number of outgrowths (or branches) after 24 hours and 72 hours with the control (DMSO), Ro5-3335, and combination of methotrexate and Ro5-3335.
Figure 34A:
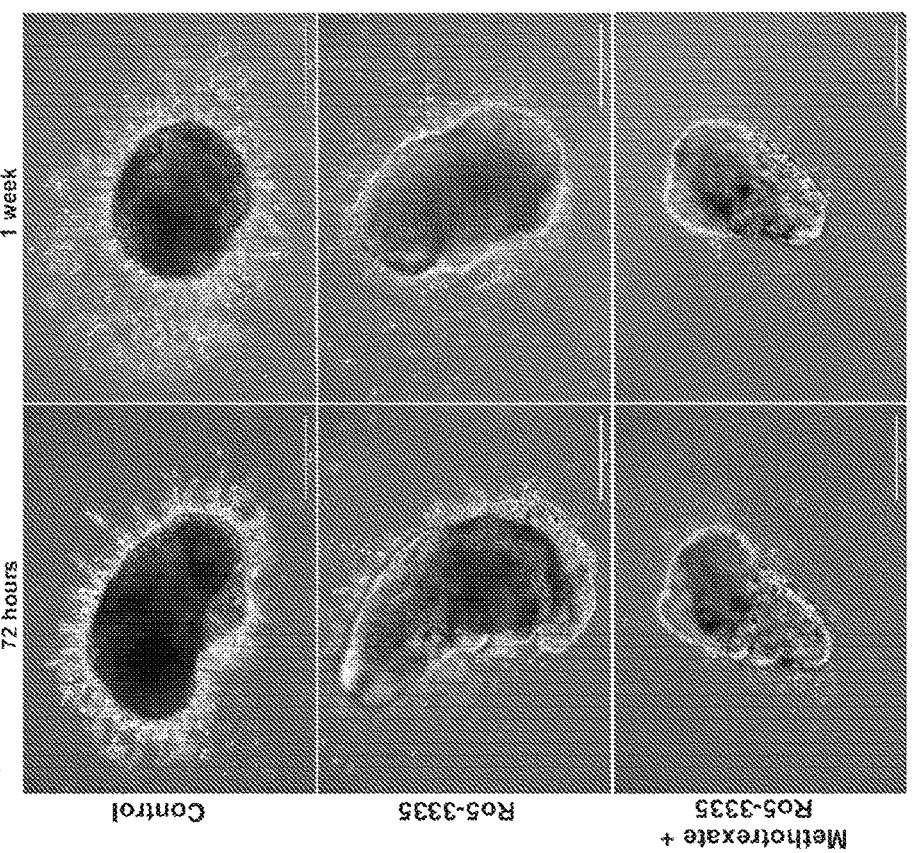
FIG. 34A is a series of images indicating that the RUNX1 inhibitor, Ro5-3335 reduced growth of human PVR membranes in an explant model. A synergistic effect was observed with methotrexate+Ro5-3335. Less branching, a faster regression of the branches and apoptosis was observed in human PVR explants treated with RUNX1 inhibitor (Ro5-3335 at 150 μM), or a combination of Ro5-3335 (150 μM) and methotrexate (400 μM). Detachment of the branches from the primary tissue was also observed in Ro-3335 alone, but the combination (synergistic) effect of the drugs was surprising and even more significant. Top panels showed explant treated with DMSO (vehicle), middle panels showed explant after treatment with Ro5-3335 and bottom panels showed the effect of combination treatment (Ro5-3335 and methotrexate).

Synergistic Effect was Observed with the Combination of RUNX1 Inhibition and Methotrexate Explant data reveled the reduction of the growth of PVR membranes in an explant model. Furthermore, a synergistic effect was observed, when RUNX1 inhibition (e.g., with Ro5-3335) was combined with methotrexate (FIGS. 34A and 34B). PVR membranes were freshly obtained from patients, placed in growth factor-reduced Matrigel (BD Biosciences), and seeded in 24 well plates. 30 μl of matrigel was used to coat the bottom of 24 well plates without touching the edges of the well. After seeding, the PVR membrane explant plates were incubated in a 37° C. cell incubator without medium for 10 minutes in order for the Matrigel to solidify. 500 µl of medium was added to each well and incubated at 37° C. with 5% $CO_2$. The explants were treated with RUNX1 inhibitor (Ro5-3335) or a combination of Ro5-3335 and methotrexate. Phase contrast photos of individual explants were taken daily.

Lenlidomide Inhibited Proliferation in C-PVR Cells

C-PVR cells were treated with lenalidomide, and it was found that lenalidomide treatment significantly reduced proliferation of C-PVR cells. Lenalidomide treatment alone or in combination with a RUNX1 inhibitor may be used for the treatment of PVR.

Lenlidomide inhibited proliferation in C-PVR cells at 48 and 72 hours, with 40 and 80 nM (FIG. 35A-35D). A CyQuant Cell Proliferation Assay was performed 48 and 72 hours post-treatment, with lenalidomide at 40 nM, and 80 nM. The data were compared to vehicle treated, and showed a significant reduction in percent live cells at 72 hours. C-PVR cells were cultured in 96 well plates for 8 hours, followed by treatment with lenalidomide (Sigma-Aldrich) in growth media or vehicle only for a period of 48 or 72 hours. The cells were washed, and CyQuant Direct and nucleic acid stain was added and incubated at 37° C. Fluorescence read outs were measured at wavelengths as instructed in the protocol.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for preventing or reducing proliferation or migration of retinal pigment epithelial (RPE) cells in a subject who has not been diagnosed with aberrant angiogenesis or small vessel disease and who comprises a retinal hole or retinal tear, the method comprising administering to the subject a composition comprising a small molecule selected from the group consisting of:

a small molecule comprising the structure of Formula I:

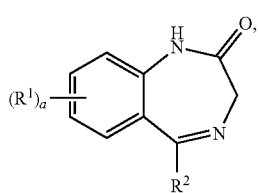

or a pharmaceutically acceptable salt or ester thereof, wherein
each $R^1$ is individually selected from halogen, alkyl, aryl, heteroaryl, or alkoxy,
and $R^1$ is selected from aryl or heteroaryl, and
a is 0 to 4; or a small molecule comprising the structure of Formula III:

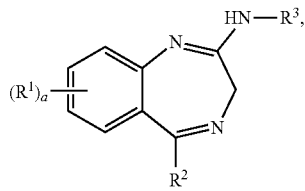

or a pharmaceutically acceptable salt or ester thereof, wherein
each $R^1$ is individually selected from halogen, alkyl, aryl, heteroaryl, or alkoxy,
$R^2$ is selected from aryl or heteroaryl;
$R^3$ is alkyl or aryl, and
a is 0 to 4; or a small molecule comprising the structure of Formula V:

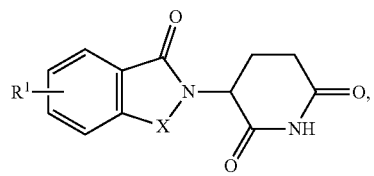

or a pharmaceutically acceptable salt or ester thereof, wherein
$R^1$ is $H_3$, $NH_2$, or $NHC(O)CH_3$, and
X is $CH_2$ or $C(O)$.

2. The method of claim 1, wherein the small molecule is Ro5-3335.

3. The method of claim 1, wherein the small molecule is Ro24-7429.

4. The method of claim 1, wherein the small molecule is lenalidomide.

5. The method of claim 1, wherein the small molecule decreases the expression and/or activity of RUNX1.

6. The method of claim 1, wherein the composition further comprises methotrexate.

7. The method of claim 1, wherein the composition further comprises an anti-inflammatory agent.

8. The method of claim 7, wherein the anti-inflammatory agent comprises a steroid or a nonsteroidal anti-inflammatory drug (NSAID).

9. The method of claim 1, wherein the composition is administered topically or by intravitreal injection.

10. The method of claim 1, wherein the subject is a human.

11. The method of claim 1, wherein the subject has not undergone surgery.

12. The method of claim 1, wherein the inhibitor is administered prior to a surgery, during a surgery or after a surgery.

13. The method of claim 12, wherein the surgery comprises retinal detachment surgery.

14. The method of claim 1, wherein the subject has suffered a trauma to the eye.

15. The method of claim 1, wherein the composition comprises a carrier or excipient suitable for administration to ocular tissue.

16. A method for preventing or reducing proliferation or migration of retinal pigment epithelial (RPE) cells in a subject who has not been diagnosed with aberrant angiogenesis or small vessel disease and who comprises a retinal hole or retinal tear, the method comprising administering to the subject a composition comprising an RNA encoding the dominant negative CBF-Beta protein CBFB-MYH11.

17. The method of claim 16, wherein the RNA encoding the dominant negative CBF-Beta protein CBFB-MYH11 decreases the expression and/or activity of RUNX1.

18. The method of claim 16, wherein the composition further comprises methotrexate.

19. The method of claim 16, wherein the composition further comprises an anti-inflammatory agent.

20. The method of claim 19, wherein the anti-inflammatory agent comprises a steroid or a nonsteroidal anti-inflammatory drug (NSAID).

21. The method of claim 16, wherein the composition is administered topically or by intravitreal injection.

22. The method of claim 16, wherein the subject is a human.

23. The method of claim 16, wherein the subject has not undergone surgery.

24. The method of claim 16, wherein the inhibitor is administered prior to a surgery, during a surgery or after a surgery.

25. The method of claim 24, wherein the surgery comprises retinal detachment surgery.

26. The method of claim 16, wherein the subject has suffered a trauma to the eye.

27. The method of claim 16, wherein the composition comprises a carrier or excipient suitable for administration to ocular tissue.

28. A method for treating or reducing the severity of PVR in a subject, said method comprising:
    (a) identifying a subject comprising PVR, and
    (b) administering to said subject a small molecule selected from the group consisting of:

a small molecule comprising the structure of Formula I:

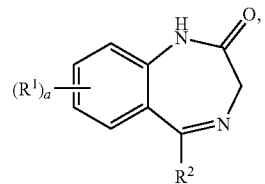

or a pharmaceutically acceptable salt or ester thereof, wherein
    each $R^1$ is individually selected from halogen, alkyl, aryl, heteroaryl, or alkoxy,
    and $R^2$ is selected from aryl or heteroaryl, and
    a is 0 to 4; or a small molecule comprising the structure of Formula III:

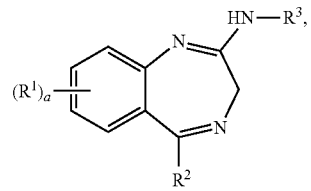

or a pharmaceutically acceptable salt or ester thereof, wherein
    each $R^1$ is individually selected from halogen, alkyl, aryl, heteroaryl, or alkoxy,
    $R^2$ is selected from aryl or heteroaryl;
    $R^3$ is alkyl or aryl, and
    a is 0 to 4; or a small molecule comprising the structure of Formula V:

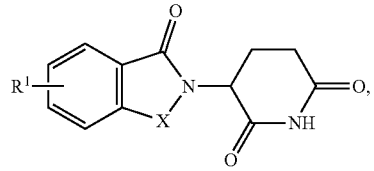

or a pharmaceutically acceptable salt or ester thereof, wherein
    $R^1$ is $H_3$, $NH_2$, or $NHC(O)CH_3$, and
    X is $CH_2$ or $C(O)$.

29. A method for treating or reducing the severity of PVR in a subject, said method comprising:
    (a) identifying a subject comprising PVR, and
    (b) administering to said subject an RNA encoding the dominant negative CBF-Beta protein CBFB-MYH11.

30. A method of reducing proliferation and migration of cells undergoing epithelial to mesenchymal transition (EMT) within an eye in a subject or treating or preventing an EMT related disease, comprising administrating to the subject a small molecule selected from the group consisting of:

a small molecule comprising the structure of Formula I:

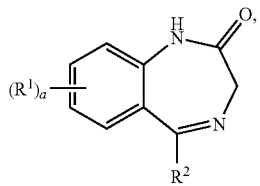

or a pharmaceutically acceptable salt or ester thereof, wherein
each $R^1$ is individually selected from halogen, alkyl, aryl, heteroaryl, or alkoxy,
and $R^2$ is selected from aryl or heteroaryl, and
a is 0 to 4; or
a small molecule comprising the structure of Formula III:

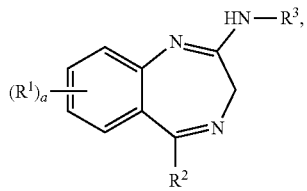

or a pharmaceutically acceptable salt or ester thereof, wherein
each $R^1$ is individually selected from halogen, alkyl, aryl, heteroaryl, or alkoxy,
$R^2$ is selected from aryl or heteroaryl;
$R^3$ is alkyl or aryl, and
a is 0 to 4; or
a small molecule comprising the structure of Formula V:

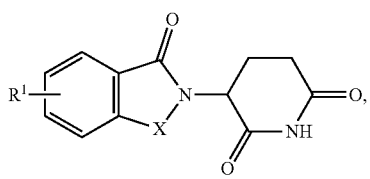

or a pharmaceutically acceptable salt or ester thereof, wherein
$R^1$ is H, $NH_2$, or $NHC(O)CH_3$, and
X is $CH_2$ or $C(O)$,
wherein the EMT related disease comprises pathologic ocular fibrosis-associated proliferation, conjunctival fibrosis, ocular cicatricial pemphigoid, corneal scarring, corneal epithelial down growth, or aberrant post-surgical fibrosis,
wherein said inhibitor is administered during or after intraocular surgery.

31. A method of reducing proliferation and migration of cells undergoing epithelial to mesenchymal transition (EMT) within an eye in a subject or treating or preventing an EMT related disease, comprising administrating to the subject a small molecule selected from the group consisting of:

a small molecule comprising the structure of Formula I:

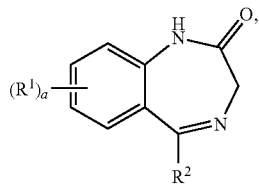

or a pharmaceutically acceptable salt or ester thereof, wherein
each $R^1$ is individually selected from halogen, alkyl, aryl, heteroaryl, or alkoxy,
and $R^2$ is selected from aryl or heteroaryl, and
a is 0 to 4; or
a small molecule comprising the structure of Formula III:

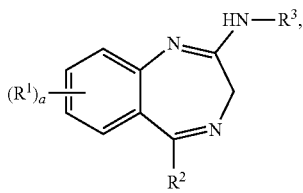

or a pharmaceutically acceptable salt or ester thereof, wherein
each $R^1$ is individually selected from halogen, alkyl, aryl, heteroaryl, or alkoxy,
$R^2$ is selected from aryl or heteroaryl;
$R^3$ is alkyl or aryl, and
a is 0 to 4; or
a small molecule comprising the structure of Formula V:

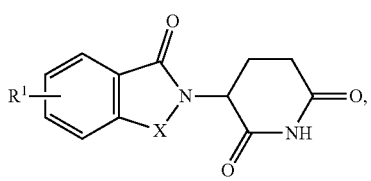

or a pharmaceutically acceptable salt or ester thereof, wherein
$R^1$ is $H_3$, $NH_2$, or $NHC(O)CH_3$, and
X is $CH_2$ or $C(O)$,
wherein the EMT related disease comprises pathologic ocular fibrosis-associated proliferation, conjunctival fibrosis, ocular cicatricial pemphigoid, corneal scarring, corneal epithelial down growth, or aberrant post-surgical fibrosis,
wherein said inhibitor is administered during or after glaucoma surgery, cataract surgery, or Laser-Assisted In Situ Keratomileusis (LASIK).

32. A method of reducing proliferation and migration of cells undergoing epithelial to mesenchymal transition (EMT) within an eye in a subject or treating or preventing an EMT related disease, comprising administrating to the subject a an RNA encoding the dominant negative CBF-Beta protein CBFB-MYH11, wherein the EMT related disease comprises pathologic ocular fibrosis-associated proliferation, conjunctival fibrosis, ocular cicatricial pemphigoid, corneal scarring, corneal epithelial down growth, or aberrant post-surgical fibrosis, wherein said inhibitor is administered during or after intraocular surgery.

33. A method of reducing proliferation and migration of cells undergoing epithelial to mesenchymal transition (EMT) within an eye in a subject or treating or preventing an EMT related disease, comprising administrating to the subject a an RNA encoding the dominant negative CBF-Beta protein CBFB-MYH11, wherein the EMT related disease comprises pathologic ocular fibrosis-associated proliferation, conjunctival fibrosis, ocular cicatricial pemphigoid, corneal scarring, corneal epithelial down growth, or aberrant post-surgical fibrosis, wherein said inhibitor is administered during or after glaucoma surgery, cataract surgery, or Laser-Assisted In Situ Keratomileusis (LASIK).

* * * * *

UNITED STATES PATENT AND TRADEMARK OFFICE
CERTIFICATE OF CORRECTION

| | |
|---|---|
| PATENT NO. | : 11,739,326 B2 |
| APPLICATION NO. | : 16/763880 |
| DATED | : August 29, 2023 |
| INVENTOR(S) | : Kim et al. |

Page 1 of 2

It is certified that error appears in the above-identified patent and that said Letters Patent is hereby corrected as shown below:

On the Title Page:

In Column 1 item (72) (Inventors), Line 3, delete "Newtown," and insert -- Newton, --

The first or sole Notice should read --

Subject to any disclaimer, the term of this patent is extended or adjusted under 35 U.S.C. 154(b) by 149 days.

In Column 2 item (56) (Other Publications), Line 13, delete "VEGR" and insert -- VEGF --

In the Specification

In Column 1, Lines 6-12, below "TRANSITION" delete "RELATED APPLICATIONS
This application claims benefit of priority to U.S. Provisional Application No. 62/586,067, filed Nov. 14, 2017, the entire contents of which is incorporated herein by reference."

In Column 1, Lines 22-32, delete "CROSS-REFERENCES TO RELATED APPLICATIONS
This application is a national stage application filed under 35 U.S.C. § 371, of International Patent Application No PCT/US2018/061110, filed on Nov. 14, 2018, which claims the benefit of and priority to U.S. Provisional Application No. 62/586,067, filed on Nov. 14, 2017, the entire contents of which are incorporated herein by reference in their entirety." and insert the same on Column 1, Line 6, as a new paragraph In the Claims In Column 197, Line 66, Claim 1, delete "$R^1$" and insert -- $R^2$ --

In Column 201, Line 52, Claim 30, delete "H," and insert -- $H_3$, --

Signed and Sealed this
Sixteenth Day of April, 2024

*Katherine Kelly Vidal*

Katherine Kelly Vidal
*Director of the United States Patent and Trademark Office*

In Column 202, Line 64, Claim 32, delete "a an" and insert -- an --

In Column 203, Line 8, Claim 33, delete "a an" and insert -- an --

SEQUENCE LISTING

```
<160> NUMBER OF SEQ ID NOS: 39

<210> SEQ ID NO 1
<211> LENGTH: 453
<212> TYPE: PRT
<213> ORGANISM: Homo sapiens

<400> SEQUENCE: 1

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
        35                  40                  45

Arg Ser Met Val Glu Val Leu Ala Asp His Pro Gly Glu Leu Val Arg
    50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
        115                 120                 125

Ala Arg Phe Asn Asp Leu Arg Phe Val Gly Arg Ser Gly Arg Gly Lys
    130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Arg His Arg Gln Lys Leu Asp Asp Gln Thr Lys Pro Gly Ser Leu
            180                 185                 190
```

```
Ser Phe Ser Glu Arg Leu Ser Glu Leu Glu Gln Leu Arg Thr Ala
            195                 200                 205

Met Arg Val Ser Pro His His Pro Ala Pro Thr Pro Asn Pro Arg Ala
210                 215                 220

Ser Leu Asn His Ser Thr Ala Phe Asn Pro Gln Pro Gln Ser Gln Met
225                 230                 235                 240

Gln Asp Thr Arg Gln Ile Gln Pro Ser Pro Trp Ser Tyr Asp Gln
            245                 250                 255

Ser Tyr Gln Tyr Leu Gly Ser Ile Ala Ser Pro Ser Val His Pro Ala
                260                 265                 270

Thr Pro Ile Ser Pro Gly Arg Ala Ser Gly Met Thr Thr Leu Ser Ala
            275                 280                 285

Glu Leu Ser Ser Arg Leu Ser Thr Ala Pro Asp Leu Thr Ala Phe Ser
290                 295                 300

Asp Pro Arg Gln Phe Pro Ala Leu Pro Ser Ile Ser Asp Pro Arg Met
305                 310                 315                 320

His Tyr Pro Gly Ala Phe Thr Tyr Ser Pro Thr Pro Val Thr Ser Gly
                325                 330                 335

Ile Gly Ile Gly Met Ser Ala Met Gly Ser Ala Thr Arg Tyr His Thr
            340                 345                 350

Tyr Leu Pro Pro Pro Tyr Pro Gly Ser Ser Gln Ala Gln Gly Gly Pro
            355                 360                 365

Phe Gln Ala Ser Ser Pro Ser Tyr His Leu Tyr Tyr Gly Ala Ser Ala
370                 375                 380

Gly Ser Tyr Gln Phe Ser Met Val Gly Gly Glu Arg Ser Pro Pro Arg
385                 390                 395                 400

Ile Leu Pro Pro Cys Thr Asn Ala Ser Thr Gly Ser Ala Leu Leu Asn
                405                 410                 415

Pro Ser Leu Pro Asn Gln Ser Asp Val Val Glu Ala Glu Gly Ser His
            420                 425                 430

Ser Asn Ser Pro Thr Asn Met Ala Pro Ser Ala Arg Leu Glu Glu Ala
            435                 440                 445

Val Trp Arg Pro Tyr
    450

<210> SEQ ID NO 2
<211> LENGTH: 472
<212> TYPE: PRT
<213> ORGANISM: Homo sapiens

<400> SEQUENCE: 2

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
            35                  40                  45

Arg Ser Met Val Glu Val Leu Ala Asp His Pro Gly Glu Leu Val Arg
        50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110
```

```
Tyr Ser Ala Glu Leu Arg Asn Ala Thr Ala Ala Met Lys Asn Gln Val
        115                 120                 125

Ala Arg Phe Asn Asp Leu Arg Phe Val Gly Arg Ser Gly Arg Gly Lys
130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Arg His Arg Gln Lys Leu Asp Asp Gln Thr Lys Pro Gly Ser Leu
                180                 185                 190

Ser Phe Ser Glu Arg Leu Ser Glu Leu Glu Gln Leu Arg Arg Thr Ala
        195                 200                 205

Met Arg Val Ser Pro His His Pro Ala Pro Thr Pro Asn Pro Arg Ala
210                 215                 220

Ser Leu Asn His Ser Thr Ala Phe Asn Pro Gln Pro Gln Ser Gln Met
225                 230                 235                 240

Gln Asp Thr Arg Gln Ile Gln Pro Ser Pro Pro Trp Ser Tyr Asp Gln
                245                 250                 255

Ser Tyr Gln Tyr Leu Gly Ser Ile Ala Ser Pro Ser Val His Pro Ala
                260                 265                 270

Thr Pro Ile Ser Pro Gly Arg Ala Ser Gly Met Thr Thr Leu Ser Ala
                275                 280                 285

Glu Leu Ser Ser Arg Leu Ser Thr Ala Pro Asp Leu Thr Ala Phe Ser
        290                 295                 300

Asp Pro Arg Gln Phe Pro Ala Leu Pro Ser Ile Ser Asp Pro Arg Met
305                 310                 315                 320

His Tyr Pro Gly Ala Phe Thr Tyr Ser Pro Thr Pro Val Thr Ser Gly
                325                 330                 335

Ile Gly Ile Gly Met Ser Ala Met Gly Ser Ala Thr Arg Tyr His Thr
                340                 345                 350

Tyr Leu Pro Pro Pro Tyr Pro Gly Ser Ser Gln Ala Gln Gly Gly Pro
        355                 360                 365

Phe Gln Ala Ser Ser Pro Ser Tyr His Leu Tyr Tyr Gly Ala Ser Ala
        370                 375                 380

Gly Ser Tyr Gln Phe Ser Met Val Gly Gly Glu Arg Ser Pro Pro Arg
385                 390                 395                 400

Ile Leu Pro Pro Cys Thr Asn Ala Ser Thr Gly Ser Ala Leu Leu Asn
                405                 410                 415

Pro Ser Leu Pro Asn Gln Ser Asp Val Val Glu Ala Glu Gly Ser His
                420                 425                 430

Ser Asn Ser Pro Thr Asn Met Gly Gly Ala Ser Cys Ser Arg Gln Ala
        435                 440                 445

Arg Arg Asp Pro Gly Pro Trp Ala Arg Thr Pro Ser Trp Gly Arg Gly
450                 455                 460

Arg Pro Thr Asp Arg Ile Ser Leu
465                 470

<210> SEQ ID NO 3
<211> LENGTH: 250
<212> TYPE: PRT
<213> ORGANISM: Homo sapiens

<400> SEQUENCE: 3

Met Arg Ile Pro Val Asp Ala Ser Thr Ser Arg Arg Phe Thr Pro Pro
```

```
1               5                   10                  15
Ser Thr Ala Leu Ser Pro Gly Lys Met Ser Glu Ala Leu Pro Leu Gly
                20                  25                  30

Ala Pro Asp Ala Gly Ala Ala Leu Ala Gly Lys Leu Arg Ser Gly Asp
            35                  40                  45

Arg Ser Met Val Glu Val Leu Ala Asp His Pro Gly Glu Leu Val Arg
        50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
        115                 120                 125

Ala Arg Phe Asn Asp Leu Arg Phe Val Gly Arg Ser Gly Arg Gly Lys
    130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Arg His Arg Gln Lys Leu Asp Asp Gln Thr Lys Pro Gly Ser Leu
            180                 185                 190

Ser Phe Ser Glu Arg Leu Ser Glu Leu Glu Gln Leu Arg Arg Thr Ala
        195                 200                 205

Met Arg Val Ser Pro His His Pro Ala Pro Thr Pro Asn Pro Arg Ala
    210                 215                 220

Ser Leu Asn His Ser Thr Ala Phe Asn Pro Gln Pro Gln Ser Gln Met
225                 230                 235                 240

Gln Glu Glu Asp Thr Ala Pro Trp Arg Cys
                245                 250

<210> SEQ ID NO 4
<211> LENGTH: 257
<212> TYPE: PRT
<213> ORGANISM: Homo sapiens

<400> SEQUENCE: 4

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
                20                  25                  30

Ala Pro Asp Ala Gly Ala Ala Leu Ala Gly Lys Leu Arg Ser Gly Asp
            35                  40                  45

Arg Ser Met Val Glu Val Leu Ala Asp His Pro Gly Glu Leu Val Arg
        50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
        115                 120                 125
```

```
Ala Arg Phe Asn Asp Leu Arg Phe Val Gly Arg Ser Gly Arg Gly Lys
    130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Arg His Arg Gln Lys Leu Asp Asp Gln Thr Lys Pro Gly Ser Leu
                180                 185                 190

Ser Phe Ser Glu Arg Leu Ser Glu Leu Glu Gln Leu Arg Thr Ala
            195                 200                 205

Met Arg Val Ser Pro His His Pro Ala Pro Thr Pro Asn Pro Arg Ala
    210                 215                 220

Ser Leu Asn His Ser Thr Ala Phe Asn Pro Gln Pro Gln Ser Gln Met
225                 230                 235                 240

Gln Asp Thr Arg Gln Ile Gln Pro Ser Pro Pro Trp Ser Tyr Asp Gln
                245                 250                 255

Ser

<210> SEQ ID NO 5
<211> LENGTH: 224
<212> TYPE: PRT
<213> ORGANISM: Homo sapiens

<400> SEQUENCE: 5

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
                20                  25                  30

Ala Pro Asp Ala Gly Ala Ala Leu Ala Gly Lys Leu Arg Ser Gly Asp
            35                  40                  45

Arg Ser Met Val Glu Val Leu Ala Asp His Pro Gly Glu Leu Val Arg
        50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
        115                 120                 125

Ala Arg Phe Asn Asp Leu Arg Phe Val Gly Arg Ser Gly Arg Gly Lys
    130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Ser Lys Cys Ile His Leu Gly Leu Val His Pro Pro Gly Trp Tyr
                180                 185                 190

Thr Leu Gln Ala Gly Ile Leu Arg Asp His Val Ser Asp Ser Leu Gly
            195                 200                 205

Ser Thr Phe Pro Pro Gly Gly Trp Gln Ala Pro Val Lys Pro Lys Ser
        210                 215                 220

<210> SEQ ID NO 6
<211> LENGTH: 188
```

<212> TYPE: PRT
<213> ORGANISM: Homo sapiens

<400> SEQUENCE: 6

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
        35                  40                  45

Arg Ser Met Val Glu Val Leu Ala Asp His Pro Gly Glu Leu Val Arg
    50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
        115                 120                 125

Ala Arg Phe Asn Asp Leu Arg Phe Val Gly Arg Ser Gly Arg Gly Lys
    130                 135                 140

Ser Phe Thr Leu Thr Ile Thr Val Phe Thr Asn Pro Pro Gln Val Ala
145                 150                 155                 160

Thr Tyr His Arg Ala Ile Lys Ile Thr Val Asp Gly Pro Arg Glu Pro
                165                 170                 175

Arg Asn Ser Leu Thr Trp Pro Arg Tyr Pro His Ile
            180                 185

<210> SEQ ID NO 7
<211> LENGTH: 242
<212> TYPE: PRT
<213> ORGANISM: Homo sapiens

<400> SEQUENCE: 7

Met Arg Ile Pro Val Asp Ala Ser Thr Ser Arg Arg Phe Thr Pro Pro
1               5                   10                  15

Ser Thr Ala Leu Ser Pro Gly Lys Met Ser Glu Ala Leu Pro Leu Gly
            20                  25                  30

Ala Pro Asp Ala Gly Ala Ala Leu Ala Gly Lys Leu Arg Ser Gly Asp
        35                  40                  45

Arg Ser Met Val Glu Val Leu Ala Asp His Pro Gly Glu Leu Val Arg
    50                  55                  60

Thr Asp Ser Pro Asn Phe Leu Cys Ser Val Leu Pro Thr His Trp Arg
65                  70                  75                  80

Cys Asn Lys Thr Leu Pro Ile Ala Phe Lys Val Val Ala Leu Gly Asp
                85                  90                  95

Val Pro Asp Gly Thr Leu Val Thr Val Met Ala Gly Asn Asp Glu Asn
            100                 105                 110

Tyr Ser Ala Glu Leu Arg Asn Ala Thr Ala Ala Met Lys Asn Gln Val
        115                 120                 125

Ala Arg Phe Asn Asp Leu Arg Phe Val Asp Gly Pro Arg Glu Pro Arg
    130                 135                 140

Arg His Arg Gln Lys Leu Asp Asp Gln Thr Lys Pro Gly Ser Leu Ser
145                 150                 155                 160

```
Phe Ser Glu Arg Leu Ser Glu Leu Glu Gln Leu Arg Arg Thr Ala Met
                165                 170                 175
Arg Val Ser Pro His His Pro Ala Pro Thr Pro Asn Pro Arg Ala Ser
            180                 185                 190
Leu Asn His Ser Thr Ala Phe Asn Pro Gln Pro Gln Ser Gln Met Gln
        195                 200                 205
Asp Thr Arg Gln Ile Gln Pro Ser Pro Pro Trp Ser Tyr Asp Gln Ser
    210                 215                 220
Tyr Gln Tyr Leu Gly Ser Ile Ala Ser Pro Ser Val His Pro Ala Thr
225                 230                 235                 240
Pro Ile

<210> SEQ ID NO 8
<211> LENGTH: 480
<212> TYPE: PRT
<213> ORGANISM: Homo sapiens

<400> SEQUENCE: 8

Met Ala Ser Asp Ser Ile Phe Glu Ser Phe Pro Ser Tyr Pro Gln Cys
1               5                   10                  15
Phe Met Arg Glu Cys Ile Leu Gly Met Asn Pro Ser Arg Asp Val His
            20                  25                  30
Asp Ala Ser Thr Ser Arg Arg Phe Thr Pro Pro Ser Thr Ala Leu Ser
        35                  40                  45
Pro Gly Lys Met Ser Glu Ala Leu Pro Leu Gly Ala Pro Asp Ala Gly
    50                  55                  60
Ala Ala Leu Ala Gly Lys Leu Arg Ser Gly Asp Arg Ser Met Val Glu
65                  70                  75                  80
Val Leu Ala Asp His Pro Gly Glu Leu Val Arg Thr Asp Ser Pro Asn
                85                  90                  95
Phe Leu Cys Ser Val Leu Pro Thr His Trp Arg Cys Asn Lys Thr Leu
            100                 105                 110
Pro Ile Ala Phe Lys Val Val Ala Leu Gly Asp Val Pro Asp Gly Thr
        115                 120                 125
Leu Val Thr Val Met Ala Gly Asn Asp Glu Asn Tyr Ser Ala Glu Leu
    130                 135                 140
Arg Asn Ala Thr Ala Ala Met Lys Asn Gln Val Ala Arg Phe Asn Asp
145                 150                 155                 160
Leu Arg Phe Val Gly Arg Ser Gly Arg Gly Lys Ser Phe Thr Leu Thr
                165                 170                 175
Ile Thr Val Phe Thr Asn Pro Pro Gln Val Ala Thr Tyr His Arg Ala
            180                 185                 190
Ile Lys Ile Thr Val Asp Gly Pro Arg Glu Pro Arg Arg His Arg Gln
        195                 200                 205
Lys Leu Asp Asp Gln Thr Lys Pro Gly Ser Leu Ser Phe Ser Glu Arg
    210                 215                 220
Leu Ser Glu Leu Glu Gln Leu Arg Arg Thr Ala Met Arg Val Ser Pro
225                 230                 235                 240
His His Pro Ala Pro Thr Pro Asn Pro Arg Ala Ser Leu Asn His Ser
                245                 250                 255
Thr Ala Phe Asn Pro Gln Pro Gln Ser Gln Met Gln Asp Thr Arg Gln
            260                 265                 270
Ile Gln Pro Ser Pro Pro Trp Ser Tyr Asp Gln Ser Tyr Gln Tyr Leu
        275                 280                 285
```

```
Gly Ser Ile Ala Ser Pro Ser Val His Pro Ala Thr Pro Ile Ser Pro
    290                 295                 300

Gly Arg Ala Ser Gly Met Thr Thr Leu Ser Ala Glu Leu Ser Ser Arg
305                 310                 315                 320

Leu Ser Thr Ala Pro Asp Leu Thr Ala Phe Ser Asp Pro Arg Gln Phe
                325                 330                 335

Pro Ala Leu Pro Ser Ile Ser Asp Pro Arg Met His Tyr Pro Gly Ala
            340                 345                 350

Phe Thr Tyr Ser Pro Thr Pro Val Thr Ser Gly Ile Gly Ile Gly Met
        355                 360                 365

Ser Ala Met Gly Ser Ala Thr Arg Tyr His Thr Tyr Leu Pro Pro Pro
370                 375                 380

Tyr Pro Gly Ser Ser Gln Ala Gln Gly Gly Pro Phe Gln Ala Ser Ser
385                 390                 395                 400

Pro Ser Tyr His Leu Tyr Tyr Gly Ala Ser Ala Gly Ser Tyr Gln Phe
                405                 410                 415

Ser Met Val Gly Gly Glu Arg Ser Pro Pro Arg Ile Leu Pro Pro Cys
            420                 425                 430

Thr Asn Ala Ser Thr Gly Ser Ala Leu Leu Asn Pro Ser Leu Pro Asn
        435                 440                 445

Gln Ser Asp Val Val Glu Ala Glu Gly Ser His Ser Asn Ser Pro Thr
    450                 455                 460

Asn Met Ala Pro Ser Ala Arg Leu Glu Glu Ala Val Trp Arg Pro Tyr
465                 470                 475                 480

<210> SEQ ID NO 9
<211> LENGTH: 456
<212> TYPE: PRT
<213> ORGANISM: Homo sapiens

<400> SEQUENCE: 9

Met Asn Pro Ser Arg Asp Val His Asp Ala Ser Thr Ser Arg Arg Phe
1               5                   10                  15

Thr Pro Pro Ser Thr Ala Leu Ser Pro Gly Lys Met Ser Glu Ala Leu
                20                  25                  30

Pro Leu Gly Ala Pro Asp Ala Gly Ala Ala Leu Ala Gly Lys Leu Arg
            35                  40                  45

Ser Gly Asp Arg Ser Met Val Glu Val Leu Ala Asp His Pro Gly Glu
        50                  55                  60

Leu Val Arg Thr Asp Ser Pro Asn Phe Leu Cys Ser Val Leu Pro Thr
65                  70                  75                  80

His Trp Arg Cys Asn Lys Thr Leu Pro Ile Ala Phe Lys Val Val Ala
                85                  90                  95

Leu Gly Asp Val Pro Asp Gly Thr Leu Val Thr Val Met Ala Gly Asn
            100                 105                 110

Asp Glu Asn Tyr Ser Ala Glu Leu Arg Asn Ala Thr Ala Ala Met Lys
        115                 120                 125

Asn Gln Val Ala Arg Phe Asn Asp Leu Arg Phe Val Gly Arg Ser Gly
    130                 135                 140

Arg Gly Lys Ser Phe Thr Leu Thr Ile Thr Val Phe Thr Asn Pro Pro
145                 150                 155                 160

Gln Val Ala Thr Tyr His Arg Ala Ile Lys Ile Thr Val Asp Gly Pro
                165                 170                 175

Arg Glu Pro Arg Arg His Arg Gln Lys Leu Asp Asp Gln Thr Lys Pro
            180                 185                 190
```

```
Gly Ser Leu Ser Phe Ser Glu Arg Leu Ser Glu Leu Glu Gln Leu Arg
            195                 200                 205

Arg Thr Ala Met Arg Val Ser Pro His His Pro Ala Pro Thr Pro Asn
210                 215                 220

Pro Arg Ala Ser Leu Asn His Ser Thr Ala Phe Asn Pro Gln Pro Gln
225                 230                 235                 240

Ser Gln Met Gln Asp Thr Arg Gln Ile Gln Pro Ser Pro Pro Trp Ser
            245                 250                 255

Tyr Asp Gln Ser Tyr Gln Tyr Leu Gly Ser Ile Ala Ser Pro Ser Val
        260                 265                 270

His Pro Ala Thr Pro Ile Ser Pro Gly Arg Ala Ser Gly Met Thr Thr
                275                 280                 285

Leu Ser Ala Glu Leu Ser Ser Arg Leu Ser Thr Ala Pro Asp Leu Thr
    290                 295                 300

Ala Phe Ser Asp Pro Arg Gln Phe Pro Ala Leu Pro Ser Ile Ser Asp
305                 310                 315                 320

Pro Arg Met His Tyr Pro Gly Ala Phe Thr Tyr Ser Pro Thr Pro Val
            325                 330                 335

Thr Ser Gly Ile Gly Ile Gly Met Ser Ala Met Gly Ser Ala Thr Arg
        340                 345                 350

Tyr His Thr Tyr Leu Pro Pro Pro Tyr Pro Gly Ser Ser Gln Ala Gln
                355                 360                 365

Gly Gly Pro Phe Gln Ala Ser Ser Pro Ser Tyr His Leu Tyr Tyr Gly
    370                 375                 380

Ala Ser Ala Gly Ser Tyr Gln Phe Ser Met Val Gly Gly Glu Arg Ser
385                 390                 395                 400

Pro Pro Arg Ile Leu Pro Pro Cys Thr Asn Ala Ser Thr Gly Ser Ala
            405                 410                 415

Leu Leu Asn Pro Ser Leu Pro Asn Gln Ser Asp Val Val Glu Ala Glu
        420                 425                 430

Gly Ser His Ser Asn Ser Pro Thr Asn Met Ala Pro Ser Ala Arg Leu
                435                 440                 445

Glu Glu Ala Val Trp Arg Pro Tyr
    450                 455

<210> SEQ ID NO 10
<211> LENGTH: 468
<212> TYPE: PRT
<213> ORGANISM: Homo sapiens

<400> SEQUENCE: 10

Met Pro Ala Ala Pro Arg Gly Pro Ala Gln Gly Glu Ala Ala Ala Arg
1               5                   10                  15

Thr Arg Ser Arg Asp Ala Ser Thr Ser Arg Arg Phe Thr Pro Pro Ser
            20                  25                  30

Thr Ala Leu Ser Pro Gly Lys Met Ser Glu Ala Leu Pro Leu Gly Ala
        35                  40                  45

Pro Asp Ala Gly Ala Ala Leu Ala Gly Lys Leu Arg Ser Gly Asp Arg
    50                  55                  60

Ser Met Val Glu Val Leu Ala Asp His Pro Gly Glu Leu Val Arg Thr
65                  70                  75                  80

Asp Ser Pro Asn Phe Leu Cys Ser Val Leu Pro Thr His Trp Arg Cys
            85                  90                  95

Asn Lys Thr Leu Pro Ile Ala Phe Lys Val Val Ala Leu Gly Asp Val
```

```
            100                 105                 110
Pro Asp Gly Thr Leu Val Thr Val Met Ala Gly Asn Asp Glu Asn Tyr
            115                 120                 125

Ser Ala Glu Leu Arg Asn Ala Thr Ala Met Lys Asn Gln Val Ala
130                 135                 140

Arg Phe Asn Asp Leu Arg Phe Val Gly Arg Ser Gly Arg Gly Lys Ser
145                 150                 155                 160

Phe Thr Leu Thr Ile Thr Val Phe Thr Asn Pro Pro Gln Val Ala Thr
                    165                 170                 175

Tyr His Arg Ala Ile Lys Ile Thr Val Asp Gly Pro Arg Glu Pro Arg
                    180                 185                 190

Arg His Arg Gln Lys Leu Asp Asp Gln Thr Lys Pro Gly Ser Leu Ser
                    195                 200                 205

Phe Ser Glu Arg Leu Ser Glu Leu Glu Gln Leu Arg Arg Thr Ala Met
210                 215                 220

Arg Val Ser Pro His His Pro Ala Pro Thr Pro Asn Pro Arg Ala Ser
225                 230                 235                 240

Leu Asn His Ser Thr Ala Phe Asn Pro Gln Pro Gln Ser Gln Met Gln
                    245                 250                 255

Asp Thr Arg Gln Ile Gln Pro Ser Pro Pro Trp Ser Tyr Asp Gln Ser
                    260                 265                 270

Tyr Gln Tyr Leu Gly Ser Ile Ala Ser Pro Ser Val His Pro Ala Thr
                    275                 280                 285

Pro Ile Ser Pro Gly Arg Ala Ser Gly Met Thr Thr Leu Ser Ala Glu
290                 295                 300

Leu Ser Ser Arg Leu Ser Thr Ala Pro Asp Leu Thr Ala Phe Ser Asp
305                 310                 315                 320

Pro Arg Gln Phe Pro Ala Leu Pro Ser Ile Ser Asp Pro Arg Met His
                    325                 330                 335

Tyr Pro Gly Ala Phe Thr Tyr Ser Pro Thr Pro Val Thr Ser Gly Ile
                    340                 345                 350

Gly Ile Gly Met Ser Ala Met Gly Ser Ala Thr Arg Tyr His Thr Tyr
                    355                 360                 365

Leu Pro Pro Tyr Pro Gly Ser Ser Gln Ala Gln Gly Gly Pro Phe
370                 375                 380

Gln Ala Ser Ser Pro Ser Tyr His Leu Tyr Tyr Gly Ala Ser Ala Gly
385                 390                 395                 400

Ser Tyr Gln Phe Ser Met Val Gly Gly Glu Arg Ser Pro Pro Arg Ile
                    405                 410                 415

Leu Pro Pro Cys Thr Asn Ala Ser Thr Gly Ser Ala Leu Leu Asn Pro
                    420                 425                 430

Ser Leu Pro Asn Gln Ser Asp Val Val Glu Ala Glu Gly Ser His Ser
                    435                 440                 445

Asn Ser Pro Thr Asn Met Ala Pro Ser Ala Arg Leu Glu Glu Ala Val
                    450                 455                 460

Trp Arg Pro Tyr
465

<210> SEQ ID NO 11
<211> LENGTH: 348
<212> TYPE: PRT
<213> ORGANISM: Homo sapiens

<400> SEQUENCE: 11
```

```
Met Ala Gly Asn Asp Glu Asn Tyr Ser Ala Glu Leu Arg Asn Ala Thr
1               5                   10                  15

Ala Ala Met Lys Asn Gln Val Ala Arg Phe Asn Asp Leu Arg Phe Val
            20                  25                  30

Gly Arg Ser Gly Arg Gly Lys Ser Phe Thr Leu Thr Ile Thr Val Phe
        35                  40                  45

Thr Asn Pro Pro Gln Val Ala Thr Tyr His Arg Ala Ile Lys Ile Thr
    50                  55                  60

Val Asp Gly Pro Arg Glu Pro Arg Arg His Arg Gln Lys Leu Asp Asp
65                  70                  75                  80

Gln Thr Lys Pro Gly Ser Leu Ser Phe Ser Glu Arg Leu Ser Glu Leu
                85                  90                  95

Glu Gln Leu Arg Arg Thr Ala Met Arg Val Ser Pro His His Pro Ala
            100                 105                 110

Pro Thr Pro Asn Pro Arg Ala Ser Leu Asn His Ser Thr Ala Phe Asn
        115                 120                 125

Pro Gln Pro Gln Ser Gln Met Gln Asp Thr Arg Gln Ile Gln Pro Ser
    130                 135                 140

Pro Pro Trp Ser Tyr Asp Gln Ser Tyr Gln Tyr Leu Gly Ser Ile Ala
145                 150                 155                 160

Ser Pro Ser Val His Pro Ala Thr Pro Ile Ser Pro Gly Arg Ala Ser
                165                 170                 175

Gly Met Thr Thr Leu Ser Ala Glu Leu Ser Ser Arg Leu Ser Thr Ala
            180                 185                 190

Pro Asp Leu Thr Ala Phe Ser Asp Pro Arg Gln Phe Pro Ala Leu Pro
        195                 200                 205

Ser Ile Ser Asp Pro Arg Met His Tyr Pro Gly Ala Phe Thr Tyr Ser
    210                 215                 220

Pro Thr Pro Val Thr Ser Gly Ile Gly Ile Gly Met Ser Ala Met Gly
225                 230                 235                 240

Ser Ala Thr Arg Tyr His Thr Tyr Leu Pro Pro Tyr Pro Gly Ser
                245                 250                 255

Ser Gln Ala Gln Gly Gly Pro Phe Gln Ala Ser Ser Pro Ser Tyr His
            260                 265                 270

Leu Tyr Tyr Gly Ala Ser Ala Gly Ser Tyr Gln Phe Ser Met Val Gly
        275                 280                 285

Gly Glu Arg Ser Pro Pro Arg Ile Leu Pro Pro Cys Thr Asn Ala Ser
    290                 295                 300

Thr Gly Ser Ala Leu Leu Asn Pro Ser Leu Pro Asn Gln Ser Asp Val
305                 310                 315                 320

Val Glu Ala Glu Gly Ser His Ser Asn Ser Pro Thr Asn Met Ala Pro
                325                 330                 335

Ser Ala Arg Leu Glu Glu Ala Val Trp Arg Pro Tyr
            340                 345

<210> SEQ ID NO 12
<211> LENGTH: 7274
<212> TYPE: DNA
<213> ORGANISM: Homo sapiens

<400> SEQUENCE: 12
catagagcca gcgggcgcgg gcgggacggg cgccccgcgg ccggacccag ccagggcacc    60
acgctgcccg gccctgcgcc gccaggcact tctttccggg gctcctaggg acgccagaag   120
gaagtcaacc tctgctgctt ctccttggcc tgcgttggac cttcctttt ttgttgtttt   180
```

```
tttttgtttt tccccttttct tccttttgaa ttaactggct tcttggctgg atgttttcaa      240
cttctttcct ggctgcgaac ttttccccaa ttgttttcct tttacaacag ggggagaaag      300
tgctctgtgg tccgaggcga gccgtgaagt tgcgtgtgcg tggcagtgtg cgtggcagga      360
tgtgcgtgcg tgtgtaaccc gagccgcccg atctgtttcg atctgcgccg cggagccctc      420
cctcaaggcc cgctccacct gctgcggtta cgcggcgctc gtgggtgttc gtgcctcgga      480
gcagctaacc ggcgggtgct gggcgacggt ggaggagtat cgtctcgctg ctgcccgagt      540
cagggctgag tcacccagct gatgtagaca gtggctgcct tccgaagagt gcgtgtttgc      600
atgtgtgtga ctctgcggct gctcaactcc caacaaacca gaggaccagc cacaaactta      660
accaacatcc ccaaacccga gttcacagat gtgggagagc tgtagaaccc tgagtgtcat      720
cgactgggcc ttcttatgat tgttgtttta agattagctg aagatctctg aaacgctgaa      780
ttttctgcac tgagcgtttt gacagaattc attgagagaa cagagaacat gacaagtact      840
tctagctcag cactgctcca actactgaag ctgattttca aggctactta aaaaaatctg      900
cagcgtacat taatggattt ctgttgtgtt taaattctcc acagattgta ttgtaaatat      960
tttatgaagt agagcatatg tatatattta tatatacgtg cacatacatt agtagcacta     1020
cctttggaag tctcagctct tgcttttcgg gactgaagcc agttttgcat gataaaagtg     1080
gccttgttac gggagataat tgtgttctgt tgggacttta gacaaaactc acctgcaaaa     1140
aactgacagg cattaactac tggaacttcc aaataatgtg tttgctgatc gttttactct     1200
tcgcataaat attttaggaa gtgtatgaga attttgcctt caggaacttt tctaacagcc     1260
aaagacagaa cttaacctct gcaagcaaga ttcgtggaag atagtctcca cttttaatg     1320 cactaagcaa tcggttgcta ggagcccatc ctgggtcaga ggccgatccg cagaaccaga     1380
acgttttccc ctcctggact gttagtaact tagtctccct cctccctaa ccaccccgc      1440 cccccccac cccccgcagt aataaaggcc cctgaacgtg tatgttggtc tcccgggagc     1500
tgcttgctga agatccgcgc ccctgtcgcc gtctggtagg agctgtttgc agggtcctaa     1560
ctcaatcggc ttgttgtgat gcgtatcccc gtagatgcca gcacgagccg ccgcttcacg     1620
ccgccttcca ccgcgctgag cccaggcaag atgagcgagg cgttgccgct gggcgccccg     1680
gacgccggcg ctgccctggc cggcaagctg aggagcggcg accgcagcat ggtggaggtg     1740
ctggccgacc acccgggcga gctggtgcgc accgacagcc ccaacttcct ctgctccgtg     1800
ctgcctacgc actggcgctg caacaagacc ctgcccatcg ctttcaaggt ggtggcccta     1860
ggggatgttc cagatggcac tctggtcact gtgatggctg gcaatgatga aaactactcg     1920
gctgagctga gaaatgctac cgcagccatg aagaaccagg ttgcaagatt taatgacctc     1980
aggtttgtcg gtcgaagtgg aagagggaaa agcttcactc tgaccatcac tgtcttcaca     2040
aacccaccgc aagtcgccac ctaccacaga gccatcaaaa tcacagtgga tgggccccga     2100
gaacctcgaa gacatcggca gaaactagat gatcagacca gcccgggag cttgtccttt     2160 tccgagcggc tcagtgaact ggagcagctg cggcgcacag ccatgagggt cagcccacac     2220
cacccagccc ccacgcccaa ccctcgtgcc tccctgaacc actccactgc ctttaaccct     2280
cagcctcaga gtcagatgca ggatacaagg cagatccaac catccccacc gtggtcctac     2340
gatcagtcct accaataccct gggatccatt gcctctcctt ctgtgcaccc agcaacgccc     2400
atttcacctg gacgtgccag cggcatgaca acccctctg cagaactttc cagtcgactc     2460
tcaacggcac ccgacctgac agcgttcagc gaccgcgcc agttcccgc gctgccctcc      2520
```

-continued

```
atctccgacc cccgcatgca ctatccaggc gccttcacct actccccgac gccggtcacc    2580
tcgggcatcg gcatcggcat gtcggccatg ggctcggcca cgcgctacca cacctacctg    2640
ccgccgccct accccggctc gtcgcaagcg cagggaggcc cgttccaagc cagctcgccc    2700
tcctaccacc tgtactacgg cgcctcggcc ggctcctacc agttctccat ggtgggcggc    2760
gagcgctcgc cgccgcgcat cctgccgccc tgcaccaacg cctccaccgg ctccgcgctg    2820
ctcaacccca gcctcccgaa ccagagcgac gtggtggagg ccgagggcag ccacagcaac    2880
tcccccacca acatggcgcc ctccgcgcgc ctggaggagg ccgtgtggag gccctactga    2940
ggcgccaggc ctggcccggc tgggcccgcg gggccgccgc cttcgcctcc gggcgcgcgg    3000
gcctcctgtt cgcgacaagc ccgccgggat cccgggccct gggcccggcc accgtcctgg    3060
ggccgagggc gcccgacggc caggatctcg ctgtaggtca ggcccgcgca gcctcctgcg    3120
cccagaagcc cacgccgccg ccgtctgctg gcgcccccgg cctcgcggag gtgtccgagg    3180
cgacgcacct cgagggtgtc cgccggcccc agcacccagg ggacgcgctg gaaagcaaac    3240
aggaagattc ccgagggaa  actgtgaatg cttctgattt agcaatgctg tgaataaaaa    3300
gaaagatttt ataccttga  cttaactttt taaccaagtt gtttattcca aagagtgtgg    3360
aattttggtt ggggtgggg  gagaggaggg atgcaactcg ccctgtttgg catctaattc    3420
ttatttttaa tttttccgca ccttatcaat tgcaaaatgc gtatttgcat ttgggtggtt    3480
tttatttta  tatacgttta tataaatata tataaattga gcttgcttct ttcttgcttt    3540
gaccatggaa agaaatatga ttcccttttc tttaagtttt atttaacttt tcttttggac    3600
ttttgggtag ttgttttttt ttgttttgtt ttgtttttt  gagaaacagc tacagctttg    3660
ggtcatttt  aactactgta ttcccacaag gaatccccag atatttatgt atcttgatgt    3720
tcagacattt atgtgttgat aattttttaa ttatttaaat gtactatat  taagaaaat    3780
atcaagtact acattttctt ttgttcttga tagtagccaa agttaaatgt atcacattga    3840
agaaggctag aaaaaaagaa tgagtaatgt gatcgcttgg ttatccagaa gtattgttta    3900
cattaaactc cctttcatgt taatcaaaca agtgagtagc tcacgcagca acgtttttaa    3960
taggatttt  agacactgag ggtcactcca aggatcagaa gtatggaatt ttctgccagg    4020
ctcaacaagg gtctcatatc taacttcctc cttaaaacag agaaggtcaa tctagttcca    4080
gagggttgag gcaggtgcca ataattacat cttggagag  gatttgattt ctgcccaggg    4140
atttgctcac cccaaggtca tctgataatt tcacagatgc tgtgtaacag aacacagcca    4200
aagtaaactg tgtaggggag ccacatttac ataggaacca aatcaatgaa tttagggtt    4260
acgattatag caatttaagg gcccaccaga agcaggcctc gaggagtcaa tttgcctctg    4320
tgtgcctcag tggagacaag tgggaaaaca tggtcccacc tgtgcgagac ccctgtcct   4380
gtgctgctca ctcaacaaca tctttgtgtt gctttcacca ggctgagacc ctaccctatg    4440
gggtatatgg gcttttacct gtgcaccagt gtgacaggaa agattcatgt cactactgtc    4500
cgtggctaca attcaaaggt atccaatgtc gctgtaaatt ttatggcact attttattg    4560
gaggatttgg tcagaatgca gttgttgtac aactcataaa tactaactgc tgattttgac    4620
acatgtgtgc tccaaatgat ctggtggtta tttaacgtac ctcttaaaat tcgttgaaac    4680
gatttcaggt caactctgaa gagtatttga aagcaggact tcagaacagt gtttgatttt    4740
tatttttataa atttaagcat tcaaattagg caaatctttg gctgcaggca gcaaaaacag    4800
ctggacttat ttaaaacaac ttgttttga  gttttcttat atatatattg attatttgtt    4860
ttacacacat gcagtagcac tttggtaaga gttaaagagt aaagcagctt atgttgtcag    4920
```

```
gtcgttctta tctagagaag agctatagca gatctcggac aaactcagaa tatattcact    4980
ttcatttttg acaggattcc ctccacaact cagtttcata tattattccg tattacattt    5040
ttgcagctaa attaccataa aatgtcagca aatgtaaaaa tttaatttct gaaaagcacc    5100
attagcccat ttcccccaaa ttaaacgtaa atgttttttt tcagcacatg ttaccatgtc    5160
tgacctgcaa aaatgctgga gaaaatgaa ggaaaaaatt atgttttca gtttaattct     5220 gttaactgaa gatattccaa ctcaaaacca gcctcatgct ctgattagat aatcttttac    5280
attgaacctt tactctcaaa gccatgtgtg gaggggcctt gtcactattg taggctcact    5340
ggattggtca tttagagttt cacagactct taccagcata tatagtattt aattgtttca    5400
aaaaaaatca aactgtagtt gttttggcga taggtctcac gcaacacatt tttgtatgtg    5460
tgtgtgtgtg cgtgtgtgtg tgtgtgtgtg aaaaattgca ttcattgact tcaggtagat    5520
taaggtatct ttttattcat tgccctcagg aaagttaagg tatcaatgag acccttaagc    5580
caatcatgta ataactgcat gtgtctggtc caggagaagt attgaataag ccatttctac    5640
tgcttactca tgtccctatt tatgatttca acatggatac atatttcagt tctttctttt    5700
tctcactatc tgaaaataca tttccctccc tctcttcccc ccaatatctc cctttttttc    5760
tctcttcctc tatcttccaa accccacttt ctccctcctc cttttcctgt gttctcttaa    5820
gcagatagca catacccca cccagtacca aatttcagaa cacaagaagg tccagttctt     5880
cccccttcac ataaaggaac atggtttgtc agcctttctc ctgtttatgg gtttcttcca    5940
gcagaacaga gacattgcca accatattgg atctgcttgc tgtccaaacc agcaaacttt    6000
cctgggcaaa tcacaatcag tgagtaaata gacagccttt ctgctgcctt gggtttctgt    6060
gcagataaac agaaatgctc tgattagaaa ggaaatgaat ggttccactc aaatgtcctg    6120
caatttagga ttgcagattt ctgccttgaa atacctgttt ctttgggaca ttccgtcctg    6180 atgatttta ttttgttgg ttttttatttt tgggggaat gacatgtttg ggtcttttat      6240
acatgaaaat ttgtttgaca ataatctcac aaaacatatt ttacatctga acaaaatgcc    6300
tttttgttta ccgtagcgta tacatttgtt ttgggatttt tgtgtgtttg ttgggaattt    6360 tgttttagc caggtcagta ttgatgaggc tgatcatttg gctctttttt tccttccaga    6420
agagttgcat caacaaagtt aattgtattt atgtatgtaa atagatttta gcttcatta    6480 taaaatattg ttaatgccta taactttttt tcaattttt tgtgtgtgtt tctaaggact     6540
ttttcttagg tttgctaaat actgtaggga aaaaatgct tctttctact ttgtttattt     6600
tagactttaa aatgagctac ttcttattca cttttgtaaa cagctaatag catggttcca    6660
atttttttta agttcacttt ttttgttcta ggggaaatga atgtgcaaaa aaagaaaaag    6720
aactgttggt tatttgtgtt attctggatg tataaaaatc aatggaaaaa ataaacttt     6780 caaattgaaa tgacggtata acacatctac tgaaaagca acgggaaatg tggtcctatt     6840
taagccagcc cccacctagg gtctatttgt gtggcagtta ttgggtttgg tcacaaaaca    6900
tcctgaaaat tcgtgcgtgg gcttctttct ccctggtaca aacgtatgga atgcttctta    6960
aaggggaact gtcaagctgg tgtcttcagc cagatgacat gagagaatat cccagaaccc    7020
tctctccaag gtgtttctag atagcacagg agagcaggca ctgcactgtc cacagtccac    7080
ggtacacagt cgggtgggcc gcctcccctc tcctgggagc attcgtcgtg cccagcctga    7140
gcagggcagc tggactgctg ctgttcagga gccaccagag ccttcctctc tttgtaccac    7200
agtttcttct gtaaatccag tgttacaatc agtgtgaatg gcaaataaac agtttgacaa    7260
```

```
gtacatacac cata                                                  7274

<210> SEQ ID NO 13
<211> LENGTH: 5967
<212> TYPE: DNA
<213> ORGANISM: Homo sapiens

<400> SEQUENCE: 13
ctttgggcct cataaacaac cacagaacca caagttgggt agcctggcag tgtcagaagt    60
ctgaacccag catagtggtc agcaggcagg acgaatcaca ctgaatgcaa accacagggt   120
ttcgcagcgt ggtaaaagaa atcattgagt cccccgcctt cagaagaggg tgcattttca   180
ggaggaagcg atggcttcag acagcatatt tgagtcattt ccttcgtacc cacagtgctt   240
catgagagaa tgcatacttg gaatgaatcc ttctagagac gtccacgatg ccagcacgag   300
ccgccgcttc acgccgcctt ccaccgcgct gagcccaggc aagatgagcg aggcgttgcc   360
gctgggcgcc ccggacgccg cgcgctgccct ggccggcaag ctgaggagcg cgaccgcag   420 catggtggag gtgctggccg accacccggg cgagctggtg cgcaccgaca gccccaactt   480
cctctgctcc gtgctgccta cgcactggcg ctgcaacaag accctgccca tcgcttttcaa   540 ggtggtggcc ctaggggatg ttccagatgg cactctggtc actgtgatgg ctggcaatga   600
tgaaaactac tcggctgagc tgagaaatgc taccgcagcc atgaagaacc aggttgcaag   660
atttaatgac ctcaggtttg tcggtcgaag tggaagaggg aaaagcttca ctctgaccat   720
cactgtcttc acaaacccac cgcaagtcgc cacctaccac agagccatca aaatcacagt   780
ggatgggccc cgagaacctc gaagacatcg gcagaaacta gatgatcaga ccaagcccgg   840
gagcttgtcc tttttccgagc ggctcagtga actggagcag ctgcggcgca cagccatgag   900
ggtcagccca caccacccag cccccacgcc caaccctcgt gcctccctga ccactccac   960 tgcctttaac cctcagcctc agagtcagat gcaggataca aggcagatcc aaccatcccc  1020
accgtggtcc tacgatcagt cctaccaata cctgggatcc attgcctctc cttctgtgca  1080
cccagcaacg cccatttcac ctggacgtgc cagcggcatg acaaccctct ctgcagaact  1140
ttccagtcga ctctcaacgg cacccgacct gacagcgttc agcgacccgc gccagttccc  1200
cgcgctgccc tccatctccg acccccgcat gcactatcca ggcgccttca cctactcccc  1260
gacgccggtc acctcgggca tcggcatcgg catgtcggcc atgggctcgg ccacgcgcta  1320
ccacacctac ctgccgccgc cctacccgg ctcgtcgcaa gcgcagggag gcccgttcca  1380
agccagctcg ccctcctacc acctgtacta cggcgcctcg gccggctcct accagttctc  1440
catggtgggc ggcgagcgct cgccgccgcg catcctgccg ccctgcacca acgcctccac  1500
cggctccgcg ctgctcaacc ccagcctccc gaaccagagc gacgtggtgg aggccgaggg  1560
cagccacagc aactccccca ccaacatggc gccctccgcg cgcctggagg aggccgtgtg  1620
gagggcctac tgaggcgcca ggcctggccc ggctgggccc cgcgggccgc cgccttcgcc  1680
tccgggcgcg cgggcctcct gttcgcgaca agcccgccgg gatcccgggc cctgggcccg  1740
gccaccgtcc tggggccgag ggcgcccgac ggccaggatc tcgctgtagg tcaggcccgc  1800
gcagcctcct gcgcccagaa gcccacgccg ccgccgtctg ctggcgcccc ggccctcgcg  1860
gaggtgtccg aggcgacgca cctcgagggt gtccgccggc cccagcaccc aggggacgcg  1920
ctggaaagca aacaggaaga ttcccggagg gaaactgtga atgcttctga tttagcaatg  1980
ctgtgaataa aaagaaagat tttataccct tgacttaact ttttaaccaa gttgtttatt  2040
ccaaagagtg tggaattttg gttggggtgg ggggagagga gggatgcaac tcgccctgtt  2100
```

-continued

```
tggcatctaa ttcttatttt taattttttcc gcaccttatc aattgcaaaa tgcgtatttg    2160
catttgggtg gtttttattt ttatatacgt ttatataaat atatataaat tgagcttgct    2220
tctttcttgc tttgaccatg gaaagaaata tgattccctt ttctttaagt tttatttaac    2280
ttttcttttg gactttgggg tagttgtttt tttttgtttt gttttgtttt tttgagaaac    2340
agctacagct ttgggtcatt tttaactact gtattcccac aaggaatccc cagatattta    2400
tgtatcttga tgttcagaca tttatgtgtt gataattttt taattattta aatgtactta    2460
tattaagaaa aatatcaagt actacatttt cttttgttct tgatagtagc caaagttaaa    2520
tgtatcacat tgaagaaggc tagaaaaaaa gaatgagtaa tgtgatcgct tggttatcca    2580
gaagtattgt ttacattaaa ctccctttca tgttaatcaa acaagtgagt agctcacgca    2640
gcaacgtttt taataggatt tttagacact gagggtcact ccaaggatca gaagtatgga    2700
attttctgcc aggctcaaca agggtctcat atctaacttc ctccttaaaa cagagaaggt    2760
caatctagtt ccagagggtt gaggcaggtg ccaataatta catctttgga gaggatttga    2820
tttctgccca gggatttgct caccccaagg tcatctgata atttcacaga tgctgtgtaa    2880
cagaacacag ccaaagtaaa ctgtgtaggg gagccacatt tacataggaa ccaaatcaat    2940
gaatttaggg gttacgatta tagcaattta agggcccacc agaagcaggc ctcgaggagt    3000
caatttgcct ctgtgtgcct cagtggagac aagtgggaaa acatggtccc acctgtgcga    3060 gacccctgt cctgtgctgc tcactcaaca acatctttgt gttgctttca ccaggctgag    3120
accctaccct atggggtata tgggctttta cctgtgcacc agtgtgacag gaaagattca    3180
tgtcactact gtccgtggct acaattcaaa ggtatccaat gtcgctgtaa atttttatggc    3240 actatttta ttggaggatt tggtcagaat gcagttgttg tacaactcat aaatactaac    3300
tgctgatttt gacacatgtg tgctccaaat gatctggtgg ttatttaacg tacctcttaa    3360
aattcgttga aacgatttca ggtcaactct gaagagtatt tgaaagcagg acttcagaac    3420
agtgtttgat ttttatttta taaatttaag cattcaaatt aggcaaatct ttggctgcag    3480
gcagcaaaaa cagctggact tatttaaaac aacttgtttt tgagttttct tatatatata    3540
ttgattattt gttttacaca catgcagtag cactttggta agagttaaag agtaaagcag    3600
cttatgttgt caggtcgttc ttatctagag aagagctata gcagatctcg gacaaactca    3660
gaatatattc actttcattt ttgacaggat tccctccaca actcagtttc atatattatt    3720
ccgtattaca tttttgcagc taaattacca taaaatgtca gcaaatgtaa aaatttaatt    3780
tctgaaaagc accattagcc catttccccc aaattaaacg taaatgtttt ttttcagcac    3840
atgttaccat gtctgacctg caaaaatgct ggagaaaaat gaaggaaaaa attatgtttt    3900
tcagtttaat tctgttaact gaagatattc caactcaaaa ccagcctcat gctctgatta    3960
gataatcttt tacattgaac ctttactctc aaagccatgt gtggagggggg cttgtcacta    4020 ttgtaggctc actggattgg tcatttagag tttcacagac tcttaccagc atatatagta    4080
tttaattgtt tcaaaaaaaa tcaaactgta gttgttttgg cgataggtct cacgcaacac    4140 attttttgtat gtgtgtgtgt gtgcgtgtgt gtgtgtgtgt gtgaaaaatt gcattcattg    4200
acttcaggta gattaaggta tctttttatt cattgccctc aggaaagtta aggtatcaat    4260 gagacccttta agccaatcat gtaataactg catgtgtctg gtccaggaga agtattgaat    4320
aagccatttc tactgcttac tcatgtccct atttatgatt tcaacatgga tacatatttc    4380
agttctttct ttttctcact atctgaaaat acatttccct ccctctcttc cccccaatat    4440
```

```
ctcccttttt ttctctcttc ctctatcttc caaaccccac tttctccctc ctccttttcc      4500
tgtgttctct taagcagata gcacataccc ccacccagta ccaaatttca gaacacaaga      4560
aggtccagtt cttcccccctt cacataaagg aacatggttt gtcagccttt ctcctgttta    4620
tgggtttctt ccagcagaac agagacattg ccaaccatat tggatctgct tgctgtccaa      4680
accagcaaac tttcctgggc aaatcacaat cagtgagtaa atagacagcc tttctgctgc     4740
cttgggtttc tgtgcagata aacagaaatg ctctgattag aaaggaaatg aatggttcca     4800
ctcaaatgtc ctgcaattta ggattgcaga tttctgcctt gaaatacctg tttctttggg     4860
acattccgtc ctgatgattt ttattttttgt tggttttttat ttttgggggg aatgacatgt   4920
ttgggtcttt tatacatgaa aatttgtttg acaataatct cacaaaacat attttacatc    4980
tgaacaaaat gccttttttgt ttaccgtagc gtatacattt gttttgggat ttttgtgtgt   5040
ttgttgggaa ttttgttttt agccaggtca gtattgatga ggctgatcat ttggctcttt    5100
ttttccttcc agaagagttg catcaacaaa gttaattgta tttatgtatg taaatagatt    5160
ttaagcttca ttataaaata ttgttaatgc ctataacttt ttttcaattt ttttgtgtgt    5220
gtttctaagg acttttttctt aggtttgcta aatactgtag ggaaaaaaat gcttctttct   5280
actttgttta tttttagactt taaaatgagc tacttcttat tcactttttgt aaacagctaa  5340
tagcatggtt ccaattttttt ttaagttcac ttttttttgtt ctaggggaaa tgaatgtgca  5400
aaaaaagaaa aagaactgtt ggttatttgt gttattctgg atgtataaaa atcaatggaa    5460
aaaaataaac tttcaaattg aaatgacggt ataacacatc tactgaaaaa gcaacgggaa    5520
atgtggtcct atttaagcca gcccccacct agggtctatt tgtgtggcag ttattgggtt    5580
tggtcacaaa acatcctgaa aattcgtgcg tgggcttctt tctccctggt acaaacgtat    5640
ggaatgcttc ttaaagggga actgtcaagc tggtgtcttc agccagatga catgagagaa    5700
tatcccagaa ccctctctcc aaggtgtttc tagatagcac aggagagcag gcactgcact    5760
gtccacagtc cacggtacac agtcgggtgg gccgcctccc ctctcctggg agcattcgtc    5820
gtgcccagcc tgagcagggc agctggactg ctgctgttca ggagccacca gagccttcct   5880
ctctttgtac cacagtttct tctgtaaatc cagtgttaca atcagtgtga atggcaaata    5940
aacagtttga caagtacata caccata                                        5967
```

<210> SEQ ID NO 14
<211> LENGTH: 2722
<212> TYPE: DNA
<213> ORGANISM: Homo sapiens

<400> SEQUENCE: 14

```
catagagcca gcgggcgcgg gcgggacggg cgccccgcgg ccggacccag ccagggcacc       60
acgctgcccg gccctgcgcc gccaggcact tctttccggg gctcctaggg acgccagaag      120
gaagtcaacc tctgctgctt ctccttggcc tgcgttggac cttccttttt ttgttgtttt     180
tttttgtttt tccccttttct tccttttgaa ttaactggct tcttggctgg atgttttcaa    240
cttctttcct ggctgcgaac ttttccccaa ttgttttcct tttacaacag ggggagaaag    300
tgctctgtgg tccgaggcga gccgtgaagt tgcgtgtgcg tggcagtgtg cgtggcagga    360
tgtgcgtgcg tgtgtaaccc gagccgcccg atctgtttcg atctgcgccg cggagccctc    420
cctcaaggcc cgctccacct gctgcggtta cgcggcgctc gtgggtgttc gtgcctcgga     480
gcagctaacc ggcgggtgct gggcgacggt ggaggagtat cgtctcgctg ctgcccgagt    540
cagggctgag tcacccagct gatgtagaca gtggctgcct tccgaagagt gcgtgtttgc     600
```

```
atgtgtgtga ctctgcggct gctcaactcc caacaaacca gaggaccagc cacaaactta    660
accaacatcc ccaaacccga gttcacagat gtgggagagc tgtagaaccc tgagtgtcat    720
cgactgggcc ttcttatgat tgttgtttta agattagctg aagatctctg aaacgctgaa    780
ttttctgcac tgagcgtttt gacagaattc attgagagaa cagagaacat gacaagtact    840
tctagctcag cactgctcca actactgaag ctgattttca aggctactta aaaaaatctg    900
cagcgtacat taatggattt ctgttgtgtt taaattctcc acagattgta ttgtaaatat    960
tttatgaagt agagcatatg tatatattta tatacgtgt cacatacatt agtagcacta   1020
cctttggaag tctcagctct tgcttttcgg gactgaagcc agttttgcat gataaaagtg   1080
gccttgttac gggagataat tgtgttctgt tgggactttta gacaaaactc acctgcaaaa   1140
aactgacagg cattaactac tggaacttcc aaataatgtg tttgctgatc gttttactct   1200
tcgcataaat atttttaggaa gtgtatgaga attttgcctt caggaacttt tctaacagcc   1260
aaagacagaa cttaacctct gcaagcaaga ttcgtggaag atagtctcca cttttttaatg   1320
cactaagcaa tcggttgcta ggagcccatc ctgggtcaga ggccgatccg cagaaccaga   1380
acgttttccc ctcctggact gttagtaact tagtctccct cctcccctaa ccaccccgc    1440
cccccccac ccccgcagt aataaaggcc cctgaacgtg tatgttggtc tcccgggagc     1500
tgcttgctga agatccgcgc ccctgtcgcc gtctggtagg agctgtttgc agggtcctaa   1560
ctcaatcggc ttgttgtgat gcgtatcccc gtagatgcca gcacgagccg ccgcttcacg   1620
ccgccttcca ccgcgctgag cccaggcaag atgagcgagg cgttgccgct gggcgccccg   1680
gacgccggcg ctgccctggc cggcaagctg aggagcggcg accgcagcat ggtggaggtg   1740
ctggccgacc acccgggcga gctggtgcgc accgacagcc caacttcct ctgctccgtg    1800
ctgcctacgc actggcgctg caacaagacc ctgcccatcg ctttcaaggt ggtggcccta   1860
ggggatgttc cagatggcac tctggtcact gtgatggctg gcaatgatga aaactactcg   1920
gctgagctga gaaatgctac cgcagccatg aagaaccagg ttgcaagatt taatgaccctc  1980
aggtttgtcg gtcgaagtgg aagagggaaa agcttcactc tgaccatcac tgtcttcaca   2040
aacccaccgc aagtcgccac ctaccacaga gccatcaaaa tcacagtgga tgggccccga   2100
gaacctcgaa gacatcggca gaaactagat gatcagacca gcccgggag cttgtccttt    2160
tccgagcggc tcagtgaact ggagcagctg cggcgcacag ccatgagggt cagcccacac   2220
cacccagccc ccacgcccaa ccctcgtgcc tccctgaacc actccactgc ctttaaccct   2280
cagcctcaga gtcagatgca ggaggaagac acagcaccct ggagatgtta aggcagaagt   2340
cagttcttct gtccatccct ctccccagcc aggatagagc tatctttcc atctcatcct    2400
cagaagagac tcagaagaaa gatgacagcc ctcagaatgc acgttatgag gaaggcagaa   2460
tgtgggtctg taattcctcc gtgtcccttc tcccctctg caaaccgtcg taacaataat    2520
agttcctaac acatgggaca attgtgagga ttaaatgagt tagcctgcag aaatcacttg   2580
atgcacagca catgggaagc attgtgtgta tttattaatc cttcacaaag tctttgagat   2640
atattttat caaatattta gcatggatcc cggtacactt tcaatactta ataaatggtc    2700
aatgttattc ttttcacta tt                                             2722
```

<210> SEQ ID NO 15
<211> LENGTH: 6230
<212> TYPE: DNA
<213> ORGANISM: Homo sapiens

<400> SEQUENCE: 15

```
agggcggctg ctgccccctg gcgtccgcca gagcccgcgg cgcgtcccga cagctccgcg      60
cagtccgggc ccgcccggga aaggcctcca cgccagtcaa ccccggcccc ctcctgcgtc     120
cgggcccgcg gcaacgcccg gggacagtcc ctgcgcggca gcggccacag caccctagcc     180
ctggggagg gaggagcggg cgtcaggggc cccgtgaggt cggcgaggga ccccgcgcc      240
ggggagctta attgagggc tccgcgggga ccacaaagca gcccgcggtg aacggggcc      300
gggatccggg gactgggttg cagccccggg gtggatgaga ggccccggga ggtgcagggc     360
ccggcaggga gggcgtggag ggactcatgg tgacgggagc agcctccgct gggagggagc     420
cccgccgggc ggggtcggag ttggcagcgc acgccggacc gggggcgggg ccctccgagc     480
tccgcgaaaa tgcccgcagc accgcgggga ccggcgcagg gggaagcggc cgcccgcacg     540
cgaagccggg atgccagcac gagccgccgc ttcacgccgc cttccaccgc gctgagccca     600
ggcaagatga gcgaggcgtt gccgctgggc gccccgacg ccggcgctgc cctggccggc      660
aagctgagga gcggcgaccg cagcatggtg gaggtgctgg ccgaccaccc gggcgagctg     720
gtgcgcaccg acagccccaa cttcctctgc tccgtgctgc ctacgcactg gcgctgcaac     780
aagaccctgc ccatcgcttt caaggtggtg gcccctaggg g atgttccaga tggcactctg    840
gtcactgtga tggctggcaa tgatgaaaac tactcggctg agctgagaaa tgctaccgca    900
gccatgaaga accaggttgc aagatttaat gacctcaggt ttgtcggtcg aagtggaaga    960
gggaaaagct tcactctgac catcactgtc ttcacaaacc caccgcaagt cgccacctac   1020
cacagagcca tcaaaatcac agtggatggg ccccgagaac ctcgaagaca tcggcagaaa   1080
ctagatgatc agaccaagcc cgggagcttg tccttttccg agcggctcag tgaactggag   1140
cagctgcggc gcacagccat gagggtcagc ccacaccacc cagcccccac gcccaaccct   1200
cgtgcctccc tgaaccactc cactgccttt aaccctcagc ctcagagtca gatgcaggat   1260
acaaggcaga tccaaccatc cccaccgtgg tcctacgatc agtcctacca ataccctggga   1320
tccattgcct ctccttctgt gcacccagca acgcccattt cacctggacg tgccagcggc   1380
atgacaaccc tctctgcaga actttccagt cgactctcaa cggcaccgga cctgacagcg   1440
ttcagcgacc cgcgccagtt ccccgcgctg ccctccatct ccgaccccccg catgcactat   1500
ccaggcgcct tcacctactc cccgacgccg gtcacctcgg gcatcggcat cggcatgtcg   1560
gccatgggct cggccacgcg ctaccacacc tacctgccgc cgccctaccc cggctcgtcg   1620
caagcgcagg gaggcccgtt ccaagccagc tcgccctcct accacctgta ctacggcgcc   1680
tcggccggct cctaccagtt ctccatggtg ggcggcgagc gctcgccgcc gcgcatcctg   1740
ccgcctgca ccaacgcctc caccggctcc gcgctgctca cccagagcct cccgaaccag   1800
agcgacgtgg tggaggccga gggcagccac agcaactccc ccaccaacat ggcgccctcc   1860
gcgcgcctgg aggaggccgt gtggaggccc tactgaggcg ccaggcctgg cccggctggg   1920
ccccgcgggc cgccgccttc gcctccgggc gcgcggggcct cctgttcgcg acaagcccgc   1980
cgggatcccg ggccctgggc ccggccaccg tcctggggcc gagggcgccc gacggccagg   2040
atctcgctgt aggtcaggcc cgcgcagcct cctgcgccca gaagcccacg ccgccgccgt   2100
ctgctggcgc cccggccctc gcggaggtgt ccgaggcgac gcacctcgag ggtgtccgcc   2160
ggccccagca cccaggggac gcgctggaaa gcaaacagga agattcccgg agggaaactg   2220
tgaatgcttc tgatttagca atgctgtgaa taaaagaaa gatttatac ccttgactta      2280
acttttaac caagttgttt attccaaaga gtgtggaatt ttggttgggg tgggggaga   2340
```

```
ggagggatgc aactcgccct gtttggcatc taattcttat ttttaatttt tccgcacctt    2400
atcaattgca aaatgcgtat ttgcatttgg gtggttttta tttttatata cgtttatata    2460
aatatatata aattgagctt gcttctttct tgctttgacc atggaaagaa atatgattcc    2520
cttttcttta agtttatttt aacttttctt ttggactttt gggtagttgt ttttttttgt    2580
tttgttttgt tttttttgaga aacagctaca gctttgggtc attttttaact actgtattcc    2640 cacaaggaat ccccagatat ttatgtatct tgatgttcag acatttatgt gttgataatt    2700
ttttaattat ttaaatgtac ttatattaag aaaaatatca agtactacat tttcttttgt    2760
tcttgatagt agccaaagtt aaatgtatca cattgaagaa ggctagaaaa aaagaatgag    2820
taatgtgatc gcttggttat ccagaagtat tgtttacatt aaactcccctt tcatgttaat    2880 caaacaagtg agtagctcac gcagcaacgt ttttaatagg attttttagac actgagggtc    2940 actccaagga tcagaagtat ggaatttttct gccaggctca acaagggtct catatctaac    3000
ttcctcctta aaacagagaa ggtcaatcta gttccagagg gttgaggcag gtgccaataa    3060
ttacatcttt ggagaggatt tgatttctgc ccagggattt gctcacccca aggtcatctg    3120 ataattttcac agatgctgtg taacagaaca cagccaaagt aaactgtgta ggggagccac    3180
atttacatag gaaccaaatc aatgaattta ggggttacga ttatagcaat ttaagggccc    3240
accagaagca ggcctcgagg agtcaattttg cctctgtgtg cctcagtgga gacaagtggg    3300
aaaacatggt cccacctgtg cgagaccccc tgtcctgtgc tgctcactca acaacatctt    3360
tgtgttgctt tcaccaggct gagaccctac cctatggggt atatgggctt ttacctgtgc    3420
accagtgtga caggaaagat tcatgtcact actgtccgtg gctacaattc aaaggtatcc    3480
aatgtcgctg taaattttat ggcactattt ttattggagg atttggtcag aatgcagttg    3540
ttgtacaact cataaatact aactgctgat tttgacacat gtgtgctcca aatgatctgg    3600
tggttattta acgtacctct taaaattcgt tgaaacgatt tcaggtcaac tctgaagagt    3660
atttgaaagc aggacttcag aacagtgttt gattttttat ttataaattt aagcattcaa    3720
attaggcaaa tctttggctg caggcagcaa aaacagctgg acttatttaa aacaacttgt    3780
ttttgagttt tcttatatat atattgatta tttgttttac acacatgcag tagcactttg    3840
gtaagagtta aagagtaaag cagcttatgt tgtcaggtcg ttcttatcta gagaagagct    3900
atagcagatc tcggacaaac tcagaatata ttcactttca ttttttgacag gattccctcc    3960 acaactcagt ttcatatatt attccgtatt acatttttgc agctaaatta ccataaaatg    4020
tcagcaaatg taaaaattta atttctgaaa agcaccatta gcccatttcc cccaaattaa    4080
acgtaaatgt ttttttttcag cacatgttac catgtctgac ctgcaaaaat gctggagaaa    4140
aatgaaggaa aaaattatgt ttttcagttt aattctgtta actgaagata ttccaactca    4200
aaaccagcct catgctctga ttagataatc ttttacattg aacctttact ctcaaagcca    4260
tgtgtggagg gggcttgtca ctattgtagg ctcactggat tggtcattta gagtttcaca    4320
gactcttacc agcatatata gtatttaatt gtttcaaaaa aaatcaaact gtagttgttt    4380
tggcgatagg tctcacgcaa cacatttttg tatgtgtgtg tgtgtgcgtg tgtgtgtgtg    4440
tgtgtgaaaa attgcattca ttgacttcag gtagattaag gtatctttt attcattgcc    4500 ctcaggaaag ttaaggtatc aatgagaccc ttaagccaat catgtaataa ctgcatgtgt    4560
ctggtccagg agaagtattg aataagccat ttctactgct tactcatgtc cctatttatg    4620
atttcaacat ggatacatat ttcagttctt tcttttttctc actatctgaa aatacatttc    4680
```

```
cctccctctc ttccccccaa tatctccctt tttttctctc ttcctctatc ttccaaaccc    4740
cactttctcc ctcctccttt tcctgtgttc tcttaagcag atagcacata cccccaccca    4800
gtaccaaatt tcagaacaca agaaggtcca gttcttcccc cttcacataa aggaacatgg    4860
tttgtcagcc tttctcctgt ttatgggttt cttccagcag aacagagaca ttgccaacca    4920
tattggatct gcttgctgtc caaaccagca aactttcctg ggcaaatcac aatcagtgag    4980
taaatagaca gcctttctgc tgccttgggt ttctgtgcag ataaacagaa atgctctgat    5040
tagaaaggaa atgaatggtt ccactcaaat gtcctgcaat ttaggattgc agatttctgc    5100
cttgaaatac ctgtttcttt gggacattcc gtcctgatga ttttttatttt tgttggtttt    5160 tatttttggg gggaatgaca tgtttgggtc ttttatacat gaaaatttgt ttgacaataa    5220
tctcacaaaa catattttac atctgaacaa aatgcctttt tgtttaccgt agcgtataca    5280
tttgttttgg gattttttgtg tgtttgttgg gaattttgtt tttagccagg tcagtattga    5340
tgaggctgat catttggctc tttttttcct tccagaagag ttgcatcaac aaagttaatt    5400
gtatttatgt atgtaaatag atttttaagct tcattataaa atattgttaa tgcctataac    5460 ttttttttcaa tttttttgtg tgtgtttcta aggacttttt cttaggtttg ctaaatactg    5520
tagggaaaaa aatgcttctt tctactttgt ttatttttaga cttaaaaatg agctacttct    5580
tattcacttt tgtaaacagc taatagcatg gttccaattt tttttaagtt cactttttttt    5640 gttctagggg aaatgaatgt gcaaaaaaag aaaaagaact gttggttatt tgtgttattc    5700
tggatgtata aaaatcaatg gaaaaaaata aactttcaaa ttgaaatgac ggtataacac    5760
atctactgaa aaagcaacgg gaaatgtggt cctatttaag ccagccccca cctagggtct    5820
atttgtgtgg cagttattgg gtttggtcac aaaacatcct gaaaattcgt gcgtgggctt    5880 cttttctccct ggtacaaacg tatggaatgc ttccttaaagg ggaactgtca agctggtgtc    5940
ttcagccaga tgacatgaga gaatatccca gaaccctctc tccaaggtgt ttctagatag    6000
cacaggagag caggcactgc actgtccaca gtccacggta cacagtcggg tgggccgcct    6060
cccctctcct gggagcattc gtcgtgccca gcctgagcag ggcagctgga ctgctgctgt    6120
tcaggagcca ccagagcctt cctctctttg taccacagtt tcttctgtaa atccagtgtt    6180
acaatcagtg tgaatggcaa ataaacagtt tgacaagtac atacaccata              6230

<210> SEQ ID NO 16
<211> LENGTH: 1452
<212> TYPE: DNA
<213> ORGANISM: Homo sapiens

<400> SEQUENCE: 16
acagttaaat ttgtaatttg ggttgtgtga aaacttcttt gggcctcata acaaccaca      60 gaaccacaag ttgggtagcc tggcagtgtc agaagtctga acccagcata gtggtcagca    120
ggcaggacga atcacactga atgcaaacca caggggtttcg cagcgtggta aaagaaatca    180
ttgagtcccc cgccttcaga agagggtgca ttttcaggag gaagcgatgg cttcagacag    240
catatttgag tcatttcctt cgtacccaca gtgcttcatg agagaatgca tacttggaat    300
gaatccttct agagacgtcc acgatgccag cacgagccgc cgcttcacgc cgccttccac    360
cgcgctgagc ccaggcaaga tgagcgaggc gttgccgctg ggcgccccgg acgccggcgc    420
tgccctggcc ggcaagctga gggagcggcga ccgcagcatg gtggaggtgc tggccgacca    480
cccgggcgag ctggtgcgca ccgacagccc caacttcctc tgctccgtgc tgcctacgca    540
ctggcgctgc aacaagaccc tgcccatcgc tttcaaggtg gtggccctag ggatgttcc    600
```

```
agatggcact ctggtcactg tgatggctgg caatgatgaa aactactcgg ctgagctgag        660
aaatgctacc gcagccatga agaaccaggt tgcaagattt aatgacctca ggtttgtcgg        720
tcgaagtgga agagggaaaa gcttcactct gaccatcact gtcttcacaa acccaccgca        780
agtcgccacc taccacagag ccatcaaaat cacagtggat gggccccgag aacctcgaag        840
acatcggcag aaactagatg atcagaccaa gcccgggagc ttgtcctttt ccgagcggct        900
cagtgaactg gagcagctgc ggcgcacagc catgagggtc agcccacacc acccagcccc        960
cacgcccaac cctcgtgcct ccctgaacca ctccactgcc tttaaccctc agcctcagag       1020
tcagatgcag gaggaagaca cagcaccctg gagatgttaa ggcagaagtc agttcttctg       1080
tccatccctc tccccagcca ggatagagct atcttttcca tctcatcctc agaagagact       1140
cagaagaaag atgacagccc tcagaatgca cgttatgagg aaggcagaat gtgggtctgt       1200
aattcctccg tgtcccttct cccccctctgc aaaccgtcgt aacaataata gttcctaaca       1260
catgggacaa ttgtgaggat taaatgagtt agcctgcaga aatcacttga tgcacagcac       1320
atgggaagca ttgtgtgtat ttattaatcc ttcacaaagt ctttgagata tattttttatc       1380 aaatatttag catggatccc ggtacacttt caatacttaa taaatggtca atgttattct       1440 tttcactat ta                                                             1452

<210> SEQ ID NO 17
<211> LENGTH: 4693
<212> TYPE: DNA
<213> ORGANISM: Homo sapiens

<400> SEQUENCE: 17
acagttaaat ttgtaatttg ggttgtgtga aaacttcttt gggcctcata aacaaccaca         60
gaaccacaag ttgggtagcc tggcagtgtc agaagtctga acccagcata gtggtcagca        120
ggcaggacga atcacactga atgcaaacca cagggtttcg cagcgtggta aaagaaatca        180
ttgagtcccc cgccttcaga agagggtgca ttttcaggag gaagcgatgg cttcagacag        240
catatttgag tcatttcctt cgtacccaca gtgcttcatg agagaatgca tacttggaat        300
gaatccttct agagacgtcc acgatgccag cacgagccgc cgcttcacgc cgccttccac        360
cgcgctgagc ccaggcaaga tgagcgaggc gttgccgctg ggcgcccggg acgccggcgc        420
tgccctggcc ggcaagctga ggagcggcga ccgcagcatg tggaggtgc tggccgacca        480 cccgggcgag ctggtgcgca ccgacagccc caacttcctc tgctccgtgc tgcctacgca        540
ctggcgctgc aacaagaccc tgcccatcgc tttcaaggtg gtggccctag ggatgttcc        600 agatggcact ctggtcactg tgatggctgg caatgatgaa aactactcgg ctgagctgag        660
aaatgctacc gcagccatga agaaccaggt tgcaagattt aatgacctca ggtttgtcgg        720
tcgaagtgga agagggaaaa gcttcactct gaccatcact gtcttcacaa acccaccgca        780
agtcgccacc taccacagag ccatcaaaat cacagtggat gggccccgag aacctcgaag        840
acatcggcag aaactagatg atcagaccaa gcccgggagc ttgtcctttt ccgagcggct        900
cagtgaactg gagcagctgc ggcgcacagc catgagggtc agcccacacc acccagcccc        960
cacgcccaac cctcgtgcct ccctgaacca ctccactgcc tttaaccctc agcctcagag       1020
tcagatgcag gatacaaggc agatccaacc atccccaccg tggtcctacg atcagtccta       1080
ccaatacctg ggatccattg cctctccttc tgtgcaccca gcaacgccca tttcacctgg       1140
acgtgccagc ggcatgacaa ccctctctgc agaactttcc agtcgactct caaacagttg       1200
```

-continued

```
tgattacttc aggtttcacc agatgcctta gctgctgttc agagcttcac agaatgcctt    1260
ctaagagctt cacaacggca gtactattga catttggggc caaataattc tttgttgggg    1320
ggggtctgtc ctgagcatcg gagaatattt agcagcatcc ttggcctcta gatgccaata    1380
gcatcccct caccccagtt aggacaataa aaaatgtttc cagacattgc caaatttccc     1440
aaggggcaaa actgtcccca ggtgagaacc actgccttcc agtgttcttg ggtggtacag    1500
taaaatagga aaaccaactt aagtgcttgg ttttcacatt acttttggcc attaatgcca    1560
atattttcat ggtacattct gctccaaggc attgagagta gcacaggtat cttggcatct    1620
tgtttagctt gtggtttcta gaagcttatc cctcaagaac aaaggcactt gtcagctttt    1680
actgattgtt ctcagggcac ccctctgcac accggctacg gtcttcacct gaaataatgc    1740
ctgttctcct tcaaatgttc ctgctatggg tctatccttt ggaatttatt acataagtct    1800
tttgacttgg tcatcaccca agatcagcac cttatagtcc aagaacccta ggggccaact    1860
cctccagctg actggtgttc agatggtagg gtgactttt aaataaaagg aatgagtaac     1920
atgtgcactc caaagtccca tatcacagtt acatttgtga atatcctgga cttcaatcac    1980
ccaaggagta agagagaaca ttttatggca tgggagtgtg aagtagataa aaaccatgcc    2040
tcatttcaga acccaagaat gattcttttc tttttggagg gaggacagaa ttccagatga    2100
gctttcacag tggcatagaa cagtatggga gactgctctt caatttggca gaactccctc    2160
tgagaaatca agcctggagc acaggcctga aaagtgttgt cataaacctg gaggcaggag    2220
gggggtggaa tacataaaag gaaagtggct gcctggccga cagctttgag aacctgacac    2280
tgctctgtgg ctgctttgcc ttttaatcca gcccgacagc tttgtgctct gcccctcttc    2340
ccggccccag ccccacctgg gcttccttct gcgctgggga cttggactct gtctgtctct    2400
ctctctctat cctttgcaga cagactccac accttgtctg aaaagagttg tcatctagag    2460
gtttactttt ttttttcttt ttcaaaaaaa attaatgttt agctgccaac ctgggcgaca    2520
gacagcatgc attaatctga gtcatgcaaa agctcctttt aaggcagcca ttacctgctc    2580
aggttgttta atcctctggg ggcagtagga ggggccctgt agcgaggctg ctttcatcca    2640
tgtcaagctg gagagcgaag acttgagctg tcatggcaaa tatttagccc catcaatggg    2700
aaaacacttc caaccaaaat acctggacct cctaagcccc agatttccta ctcttaaaaa    2760
ctctctgtga atatcagggg atcccaactc cccccacact tctgctgaat caggggacac    2820
caggccagcc aaaaggacag aagagctaca gctggatggg tgaactgcgc agactgatgg    2880
gtttgaataa gggatctgag acaagacaca aagatgaaaa ccaacatttg aatatagcat    2940
ttgaatctga gcatatctag aaggcctaag atattgtatt atcaaaatgt gtgtaaaaaa    3000
gatagtttga ccaaatggat ggtcttttgt agtatgacgt tgctcatgtg tacatagaag    3060
aaggatcaca ggcagcattg cagctctttc ttttggatgt tctcctcaca agtgaaagaa    3120
ctatttcccc ccaacagctg agaccataac atcattccag tacttatgtc catgacaaat    3180
cacggactca ctctggattc cagtaacttg gtaccatcac cacattacca gtagtagtt    3240
ggaacctact ggcagagcat gtccagacat tgctgtaaaa cagggtgacc tttcgttcat    3300
tttccagtgg attcaccttt ttgtctcagg gcaaatgaag caagaggaat aatgggcaga    3360
gtcatttatt tgtgtccaga gtattgcatc agatgacaac aaactgactg tatttgccta    3420
atgcttttcc tcctgtccca gcttctccgt agactctata aatctaaatg gaaaatgga    3480
gtaaagcttc ctgttaactc tcaaacatgt cacagctctc catgtcagca aaacaagtg    3540
acacagggct tgctcacaga tggccccaaa gagcgggcag ggatgaaccc tgtggaatga    3600
```

-continued

| | | |
|---|---|---|
| ggtgtggcct ggctcgagaa tgactagagt gtggccaagg aagggcagcc tcagaaccac | 3660 |
| tgtccgttta caacgttttc cctgcccaca tgtctgcctg gctttgaaaa gattaacagg | 3720 |
| agtgtttgtt tgaaagtcag actcctggtt tcctcattag tgaagggatc tgctacagac | 3780 |
| ttgggctgtt tctataaact ttaattacct ctgatgagga gtgtatcccc tcatcacatt | 3840 |
| cacccccaaag gtacagagga gttcattttt aaaaatgtgt tagagcaata aaaggccatt | 3900 |
| agagggaggg aggatggggt gtggaagaga cgagagagcg agcgagagag agagaaaaca | 3960 |
| cactagctct ccctgctgga ataataggct tgaaatatga ggaagttgat caactgccgc | 4020 |
| tgccttccaa aaacagatta atccaccttg gtagctttcc tttcagagca agcttttggc | 4080 |
| tctgtcgact ttctctatca gcctgaactc aaaaggacac aggccacatg ccatctgagc | 4140 |
| ttaagagtta ttttgtgtgt tgatctgaga acttcacatt ttaaaacaat gaattcatgt | 4200 |
| ttctactgtt tgttgctgtc tgtggatttg ctgatataaa aggagagtc ctagcctggt | 4260 |
| catttaatga ataattctaa ggaacctgaa cttctccagg gtgcccttct acatctgcag | 4320 |
| tggtggttct cagctggggt gactttgctt ccgtcacccc acccgcagga tatctggcaa | 4380 |
| tgtctggaga cattctgagt tgtcacaaga ggggcgggcg atgctactaa cacctaatgg | 4440 |
| gtaaagcaga gatgctgcca cacatcctac gatgaacgag acagcccct ccacccagc | 4500 |
| aaatcatgat ctggcccaaa atgtcaacag tgtcaacagt tgagaaactc tgatctacag | 4560 |
| atatagggaa ccctgcctaa tacacaaatc ctccgtagtt cccaagggcg gcctgtagcg | 4620 |
| gcacccgacc tgacagcgtt cagcgacccg cgccagttcc ccgcgctgcc ctccatctcc | 4680 |
| gaccccgca tgc | 4693 |

<210> SEQ ID NO 18
<211> LENGTH: 5772
<212> TYPE: DNA
<213> ORGANISM: Homo sapiens

<400> SEQUENCE: 18

| | | |
|---|---|---|
| acagttaaat ttgtaatttg ggttgtgtga aaacttctttt gggcctcata aacaaccaca | 60 |
| gaaccacaag ttgggtagcc tggcagtgtc agaagtctga acccagcata gtggtcagca | 120 |
| ggcaggacga atcacactga atgcaaacca cagggtttcg cagcgtggta aaagaaatca | 180 |
| ttgagtcccc cgccttcaga agagggtgca ttttcaggag gaagcgatgg cttcagacag | 240 |
| catatttgag tcatttcctt cgtacccaca gtgcttcatg agagatgcca gcacgagccg | 300 |
| ccgcttcacg ccgccttcca ccgcgctgag cccaggcaag atgagcgagg cgttgccgct | 360 |
| gggcgccccg gacgccggcg ctgccctggc cggcaagctg aggagcggcg accgcagcat | 420 |
| ggtggaggtg ctgccgacc accccgggcga gctggtgcgc accgacagcc caacttcct | 480 |
| ctgctccgtg ctgcctacgc actggcgctg caacaagacc ctgcccatcg ctttcaaggt | 540 |
| ggtgccccta ggggatgttc cagatggcac tctggtcact gtgatggctg caatgatga | 600 |
| aaactactcg gctgagctga gaaatgctac cgcagccatg aagaaccagg ttgcaagatt | 660 |
| taatgacctc aggtttgtcg gtcgaagtgg aagagggaaa agcttcactc tgaccatcac | 720 |
| tgtcttcaca aacccaccgc aagtcgccac ctaccacaga gccatcaaaa tcacagtgga | 780 |
| tgggccccga gaacctcgaa atacaaggca gatccaacca tccccaccgt ggtcctacga | 840 |
| tcagtcctac caatacctgg gatccattgc ctctccttct gtgcacccag caacgcccat | 900 |
| ttcacctgga cgtgccagcg gcatgacaac cctctctgca gaactttcca gtcgactctc | 960 |

-continued

```
aacggcaccc gacctgacag cgttcagcga cccgcgccag ttccccgcgc tgccctccat    1020
ctccgacccc cgcatgcact atccaggcgc cttcacctac tccccgacgc cggtcacctc    1080
gggcatcggc atcggcatgt cggccatggg ctcggccacg cgctaccaca cctacctgcc    1140
gccgccctac cccggctcgt cgcaagcgca gggaggcccg ttccaagcca gctcgccctc    1200
ctaccacctg tactacggcg cctcggccgg ctcctaccag ttctccatgg tgggcggcga    1260
gcgctcgccg ccgcgcatcc tgccgccctg caccaacgcc tccaccggct ccgcgctgct    1320 caacccagc ctcccgaacc agagcgacgt ggtggaggcc gagggcagcc acagcaactc    1380
ccccaccaac atggcgccct ccgcgcgcct ggaggaggcc gtgtggaggc cctactgagg    1440
cgccaggcct ggcccggctg ggccccgcgg gccgccgcct tcgcctccgg gcgcgcgggc    1500
ctcctgttcg cgacaagccc gccgggatcc cgggccctgg gcccggccac cgtcctgggg    1560
ccgagggcgc ccgacggcca ggatctcgct gtaggtcagg cccgcgcagc ctcctgcgcc    1620
cagaagccca cgccgccgcc gtctgctggc gccccggccc tcgcggaggt gtccgaggcg    1680
acgcacctcg agggtgtccg ccggccccag cacccagggg acgcgctgga aagcaaacag    1740
gaagattccc ggagggaaac tgtgaatgct tctgatttag caatgctgtg aataaaaaga    1800
aagattttat acccttgact taacttttta accaagttgt ttattccaaa gagtgtggaa    1860
ttttggttgg ggtggggga gaggagggat gcaactcgcc ctgtttggca tctaattctt    1920 attttaatt tttccgcacc ttatcaattg caaaatgcgt atttgcattt gggtggtttt    1980 tattttata tacgtttata taaatatata taaattgagc ttgcttcttt cttgctttga    2040
ccatggaaag aaatatgatt cccttttctt taagttttat ttaacttttc ttttggactt    2100
ttgggtagtt gttttttttt gttttgtttt gtttttttga gaaacagcta cagctttggg    2160
tcatttttaa ctactgtatt cccacaagga atccccagat atttatgtat cttgatgttc    2220
agacatttat gtgttgataa ttttttaatt atttaaatgt acttatatta agaaaaatat    2280
caagtactac atttttcttt gttcttgata gtagccaaag ttaaatgtat cacattgaag    2340
aaggctagaa aaaagaatg agtaatgtga tcgcttggtt atccagaagt attgtttaca    2400
ttaaactccc tttcatgtta atcaaacaag tgagtagctc acgcagcaac gttttaata    2460 ggattttag acactgaggg tcactccaag gatcagaagt atggaatttt ctgccaggct    2520
caacaagggt ctcatatcta acttcctcct taaaacagag aaggtcaatc tagttccaga    2580
gggttgaggc aggtgccaat aattacatct ttggagagga tttgatttct gcccagggat    2640
ttgctcaccc caaggtcatc tgataatttc acagatgctg tgtaacagaa cacagccaaa    2700
gtaaactgtg tagggagcc acatttacat aggaaccaaa tcaatgaatt tagggggttac    2760 gattatagca atttaagggc ccaccagaag caggcctcga ggagtcaatt tgcctctgtg    2820
tgcctcagtg gagacaagtg ggaaaacatg gtcccacctg tgcgagaccc cctgtcctgt    2880
gctgctcact caacaacatc tttgtgttgc tttcaccagg ctgagaccct accctatggg    2940
gtatatgggc ttttacctgt gcaccagtgt gacaggaaag attcatgtca ctactgtccg    3000
tggctacaat tcaaaggtat ccaatgtcgc tgtaaatttt atggcactat ttttattgga    3060
ggatttggtc agaatgcagt tgttgtacaa ctcataaata ctaactgctg attttgacac    3120
atgtgtgctc caaatgatct ggtggttatt taacgtacct cttaaaattc gttgaaacga    3180
tttcaggtca actctgaaga gtatttgaaa gcaggacttc agaacagtgt ttgatttta    3240 ttttataaat ttaagcattc aaattaggca aatcttggc tgcaggcagc aaaaacagct    3300
ggacttattt aaaacaactt gttttttgagt tttcttatat atatattgat tatttgtttt    3360
```

```
acacacatgc agtagcactt tggtaagagt taaagagtaa agcagcttat gttgtcaggt    3420
cgttcttatc tagagaagag ctatagcaga tctcggacaa actcagaata tattcacttt    3480
catttttgac aggattccct ccacaactca gtttcatata ttattccgta ttacattttt    3540
gcagctaaat taccataaaa tgtcagcaaa tgtaaaaatt taatttctga aaagcaccat    3600
tagcccattt cccccaaatt aaacgtaaat gttttttttc agcacatgtt accatgtctg    3660
acctgcaaaa atgctggaga aaaatgaagg aaaaaattat gttttcagt ttaattctgt     3720 taactgaaga tattccaact caaaaccagc tcatgctct gattagataa tcttttacat      3780 tgaacccttta ctctcaaagc catgtgtgga gggggcttgt cactattgta ggctcactgg   3840
attggtcatt tagagtttca cagactctta ccagcatata tagtatttaa ttgtttcaaa    3900
aaaaatcaaa ctgtagttgt tttggcgata ggtctcacgc aacacatttt tgtatgtgtg    3960
tgtgtgtgcg tgtgtgtgtg tgtgtgtgaa aaattgcatt cattgacttc aggtagatta    4020
aggtatcttt ttattcattg ccctcaggaa agttaaggta tcaatgagac ccttaagcca    4080
atcatgtaat aactgcatgt gtctggtcca ggagaagtat tgaataagcc atttctactg    4140
cttactcatg tccctatta tgatttcaac atggatacat atttcagttc tttcttttc       4200 tcactatctg aaaatacatt tccctccctc tcttccccc aatatctccc tttttttctc       4260
tcttcctcta tcttccaaac cccactttct ccctcctcct tttcctgtgt tctcttaagc     4320
agatagcaca taccccacc cagtaccaaa tttcagaaca caagaaggtc cagttcttcc      4380
cccttcacat aaaggaacat ggtttgtcag cctttctcct gtttatgggt ttcttccagc    4440
agaacagaga cattgccaac catattggat ctgcttgctg tccaaaccag caaactttcc    4500
tgggcaaatc acaatcagtg agtaaataga cagcctttct gctgccttgg gtttctgtgc    4560
agataaacag aaatgctctg attagaaagg aaatgaatgg ttccactcaa atgtcctgca    4620
atttaggatt gcagatttct gccttgaaat acctgtttct ttgggacatt ccgtcctgat    4680
gatttttatt tttgttggtt tttatttttg gggggaatga catgtttggg tcttttatac    4740
atgaaaattt gtttgacaat aatctcacaa aacatatttt acatctgaac aaaatgcctt    4800
tttgtttacc gtagcgtata catttgtttt gggattttg tgtgtttgtt gggaattttg      4860
tttttagcca ggtcagtatt gatgaggctg atcatttggc tcttttttc cttccagaag      4920 agttgcatca acaaagttaa ttgtatttat gtatgtaaat agattttaag cttcattata     4980
aaatattgtt aatgcctata acttttttc aatttttttg tgtgtgtttc taaggacttt       5040
ttcttaggtt tgctaaatac tgtagggaaa aaaatgcttc tttctacttt gtttatttta    5100
gactttaaaa tgagctactt cttattcact tttgtaaaca gctaatagca tggttccaat    5160
tttttttaag ttcactttt ttgttctagg ggaaatgaat gtgcaaaaaa agaaaaagaa      5220
ctgttggtta tttgtgttat tctggatgta taaaaatcaa tggaaaaaaa taaactttca    5280
aattgaaatg acggtataac acatctactg aaaaagcaac gggaaatgtg gtcctattta    5340
agccagcccc cacctagggt ctatttgtgt ggcagttatt gggtttggtc acaaaacatc    5400
ctgaaaattc gtgcgtgggc ttctttctcc ctggtacaaa cgtatggaat gcttcttaaa    5460
ggggaactgt caagctggtg tcttcagcca gatgacatga gagaatatcc cagaaccctc    5520
tctccaaggt gtttctagat agcacaggag agcaggcact gcactgtcca cagtccacgg    5580
tacacagtcg ggtgggccgc ctcccctctc ctgggagcat tcgtcgtgcc cagcctgagc    5640
agggcagctg gactgctgct gttcaggagc caccagagcc ttcctctctt tgtaccacag    5700
```

<210> SEQ ID NO 19
<211> LENGTH: 5811
<212> TYPE: DNA
<213> ORGANISM: Homo sapiens

<400> SEQUENCE: 19

```
tttcttctgt aaatccagtg ttacaatcag tgtgaatggc aaataaacag tttgacaagt    5760
acatacacca ta                                                        5772
```

<210> SEQ ID NO 19
<211> LENGTH: 5811
<212> TYPE: DNA
<213> ORGANISM: Homo sapiens

<400> SEQUENCE: 19

```
acagttaaat ttgtaatttg ggttgtgtga aaacttcttt gggcctcata acaaccaca      60
gaaccacaag ttgggtagcc tggcagtgtc agaagtctga acccagcata gtggtcagca    120
ggcaggacga atcacactga atgcaaacca cagggtttcg cagcgtggta aaagaaatca    180
ttgagtcccc cgccttcaga agagggtgca ttttcaggag gaagcgatgg cttcagacag    240
catatttgag tcatttcctt cgtacccaca gtgcttcatg agagaatgca tacttggaat    300
gaatccttct agagacgtcc acgatgccag cacgagccgc cgcttcacgc cgccttccac    360
cgcgctgagc ccaggcaaga tgagcgaggc gttgccgctg ggcgccccgg acgccggcgc    420
tgccctggcc ggcaagctga ggagcggcga ccgcagcatg gtggaggtgc tggccgacca    480
cccgggcgag ctggtgcgca ccgacagccc caacttcctc tgctccgtgc tgcctacgca    540
ctggcgctgc aacaagaccc tgcccatcgc tttcaaggtg gtgggcctag ggatgttcc    600
agatggcact ctggtcactg tgatggctgg caatgatgaa aactactcgg ctgagctgag    660
aaatgctacc gcagccatga agaaccaggt tgcaagattt aatgacctca ggtttgtcgg    720
tcgaagtgga gagggaaaaa gcttcactct gaccatcact gtcttcacaa acccaccgca    780
agtcgccacc taccacagag ccatcaaaat cacagtggat gggccccgag aacctcgaaa    840
tacaaggcag atccaaccat ccccaccgtg gtcctacgat cagtcctacc aatacctggg    900
atccattgcc tctccttctg tgcacccagc aacgcccatt tcacctggac gtgccagcgg    960
catgacaacc ctctctgcag aactttccag tcgactctca acggcacccg acctgacagc   1020
gttcagcgac ccgcgccagt tccccgcgct gccctccatc tccgaccccc gcatgcacta   1080
tccaggcgc ttcacctact ccccgacgcc ggtcacctcg gcatcggca tcggcatgtc    1140
ggccatgggc tcggccacgc gctaccacac ctacctgccg ccgcccacc ccggctcgtc    1200
gcaagcgcag ggaggcccgt tccaagccag ctcgcccctc cctaccacctgt actacgcgc   1260
ctcggccggc tcctaccagt tctccatggt gggcggcgag cgctcgccgc gcgcatcct    1320
gccgccctgc accaacgcct ccaccggctc cgcgctgctc aaccccagcc tccgaacca   1380
gagcgacgtg gtggaggccg agggcagcca cagcaactcc cccaccaaca tggcgccctc   1440
cgcgcgcctg gaggaggccg tgtggaggcc ctactgaggc gccaggcctg ccccggctgg   1500
gccccgcggg ccgccgcctt cgcctccggg cgcgcgggcc tcctgttcgc gacaagcccg   1560
ccgggatccc gggccctggg cccggccacc gtcctgggc cgaggcgcc cgacggccag    1620
gatctcgctg taggtcaggc ccgcgcagcc tcctgcgccc agaagcccac gccgccgccg   1680
tctgctggcg ccccggccct cgcggaggtg tccgaggcga cgcacctcga gggtgtccgc   1740
cggccccagc acccagggga cgcgctggaa agcaaacagg aagattcccg gagggaaact   1800
gtgaatgctt ctgatttagc aatgctgtga ataaaaagaa agatttttata cccttgactt   1860
aactttttaa ccaagttgtt tattccaaag agtgtggaat tttggttggg gtgggggag   1920
aggagggatg caactcgccc tgtttggcat ctaattctta ttttaatttt ttccgcacct   1980
tatcaattgc aaaatgcgta tttgcatttg ggtggttttt attttatat acgtttatat   2040
```

```
aaatatatat aaattgagct tgcttctttc ttgctttgac catggaaaga aatatgattc    2100
ccttttcttt aagttttatt taacttttct tttggacttt tgggtagttg ttttttttg     2160 ttttgttttg ttttttgag aaacagctac agctttgggt cattttaac tactgtattc     2220 ccacaaggaa tccccagata tttatgtatc ttgatgttca gacatttatg tgttgataat    2280
tttttaatta tttaaatgta cttatattaa gaaaatatc aagtactaca ttttcttttg     2340
ttcttgatag tagccaaagt taaatgtatc acattgaaga aggctagaaa aaagaatga     2400 gtaatgtgat cgcttggtta tccagaagta ttgtttacat taaactccct ttcatgttaa    2460
tcaaacaagt gagtagctca cgcagcaacg ttttaatag gattttaga cactgagggt      2520 cactccaagg atcagaagta tggaattttc tgccaggctc aacaagggtc tcatatctaa    2580
cttcctcctt aaaacagaga aggtcaatct agttccagag ggttgaggca ggtgccaata    2640
attacatctt tggagaggat tgatttctg cccagggatt tgctcacccc aaggtcatct     2700
gataatttca cagatgctgt gtaacagaac acagccaaag taaactgtgt aggggagcca    2760
catttacata ggaaccaaat caatgaattt aggggttacg attatagcaa tttaagggcc    2820
caccagaagc aggcctcgag gagtcaattt gcctctgtgt gcctcagtgg agacaagtgg    2880
gaaaacatgg tcccacctgt gcgagacccc ctgtcctgtg ctgctcactc aacaacatct    2940
ttgtgttgct ttcaccaggc tgagacccta ccctatgggg tatatgggct tttacctgtg    3000
caccagtgtg acaggaaaga ttcatgtcac tactgtccgt ggctacaatt caaaggtatc    3060
caatgtcgct gtaaatttta tggcactatt tttattggag gatttggtca gaatgcagtt    3120
gttgtacaac tcataaatac taactgctga ttttgacaca tgtgtgctcc aaatgatctg    3180
gtggttattt aacgtacctc ttaaaattcg ttgaaacgat ttcaggtcaa ctctgaagag    3240
tatttgaaag caggacttca gaacagtgtt tgattttat tttataaatt taagcattca     3300
aattaggcaa atctttggct gcaggcagca aaaacagctg gacttattta aaacaacttg    3360
tttttgagtt ttcttatata tatattgatt atttgtttta cacacatgca gtagcacttt    3420
ggtaagagtt aaagagtaaa gcagcttatg ttgtcaggtc gttcttatct agagaagagc    3480
tatagcagat ctcggacaaa ctcagaatat attcactttc attttttgaca ggattccctc   3540 cacaactcag tttcatatat tattccgtat tacattttg cagctaaatt accataaaat     3600
gtcagcaaat gtaaaaattt aatttctgaa aagcaccatt agcccatttc ccccaaatta    3660
aacgtaaatg ttttttttca gcacatgtta ccatgtctga cctgcaaaaa tgctggagaa    3720
aaatgaagga aaaaattatg ttttttcagtt taattctgtt aactgaagat attccaactc   3780
aaaaccagcc tcatgctctg attagataat cttttacatt gaacctttac tctcaaagcc    3840
atgtgtggag ggggcttgtc actattgtag gctcactgga ttggtcattt agagtttcac    3900
agactcttac cagcatatat agtatttaat tgtttcaaaa aaaatcaaac tgtagttgtt    3960
ttggcgatag gtctcacgca acacattttt gtatgtgtgt gtgtgtgcgt gtgtgtgtgt    4020
gtgtgtgaaa aattgcattc attgacttca ggtagattaa ggtatctttt tattcattgc    4080
cctcaggaaa gttaaggtat caatgagacc cttaagccaa tcatgtaata actgcatgtg    4140
tctggtccag gagaagtatt gaataagcca tttctactgc ttactcatgt ccctatttat    4200
gatttcaaca tggatacata tttcagttct ttcttttttct cactatctga aaatacatt    4260 ccctccctct cttccccccca atatctccct tttttctct cttcctctat cttccaaacc    4320
ccactttctc cctcctcctt ttcctgtgtt ctcttaagca gatagcacat acccccaccc    4380
```

```
agtaccaaat tcagaacac aagaaggtcc agttcttccc ccttcacata aaggaacatg    4440
gtttgtcagc ctttctcctg tttatgggtt tcttccagca gaacagagac attgccaacc    4500
atattggatc tgcttgctgt ccaaaccagc aaactttcct gggcaaatca caatcagtga    4560
gtaaatagac agcctttctg ctgccttggg tttctgtgca gataaacaga aatgctctga    4620
ttagaaagga aatgaatggt tccactcaaa tgtcctgcaa tttaggattg cagatttctg    4680
ccttgaaata cctgtttctt tgggacattc cgtcctgatg attttttattt ttgttggttt    4740 ttatttttgg ggggaatgac atgtttgggt cttttataca tgaaaatttg tttgacaata    4800
atctcacaaa acatatttta catctgaaca aaatgccttt ttgtttaccg tagcgtatac    4860
atttgttttg ggattttgt gtgtttgttg ggaattttgt tttagccag gtcagtattg    4920 atgaggctga tcatttggct ctttttttcc ttccagaaga gttgcatcaa caaagttaat    4980
tgtatttatg tatgtaaata gattttaagc ttcattataa aatattgtta atgcctataa    5040
ctttttttca attttttgt gtgtgtttct aaggactttt tcttaggttt gctaaatact    5100
gtagggaaaa aaatgcttct ttctactttg tttattttag actttaaaat gagctacttc    5160
ttattcactt ttgtaaacag ctaatagcat ggttccaatt tttttaagt tcactttttt    5220 tgttctaggg gaaatgaatg tgcaaaaaaa gaaaagaaac tgttggttat ttgtgttatt    5280
ctggatgtat aaaaatcaat ggaaaaaat aaactttcaa attgaaatga cggtataaca    5340
catctactga aaaagcaacg ggaaatgtgg tcctatttaa gccagccccc acctagggtc    5400
tatttgtgtg gcagttattg ggtttggtca caaacatcc tgaaaattcg tgcgtgggct    5460
tctttctccc tggtacaaac gtatggaatg cttcttaaag gggaactgtc aagctggtgt    5520
cttcagccag atgacatgag agaatatccc agaaccctct ctccaaggtg tttctagata    5580
gcacaggaga gcaggcactg cactgtccac agtccacggt acacagtcgg gtgggccgcc    5640 tccctctcc tgggagcatt cgtcgtgccc agcctgagca gggcagctgg actgctgctg    5700
ttcaggagcc accagagcct tcctctcttt gtaccacagt ttcttctgta aatccagtgt    5760
tacaatcagt gtgaatggca aataaacagt ttgacaagta catacaccat a             5811
```

<210> SEQ ID NO 20
<211> LENGTH: 5772
<212> TYPE: DNA
<213> ORGANISM: Homo sapiens

<400> SEQUENCE: 20

```
cacttttta a tgcactaagc aatcggttgc taggagccca tcctgggtca gaggccgatc     60
cgcagaacca gaacgttttc ccctcctgga ctatgccagc acgagccgcc gcttcacgcc    120
gccttccacc gcgctgagcc caggcaagat gagcgaggcg ttgccgctgg gcgcccgga    180 cgccggcgct gccctggccg gcaagctgag gagcggcgac cgcagcatgg tggaggtgct    240
ggccgaccac ccgggcgagc tggtgcgcac cgacagcccc aacttcctct gctccgtgct    300
gcctacgcac tggcgctgca acaagaccct gcccatcgct ttcaaggtgg tggccctagg    360
ggatgttcca gatggcactc tggtcactgt gatggctggc aatgatgaaa actactcggc    420
tgagctgaga aatgctaccg cagccatgaa gaaccaggtt gcaagattta atgacctcag    480
gtttgtcggt cgaagtggaa gagggaaaag cttcactctg accatcactg tcttcacaaa    540
cccaccgcaa gtcgccacct accacagagc catcaaaatc acagtggatg gccccgaga    600 acctcgaaga catcggcaga aactagatga tcagaccaag cccgggagct tgtccttttc    660
cgagcggctc agtgaactgg agcagctgcg gcgcacagcc atgagggtca gcccacacca    720
```

```
cccagccccc acgcccaacc ctcgtgcctc cctgaaccac tccactgcct ttaaccctca    780
gcctcagagt cagatgcagg atacaaggca gatccaacca tccccaccgt ggtcctacga    840
tcagtcctac caatacctgg gatccattgc ctctccttct gtgcacccag caacgcccat    900
ttcacctgga cgtgccagcg gcatgacaac cctctctgca gaactttcca gtcgactctc    960
aacggcaccc gacctgacag cgttcagcga cccgcgccag ttccccgcgc tgccctccat   1020
ctccgacccc cgcatgcact atccaggcgc cttcacctac tccccgacgc cggtcacctc   1080
gggcatcggc atcggcatgt cggccatggg ctcggccacg cgctaccaca cctacctgcc   1140
gccgccctac cccggctcgt cgcaagcgca gggaggcccg ttccaagcca gctcgccctc   1200
ctaccacctg tactacggcg cctcggccgg ctcctaccag ttctccatgg tgggcggcga   1260
gcgctcgccg ccgcgcatcc tgccgccctg caccaacgcc tccaccggct ccgcgctgct   1320
caaccccagc ctcccgaacc agagcgacgt ggtggaggcc gagggcagcc acagcaactc   1380
ccccaccaac atggcgccct ccgcgcgcct ggaggaggcc gtgtggaggc cctactgagg   1440
cgccaggcct ggcccggctg gccccgcgg gccgccgcct tcgcctccgg gcgcgcgggc    1500
ctcctgttcg cgacaagccc gccgggatcc cgggccctgg gcccggccac cgtcctgggg   1560
ccgagggcgc ccgacggcca ggatctcgct gtaggtcagg cccgcgcagc ctcctgcgcc   1620
cagaagccca cgccgccgcc gtctgctggc gccccggccc tcgcggaggt gtccgaggcg   1680
acgcacctcg agggtgtccg ccggccccag cacccagggg acgcgctgga aagcaaacag   1740
gaagattccc ggagggaaac tgtgaatgct tctgatttag caatgctgtg aataaaaaga   1800
aagattttat acccttgact taacttttta accaagttgt ttattccaaa gagtgtggaa   1860
tttttggttgg ggtgggggga gaggagggat gcaactcgcc ctgtttggca tctaattctt   1920
atttttaatt tttccgcacc ttatcaattg caaaatgcgt atttgcattt gggtggtttt   1980
tatttttata tacgtttata taaatatata taaattgagc ttgcttcttt cttgctttga   2040
ccatggaaag aaatatgatt cccttttctt taagttttat ttaactttc ttttggactt   2100
ttgggtagtt gttttttttt gttttgtttt gttttttga gaaacagcta cagctttggg    2160
tcatttttaa ctactgtatt cccacaagga atccccagat atttatgtat cttgatgttc   2220
agacatttat gtgttgataa ttttttaatt atttaaatgt acttatatta agaaaaatat   2280
caagtactac attttctttt gttcttgata gtagccaaag ttaaatgtat cacattgaag   2340
aaggctagaa aaaagaatg agtaatgtga tcgcttggtt atccagaagt attgtttaca    2400
ttaaactccc tttcatgtta atcaaacaag tgagtagctc acgcagcaac gttttaata    2460
ggattttttag acactgaggg tcactccaag gatcagaagt atggaatttt ctgccaggct   2520
caacaagggt ctcatatcta acttcctcct taaaacagag aaggtcaatc tagttccaga   2580
gggttgaggc aggtgccaat aattacatct ttggagagga tttgatttct gcccagggat   2640
ttgctcaccc caaggtcatc tgataatttc acagatgctg tgtaacagaa cacagccaaa   2700
gtaaactgtg taggggagcc acatttacat aggaaccaaa tcaatgaatt tagggggttac   2760
gattatagca atttaagggc ccaccagaag caggcctcga ggagtcaatt tgcctctgtg   2820
tgcctcagtg gagacaagtg ggaaaacatg gtcccacctg tgcgagaccc cctgtcctgt   2880
gctgctcact caacaacatc tttgtgttgc tttcaccagg ctgagaccct accctatggg   2940
gtatatgggc ttttacctgt gcaccagtgt gacaggaaag attcatgtca ctactgtccg   3000
tggctacaat tcaaaggtat ccaatgtcgc tgtaaatttt atggcactat ttttattgga   3060
```

```
ggatttggtc agaatgcagt tgttgtacaa ctcataaata ctaactgctg attttgacac    3120
atgtgtgctc caaatgatct ggtggttatt taacgtacct cttaaaattc gttgaaacga    3180
tttcaggtca actctgaaga gtatttgaaa gcaggacttc agaacagtgt tgattttta     3240 ttttataaat ttaagcattc aaattaggca aatctttggc tgcaggcagc aaaaacagct    3300
ggacttattt aaaacaactt gttttgagt tttcttatat atatattgat tatttgtttt     3360
acacacatgc agtagcactt tggtaagagt taaagagtaa agcagcttat gttgtcaggt    3420
cgttcttatc tagagaagag ctatagcaga tctcggacaa actcagaata tattcacttt    3480 cattttgac aggattccct ccacaactca gtttcatata ttattccgta ttacatttt      3540 gcagctaaat taccataaaa tgtcagcaaa tgtaaaaatt taatttctga aaagcaccat    3600
tagcccattt cccccaaatt aaacgtaaat gttttttttc agcacatgtt accatgtctg    3660
acctgcaaaa atgctggaga aaaatgaagg aaaaaattat gttttcagt ttaattctgt      3720 taactgaaga tattccaact caaaaccagc ctcatgctct gattagataa tcttttacat    3780 tgaacccttta ctctcaaagc catgtgtgga ggggcttgt cactattgta ggctcactgg     3840
attggtcatt tagagtttca cagactctta ccagcatata tagtatttaa ttgtttcaaa    3900
aaaaatcaaa ctgtagttgt tttggcgata ggtctcacgc aacacatttt tgtatgtgtg    3960
tgtgtgtgcg tgtgtgtgtg tgtgtgtgaa aaattgcatt cattgacttc aggtagatta    4020 aggtatctt ttattcattg ccctcaggaa agttaaggta tcaatgagac ccttaagcca      4080
atcatgtaat aactgcatgt gtctggtcca ggagaagtat tgaataagcc atttctactg    4140
cttactcatg tccctattta tgatttcaac atggatacat atttcagttc tttctttttc    4200
tcactatctg aaaatacatt tccctccctc tcttccccc aatatctccc ttttttctc       4260 tcttcctcta tcttccaaac cccactttct ccctcctcct tttcctgtgt tctcttaagc    4320
agatagcaca tacccccacc cagtaccaaa tttcagaaca caagaaggtc cagttcttcc    4380
cccttcacat aaaggaacat ggtttgtcag ccttttctcct gtttatgggt ttcttccagc    4440
agaacagaga cattgccaac catattggat ctgcttgctg tccaaaccag caaactttcc    4500
tgggcaaatc acaatcagtg agtaaataga cagccttttct gctgccttgg gtttctgtgc    4560
agataaacag aaatgctctg attagaaagg aaatgaatgg ttccactcaa atgtcctgca    4620
atttaggatt gcagatttct gccttgaaat acctgtttct ttgggacatt ccgtcctgat    4680
gatttttatt tttgttggtt tttatttttg gggggaatga catgtttggg tcttttatac    4740
atgaaaattt gtttgacaat aatctcacaa aacatatttt acatctgaac aaaatgcctt    4800
tttgtttacc gtagcgtata catttgtttt gggatttttg tgtgtttgtt gggaattttg    4860
ttttagccca ggtcagtatt gatgaggctg atcatttggc tctttttttc cttccagaag    4920
agttgcatca acaaagttaa ttgtatttat gtatgtaaat agattttaag cttcattata    4980
aaatattgtt aatgcctata acttttttc aattttttg tgtgtgtttc taaggacttt       5040
ttcttaggtt tgctaaatac tgtagggaaa aaatgcttc tttctacttt gtttattta       5100 gactttaaaa tgagctactt cttattcact tttgtaaaca gctaatagca tggttccaat    5160 ttttttttaag ttcactttt ttgttctagg ggaaatgaat gtgcaaaaaa agaaaaagaa     5220
ctgttggtta tttgtgttat tctggatgta taaaaatcaa tggaaaaaa taaactttca      5280 aattgaaatg acggtataac acatctactg aaaaagcaac gggaaatgtg gtcctattta    5340
agccagcccc cacctagggt ctatttgtgt ggcagttatt gggtttggtc acaaaacatc    5400
ctgaaaattc gtgcgtgggc ttcttttctcc ctggtacaaa cgtatggaat gcttcttaaa    5460
```

-continued

| | |
|---|---|
| gggggaactgt caagctggtg tcttcagcca gatgacatga gagaatatcc cagaaccctc | 5520 |
| tctccaaggt gtttctagat agcacaggag agcaggcact gcactgtcca cagtccacgg | 5580 |
| tacacagtcg ggtgggccgc ctcccctctc ctgggagcat tcgtcgtgcc cagcctgagc | 5640 |
| agggcagctg gactgctgct gttcaggagc caccagagcc ttcctctctt tgtaccacag | 5700 |
| tttcttctgt aaatccagtg ttacaatcag tgtgaatggc aaataaacag tttgacaagt | 5760 |
| acatacacca ta | 5772 |

<210> SEQ ID NO 21
<211> LENGTH: 5964
<212> TYPE: DNA
<213> ORGANISM: Homo sapiens

<400> SEQUENCE: 21

| | |
|---|---|
| acagttaaat ttgtaatttg ggttgtgtga aaacttcttt gggcctcata acaaccaca | 60 |
| gaaccacaag ttgggtagcc tggcagtgtc agaagtctga acccagcata gtggtcagca | 120 |
| ggcaggacga atcacactga atgcaaacca cagggtttcg cagcgtggta aaagaaatca | 180 |
| ttgagtcccc cgccttcaga agagggtgca ttttcaggag gaagcgatgg cttcagacag | 240 |
| catatttgag tcatttcctt cgtacccaca gtgcttcatg agagatgcca gcacgagccg | 300 |
| ccgcttcacg ccgccttcca ccgcgctgag cccaggcaag atgagcgagg cgttgccgct | 360 |
| gggcgccccg gacgccggcg ctgccctggc cggcaagctg aggagcggcg accgcagcat | 420 |
| ggtggaggtg ctggccgacc acccgggcga gctggtgcgc accgacagcc ccaacttcct | 480 |
| ctgctccgtg ctgcctacgc actggcgctg caacaagacc ctgcccatcg ctttcaaggt | 540 |
| ggtggcccta ggggatgttc cagatggcac tctggtcact gtgatggctg caatgatga | 600 |
| aaactactcg gctgagctga gaaatgctac cgcagccatg aagaaccagg ttgcaagatt | 660 |
| taatgacctc aggtttgtcg gtcgaagtgg aagagggaaa agcttcactc tgaccatcac | 720 |
| tgtcttcaca aacccaccgc aagtcgccac ctaccacaga gccatcaaaa tcacagtgga | 780 |
| tgggccccga gaacctcgaa gacatcggca gaaactagat gatcagacca agcccgggag | 840 |
| cttgtccttt tccgagcggc tcagtgaact ggagcagctg cggcgcacag ccatgagggt | 900 |
| cagcccacac cacccagccc ccacgcccaa ccctcgtgcc tccctgaacc actccactgc | 960 |
| cttaacccct cagcctcaga gtcagatgca ggatacaagg cagatccaac catccccacc | 1020 |
| gtggtcctac gatcagtcct accaatacct gggatccatt gcctctcctt ctgtgcaccc | 1080 |
| agcaacgccc atttcacctg gacgtgccag cggcatgaca ccctctctg cagaactttc | 1140 |
| cagtcgactc tcaacggcac ccgacctgac agcgttcagc gacccgcgcc agttccccgc | 1200 |
| gctgccctcc atctccgacc cccgcatgca ctatccaggc gccttcacct actccccgac | 1260 |
| gccggtcacc tcgggcatcg gcatcggcat gtcggccatg ggctcggcca cgcgctacca | 1320 |
| cacctacctg ccgccgccct accccggctc gtcgcaagcg cagggaggcc cgttccaagc | 1380 |
| cagctcgccc tcctaccacc tgtactacgg cgcctcggcc ggctcctacc agttctccat | 1440 |
| ggtgggcggc gagcgctcgc cgccgcgcat cctgccgccc tgcaccaacg cctccaccgg | 1500 |
| ctccgcgctc tcaacccca gcctcccgaa ccagagcgac gtggtggagg ccgagggcag | 1560 |
| ccacagcaac tccccccacc acatggcgcc ctccgcgcgc ctggaggagg ccgtgtggag | 1620 |
| gccctactga ggcgcaggc ctggcccggc tgggccccgc gggccgccgc cttcgcctcc | 1680 |
| gggcgcgcgg gcctcctgtt cgcgacaagc ccgccgggat cccgggccct gggcccggcc | 1740 |

-continued

```
accgtcctgg ggccgagggc gcccgacggc caggatctcg ctgtaggtca ggcccgcgca   1800
gcctcctgcg cccagaagcc cacgccgccg ccgtctgctg gcgccccggc cctcgcggag   1860
gtgtccgagg cgacgcacct cgagggtgtc cgccggcccc agcacccagg ggacgcgctg   1920
gaaagcaaac aggaagattc ccggaggaa actgtgaatg cttctgattt agcaatgctg    1980
tgaataaaaa gaaagatttt ataccttga cttaactttt taaccaagtt gtttattcca    2040
aagagtgtgg aattttggtt ggggtggggg gagaggaggg atgcaactcg ccctgtttgg   2100
catctaattc ttattttaa ttttccgca ccttatcaat tgcaaaatgc gtatttgcat     2160
ttgggtggtt tttattttta tatacgttta tataaatata tataaattga gcttgcttct   2220
ttcttgcttt gaccatggaa agaaatatga ttcccttttc tttaagtttt atttaacttt   2280
tcttttggac ttttgggtag ttgttttttt ttgttttgtt ttgttttttt gagaaacagc   2340
tacagctttg ggtcattttt aactactgta ttcccacaag gaatcccag atatttatgt    2400
atcttgatgt tcagacattt atgtgttgat aatttttaa ttatttaaat gtacttatat    2460
taagaaaaat atcaagtact acattttctt ttgttcttga tagtagccaa agttaaatgt   2520
atcacattga agaaggctag aaaaaaagaa tgagtaatgt gatcgcttgg ttatccagaa   2580
gtattgttta cattaaactc cctttcatgt taatcaaaca agtgagtagc tcacgcagca   2640
acgttttaa taggattttt agacactgag ggtcactcca aggatcagaa gtatggaatt    2700
ttctgccagg ctcaacaagg gtctcatatc taacttcctc cttaaaacag agaaggtcaa   2760
tctagttcca gagggttgag gcaggtgcca ataattacat cttttggagag gatttgattt  2820
ctgcccaggg atttgctcac cccaaggtca tctgataatt tcacagatgc tgtgtaacag   2880
aacacagcca agtaaactg tgtaggggag ccacatttac ataggaacca aatcaatgaa    2940
tttaggggtt acgattatag caatttaagg gcccaccaga agcaggcctc gaggagtcaa   3000
tttgcctctg tgtgcctcag tggagacaag tgggaaaaca tggtcccacc tgtgcgagac   3060
cccctgtcct gtgctgctca ctcaacaaca tcttttgtgtt gctttcacca ggctgagacc  3120
ctaccctatg gggtatatgg gcttttacct gtgcaccagt gtgacaggaa agattcatgt   3180
cactactgtc cgtggctaca attcaaaggt atccaatgtc gctgtaaatt ttatggcact   3240
attttattg gaggatttgg tcagaatgca gttgttgtac aactcataaa tactaactgc    3300
tgattttgac acatgtgtgc tccaaatgat ctggtggtta tttaacgtac ctcttaaaat   3360
tcgttgaaac gatttcaggt caactctgaa gagtatttga aagcaggact tcagaacagt   3420
gttttgatttt tattttataa atttaagcat tcaaattagg caaatctttg gctgcaggca  3480
gcaaaaacag ctggacttat ttaaaacaac ttgttttgttga gttttcttat atatatattg 3540
attatttgtt ttacacacat gcagtagcac tttggtaaga gttaaagagt aaagcagctt   3600
atgttgtcag gtcgttctta tctagagaag agctatagca gatctcggac aaactcagaa   3660
tatattcact ttcattttg acaggattcc ctccacaact cagtttcata tattattccg    3720
tattacattt ttgcagctaa attaccataa aatgtcagca aatgtaaaaa tttaattct    3780
gaaaagcacc attagcccat ttccccaaa ttaaacgtaa atgtttttt tcagcacatg     3840
ttaccatgtc tgacctgcaa aaatgctgga gaaaatgaa ggaaaaaatt atgttttca    3900
gtttaattct gttaactgaa gatattccaa ctcaaaacca gcctcatgct ctgattagat   3960
aatcttttac attgaacctt tactctcaaa gccatgtgtg gaggggcgtt gtcactattg   4020
taggctcact ggattggtca tttagagttt cacagactct taccagcata tatagtattt   4080
aattgtttca aaaaaaatca aactgtagtt gttttggcga taggtctcac gcaacacatt   4140
```

```
tttgtatgtg tgtgtgtgtg cgtgtgtgtg tgtgtgtgtg aaaaattgca ttcattgact    4200
tcaggtagat taaggtatct ttttattcat tgccctcagg aaagttaagg tatcaatgag    4260
acccttaagc caatcatgta ataactgcat gtgtctggtc caggagaagt attgaataag    4320
ccatttctac tgcttactca tgtcccctatt tatgatttca acatggatac atatttcagt    4380 tctttcttttt tctcactatc tgaaaataca tttcctccc tctcttcccc ccaatatctc    4440
cctttttttc tctcttcctc tatcttccaa accccacttt ctccctcctc cttttcctgt    4500
gttctcttaa gcagatagca cataccccca cccagtacca aatttcagaa cacaagaagg    4560
tccagttctt cccccttcac ataaaggaac atggtttgtc agccttctc ctgtttatgg    4620 gtttcttcca gcagaacaga gacattgcca accatattgg atctgcttgc tgtccaaacc    4680
agcaaacttt cctgggcaaa tcacaatcag tgagtaaata dacagccttt ctgctgcctt    4740
gggtttctgt gcagataaac agaaatgctc tgattagaaa ggaaatgaat ggttccactc    4800
aaatgtcctg caatttagga ttgcagattt ctgccttgaa atacctgttt ctttgggaca    4860
ttccgtcctg atgatttta ttttgttgg tttttattt tgggggaat gacatgtttg    4920 ggtctttat acatgaaaat ttgtttgaca ataatctcac aaaacatatt ttacatctga    4980
acaaaatgcc tttttgttta ccgtagcgta tacatttgtt ttgggatttt tgtgtgtttg    5040
ttgggaattt tgtttttagc caggtcagta ttgatgaggc tgatcatttg gctctttttt    5100
tccttccaga agagttgcat caacaaagtt aattgtattt atgtatgtaa atagatttta    5160
agcttcatta taaatattg ttaatgccta taactttttt tcaatttttt tgtgtgtgtt    5220
tctaaggact ttttcttagg tttgctaaat actgtaggga aaaaatgct tctttctact    5280 ttgttttattt tagactttaa aatgagctac ttcttattca cttttgtaaa cagctaatag    5340
catggttcca attttttta agttcacttt ttttgttcta ggggaaatga atgtgcaaaa    5400
aaagaaaaag aactgttggt tatttgtgtt attctggatg tataaaatc aatgaaaaa    5460 aataaacttt caaattgaaa tgacggtata acacatctac tgaaaagca acgggaaatg    5520 tggtcctatt taagccagcc cccacctagg gtctatttgt gtggcagtta ttgggtttgg    5580
tcacaaaaca tcctgaaaat tcgtgcgtgg gcttctttct ccctggtaca aacgtatgga    5640
atgcttctta aagggaact gtcaagctgg tgtcttcagc cagatgacat gagagaatat    5700
cccagaaccc tctctccaag gtgtttctag atagcacagg agagcaggca ctgcactgtc    5760
cacagtccac ggtacacagt cgggtgggcc gcctcccctc tcctgggagc attcgtcgtg    5820
cccagcctga gcagggcagc tggactgctg ctgttcagga gccaccagag ccttcctctc    5880
tttgtaccac agtttcttct gtaaatccag tgttacaatc agtgtgaatg caaataaac    5940 agtttgacaa gtacatacac cata    5964
```

<210> SEQ ID NO 22
<211> LENGTH: 6078
<212> TYPE: DNA
<213> ORGANISM: Homo sapiens

<400> SEQUENCE: 22

```
gtaatttggg ttgtgtgaaa acttctttgg gcctcataaa caaccacaga accacaagtt     60
gggtagcctg gcagtgtcag aagtctgaac ccagcatagt ggtcagcagg caggacgaat    120
cacactgaat gcaaaccaca gggtttcgca gcgtggtgag catcaccaac ccacagccaa    180
ggcggcgctg gctttttttt ttttttaat ctttaacaat ttgaatattt gttttacaa    240
```

| | |
|---|---|
| aggtaaaaga aatcattgag tccccgcct tcagaagagg gtgcattttc aggaggaagc | 300 |
| gatggcttca gacagcatat ttgagtcatt tccttcgtac ccacagtgct tcatgagaga | 360 |
| atgcatactt ggaatgaatc cttctagaga cgtccacgat gccagcacga gccgccgctt | 420 |
| cacgccgcct tccaccgcgc tgagcccagg caagatgagc gaggcgttgc cgctgggcgc | 480 |
| cccggacgcc ggcgctgccc tggccggcaa gctgaggagc ggcgaccgca gcatggtgga | 540 |
| ggtgctggcc gaccacccgg gcgagctggt gcgcaccgac agccccaact tcctctgctc | 600 |
| cgtgctgcct acgcactggc gctgcaacaa gaccctgccc atcgctttca aggtggtggc | 660 |
| cctaggggat gttccagatg gcactctggt cactgtgatg gctggcaatg atgaaaacta | 720 |
| ctcggctgag ctgagaaatg ctaccgcagc catgaagaac caggttgcaa gatttaatga | 780 |
| cctcaggttt gtcggtcgaa gtggaagagg gaaaagcttc actctgacca tcactgtctt | 840 |
| cacaaaccca ccgcaagtcg ccacctacca cagagccatc aaaatcacag tggatgggcc | 900 |
| ccgagaacct cgaagacatc ggcagaaact agatgatcag accaagcccg ggagcttgtc | 960 |
| cttttccgag cggctcagtg aactggagca gctgcggcgc acagccatga gggtcagccc | 1020 |
| acaccaccca gccccacgc ccaaccctcg tgcctccctg aaccactcca ctgcctttaa | 1080 |
| ccctcagcct cagagtcaga tgcaggatac aaggcagatc caaccatccc caccgtggtc | 1140 |
| ctacgatcag tcctaccaat acctgggatc cattgcctct ccttctgtgc acccagcaac | 1200 |
| gcccatttca cctggacgtg ccagcggcat gacaaccctc tctgcagaac tttccagtcg | 1260 |
| actctcaacg gcacccgacc tgacagcgtt cagcgacccg cgccagttcc ccgcgctgcc | 1320 |
| ctccatctcc gaccccgca tgcactatcc aggcgccttc acctactccc cgacgccggt | 1380 |
| cacctcgggc atcggcatcg gcatgtcggc catgggctcg gccacgcgct accacaccta | 1440 |
| cctgccgccg ccctacccg gctcgtcgca agcgcaggga ggcccgttcc aagccagctc | 1500 |
| gccctcctac cacctgtact acggcgcctc ggccggctcc taccagttct ccatggtggg | 1560 |
| cggcgagcgc tcgccgccgc gcatcctgcc gccctgcacc aacgcctcca ccggctccgc | 1620 |
| gctgctcaac cccagcctcc gaaccagag cgacgtggtg gaggccgagg gcagccacag | 1680 |
| caactccccc accaacatgg cgccctccgc gcgcctggag gaggccgtgt ggaggcccta | 1740 |
| ctgaggcgcc aggcctggcc cggctgggcc ccgcgggccg ccgccttcgc ctccgggcgc | 1800 |
| gcgggcctcc tgttcgcgac aagcccgccg ggatcccggg ccctgggccc ggccaccgtc | 1860 |
| ctggggccga gggcgcccga cggccaggat ctcgctgtag gtcaggcccg cgcagcctcc | 1920 |
| tgcgcccaga agcccacgcc gccgccgtct gctggcgccc cggccctcgc ggaggtgtcc | 1980 |
| gaggcgacgc acctcgaggg tgtccgccgg ccccagcacc caggggacgc gctggaaagc | 2040 |
| aaacaggaag attcccggag ggaaactgtg aatgcttctg atttagcaat gctgtgaata | 2100 |
| aaaagaaaga ttttataccc ttgacttaac ttttaacca agttgtttat tccaaagagt | 2160 |
| gtggaatttt ggttggggtg gggggagagg agggatgcaa ctcgccctgt ttggcatcta | 2220 |
| attcttattt ttaattttc cgcaccttat caattgcaaa atgcgtattt gcatttgggt | 2280 |
| ggttttatt tttatatacg tttatataaa tatatataaa ttgagcttgc ttctttcttg | 2340 |
| ctttgaccat ggaagaaat atgattccct tttctttaag ttttatttaa cttttctttt | 2400 |
| ggacttttgg gtagttgttt ttttttgttt tgttttgttt tttgagaaa cagctacagc | 2460 |
| tttgggtcat tttaactac tgtattccca caaggaatcc ccagatattt atgtatcttg | 2520 |
| atgttcagac atttatgtgt tgataatttt ttaattattt aaatgtactt atattaagaa | 2580 |
| aaatatcaag tactacattt tcttttgttc ttgatagtag ccaaagttaa atgtatcaca | 2640 |

```
ttgaagaagg ctagaaaaaa agaatgagta atgtgatcgc ttggttatcc agaagtattg   2700
tttacattaa actcccttc atgttaatca aacaagtgag tagctcacgc agcaacgttt    2760
ttaataggat ttttagacac tgagggtcac tccaaggatc agaagtatgg aattttctgc   2820
caggctcaac aagggtctca tatctaactt cctccttaaa acagagaagg tcaatctagt   2880
tccagagggt tgaggcaggt gccaataatt acatctttgg agaggatttg atttctgccc   2940
agggatttgc tcacccaag gtcatctgat aatttcacag atgctgtgta acagaacaca    3000
gccaaagtaa actgtgtagg ggagccacat ttacatagga accaaatcaa tgaatttagg   3060
ggttacgatt atagcaattt aagggcccac cagaagcagg cctcgaggag tcaatttgcc   3120
tctgtgtgcc tcagtggaga caagtgggaa acatggtcc cacctgtgcg agacccctg     3180 tcctgtgctg ctcactcaac aacatctttg tgttgctttc accaggctga gaccctaccc   3240
tatggggtat atgggctttt acctgtgcac cagtgtgaca ggaaagattc atgtcactac   3300
tgtccgtggc tacaattcaa aggtatccaa tgtcgctgta aattttatgg cactattttt   3360
attggaggat ttggtcagaa tgcagttgtt gtacaactca taaatactaa ctgctgattt   3420
tgacacatgt gtgctccaaa tgatctggtg gttatttaac gtacctctta aaattcgttg   3480 aaacgattc aggtcaactc tgaagagtat ttgaaagcag acttcagaa cagtgtttga     3540 tttttatttt ataaatttaa gcattcaaat taggcaaatc tttggctgca ggcagcaaaa   3600
acagctggac ttatttaaaa caacttgttt ttgagttttc ttatatatat attgattatt   3660
tgttttacac acatgcagta gcactttggt aagagttaaa gagtaaagca gcttatgttg   3720
tcaggtcgtt cttatctaga aagagctat agcagatctc ggacaaactc agaatatatt    3780
cactttcatt tttgacagga ttccctccac aactcagttt catatattat tccgtattac   3840 attttgcag ctaaattacc ataaaatgtc agcaaatgta aaaatttaat ttctgaaaag     3900
caccattagc ccatttcccc caaattaaac gtaaatgttt tttttcagca catgttacca   3960
tgtctgacct gcaaaaatgc tggagaaaaa tgaaggaaaa aattatgttt ttcagtttaa   4020
ttctgttaac tgaagatatt ccaactcaaa accagcctca tgctctgatt agataatctt   4080
ttacattgaa cctttactct caaagccatg tgtggagggg gcttgtcact attgtaggct   4140
cactggattg gtcatttaga gtttcacaga ctcttaccag catatatagt atttaattgt   4200
ttcaaaaaaa atcaaactgt agttgttttg gcgataggtc tcacgcaaca cattttgtg   4260 tgtgtgtgtg tgtgcgtgtg tgtgtgtgtg tgtgaaaaat tgcattcatt gacttcaggt   4320
agattaaggt atctttttat tcattgccct caggaaagtt aaggtatcaa tgagaccctt   4380
aagccaatca tgtaataact gcatgtgtct ggtccaggag aagtattgaa taagccattt   4440
ctactgctta ctcatgtccc tatttatgat ttcaacatgg atacatattt cagttctttc   4500 ttttctcac tatctgaaaa tacatttccc tccctctctt ccccccaata tctcccttt      4560 tttctctctt cctctatctt ccaaaccca ctttctccct cctcctttc ctgtgttctc      4620 ttaagcagat agcacatacc cccacccagt accaaatttc agaacacaag aaggtccagt   4680 tcttcccct tcacataaag gaacatggtt tgtcagcctt tctcctgttt atgggtttct    4740
tccagcagaa cagagacatt gccaaccata ttggatctgc ttgctgtcca aaccagcaaa   4800
ctttcctggg caaatcacaa tcagtgagta aatagacagc ttttctgctg ccttgggtt    4860 ctgtgcagat aaacagaaat gctctgatta gaaaggaaat gaatggttcc actcaaatgt   4920
cctgcaattt aggattgcag atttctgcct tgaaatacct gtttctttgg gacattccgt   4980
```

| | | | | |
|---|---|---|---|---|
| cctgatgatt tttattttg ttggttttta tttttgggg gaatgacatg tttgggtctt | | | | 5040 |
| ttatacatga aaatttgttt gacaataatc tcacaaaaca tattttacat ctgaacaaaa | | | | 5100 |
| tgccttttg tttaccgtag cgtatacatt tgttttggga tttttgtgtg tttgttggga | | | | 5160 |
| attttgtttt tagccaggtc agtattgatg aggctgatca tttggctctt ttttccttc | | | | 5220 |
| cagaagagtt gcatcaacaa agttaattgt atttatgtat gtaaatagat tttaagcttc | | | | 5280 |
| attataaaat attgttaatg cctataactt tttttcaatt tttttgtgtg tgtttctaag | | | | 5340 |
| gacttttct taggtttgct aaatactgta ggaaaaaaa tgcttctttc tactttgttt | | | | 5400 |
| attttagact ttaaaatgag ctacttctta ttcacttttg taaacagcta atagcatggt | | | | 5460 |
| tccaattttt tttaagttca cttttttgt tctaggggaa atgaatgtgc aaaaaagaa | | | | 5520 |
| aaagaactgt tggttatttg tgttattctg gatgtataaa aatcaatgga aaaaataaa | | | | 5580 |
| ctttcaaatt gaaatgacgg tataacacat ctactgaaaa agcaacggga aatgtggtcc | | | | 5640 |
| tatttaagcc agcccccacc tagggtctat ttgtgtggca gttattgggt ttggtcacaa | | | | 5700 |
| aacatcctga aaattcgtgc gtgggcttct ttctccctgg tacaaacgta tggaatgctt | | | | 5760 |
| cttaaagggg aactgtcaag ctggtgtctt cagccagatg acatgagaga atatcccaga | | | | 5820 |
| accctctctc caaggtgttt ctagatagca caggagagca ggcactgcac tgtccacagt | | | | 5880 |
| ccacggtaca cagtcgggtg ggccgcctcc cctctcctgg gagcattcgt cgtgcccagc | | | | 5940 |
| ctgagcaggg cagctggact gctgctgttc aggagccacc agagccttcc tctctttgta | | | | 6000 |
| ccacagtttc ttctgtaaat ccagtgttac aatcagtgtg aatggcaaat aaacagtttg | | | | 6060 |
| acaagtacat acaccata | | | | 6078 |

<210> SEQ ID NO 23
<211> LENGTH: 521
<212> TYPE: PRT
<213> ORGANISM: Homo sapiens

<400> SEQUENCE: 23

```
Met Ala Ser Asn Ser Leu Phe Ser Thr Val Thr Pro Cys Gln Gln Asn
1               5                   10                  15

Phe Phe Trp Asp Pro Ser Thr Ser Arg Arg Phe Ser Pro Pro Ser Ser
            20                  25                  30

Ser Leu Gln Pro Gly Lys Met Ser Asp Val Ser Pro Val Val Ala Ala
        35                  40                  45

Gln Gln Gln Gln Gln Gln Gln Gln Gln Gln Gln Gln Gln Gln
    50                  55                  60

Gln Gln Gln Gln Gln Gln Glu Ala Ala Ala Ala Ala Ala Ala
65                  70                  75                  80

Ala Ala Ala Ala Ala Ala Ala Ala Val Pro Arg Leu Arg Pro Pro
                85                  90                  95

His Asp Asn Arg Thr Met Val Glu Ile Ile Ala Asp His Pro Ala Glu
            100                 105                 110

Leu Val Arg Thr Asp Ser Pro Asn Phe Leu Cys Ser Val Leu Pro Ser
        115                 120                 125

His Trp Arg Cys Asn Lys Thr Leu Pro Val Ala Phe Lys Val Val Ala
    130                 135                 140

Leu Gly Glu Val Pro Asp Gly Thr Val Val Thr Val Met Ala Gly Asn
145                 150                 155                 160

Asp Glu Asn Tyr Ser Ala Glu Leu Arg Asn Ala Ser Ala Val Met Lys
                165                 170                 175
```

Asn Gln Val Ala Arg Phe Asn Asp Leu Arg Phe Val Gly Arg Ser Gly
                180                 185                 190

Arg Gly Lys Ser Phe Thr Leu Thr Ile Thr Val Phe Thr Asn Pro Pro
            195                 200                 205

Gln Val Ala Thr Tyr His Arg Ala Ile Lys Val Thr Val Asp Gly Pro
        210                 215                 220

Arg Glu Pro Arg Arg His Arg Gln Lys Leu Asp Asp Ser Lys Pro Ser
225                 230                 235                 240

Leu Phe Ser Asp Arg Leu Ser Asp Leu Gly Arg Ile Pro His Pro Ser
                245                 250                 255

Met Arg Val Gly Val Pro Pro Gln Asn Pro Arg Pro Ser Leu Asn Ser
            260                 265                 270

Ala Pro Ser Pro Phe Asn Pro Gln Gly Gln Ser Gln Ile Thr Asp Pro
        275                 280                 285

Arg Gln Ala Gln Ser Ser Pro Pro Trp Ser Tyr Asp Gln Ser Tyr Pro
    290                 295                 300

Ser Tyr Leu Ser Gln Met Thr Ser Pro Ser Ile His Ser Thr Thr Pro
305                 310                 315                 320

Leu Ser Ser Thr Arg Gly Thr Gly Leu Pro Ala Ile Thr Asp Val Pro
                325                 330                 335

Arg Arg Ile Ser Asp Asp Asp Thr Ala Thr Ser Asp Phe Cys Leu Trp
            340                 345                 350

Pro Ser Thr Leu Ser Lys Lys Ser Gln Ala Gly Ala Ser Glu Leu Gly
        355                 360                 365

Pro Phe Ser Asp Pro Arg Gln Phe Pro Ser Ile Ser Ser Leu Thr Glu
    370                 375                 380

Ser Arg Phe Ser Asn Pro Arg Met His Tyr Pro Ala Thr Phe Thr Tyr
385                 390                 395                 400

Thr Pro Pro Val Thr Ser Gly Met Ser Leu Gly Met Ser Ala Thr Thr
                405                 410                 415

His Tyr His Thr Tyr Leu Pro Pro Tyr Pro Gly Ser Ser Gln Ser
            420                 425                 430

Gln Ser Gly Pro Phe Gln Thr Ser Ser Thr Pro Tyr Leu Tyr Tyr Gly
        435                 440                 445

Thr Ser Ser Gly Ser Tyr Gln Phe Pro Met Val Pro Gly Gly Asp Arg
    450                 455                 460

Ser Pro Ser Arg Met Leu Pro Pro Cys Thr Thr Thr Ser Asn Gly Ser
465                 470                 475                 480

Thr Leu Leu Asn Pro Asn Leu Pro Asn Gln Asn Asp Gly Val Asp Ala
                485                 490                 495

Asp Gly Ser His Ser Ser Ser Pro Thr Val Leu Asn Ser Ser Gly Arg
            500                 505                 510

Met Asp Glu Ser Val Trp Arg Pro Tyr
            515                 520

<210> SEQ ID NO 24
<211> LENGTH: 499
<212> TYPE: PRT
<213> ORGANISM: Homo sapiens

<400> SEQUENCE: 24

Met Ala Ser Asn Ser Leu Phe Ser Thr Val Thr Pro Cys Gln Gln Asn
1               5                   10                  15

Phe Phe Trp Asp Pro Ser Thr Ser Arg Arg Phe Ser Pro Pro Ser Ser
                20                  25                  30

```
Ser Leu Gln Pro Gly Lys Met Ser Asp Val Ser Pro Val Ala Ala
         35                  40                  45

Gln Gln Gln Gln Gln Gln Gln Gln Gln Gln Gln Gln Gln Gln Gln
 50                  55                  60

Gln Gln Gln Gln Gln Gln Glu Ala Ala Ala Ala Ala Ala Ala Ala
 65                  70                  75                  80

Ala Ala Ala Ala Ala Ala Ala Ala Val Pro Arg Leu Arg Pro Pro
                 85                  90                  95

His Asp Asn Arg Thr Met Val Glu Ile Ile Ala Asp His Pro Ala Glu
             100                 105                 110

Leu Val Arg Thr Asp Ser Pro Asn Phe Leu Cys Ser Val Leu Pro Ser
         115                 120                 125

His Trp Arg Cys Asn Lys Thr Leu Pro Val Ala Phe Lys Val Val Ala
 130                 135                 140

Leu Gly Glu Val Pro Asp Gly Thr Val Val Thr Val Met Ala Gly Asn
145                 150                 155                 160

Asp Glu Asn Tyr Ser Ala Glu Leu Arg Asn Ala Ser Ala Val Met Lys
                 165                 170                 175

Asn Gln Val Ala Arg Phe Asn Asp Leu Arg Phe Val Gly Arg Ser Gly
             180                 185                 190

Arg Gly Lys Ser Phe Thr Leu Thr Ile Thr Val Phe Thr Asn Pro Pro
         195                 200                 205

Gln Val Ala Thr Tyr His Arg Ala Ile Lys Val Thr Val Asp Gly Pro
 210                 215                 220

Arg Glu Pro Arg Arg His Arg Gln Lys Leu Asp Ser Lys Pro Ser
225                 230                 235                 240

Leu Phe Ser Asp Arg Leu Ser Asp Leu Gly Arg Ile Pro His Pro Ser
                 245                 250                 255

Met Arg Val Gly Val Pro Pro Gln Asn Pro Arg Pro Ser Leu Asn Ser
             260                 265                 270

Ala Pro Ser Pro Phe Asn Pro Gln Gly Gln Ser Gln Ile Thr Asp Pro
         275                 280                 285

Arg Gln Ala Gln Ser Ser Pro Pro Trp Ser Tyr Asp Gln Ser Tyr Pro
 290                 295                 300

Ser Tyr Leu Ser Gln Met Thr Ser Pro Ser Ile His Ser Thr Thr Pro
305                 310                 315                 320

Leu Ser Ser Thr Arg Gly Thr Gly Leu Pro Ala Ile Thr Asp Val Pro
                 325                 330                 335

Arg Arg Ile Ser Gly Ala Ser Glu Leu Gly Pro Phe Ser Asp Pro Arg
             340                 345                 350

Gln Phe Pro Ser Ile Ser Ser Leu Thr Glu Ser Arg Phe Ser Asn Pro
         355                 360                 365

Arg Met His Tyr Pro Ala Thr Phe Thr Tyr Thr Pro Pro Val Thr Ser
 370                 375                 380

Gly Met Ser Leu Gly Met Ser Ala Thr Thr His Tyr His Thr Tyr Leu
385                 390                 395                 400

Pro Pro Pro Tyr Pro Gly Ser Ser Gln Ser Gln Ser Gly Pro Phe Gln
                 405                 410                 415

Thr Ser Ser Thr Pro Tyr Leu Tyr Tyr Gly Thr Ser Gly Ser Tyr
             420                 425                 430

Gln Phe Pro Met Val Pro Gly Gly Asp Arg Ser Pro Ser Arg Met Leu
         435                 440                 445
```

```
Pro Pro Cys Thr Thr Thr Ser Asn Gly Ser Thr Leu Leu Asn Pro Asn
    450                 455                 460

Leu Pro Asn Gln Asn Asp Gly Val Asp Ala Asp Gly Ser His Ser Ser
465                 470                 475                 480

Ser Pro Thr Val Leu Asn Ser Ser Gly Arg Met Asp Glu Ser Val Trp
                485                 490                 495

Arg Pro Tyr

<210> SEQ ID NO 25
<211> LENGTH: 521
<212> TYPE: PRT
<213> ORGANISM: Homo sapiens

<400> SEQUENCE: 25

Met Ala Ser Asn Ser Leu Phe Ser Thr Val Thr Pro Cys Gln Gln Asn
1               5                   10                  15

Phe Phe Trp Asp Pro Ser Thr Ser Arg Arg Phe Ser Pro Pro Ser Ser
                20                  25                  30

Ser Leu Gln Pro Gly Lys Met Ser Asp Val Ser Pro Val Val Ala Ala
            35                  40                  45

Gln Gln Gln Gln Gln Gln Gln Gln Gln Gln Gln Gln Gln Gln Gln Gln
50                  55                  60

Gln Gln Gln Gln Gln Gln Glu Ala Ala Ala Ala Ala Ala Ala Ala Ala
65                  70                  75                  80

Ala Ala Ala Ala Ala Ala Ala Ala Val Pro Arg Leu Arg Pro Pro
                85                  90                  95

His Asp Asn Arg Thr Met Val Glu Ile Ile Ala Asp His Pro Ala Glu
                100                 105                 110

Leu Val Arg Thr Asp Ser Pro Asn Phe Leu Cys Ser Val Leu Pro Ser
            115                 120                 125

His Trp Arg Cys Asn Lys Thr Leu Pro Val Ala Phe Lys Val Val Ala
130                 135                 140

Leu Gly Glu Val Pro Asp Gly Thr Val Val Thr Val Met Ala Gly Asn
145                 150                 155                 160

Asp Glu Asn Tyr Ser Ala Glu Leu Arg Asn Ala Ser Ala Val Met Lys
                165                 170                 175

Asn Gln Val Ala Arg Phe Asn Asp Leu Arg Phe Val Gly Arg Ser Gly
            180                 185                 190

Arg Gly Lys Ser Phe Thr Leu Thr Ile Thr Val Phe Thr Asn Pro Pro
        195                 200                 205

Gln Val Ala Thr Tyr His Arg Ala Ile Lys Val Thr Val Asp Gly Pro
    210                 215                 220

Arg Glu Pro Arg Arg His Arg Gln Lys Leu Asp Asp Ser Lys Pro Ser
225                 230                 235                 240

Leu Phe Ser Asp Arg Leu Ser Asp Leu Gly Arg Ile Pro His Pro Ser
                245                 250                 255

Met Arg Val Gly Val Pro Pro Gln Asn Pro Arg Pro Ser Leu Asn Ser
            260                 265                 270

Ala Pro Ser Pro Phe Asn Pro Gln Gly Gln Ser Gln Ile Thr Asp Pro
        275                 280                 285

Arg Gln Ala Gln Ser Ser Pro Pro Trp Ser Tyr Asp Gln Ser Tyr Pro
    290                 295                 300

Ser Tyr Leu Ser Gln Met Thr Ser Pro Ser Ile His Ser Thr Thr Pro
305                 310                 315                 320
```

```
Leu Ser Ser Thr Arg Gly Thr Gly Leu Pro Ala Ile Thr Asp Val Pro
                325                 330                 335

Arg Arg Ile Ser Asp Asp Thr Ala Thr Ser Asp Phe Cys Leu Trp
            340                 345                 350

Pro Ser Thr Leu Ser Lys Lys Ser Gln Ala Gly Ala Ser Glu Leu Gly
            355                 360                 365

Pro Phe Ser Asp Pro Arg Gln Phe Pro Ser Ile Ser Ser Leu Thr Glu
    370                 375                 380

Ser Arg Phe Ser Asn Pro Arg Met His Tyr Pro Ala Thr Phe Thr Tyr
385                 390                 395                 400

Thr Pro Pro Val Thr Ser Gly Met Ser Leu Gly Met Ser Ala Thr Thr
                405                 410                 415

His Tyr His Thr Tyr Leu Pro Pro Tyr Pro Gly Ser Ser Gln Ser
            420                 425                 430

Gln Ser Gly Pro Phe Gln Thr Ser Ser Thr Pro Tyr Leu Tyr Tyr Gly
            435                 440                 445

Thr Ser Ser Gly Ser Tyr Gln Phe Pro Met Val Pro Gly Gly Asp Arg
    450                 455                 460

Ser Pro Ser Arg Met Leu Pro Pro Cys Thr Thr Thr Ser Asn Gly Ser
465                 470                 475                 480

Thr Leu Leu Asn Pro Asn Leu Pro Asn Gln Asn Asp Gly Val Asp Ala
                485                 490                 495

Asp Gly Ser His Ser Ser Ser Pro Thr Val Leu Asn Ser Ser Gly Arg
            500                 505                 510

Met Asp Glu Ser Val Trp Arg Pro Tyr
            515                 520

<210> SEQ ID NO 26
<211> LENGTH: 485
<212> TYPE: PRT
<213> ORGANISM: Homo sapiens

<400> SEQUENCE: 26

Met Arg Ile Pro Val Asp Pro Ser Thr Ser Arg Arg Phe Ser Pro Pro
1               5                   10                  15

Ser Ser Ser Leu Gln Pro Gly Lys Met Ser Asp Val Ser Pro Val Val
                20                  25                  30

Ala Ala Gln Gln Gln Gln Gln Gln Gln Gln Gln Gln Gln Gln Gln
            35                  40                  45

Gln Gln Gln Gln Gln Gln Gln Gln Glu Ala Ala Ala Ala Ala
    50                  55                  60

Ala Ala Ala Ala Ala Ala Ala Ala Ala Ala Val Pro Arg Leu Arg
65                  70                  75                  80

Pro Pro His Asp Asn Arg Thr Met Val Glu Ile Ile Ala Asp His Pro
                85                  90                  95

Ala Glu Leu Val Arg Thr Asp Ser Pro Asn Phe Leu Cys Ser Val Leu
            100                 105                 110

Pro Ser His Trp Arg Cys Asn Lys Thr Leu Pro Val Ala Phe Lys Val
    115                 120                 125

Val Ala Leu Gly Glu Val Pro Asp Gly Thr Val Val Thr Val Met Ala
130                 135                 140

Gly Asn Asp Glu Asn Tyr Ser Ala Glu Leu Arg Asn Ala Ser Ala Val
145                 150                 155                 160

Met Lys Asn Gln Val Ala Arg Phe Asn Asp Leu Arg Phe Val Gly Arg
                165                 170                 175
```

```
Ser Gly Arg Gly Lys Ser Phe Thr Leu Thr Ile Thr Val Phe Thr Asn
            180                 185                 190

Pro Pro Gln Val Ala Thr Tyr His Arg Ala Ile Lys Val Thr Val Asp
            195                 200                 205

Gly Pro Arg Glu Pro Arg Arg His Arg Gln Lys Leu Asp Asp Ser Lys
            210                 215                 220

Pro Ser Leu Phe Ser Asp Arg Leu Ser Asp Leu Gly Arg Ile Pro His
225                 230                 235                 240

Pro Ser Met Arg Val Gly Val Pro Pro Gln Asn Pro Arg Pro Ser Leu
                    245                 250                 255

Asn Ser Ala Pro Ser Pro Phe Asn Pro Gln Gly Gln Ser Gln Ile Thr
                260                 265                 270

Asp Pro Arg Gln Ala Gln Ser Ser Pro Pro Trp Ser Tyr Asp Gln Ser
                275                 280                 285

Tyr Pro Ser Tyr Leu Ser Gln Met Thr Ser Pro Ser Ile His Ser Thr
            290                 295                 300

Thr Pro Leu Ser Ser Thr Arg Gly Thr Gly Leu Pro Ala Ile Thr Asp
305                 310                 315                 320

Val Pro Arg Arg Ile Ser Gly Ala Ser Glu Leu Gly Pro Phe Ser Asp
                    325                 330                 335

Pro Arg Gln Phe Pro Ser Ile Ser Ser Leu Thr Glu Ser Arg Phe Ser
                340                 345                 350

Asn Pro Arg Met His Tyr Pro Ala Thr Phe Thr Tyr Thr Pro Pro Val
                355                 360                 365

Thr Ser Gly Met Ser Leu Gly Met Ser Ala Thr Thr His Tyr His Thr
            370                 375                 380

Tyr Leu Pro Pro Pro Tyr Pro Gly Ser Ser Gln Ser Gln Ser Gly Pro
385                 390                 395                 400

Phe Gln Thr Ser Ser Thr Pro Tyr Leu Tyr Tyr Gly Thr Ser Ser Gly
                405                 410                 415

Ser Tyr Gln Phe Pro Met Val Pro Gly Gly Asp Arg Ser Pro Ser Arg
            420                 425                 430

Met Leu Pro Pro Cys Thr Thr Thr Ser Asn Gly Ser Thr Leu Leu Asn
            435                 440                 445

Pro Asn Leu Pro Asn Gln Asn Asp Gly Val Asp Ala Asp Gly Ser His
450                 455                 460

Ser Ser Ser Pro Thr Val Leu Asn Ser Ser Gly Arg Met Asp Glu Ser
465                 470                 475                 480

Val Trp Arg Pro Tyr
            485

<210> SEQ ID NO 27
<211> LENGTH: 514
<212> TYPE: PRT
<213> ORGANISM: Mus musculus

<400> SEQUENCE: 27

Met Arg Ile Pro Val Asp Pro Ser Thr Ser Arg Arg Phe Ser Pro Pro
1               5                   10                  15

Ser Ser Ser Leu Gln Pro Gly Lys Met Ser Asp Val Ser Pro Val Val
                20                  25                  30

Ala Ala Gln Gln Gln Gln Gln Gln Gln Gln Gln Gln Gln Gln Gln Gln
            35                  40                  45

Gln Gln Gln Gln Gln Gln Gln Gln Gln Gln Gln Gln Gln Gln Gln Glu
```

```
                50                  55                  60
Ala Ala Ala Ala Ala Ala Ala Ala Ala Ala Ala Ala Ala Ala Ala Ala
 65                  70                  75                  80

Ala Ala Val Pro Arg Leu Arg Pro Pro His Asp Asn Arg Thr Met Val
                     85                  90                  95

Glu Ile Ile Ala Asp His Pro Ala Glu Leu Val Arg Thr Asp Ser Pro
                100                 105                 110

Asn Phe Leu Cys Ser Val Leu Pro Ser His Trp Arg Cys Asn Lys Thr
                115                 120                 125

Leu Pro Val Ala Phe Lys Val Ala Leu Gly Glu Val Pro Asp Gly
                130                 135                 140

Thr Val Val Thr Val Met Ala Gly Asn Asp Glu Asn Tyr Ser Ala Glu
145                 150                 155                 160

Leu Arg Asn Ala Ser Ala Val Met Lys Asn Gln Val Ala Arg Phe Asn
                165                 170                 175

Asp Leu Arg Phe Val Gly Arg Ser Gly Arg Gly Lys Ser Phe Thr Leu
                180                 185                 190

Thr Ile Thr Val Phe Thr Asn Pro Pro Gln Val Ala Thr Tyr His Arg
                195                 200                 205

Ala Ile Lys Val Thr Val Asp Gly Pro Arg Glu Pro Arg Arg His Arg
 210                 215                 220

Gln Lys Leu Asp Asp Ser Lys Pro Ser Leu Phe Ser Asp Arg Leu Ser
225                 230                 235                 240

Asp Leu Gly Arg Ile Pro His Pro Ser Met Arg Val Gly Val Pro Pro
                245                 250                 255

Gln Asn Pro Arg Pro Ser Leu Asn Ser Ala Pro Ser Pro Phe Asn Pro
                260                 265                 270

Gln Gly Gln Ser Gln Ile Thr Asp Pro Arg Gln Ala Gln Ser Ser Pro
                275                 280                 285

Pro Trp Ser Tyr Asp Gln Ser Tyr Pro Ser Tyr Leu Ser Gln Met Thr
                290                 295                 300

Ser Pro Ser Ile His Ser Thr Thr Pro Leu Ser Ser Thr Arg Gly Thr
305                 310                 315                 320

Gly Leu Pro Ala Ile Thr Asp Val Pro Arg Arg Ile Ser Asp Asp Asp
                325                 330                 335

Thr Ala Thr Ser Asp Phe Cys Leu Trp Pro Ser Ser Leu Ser Lys Lys
                340                 345                 350

Ser Gln Ala Gly Ala Ser Glu Leu Gly Pro Phe Ser Asp Pro Arg Gln
                355                 360                 365

Phe Pro Ser Ile Ser Ser Leu Thr Glu Ser Arg Phe Ser Asn Pro Arg
                370                 375                 380

Met His Tyr Pro Ala Thr Phe Thr Tyr Thr Pro Val Thr Ser Gly
385                 390                 395                 400

Met Ser Leu Gly Met Ser Ala Thr Thr His Tyr His Thr Tyr Leu Pro
                405                 410                 415

Pro Pro Tyr Pro Gly Ser Ser Gln Ser Gln Ser Gly Pro Phe Gln Thr
                420                 425                 430

Ser Ser Pro Tyr Leu Tyr Tyr Gly Thr Ser Ala Ser Tyr Gln
                435                 440                 445

Phe Pro Met Val Pro Gly Gly Asp Arg Ser Pro Ser Arg Met Val Pro
                450                 455                 460

Pro Cys Thr Thr Thr Ser Asn Gly Ser Thr Leu Leu Asn Pro Asn Leu
465                 470                 475                 480
```

```
Pro Asn Gln Asn Asp Gly Val Asp Ala Asp Gly Ser His Ser Ser Ser
                485                 490                 495

Pro Thr Val Leu Asn Ser Ser Gly Arg Met Asp Glu Ser Val Trp Arg
            500                 505                 510

Pro Tyr

<210> SEQ ID NO 28
<211> LENGTH: 528
<212> TYPE: PRT
<213> ORGANISM: Mus musculus

<400> SEQUENCE: 28

Met Ala Ser Asn Ser Leu Phe Ser Ala Val Thr Pro Cys Gln Gln Ser
1               5                   10                  15

Phe Phe Trp Asp Pro Ser Thr Ser Arg Arg Phe Ser Pro Pro Ser Ser
            20                  25                  30

Ser Leu Gln Pro Gly Lys Met Ser Asp Val Ser Pro Val Val Ala Ala
        35                  40                  45

Gln Gln Gln Gln Gln Gln Gln Gln Gln Gln Gln Gln Gln Gln Gln Gln
    50                  55                  60

Gln Gln Gln Gln Gln Gln Gln Gln Gln Gln Gln Gln Glu Ala Ala
65                  70                  75                  80

Ala Ala Ala Ala Ala Ala Ala Ala Ala Ala Ala Ala Ala Ala Ala
                85                  90                  95

Val Pro Arg Leu Arg Pro Pro His Asp Asn Arg Thr Met Val Glu Ile
            100                 105                 110

Ile Ala Asp His Pro Ala Glu Leu Val Arg Thr Asp Ser Pro Asn Phe
        115                 120                 125

Leu Cys Ser Val Leu Pro Ser His Trp Arg Cys Asn Lys Thr Leu Pro
    130                 135                 140

Val Ala Phe Lys Val Val Ala Leu Gly Glu Val Pro Asp Gly Thr Val
145                 150                 155                 160

Val Thr Val Met Ala Gly Asn Asp Glu Asn Tyr Ser Ala Glu Leu Arg
                165                 170                 175

Asn Ala Ser Ala Val Met Lys Asn Gln Val Ala Arg Phe Asn Asp Leu
            180                 185                 190

Arg Phe Val Gly Arg Ser Gly Arg Gly Lys Ser Phe Thr Leu Thr Ile
        195                 200                 205

Thr Val Phe Thr Asn Pro Pro Gln Val Ala Thr Tyr His Arg Ala Ile
    210                 215                 220

Lys Val Thr Val Asp Gly Pro Arg Glu Pro Arg Arg His Arg Gln Lys
225                 230                 235                 240

Leu Asp Asp Ser Lys Pro Ser Leu Phe Ser Asp Arg Leu Ser Asp Leu
                245                 250                 255

Gly Arg Ile Pro His Pro Ser Met Arg Val Gly Val Pro Pro Gln Asn
            260                 265                 270

Pro Arg Pro Ser Leu Asn Ser Ala Pro Ser Pro Phe Asn Pro Gln Gly
        275                 280                 285

Gln Ser Gln Ile Thr Asp Pro Arg Gln Ala Gln Ser Ser Pro Pro Trp
    290                 295                 300

Ser Tyr Asp Gln Ser Tyr Pro Ser Tyr Leu Ser Gln Met Thr Ser Pro
305                 310                 315                 320

Ser Ile His Ser Thr Thr Pro Leu Ser Ser Thr Arg Gly Thr Gly Leu
                325                 330                 335
```

```
Pro Ala Ile Thr Asp Val Pro Arg Arg Ile Ser Asp Asp Thr Ala
            340                 345                 350

Thr Ser Asp Phe Cys Leu Trp Pro Ser Ser Leu Ser Lys Lys Ser Gln
        355                 360                 365

Ala Gly Ala Ser Glu Leu Gly Pro Phe Ser Asp Pro Arg Gln Phe Pro
    370                 375                 380

Ser Ile Ser Ser Leu Thr Glu Ser Arg Phe Ser Asn Pro Arg Met His
385                 390                 395                 400

Tyr Pro Ala Thr Phe Thr Tyr Thr Pro Pro Val Thr Ser Gly Met Ser
                405                 410                 415

Leu Gly Met Ser Ala Thr Thr His Tyr His Thr Tyr Leu Pro Pro Pro
            420                 425                 430

Tyr Pro Gly Ser Ser Gln Ser Gln Ser Gly Pro Phe Gln Thr Ser Ser
        435                 440                 445

Thr Pro Tyr Leu Tyr Tyr Gly Thr Ser Ser Ala Ser Tyr Gln Phe Pro
    450                 455                 460

Met Val Pro Gly Gly Asp Arg Ser Pro Ser Arg Met Val Pro Pro Cys
465                 470                 475                 480

Thr Thr Thr Ser Asn Gly Ser Thr Leu Leu Asn Pro Asn Leu Pro Asn
                485                 490                 495

Gln Asn Asp Gly Val Asp Ala Asp Gly Ser His Ser Ser Ser Pro Thr
            500                 505                 510

Val Leu Asn Ser Ser Gly Arg Met Asp Glu Ser Val Trp Arg Pro Tyr
        515                 520                 525

<210> SEQ ID NO 29
<211> LENGTH: 528
<212> TYPE: PRT
<213> ORGANISM: Mus musculus

<400> SEQUENCE: 29

Met Ala Ser Asn Ser Leu Phe Ser Ala Val Thr Pro Cys Gln Gln Ser
1               5                   10                  15

Phe Phe Trp Asp Pro Ser Thr Ser Arg Arg Phe Ser Pro Pro Ser Ser
                20                  25                  30

Ser Leu Gln Pro Gly Lys Met Ser Asp Val Ser Pro Val Val Ala Ala
            35                  40                  45

Gln Gln Gln Gln Gln Gln Gln Gln Gln Gln Gln Gln Gln Gln Gln Gln
        50                  55                  60

Gln Gln Gln Gln Gln Gln Gln Gln Gln Gln Gln Gln Glu Ala Ala
65                  70                  75                  80

Ala Ala Ala Ala Ala Ala Ala Ala Ala Ala Ala Ala Ala Ala Ala
                85                  90                  95

Val Pro Arg Leu Arg Pro Pro His Asp Asn Arg Thr Met Val Glu Ile
            100                 105                 110

Ile Ala Asp His Pro Ala Glu Leu Val Arg Thr Asp Ser Pro Asn Phe
        115                 120                 125

Leu Cys Ser Val Leu Pro Ser His Trp Arg Cys Asn Lys Thr Leu Pro
    130                 135                 140

Val Ala Phe Lys Val Val Ala Leu Gly Glu Val Pro Asp Gly Thr Val
145                 150                 155                 160

Val Thr Val Met Ala Gly Asn Asp Glu Asn Tyr Ser Ala Glu Leu Arg
                165                 170                 175

Asn Ala Ser Ala Val Met Lys Asn Gln Val Ala Arg Phe Asn Asp Leu
```

```
                180              185              190
Arg Phe Val Gly Arg Ser Gly Arg Gly Lys Ser Phe Thr Leu Thr Ile
            195              200              205
Thr Val Phe Thr Asn Pro Pro Gln Val Ala Thr Tyr His Arg Ala Ile
        210              215              220
Lys Val Thr Val Asp Gly Pro Arg Glu Pro Arg His Arg Gln Lys
225              230              235              240
Leu Asp Asp Ser Lys Pro Ser Leu Phe Ser Asp Arg Leu Ser Asp Leu
            245              250              255
Gly Arg Ile Pro His Pro Ser Met Arg Val Gly Val Pro Gln Asn
        260              265              270
Pro Arg Pro Ser Leu Asn Ser Ala Pro Ser Pro Phe Asn Pro Gln Gly
        275              280              285
Gln Ser Gln Ile Thr Asp Pro Arg Gln Ala Gln Ser Ser Pro Pro Trp
        290              295              300
Ser Tyr Asp Gln Ser Tyr Pro Ser Tyr Leu Ser Gln Met Thr Ser Pro
305              310              315              320
Ser Ile His Ser Thr Thr Pro Leu Ser Ser Thr Arg Gly Thr Gly Leu
            325              330              335
Pro Ala Ile Thr Asp Val Pro Arg Arg Ile Ser Asp Asp Thr Ala
        340              345              350
Thr Ser Asp Phe Cys Leu Trp Pro Ser Ser Leu Ser Lys Lys Ser Gln
        355              360              365
Ala Gly Ala Ser Glu Leu Gly Pro Phe Ser Asp Pro Arg Gln Phe Pro
        370              375              380
Ser Ile Ser Ser Leu Thr Glu Ser Arg Phe Ser Asn Pro Arg Met His
385              390              395              400
Tyr Pro Ala Thr Phe Thr Tyr Thr Pro Pro Val Thr Ser Gly Met Ser
            405              410              415
Leu Gly Met Ser Ala Thr Thr His Tyr His Thr Tyr Leu Pro Pro Pro
            420              425              430
Tyr Pro Gly Ser Ser Gln Ser Gln Ser Gly Pro Phe Gln Thr Ser Ser
            435              440              445
Thr Pro Tyr Leu Tyr Tyr Gly Thr Ser Ser Ala Ser Tyr Gln Phe Pro
        450              455              460
Met Val Pro Gly Gly Asp Arg Ser Pro Ser Arg Met Val Pro Cys
465              470              475              480
Thr Thr Thr Ser Asn Gly Ser Thr Leu Leu Asn Pro Asn Leu Pro Asn
            485              490              495
Gln Asn Asp Gly Val Asp Ala Asp Gly Ser His Ser Ser Ser Pro Thr
        500              505              510
Val Leu Asn Ser Ser Gly Arg Met Asp Glu Ser Val Trp Arg Pro Tyr
        515              520              525
```

<210> SEQ ID NO 30
<211> LENGTH: 456
<212> TYPE: PRT
<213> ORGANISM: Mus musculus

<400> SEQUENCE: 30

```
Met Arg Ile Pro Val Asp Pro Ser Thr Ser Arg Arg Phe Ser Pro Pro
1               5                  10                  15
Ser Ser Ser Leu Gln Pro Gly Lys Met Ser Asp Val Ser Pro Val Val
            20                  25                  30
```

-continued

```
Ala Ala Gln Gln Gln Gln Gln Gln Gln Gln Gln Gln Gln
     35                  40                  45
Gln Gln Gln Gln Gln Gln Gln Gln Gln Gln Gln Gln Glu
 50                  55                  60
Ala Ala Ala Ala Ala Ala Ala Ala Ala Ala Ala Ala Ala Ala Ala Ala
 65                  70                  75                  80
Ala Ala Val Pro Arg Leu Arg Pro Pro His Asp Asn Arg Thr Met Val
                 85                  90                  95
Glu Ile Ile Ala Asp His Pro Ala Glu Leu Val Arg Thr Asp Ser Pro
                 100                 105                 110
Asn Phe Leu Cys Ser Val Leu Pro Ser His Trp Arg Cys Asn Lys Thr
                 115                 120                 125
Leu Pro Val Ala Phe Lys Val Val Ala Leu Gly Glu Val Pro Asp Gly
                 130                 135                 140
Thr Val Val Thr Val Met Ala Gly Asn Asp Glu Asn Tyr Ser Ala Glu
145                 150                 155                 160
Leu Arg Asn Ala Ser Ala Val Met Lys Asn Gln Val Ala Arg Phe Asn
                 165                 170                 175
Asp Leu Arg Phe Val Gly Arg Ser Gly Arg Gly Lys Ser Phe Thr Leu
                 180                 185                 190
Thr Ile Thr Val Phe Thr Asn Pro Pro Gln Val Ala Thr Tyr His Arg
                 195                 200                 205
Ala Ile Lys Val Thr Val Asp Gly Pro Arg Glu Pro Arg Asn Pro Arg
                 210                 215                 220
Gln Ala Gln Ser Ser Pro Pro Trp Ser Tyr Asp Gln Ser Tyr Pro Ser
225                 230                 235                 240
Tyr Leu Ser Gln Met Thr Ser Pro Ser Ile His Ser Thr Thr Pro Leu
                 245                 250                 255
Ser Ser Thr Arg Gly Thr Gly Leu Pro Ala Ile Thr Asp Val Pro Arg
                 260                 265                 270
Arg Ile Ser Asp Asp Asp Thr Ala Thr Ser Asp Phe Cys Leu Trp Pro
                 275                 280                 285
Ser Ser Leu Ser Lys Lys Ser Gln Ala Gly Ala Ser Glu Leu Gly Pro
                 290                 295                 300
Phe Ser Asp Pro Arg Gln Phe Pro Ser Ile Ser Ser Leu Thr Glu Ser
305                 310                 315                 320
Arg Phe Ser Asn Pro Arg Met His Tyr Pro Ala Thr Phe Thr Tyr Thr
                 325                 330                 335
Pro Pro Val Thr Ser Gly Met Ser Leu Gly Met Ser Ala Thr Thr His
                 340                 345                 350
Tyr His Thr Tyr Leu Pro Pro Tyr Pro Gly Ser Ser Gln Ser Gln
                 355                 360                 365
Ser Gly Pro Phe Gln Thr Ser Ser Thr Pro Tyr Leu Tyr Tyr Gly Thr
 370                 375                 380
Ser Ser Ala Ser Tyr Gln Phe Pro Met Val Pro Gly Gly Asp Arg Ser
385                 390                 395                 400
Pro Ser Arg Met Val Pro Pro Cys Thr Thr Thr Ser Asn Gly Ser Thr
                 405                 410                 415
Leu Leu Asn Pro Asn Leu Pro Asn Gln Asn Asp Gly Val Asp Ala Asp
                 420                 425                 430
Gly Ser His Ser Ser Ser Pro Thr Val Leu Asn Ser Ser Gly Arg Met
                 435                 440                 445
Asp Glu Ser Val Trp Arg Pro Tyr
```

```
              450                 455

<210> SEQ ID NO 31
<211> LENGTH: 421
<212> TYPE: PRT
<213> ORGANISM: Mus musculus

<400> SEQUENCE: 31

Met Arg Ile Pro Val Asp Pro Ser Thr Ser Arg Arg Phe Ser Pro Pro
1               5                   10                  15

Ser Ser Ser Leu Gln Pro Gly Lys Met Ser Asp Val Ser Pro Val Val
            20                  25                  30

Ala Ala Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln Glu
50                  55                  60

Ala Ala Ala Ala Ala Ala Ala Ala Ala Ala Ala Ala Ala Ala Ala Ala
65                  70                  75                  80

Ala Ala Val Pro Arg Leu Arg Pro Pro His Asp Asn Arg Thr Met Val
                85                  90                  95

Glu Ile Ile Ala Asp His Pro Ala Glu Leu Val Arg Thr Asp Ser Pro
            100                 105                 110

Asn Phe Leu Cys Ser Val Leu Pro Ser His Trp Arg Cys Asn Lys Thr
        115                 120                 125

Leu Pro Val Ala Phe Lys Val Val Ala Leu Gly Glu Val Pro Asp Gly
    130                 135                 140

Thr Val Val Thr Val Met Ala Gly Asn Asp Glu Asn Tyr Ser Ala Glu
145                 150                 155                 160

Leu Arg Asn Ala Ser Ala Val Met Lys Asn Gln Val Ala Arg Phe Asn
                165                 170                 175

Asp Leu Arg Phe Val Gly Arg Ser Gly Arg Asp Pro Arg Gln Ala Gln
            180                 185                 190

Ser Ser Pro Pro Trp Ser Tyr Asp Gln Ser Tyr Pro Ser Tyr Leu Ser
        195                 200                 205

Gln Met Thr Ser Pro Ser Ile His Ser Thr Thr Pro Leu Ser Ser Thr
    210                 215                 220

Arg Gly Thr Gly Leu Pro Ala Ile Thr Asp Val Pro Arg Arg Ile Ser
225                 230                 235                 240

Asp Asp Asp Thr Ala Thr Ser Asp Phe Cys Leu Trp Pro Ser Ser Leu
                245                 250                 255

Ser Lys Lys Ser Gln Ala Gly Ala Ser Glu Leu Gly Pro Phe Ser Asp
            260                 265                 270

Pro Arg Gln Phe Pro Ser Ile Ser Ser Leu Thr Glu Ser Arg Phe Ser
        275                 280                 285

Asn Pro Arg Met His Tyr Pro Ala Thr Phe Thr Tyr Thr Pro Pro Val
    290                 295                 300

Thr Ser Gly Met Ser Leu Gly Met Ser Ala Thr His Tyr His Thr
305                 310                 315                 320

Tyr Leu Pro Pro Tyr Pro Gly Ser Ser Gln Ser Gln Ser Gly Pro
                325                 330                 335

Phe Gln Thr Ser Ser Thr Pro Tyr Leu Tyr Tyr Gly Thr Ser Ser Ala
            340                 345                 350

Ser Tyr Gln Phe Pro Met Val Pro Gly Gly Asp Arg Ser Pro Ser Arg
        355                 360                 365
```

```
Met Val Pro Pro Cys Thr Thr Thr Ser Asn Gly Ser Thr Leu Leu Asn
    370                 375                 380

Pro Asn Leu Pro Asn Gln Asn Asp Gly Val Asp Ala Asp Gly Ser His
385                 390                 395                 400

Ser Ser Ser Pro Thr Val Leu Asn Ser Ser Gly Arg Met Asp Glu Ser
            405                 410                 415

Val Trp Arg Pro Tyr
            420

<210> SEQ ID NO 32
<211> LENGTH: 5487
<212> TYPE: DNA
<213> ORGANISM: Homo sapiens

<400> SEQUENCE: 32
gtgtgaatgc ttcattcgcc tcacaaacaa ccacagaacc acaagtgcgg tgcaaacttt      60
ctccaggagg acagcaagaa gtctctggtt tttaaatggt taatctccgc aggtcactac     120
cagccaccga gaccaacaga gtcatttaag gctgcaagca gtatttacaa cagagggtac     180
aagttctatc tgaaaaaaaa aggagggact atggcatcaa acagcctctt cagcacagtg     240
acaccatgtc agcaaaactt cttttgggat ccgagcacca gccggcgctt cagcccccc     300 tccagcagcc tgcagcccgg caaaatgagc gacgtgagcc cggtggtggc tgcgcaacag     360
cagcagcaac agcagcagca gcaacagcag cagcagcagc agcaacagca gcagcagcag     420
caggaggcgg cggcggcggc tgcggcggcg gcggcggctg cggcggcggc agctgcagtg     480
ccccggttgc ggccgcccca cgacaaccgc accatggtgg agatcatcgc cgaccacccg     540
gccgaactcg tccgcaccga cagccccaac ttcctgtgct cggtgctgcc ctcgcactgg     600
cgctgcaaca agaccctgcc cgtggccttc aaggtggtag ccctcggaga ggtaccagat     660
gggactgtgg ttactgtcat ggcgggtaac gatgaaaatt attctgctga gctccggaat     720
gcctctgctg ttatgaaaaa ccaagtagca aggttcaacg atctgagatt tgtgggccgg     780
agtggacgag gcaagagttt caccttgacc ataaccgtct tcacaaatcc tccccaagta     840
gctacctatc acagagcaat taaagttaca gtagatggac ctcgggaacc cagaaggcac     900
agacagaagc ttgatgactc taaacctagt ttgttctctg accgcctcag tgatttaggg     960
cgcattcctc atcccagtat gagagtaggt gtcccgcctc agaacccacg gccctccctg    1020
aactctgcac caagtccttt taatccacaa ggacagagtc agattacaga ccccaggcag    1080
gcacagtctt ccccgccgtg gtcctatgac cagtcttacc cctcctacct gagccagatg    1140
acgtccccgt ccatccactc taccaccccg ctgtcttcca cacggggcac tgggcttcct    1200
gccatcaccg atgtgcctag gcgcatttca ggtgcttcag aactgggccc tttttcagac    1260
cccaggcagt tcccaagcat ttcatccctc actgagagcc gcttctccaa cccacgaatg    1320
cactatccag ccacctttac ttacaccccg ccagtcacct caggcatgtc cctcggtatg    1380
tccgccacca ctcactacca cacctacctg ccaccaccct accccggctc ttcccaaagc    1440
cagagtggac ccttccagac cagcagcact ccatatctct actatggcac ttcgtcagga    1500
tcctatcagt ttcccatggt gccgggggga gaccggtctc cttccagaat gcttccgcca    1560
tgcaccacca cctcgaatgg cagcacgcta ttaaatccaa atttgcctaa ccagaatgat    1620
ggtgttgacg ctgatggaag ccacagcagt tccccaactg ttttgaattc tagtggcaga    1680
atggatgaat ctgtttggcg accatattga aattcctcag cagtggccca gtggtatctg    1740
ggggccacat cccacacgta tcaatatata catatataga gagagtgcat atatatgtat    1800
```

```
atcgattagc tatctacaaa gtgcctattt tttagaagat ttttcattca ctcactcagt   1860
catgatcttg cagccataag agggtagata ttgagaagca gaaggctcaa gagagacaat   1920
tgcaatcgag cttcagattg tttactattt aagatgtact tttacaaagg aacaaagaag   1980
ggaaaaggta ttttttgttt tgttgtttgg tctgttatca tcaataaccct gttcatatgc   2040 caattcagag aggtggactc caggttcagg agggagaaga gcaaagccgc ttcctctctg   2100
tgctttgaaa cttcacaccc tcacggtggc agctgtgtat ggaccagtgc cctccgcaga   2160
cagctcacaa aaccagttga ggtgcactaa agggacatga ggtagaatgg atgcttccat   2220
cacagtacca tcattcagaa taactcttcc aatttctgct ttcagacatg ctgcaggtcc   2280
tcatctgaac tgttgggttc gttttttttt ttttttttcc tgctccaaga aagtgacttc   2340
aaaaataact gatcaggata gattatttta ttttactttt taacactcct tctccccttt   2400
tcccactgaa ccaaaaagaa atcccatccc taaaacctgc cttctccttt tatgcaaaac   2460
tgaaaatggc aatacattat tatagccata atggtataga tagtgattgc gtttggctat   2520
gtgttgtttt cttttttttt aaattatgaa tatgtgtaaa atctgaggta acttgctaac   2580
gtgaatggtc atataacttt aaagatatat ttataattat ttaatgacat ttggaccctt   2640
gaaacatttc ttagtgtatt gatatgttga cttcggtctc taaaagtgct ctttattaaa   2700
taacaaattt cttcagtggt ctagagccat atctgaaata ttgctaagca atttcagttc   2760
atccaggcac aatgtgattt taaaaaatac ttccatctcc aaatattta gatatagatt   2820 gttttttgtga tgtatgaagg aaatgttatg tttagttctt tcagatcttt gaatgcctct   2880
aacacagctt tgccttctaa agcggtaatt agggatttaa aaaacaacct ttagcccttt   2940
atcagcatga aatgctggag tgatgtggtt ttctaatttc tttggggtaa ttatgactct   3000
tgtcatatta aaagacaag cacaagtaaa tcattgaact acagaaaaat gttctgtggt   3060
ttcatagtta agcaaaactc taaatcgcca ggcttcatag caaagacata gtcagctaaa   3120
agccgcacat gtggatagag ggttcaatta tgagacacct agtacaggag agcaaaattg   3180
caccagagat tcttaaccaa ccagccttac caaacaacac aacaggggaa ccccaatctg   3240
ccttacccaa ggccccactg gcagctttcc acagaatttg catttagagg agcagaatga   3300
catcactgtc ctttgggagt aggtcctctg aaaaggcagc aggttccagc aggtagctga   3360
gctgagagga catatggccc acggggacct acagacagcc tttgacattt gtatttctta   3420
caatggaggg ccaaggaggg caaggggctg tggagtttgg tgtctactag tgtgtatgaa   3480
tttgagctag agtccttctg tggcatgcac tttgaccact cctggcagtc acatggcaga   3540
tttccaagtg caaatcctta atccaaacaa ggatcatcta atgacaccac caggccaatc   3600
cctgctctcc tccccgaaaa gtcagggtcc cttcattgga atcctccacc cacccaagca   3660
gaatttagca gagatttgcc ttcaaaccct aacggccccc ttgttctctg gtccttctca   3720
aacccacctt tgtaggccac ccagcattgc aggacagcgt gtgggcagc tggacctgtg   3780 cttcctgcct gggagtctcc cttggaattc atcctgactc cttctaataa aaatggatgg   3840
gaaagcaaaa cactttgcct tctaaaggcc gtataccaag tatgcttaga taaataagcc   3900
acttttctat tacttaagta agaaggaagt agtaattgat actatttatt gtttgtgtgt   3960
ggtagcttga agcacaccac tgtccattta tttgtaagtg taaaatatgt gtgtttgttt   4020
cagcagcact taaaaaagcc agtgtctggt tacacatttc aatttaatt aattgacata   4080 aaaatgctac cgccagtgcc agctgcatcc tatttaatta aaaaggtact atatttgtac   4140
```

```
attatttttt aatgttaaaa gggctttttt aagtttacag tacacatacc gagtgacttt    4200
agggatgctt ttgtgttgaa atgttactat agtggctgca ggcagcaacc cagaaacact    4260
ttagaagctt ttttttcctt ggaaaaattc aagcacttct tccctccacc ctcactccaa    4320
ccaccccaat gggggtaatt cacatttctt agaacaaatt ctgccctttt ttggtctagg    4380
gattaaaatt ttgttttttct ttcttctt tttttttttt ttcactgaac ccttaatttg    4440
cactgggtca tgtgtttgat tgtgatttc aagaccaaag caaagtctta ctactactgt    4500 ggaccatgt actagttcct gggaattaaa atagcgtggt tctctttgta gcacaaacat    4560
tgctggaatt tgcagtcttt tcaatgcagc cacatttta tccatttcag ttgtctcaca    4620
aattttaacc catatcagag ttccagaaca ggtaccacag ctttggtttt agattagtgg    4680
aataacattc agcccagaac tgagaaactc aacagattaa ctatcgtttg ctctttagac    4740
ggtctcactg cctctcactt gccagagccc tttcaaaatg agcagagaag tccacaccat    4800
tagggaccat ctgtgataaa ttcagaaggg aggagatgtg tgtacagctt taaggattcc    4860
ctcaattccg aggaaaggga ctggcccaga atccaggtta atacatggaa acacgaagca    4920
ttagcaaaag taataattat acctatggta tttgaaagaa caataataaa agacacttct    4980
tccaaacctt gaatttgttg ttttttagaaa acgaatgcat ttaaaaatat tttctatgtg    5040 agaattttt agatgtgtgt ttacttcatg tttacaaata actgtttgct ttttaatgca    5100
gtactttgaa atatatcagc caaaaccata acttacaata atttcttagg tattctgaat    5160
aaaattccat ttcttttgga tatgctttac cattcttagg tttctgtgga acaaaaatat    5220
ttgtagcatt ttgtgtaaat acaagctttc atttttattt tttccaattg ctattgccca    5280
agaattgctt tccatgcaca tattgtaaaa attccgcttt gtgccacagg tcatgattgt    5340
ggatgagttt actcttaact tcaaagggac tatttgtatt gtatgttgca actgtaaatt    5400
gaattatttg gcattttct catgattgta atattaattt gaagtttgaa tttaattttc    5460
aataaaatgg cttttttggt tttgtta                                        5487

<210> SEQ ID NO 33
<211> LENGTH: 5553
<212> TYPE: DNA
<213> ORGANISM: Homo sapiens

<400> SEQUENCE: 33
gtgtgaatgc ttcattcgcc tcacaaacaa ccacagaacc acaagtgcgg tgcaaacttt      60
ctccaggagg acagcaagaa gtctctggtt tttaaatggt taatctccgc aggtcactac     120
cagccaccga gaccaacaga gtcatttaag gctgcaagca gtatttacaa cagagggtac     180
aagttctatc tgaaaaaaaa aggagggact atggcatcaa acagcctctt cagcacagtg     240
acaccatgtc agcaaaactt cttttgggat ccgagcacca gccggcgctt cagccccccc     300
tccagcagcc tgcagcccgg caaaatgagc gacgtgagcc cggtggtggc tgcgcaacag     360
cagcagcaac agcagcagca gcaacagcag cagcagcagc agcaacagca gcagcagcag     420
caggaggcgg cggcggcggc tgcggcggcg gcggcggctg cggcggcggc agctgcagtg     480
ccccggttgc ggccgcccca cgacaaccgc accatggtgg agatcatcgc cgaccacccg     540
gccgaactcg tccgcaccga cagccccaac ttcctgtgct cggtgctgcc ctcgcactgg     600
cgctgcaaca gagaccctgcc cgtggccttc aaggtggtag ccctcggaga ggtaccagat     660
gggactgtgg ttactgtcat ggcgggtaac gatgaaaatt attctgctga gctccggaat     720
gcctctgctg ttatgaaaaa ccaagtagca aggttcaacg atctgagatt tgtgggccgg     780
```

| | |
|---|---|
| agtggacgag gcaagagttt caccttgacc ataaccgtct tcacaaatcc tccccaagta | 840 |
| gctacctatc acagagcaat taaagttaca gtagatggac ctcgggaacc cagaaggcac | 900 |
| agacagaagc ttgatgactc taaacctagt ttgttctctg accgcctcag tgatttaggg | 960 |
| cgcattcctc atcccagtat gagagtaggt gtcccgcctc agaacccacg ccctccctg | 1020 |
| aactctgcac caagtccttt taatccacaa ggacagagtc agattacaga ccccaggcag | 1080 |
| gcacagtctt ccccgccgtg gtcctatgac cagtcttacc cctcctacct gagccagatg | 1140 |
| acgtccccgt ccatccactc taccaccccg ctgtcttcca cacggggcac tgggcttcct | 1200 |
| gccatcaccg atgtgcctag gcgcatttca gatgatgaca ctgccacctc tgacttctgc | 1260 |
| ctctggcctt ccactctcag taagaagagc caggcaggtg cttcagaact gggccctttt | 1320 |
| tcagacccca ggcagttccc aagcatttca tccctcactg agagccgctt ctccaaccca | 1380 |
| cgaatgcact atccagccac ctttacttac accccgccag tcacctcagg catgtccctc | 1440 |
| ggtatgtccg ccaccactca ctaccacacc tacctgccac cacccctaccc cggctcttcc | 1500 |
| caaagccaga gtggacccctt ccagaccagc agcactccat atctctacta tggcacttcg | 1560 |
| tcaggatcct atcagtttcc catggtgccg ggggagacc ggtctccttc cagaatgctt | 1620 |
| ccgccatgca ccaccacctc gaatggcagc acgctattaa atccaaattt gcctaaccag | 1680 |
| aatgatggtg ttgacgctga tggaagccac agcagttccc caactgtttt gaattctagt | 1740 |
| ggcagaatgg atgaatctgt ttggcgacca tattgaaatt cctcagcagt ggcccagtgg | 1800 |
| tatctggggg ccacatccca cacgtatcaa tatatacata tatagagaga gtgcatatat | 1860 |
| atgtatatcg attagctatc tacaaagtgc ctattttta gaagattttt cattcactca | 1920 |
| ctcagtcatg atcttgcagc cataagaggg tagatattga gaagcagaag gctcaagaga | 1980 |
| gacaattgca atcgagcttc agattgttta ctatttaaga tgtactttta caaaggaaca | 2040 |
| aagaagggaa aagtatttt tgtttttgtt gtttggtctg ttatcatcaa taacctgttc | 2100 |
| atatgccaat tcagagaggt ggactccagg ttcaggaggg agaagagcaa agccgcttcc | 2160 |
| tctctgtgct ttgaaacttc acaccctcac ggtggcagct gtgtatggac cagtgccctc | 2220 |
| cgcagacagc tcacaaaacc agttgaggtg cactaaaggg acatgaggta gaatggatgc | 2280 |
| ttccatcaca gtaccatcat tcagaataac tcttccaatt tctgctttca gacatgctgc | 2340 |
| aggtcctcat ctgaactgtt gggttcgttt tttttttttt ttttcctgct ccaagaaagt | 2400 |
| gacttcaaaa ataactgatc aggatagatt atttatttt actttttaac actccttctc | 2460 |
| cccttttccc actgaaccaa aaagaaatcc catccctaaa acctgccttc tccttttatg | 2520 |
| caaaactgaa aatggcaata cattattata gccataatgg tatagatagt gattgcgttt | 2580 |
| ggctatgtgt tgtttctttt ttttttaaat tatgaatatg tgtaaaatct gaggtaactt | 2640 |
| gctaacgtga atggtcatat aactttaaag atatatttat aattatttaa tgacatttgg | 2700 |
| acccttgaaa catttcttag tgtattgata tgttgacttc ggtctctaaa agtgctcttt | 2760 |
| attaaataac aaatttcttc agtggtctag agccatatct gaaatattgc taagcaattt | 2820 |
| cagttcatcc aggcacaatg tgattttaaa aaatacttcc atctccaaat attttagata | 2880 |
| tagattgttt ttgtgatgta tgaaggaaat gttatgttta gttctttcag atctttgaat | 2940 |
| gcctctaaca cagctttgcc ttctaaagcg gtaattaggg attttaaaaaa caacctttag | 3000 |
| cccttttatca gcatgaaatg ctggagtgat gtggttttct aatttctttg gggtaattat | 3060 |
| gactcttgtc atattaaaaa gacaagcaca agtaaatcat tgaactacag aaaaatgttc | 3120 |

```
tgtggtttca tagttaagca aaactctaaa tcgccaggct tcatagcaaa gacatagtca    3180
gctaaaagcc gcacatgtgg atagagggtt caattatgag acacctagta caggagagca    3240
aaattgcacc agagattctt aaccaaccag ccttaccaaa caacacaaca ggggaacccc    3300
aatctgcctt acccaaggcc ccactggcag cttttccacag aatttgcatt tagaggagca    3360
gaatgacatc actgtccttt gggagtaggt cctctgaaaa ggcagcaggt tccagcaggt    3420
agctgagctg agaggacata tggcccacgg ggacctacag acagcctttg acatttgtat    3480
ttcttacaat ggagggccaa ggagggcaag gggctgtgga gtttggtgtc tactagtgtg    3540
tatgaatttg agctagagtc cttctgtggc atgcactttg accactcctg gcagtcacat    3600
ggcagatttc caagtgcaaa tccttaatcc aaacaaggat catctaatga caccaccagg    3660
ccaatccctg ctctcctccc cgaaaagtca gggtcccttc attggaatcc tccacccacc    3720
caagcagaat ttagcagaga tttgccttca aaccctaacg gccccttgt tctctggtcc    3780
ttctcaaacc cacctttgta ggccaccag cattgcagga cagcgtgtgg ggcagctgga    3840
cctgtgcttc ctgcctggga gtctcccttg gaattcatcc tgactccttc taataaaaat    3900
ggatgggaaa gcaaaacact ttgccttcta aaggccgtat accaagtatg cttagataaa    3960
taagccactt ttctattact taagtaagaa ggaagtagta attgatacta tttattgttt    4020
gtgtgtggta gcttgaagca caccactgtc catttatttg taagtgtaaa atatgtgtgt    4080
ttgtttcagc agcacttaaa aaagccagtg tctggttaca catttcaatt ttaattaatt    4140
gacataaaaa tgctaccgcc agtgccagct gcatcctatt taattaaaaa ggtactatat    4200
ttgtacatta tttttaatg ttaaaagggc ttttttaagt ttacagtaca cataccgagt    4260
gactttaggg atgcttttgt gttgaaatgt tactatagtg gctgcaggca gcaacccaga    4320
aacactttag aagcttttt tccttgggaa aaattcaagc acttcttccc tccaccctca    4380
ctccaaccac cccaatgggg gtaattcaca tttcttagaa caaattctgc ccttttttgg    4440
tctagggatt aaaattttgt ttttcttttct ttctttttttt tttttttttca ctgaacccttt    4500
aatttgcact gggtcatgtg tttgatttgt gatttcaaga ccaaagcaaa gtcttactac    4560
tactgtggaa ccatgtacta gttcctggga attaaaatag cgtggttctc tttgtagcac    4620
aaacattgct ggaatttgca gtcttttcaa tgcagccaca ttttatccaa tttcagttgt    4680
ctcacaaatt ttaacccata tcagagttcc agaacaggta ccacagcttt ggttttagat    4740
tagtggaata acattcagcc cagaactgag aaactcaaca gattaactat cgtttgctct    4800
ttagacggtc tcactgcctc tcacttgcca gagcccttc aaaatgagca gagaagtcca    4860
caccattagg gaccatctgt gataaaattca gaagggagga gatgtgtgta cagctttaag    4920
gattccctca attccgagga aagggactgg cccagaatcc aggttaatac atggaaacac    4980
gaagcattag caaaagtaat aattatacct atggtatttg aaagaacaat aataaaagac    5040
acttcttcca aaccttgaat ttgttgtttt tagaaaacga atgcatttaa aaatattttc    5100
tatgtgagaa ttttttagat gtgtgtttac ttcatgttta caaataactg tttgcttttt    5160
aatgcagtac tttgaaatat atcagccaaa accataactt acaataattt cttaggtatt    5220
ctgaataaaa ttccatttct tttggatatg ctttaccatt cttaggtttc tgtggaacaa    5280
aaatatttgt agcattttgt gtaaatacaa gctttcattt ttattttttc caattgctat    5340
tgcccaagaa ttgcttttcca tgcacatatt gtaaaaattc cgctttgtgc cacaggtcat    5400
gattgtggat gagtttactc ttaacttcaa agggactatt tgtattgtat gttgcaactg    5460
taaattgaat tatttggcat ttttctcatg attgtaatat taatttgaag tttgaattta    5520
```

-continued

```
attttcaata aaatggcttt tttggttttg tta                                  5553
```

<210> SEQ ID NO 34
<211> LENGTH: 5235
<212> TYPE: DNA
<213> ORGANISM: Homo sapiens

<400> SEQUENCE: 34

```
atgcgtattc ccgtagatcc gagcaccagc cggcgcttca gcccccctc cagcagcctg      60
cagcccggca aaatgagcga cgtgagcccg gtggtggctg cgcaacagca gcagcaacag    120
cagcagcagc aacagcagca gcagcagcag caacagcagc agcagcagca ggaggcggcg    180
gcggcggctg cggcggcggc ggcggctgcg gcggcggcag ctgcagtgcc ccggttgcgg    240
ccgccccacg acaaccgcac catggtggag atcatcgccg accacccggc cgaactcgtc    300
cgcaccgaca gccccaactt cctgtgctcg gtgctgccct cgcactggcg ctgcaacaag    360
accctgcccg tggccttcaa ggtggtagcc ctcggagagg taccagatgg gactgtggtt    420
actgtcatgg cgggtaacga tgaaaattat tctgctgagc tccggaatgc ctctgctgtt    480
atgaaaaacc aagtagcaag gttcaacgat ctgagatttg tgggccggag tggacgaggc    540
aagagtttca ccttgaccat aaccgtcttc acaaatcctc cccaagtagc tacctatcac    600
agagcaatta agttacagt agatggacct cgggaaccca gaaggcacag acagaagctt    660
gatgactcta aacctagttt gttctctgac cgcctcagtg atttagggcg cattcctcat    720
cccagtatga gagtaggtgt cccgcctcag aacccacggc cctccctgaa ctctgcacca    780
agtcctttta atccacaagg acagagtcag attacagacc ccaggcaggc acagtcttcc    840
ccgccgtggt cctatgacca gtcttacccc tcctacctga ccagatgac gtccccgtcc    900
atccactcta ccaccccgct gtcttccaca cggggcactg ggcttcctgc catcaccgat    960
gtgcctaggc gcatttcagg tgcttcagaa ctgggccctt tttcagaccc caggcagttc   1020
ccaagcattt catccctcac tgagagccgc ttctccaacc cacgaatgca ctatccagcc   1080
acctttactt acaccccgcc agtcacctca ggcatgtccc tcggtatgtc cgccaccact   1140
cactaccaca cctacctgcc accaccctac cccggctctt cccaaagcca gagtggaccc   1200
ttccagacca gcagcactcc atatctctac tatggcactt cgtcaggatc ctatcagttt   1260
cccatggtgc cggggggaga ccggtctcct tccagaatgc ttccgccatg caccaccacc   1320
tcgaatggca gcacgctatt aaatccaaat ttgcctaacc agaatgatgg tgttgacgct   1380
gatggaagcc acagcagttc cccaactgtt ttgaattcta gtggcagaat ggatgaatct   1440
gtttggcgac atattgaaa ttcctcagca gtggcccagt ggtatctggg ggccacatcc   1500
cacacgtatc aatatataca tatatagaga gagtgcatat atatgtatat cgattagcta   1560
tctacaaagt gcctattttt tagaagattt ttcattcact cactcagtca tgatcttgca   1620
gccataagag ggtagatatt gagaagcaga aggctcaaga gagacaattg caatcgagct   1680
tcagattgtt tactatttaa gatgtacttt tacaaaggaa caagaaggg aaaaggtatt   1740
tttgttttg ttgtttggtc tgttatcatc aataacctgt tcatatgcca attcagagag   1800
gtggactcca ggttcaggag ggagaagagc aaagccgctt cctctctgtg ctttgaaact   1860
tcacaccctc acggtggcag ctgtgtatgg accagtgccc tccgcagaca gctcacaaaa   1920
ccagttgagt tgcactaaag ggacatgagg tagaatggat gcttccatca cagtaccatc   1980
attcagaata actcttccaa tttctgcttt cagacatgct gcaggtcctc atctgaactg   2040
```

```
ttgggttcgt tttttttttt tttttcctg ctccaagaaa gtgacttcaa aaataactga    2100
tcaggataga ttatttatt ttacttttta acactccttc tcccttttc ccactgaacc    2160
aaaaagaaat cccatcccta aaacctgcct tctccttta tgcaaaactg aaaatggcaa    2220
tacattatta tagccataat ggtatagata gtgattgcgt ttggctatgt gttgttttct    2280
ttttttttaa attatgaata tgtgtaaaat ctgaggtaac ttgctaacgt gaatggtcat    2340
ataactttaa agatatattt ataattattt aatgacattt ggaccttga aacatttctt    2400
agtgtattga tatgttgact tcggtctcta aaagtgctct ttattaaata acaaatttct    2460
tcagtggtct agagccatat ctgaaatatt gctaagcaat ttcagttcat ccaggcacaa    2520
tgtgatttta aaaaatactt ccatctccaa atattttaga tatagattgt ttttgtgatg    2580
tatgaaggaa atgttatgtt tagttctttc agatctttga atgcctctaa cacagctttg    2640
ccttctaaag cggtaattag ggatttaaaa acaaccttt agcccttat cagcatgaaa    2700
tgctggagtg atgtggtttt ctaatttctt tggggtaatt atgactcttg tcatattaaa    2760
aagacaagca caagtaaatc attgaactac agaaaaatgt tctgtggttt catagttaag    2820
caaaactcta aatcgccagg cttcatagca aagacatagt cagctaaaag ccgcacatgt    2880
ggatagaggg ttcaattatg agacacctag tacaggagag caaaattgca ccagagattc    2940
ttaaccaacc agccttacca aacaacacaa caggggaacc ccaatctgcc ttacccaagg    3000
ccccactggc agctttccac agaatttgca tttagaggag cagaatgaca tcactgtcct    3060
ttgggagtag gtcctctgaa aaggcagcag gttccagcag gtagctgagc tgagaggaca    3120
tatgccccac ggggacctac agacagcctt tgacatttgt atttcttaca atggagggcc    3180
aaggagggca agggggctgtg gagtttggtg tctactagtg tgtatgaatt tgagctagag    3240
tccttctgtg gcatgcactt tgaccactcc tggcagtcac atggcagatt tccaagtgca    3300
aatccttaat ccaaacaagg atcatctaat gacaccacca ggccaatccc tgctctcctc    3360
cccgaaaagt cagggtccct tcattggaat cctccaccca cccaagcaga atttagcaga    3420
gatttgcctt caaaccctaa cggccccctt gttctctggt ccttctcaaa cccacctttg    3480
taggccaccc agcattgcag acagcgtgt ggggcagctg gacctgtgct tcctgcctgg    3540
gagtctccct tggaattcat cctgactcct tctaataaaa atggatggga aagcaaaaca    3600
ctttgccttc taaaggccgt ataccaagta tgcttagata aataagccac ttttctatta    3660
cttaagtaag aaggaagtag taattgatac tatttattgt ttgtgtgtgg tagcttgaag    3720
cacaccactg tccattttatt tgtaagtgta aaatatgtgt gtttgtttca gcagcactta    3780
aaaaagccag tgtctggtta cacatttcaa ttttaattaa ttgacataaa aatgctaccg    3840
ccagtgccag ctgcatccta tttaattaaa aaggtactat atttgtacat tattttttaa    3900
tgttaaaagg gcttttttaa gtttacagta cacataccga gtgactttag ggatgctttt    3960
gtgttgaaat gttactatag tggctgcagg cagcaaccca gaaacacttt agaagctttt    4020
tttccttggg aaaaattcaa gcacttcttc cctccaccct cactccaacc accccaatgg    4080
gggtaattca catttcttag aacaaattct gcccttttt ggtctaggga ttaaaatttt    4140
gttttctttt ctttctttt tttttttttt cactgaaccc ttaatttgca ctgggtcatg    4200
tgtttgattt gtgatttcaa gaccaaagca aagtcttact actactgtgg aaccatgtac    4260
tagttcctgg gaattaaaat agcgtggttc tctttgtagc acaaacattg ctggaatttg    4320
cagtcttttc aatgcagcca cattttatc catttcagtt gtctcacaaa ttttaaccca    4380
tatcagagtt ccagaacagg taccacagct ttggttttag attagtggaa taacattcag    4440
```

```
cccagaactg agaaactcaa cagattaact atcgtttgct ctttagacgg tctcactgcc    4500
tctcacttgc cagagccctt tcaaaatgag cagagaagtc cacaccatta gggaccatct    4560
gtgataaatt cagaagggag gagatgtgtg tacagcttta aggattccct caattccgag    4620
gaaagggact ggcccagaat ccaggttaat acatggaaac acgaagcatt agcaaaagta    4680
ataattatac ctatggtatt tgaaagaaca ataataaaag acacttcttc caaaccttga    4740
atttgttgtt tttagaaaac gaatgcattt aaaaatattt tctatgtgag aattttttag    4800
atgtgtgttt acttcatgtt tacaaataac tgtttgcttt ttaatgcagt actttgaaat    4860
atatcagcca aaaccataac ttacaataat ttcttaggta ttctgaataa aattccattt    4920
cttttggata tgctttacca ttcttaggtt tctgtggaac aaaaatattt gtagcatttt    4980
gtgtaaatac aagctttcat ttttattttt tccaattgct attgcccaag aattgctttc    5040
catgcacata ttgtaaaaat tccgctttgt gccacaggtc atgattgtgg atgagtttac    5100
tcttaacttc aaagggacta tttgtattgt atgttgcaac tgtaaattga attatttggc    5160 attttctca tgattgtaat attaatttga agtttgaatt taattttcaa taaaatggct    5220
tttttggttt tgtta                                                    5235

<210> SEQ ID NO 35
<211> LENGTH: 6475
<212> TYPE: DNA
<213> ORGANISM: Mus musculus

<400> SEQUENCE: 35
ctgaagttaa caacgaaaaa ttaacgccag tcggagcagc ctgaggctct cccgcttctc      60
agctttagcg tcgtcagacc gagaagtggt tcccggtcct gagggtgaag tggggagccg     120
aggacgcagg cggcgatgtc ctaggcgggg acctcctccc tacagcttcg ggcgccgagc     180
gagcgcagcg gcgcttctag cggcggcgcg gcggcggcag cggctgcgat ccgcaggctc     240
cagatctgtc gccccgagat ccgctctccc cccgccccca cttacctccc ggcaccttga     300
aacgcgaggg gggcccgggg cactttgcaa agagcaggag agacgaggct gcgagctaga     360
cggcggcgaa ggagagggcg agaggagaag ccggggaaag gaaggactcg gcggccggag     420
gactcggagc gcgctgccgg cgcggggagc gcgcagcggc ctcggaggag gaggcggagg     480
aggcggcgcg ggcaagcgac ggcgccgcga gctgggcagc cgcgctctgc ttggcggtgg     540
cggacagcga ggagccacac gcaccgccga gatggactgc tgaacctgcg gggctccact     600
accgtactgg aacccggagc ggggcgccag cgcacccagg acacggtgcc ccaagggggcc     660 cctactgcaa gctgttaact tcaagtccct tgcggcggct gggccaaaca cgccccgcg     720 tcccgctcgt tgcagccacc gccagggact cccaagcctc ccggtggaga tccgcgcctc     780
tcgggtgtcc ccacccgcta ccccgactct gtccggtctc cagtcgccgg ccccccagcag     840 actccgcccg gcacacggct tcctcgaact tgatttctca cctcctctgt cccgtcacct     900
ccatcctctt tccgccccg tctcgcctcc accccctcga tttcctcctc ctcgcccccc     960
atttccaccc tcctccccct ccccggcca cttcgctaac ttgtggctgt tgtgatgcgt    1020
attcctgtag atccgagcac cagccggcgc ttcagccccc cctccagcag cctgcagccc    1080
ggcaagatga gcgacgtgag cccggtggtg gctgcgcagc agcagcaaca gcagcagcag    1140
cagcagcaac agcagcagca acaacagcaa cagcaacaac agcagcagca gcagcagcag    1200
caggaggcgg ccgcagcagc agcggcggca gcggcggcgg cagcagcggc ggcggccgca    1260
```

-continued

```
gtgccccgat tgaggccgcc gcacgacaac cgcaccatgg tggagatcat cgcggaccac    1320
ccggccgaac tggtccgcac cgacagtccc aacttcctgt gctccgtgct gccctcgcac    1380
tggcggtgca acaagaccct gcccgtggcc ttcaaggttg tagccctcgg agaggtacca    1440
gatgggactg tggttaccgt catggccggg aatgatgaga actactccgc cgagctccga    1500
aatgcctccg ctgttatgaa aaaccaagta gccaggttca acgatctgag atttgtgggc    1560
cggagcggac gaggcaagag tttcaccttg accataacag tcttcacaaa tcctccccaa    1620
gtggccactt accacagagc tattaaagtg acagtggacg gtccccggga accaagaagg    1680
cacagacaga agcttgatga ctctaaacct agtttgttct ctgatcgcct cagtgattta    1740
gggcgcattc ctcatcccag tatgagagta ggtgtcccgc tcagaaccca cggccctcc    1800 ctgaactctg caccaagtcc ttttaatcca caaggacaga gtcagattac agatcccagg    1860
caggcacagt cttccccacc gtggtcctat gaccagtctt acccctccta tctgagccag    1920
atgacatccc catccatcca ctccaccacg ccgctgtctt ccacacgggg caccgggcta    1980
cctgccatca ctgacgtgcc caggcgtatt tcagatgatg acactgccac ctctgacttc    2040
tgcctctggc cttcctctct cagtaagaag agccaggcag gtgcttcaga actgggccct    2100
ttttcagacc ccaggcagtt cccaagcatt tcatccctca ctgagagccg cttctccaac    2160
ccacgaatgc actacccagc cacctttacc tacaccccgc cagtcacgtc aggcatgtcc    2220
ctcggcatgt ccgccaccac tcactaccac acgtacctgc caccacccta ccccggctct    2280
tcccaaagcc agagtggacc cttccagacc agcagcactc catatctcta ctatggtact    2340
tcgtcagcat cctatcagtt cccaatggta cccgggggag accggtctcc ttccaggatg    2400
gtcccaccat gcaccaccac ctcgaatggc agcacgctat aaatccaaa tttgcctaac     2460 cagaatgatg tgttgacgc tgacggaagc cacagcagtt ccccaactgt tttgaattct     2520
agcggcagaa tggatgagtc tgtttggcgg ccatattgaa attcgtcaac catggcccag     2580
tggcatgggg gccacatccc gcatgtgtta atatatacat atataaagag agtgcctata    2640
tatgtatatt gattagctaa ctagaagatt tctcattcaa tccctagtca tgatcttgca    2700
accctaagag ggtgggggca gtcataactg ggtttcatat tgtttactat ttaagatgtc    2760 cccctttacca aggaacaaac cgtcaaaggt gttgtctggt ctgttttcat aagtgacctg    2820
ttcccacgcc ggttcagaga ggtggactct gggtctggga ggaaggagag acacttcctc    2880 tctgtgctttt gaaaccacag cctctgctgt gtggcagccg gtacactctg cagacccgct    2940
tacagagtca gatgtggtgc actcagaaag ggacaagagg cagagtggct gcttctgtcc    3000
gctgccgtcc actctgccgt ccacctgttc caaagttttc cttcagactt gctgcaggta    3060
ctcatttgaa cttttgagtt cactttttttt ttttcctatt ctaagaaagt gacttcaaaa    3120
atactgatca ggacagataa ttttatttta cctttatat tttctcactt ccccattta     3180 accaaaaaga aatcccgttc ccctcccccc gttccttctg cttctccctt tatgcaaact    3240
gaaaatggca atgccttatt attatagcca taatggtata gtgtttgagt tggctgtgtg    3300
ttatgtgttt ttttcttttt ttttcttttt taaattatga atatgtgtaa aatctgaagt    3360
aacttgctaa cgtgaatggt catataactt taaagatata tttataatta tttaatgaca    3420
tttggacatt tggaacattt cttagtgtaa tgatatgttg acttcggtct ctaaaagtgt    3480
gcttcttctt caataccaag tttcttcagt gggctagagc catatcggaa atattgctaa    3540
gcaatctcaa ttccttcagg cataatgtga tttttttttt ttttgaaga taactcccat     3600 ctccaaatag tttagatgta gtttgttttc acgatgtatg aaggagatgc tctgtttctt    3660
```

-continued

```
tctttcaggc atttgattgc ctctgacaca gctttgcctt ttaaagcaat aattagggat    3720
taaaataaca aaaacaaaac aaaagccacc tatagcccct taacacttaa cgtggccct     3780
ttactagcat gaaatgctgg agacatgtgg tttcctaatt tctccatttt gggggtggtg    3840
ggagggggga gggtggccat tatgactctt atcatattaa aaagccaagc acaagtgatt    3900
ggttgaactg cagaaaagtg ttctgtggtc tctgagttga gcaaaactct aaattgcagg    3960
cttcgtggtt gagggcctag tcagctgaaa gccacgcgtg tggtaaaggc tcaggcatgg    4020
cttggagaac ctaggaacac attaggagcc tgcacctacc agcctcacca tacagccatt    4080
caggggaacc caaaaagtgc cttacccaag gagggccccc agcagctttc caggaagtcg    4140
aatgaagtcg ctgtcctcgg ggaactggtc agctgaagta gcaaccggta gctgatgtca    4200
gtagacaaca gaacctgtgg ggacctccag gaaacctttg acattggagg ctttcattag    4260
gcagggccaa caagagcagg gaaggccatg tacccattgg tatctgccat tgtgtgtgag    4320
tttgagatcc agccctcctt ggaggatgta ctgtgatcat tcctggtacc ttagggccaa    4380
tccctaagtg tggcttccta atccaggcca gggatcattc agtgatacca ccaggccaat    4440
cccagcattc ctcctgcaca aagtgtttgt gtgtgggggg atagattggg gtggggccac    4500
cttcatttga atcctgagtc attctaagag ttctgcaagc ttttgccttc agcaccctat    4560
accccctcgc tctctgttcc ttctcaggtt gacctttgtc ccaatgcggg acagtccaga    4620
ggcagatggg gacctatgtg tgcctccaac ctgcgttttc ctcagaattc atcctgactc    4680
cctctgacac agattgaggg gggggggaag aaacccaacc cgcaccaaag caaaacactt    4740
tgccttctaa aggctgtgca ccaagtagac gcagatggtc agcccacctt tgtgtttcct    4800
taagatggaa attgtaactg atgctatta ttgtttgtgt gtggtagctt gaagcacacc    4860
acggtccatg tgtttgtctg atacctattt cagcagcatt tacaaaagcc agtgtctggt    4920
tacactttc agttttcatt aatcaacatg aaaatgttac cattggtgcc agctgcaccc    4980
tatttaattt ttttaagggc actatatttg tacatttcgt ttttaatgtt aaagggcttc    5040
ttaaagttta cagtacagtt atcaagggaa tagaggggat gcattagtgc ctaaatgtta    5100
ttctagtggc tgcaggcagc aacccagaag cagttttgaa aacaggttgt ttccctctgt    5160
cctcccttat ttgggaaaat tcaagtgctt tcttcacctt tcaggcacct cacggtgact    5220
cccgttactt agagcagtct gtcgtcgtct tcttcttctt cctcttcctc ttcctcttcc    5280
tcttcctctt cctcttcctc ttcctcttcc tcttcctctt cttcttcttc ttcttcttct    5340
tcttcttctt cttcttcctc ctagggttta aaatccccct tcctcttccc ttatctctta    5400
aactcttcat ttgcactggg tcacacgtat gatttgtggt tttaagacca agcaatgtc     5460
ttattactct tctggagccg tttatgtgta ctaaccaacc cttccctcca cttccctggg    5520
tttagatgca cacggttctc aaaggagcac aaacatggcc agattcacag tgggacccac    5580
acagccatgt taaaaaaaaa aacaaaaaaa aacctcttca cttgtctgag aattttaacc    5640
tgggcccaa ttgctaacgg gcaccatggc ttgggtttca ggttagggaa cgttgcccag     5700
tgagtaacag aaagacttaa ctgatttaat tagtttgccc tcatccttca ctccaagacc    5760
ctaagaaacc gatcagagaa acatctccac accattagag gttgagaagg gaggagccat    5820
gtgggggttc cctccgctcg gaggaaaggc actgactgac ctagttagag tggtagcaga    5880
agcacccatg gtatctgaga gagcaataaa caataaaaga tgatcctccc aagcttagaa    5940
tttgttgttc ttaaagaaga cgatgcatct aaaacaaaga atttttttt ctatgtggga    6000
```

| | | |
|---|---|---|
| actttcttcg ttgtctgttt acttcatgtt tacaaataat tgtttgcttt ttaatgcagt | 6060 | |
| actttaaaaa atatatcagc caaaaccata acttacagta atttttttag gtattctgaa | 6120 | |
| taaaattcca tgtcttttga tatgtctact gttcttaggt ttctgtggaa caacaacaac | 6180 | |
| aacaacaaca aaattgtagc attttgtgta aatacagctt tcgttcttat tttttatttt | 6240 | |
| tctgattgct attgcccaag atttgctttc tatgcacgta ttgtacaaat tgtgctttgt | 6300 | |
| gccacaggtc atgatcgtgg atgagtttac tctgaacttc aaagggacta tttgtattgt | 6360 | |
| atgttgcaac tgtaaattga attatttggc atttcccct ctcatgattg taatattaat | 6420 | |
| ttgaagtttg aatttaattt tcaataaaaa ggcttttttt ttccttttgg ttttg | 6475 | |

<210> SEQ ID NO 36
<211> LENGTH: 5740
<212> TYPE: DNA
<213> ORGANISM: Mus musculus

<400> SEQUENCE: 36

| | | |
|---|---|---|
| atgcttcatt cgcctcacaa acaaccacag aaccacaagt gcggtgcaaa ctttctccag | 60 | |
| gaagactgca agaaggctct ggcgtttaaa tggttaatct ctgcaggtca ctaccagcca | 120 | |
| ccgagaccaa ccgagtcagt gagtgctcta accacagtcc atgcaggaat atttaaggct | 180 | |
| gcaagcagta tttacaacag agggcacaag ttctatctgg aaaaaaaagg agggactatg | 240 | |
| gcgtcaaaca gcctcttcag cgcagtgaca ccgtgtcagc aaagcttctt ttgggatccg | 300 | |
| agcaccagcc ggcgcttcag ccccccctcc agcagcctgc agcccggcaa gatgagcgac | 360 | |
| gtgagcccgg tggtggctgc gcagcagcag caacagcagc agcagcagca gcaacagcag | 420 | |
| cagcaacaac agcaacagca acaacagcag cagcagcagc agcagcagga ggcggccgca | 480 | |
| gcagcagcgc cggcagcggc ggcggcagca gcggcggcgg ccgcagtgcc ccgattgagg | 540 | |
| ccgccgcacg acaaccgcac catggtggag atcatcgcgg accacccggc cgaactggtc | 600 | |
| cgcaccgaca gtcccaactt cctgtgctcc gtgctgccct cgcactggcg gtgcaacaag | 660 | |
| accctgcccg tggccttcaa ggttgtagcc ctcggagagg taccagatgg gactgtggtt | 720 | |
| accgtcatgg ccgggaatga tgagaactac tccgccgagc tccgaaatgc ctccgctgtt | 780 | |
| atgaaaaacc aagtagccag gttcaacgat ctgagatttg tgggccggag cggacgaggc | 840 | |
| aagagtttca ccttgaccat aacagtcttc acaaatcctc cccaagtggc cacttaccac | 900 | |
| agagctatta agtgacagt ggacggtccc cgggaaccaa gaaggcacag acagaagctt | 960 | |
| gatgactcta aacctagttt gttctctgat cgcctcagtg atttagggcg cattcctcat | 1020 | |
| cccagtatga gagtaggtgt cccgcctcag aacccacggc cctccctgaa ctctgcacca | 1080 | |
| agtcctttta atccacaagg acagagtcag attacagatc ccaggcaggc acagtcttcc | 1140 | |
| ccaccgtggt cctatgacca gtcttacccc tcctatctga gccagatgac atccccatcc | 1200 | |
| atccactcca ccacgccgct gtcttccaca cggggcaccg ggctacctgc catcactgac | 1260 | |
| gtgcccaggc gtatttcaga tgatgacact gccacctctg acttctgcct ctggccttcc | 1320 | |
| tctctcagta agaagagcca ggcaggtgct tcagaactgg gccctttttc agaccccagg | 1380 | |
| cagttcccaa gcattcatc cctcactgag agccgcttct ccaacccacg aatgcactac | 1440 | |
| ccagccacct ttacctacac cccgccagtc acgtcaggca tgtccctcgg catgtccgcc | 1500 | |
| accactcact accacacgta cctgccacca ccctaccccg ctcttcccca agccagagt | 1560 | |
| ggaccccttcc agaccagcag cactccatat ctctactatg gtacttcgtc agcatcctat | 1620 | |
| cagttcccaa tggtacccgg gggagaccgg tctccttcca ggatggtccc accatgcacc | 1680 | |

```
accacctcga atggcagcac gctattaaat ccaaatttgc ctaaccagaa tgatggtgtt    1740
gacgctgacg gaagccacag cagttcccca actgttttga attctagcgg cagaatggat    1800
gagtctgttt ggcggccata ttgaaattcg tcaaccatgg cccagtggca tgggggccac    1860
atcccgcatg tgttaatata tacatatata aagagagtgc ctatatatgt atattgatta    1920
gctaactaga agatttctca ttcaatccct agtcatgatc ttgcaaccct aagagggtgg    1980
gggcagtcat aactgggttt catattgttt actatttaag atgtcccctt taccaaggaa    2040
caaaccgtca aggtgttgt ctggtctgtt ttcataagtg acctgttccc acgccggttc    2100
agagaggtgg actctgggtc tgggaggaag gagagacact tcctctctgt gctttgaaac    2160
cacagcctct gctgtgtggc agccggtaca ctctgcagac ccgcttacag agtcagatgt    2220
ggtgcactca gaaagggaca agaggcagag tggctgcttc tgtccgctgc cgtccactct    2280
gccgtccacc tgttccaaag ttttccttca gacttgctgc aggtactcat ttgaactttt    2340
gagttcactt ttttttttc ctattctaag aaagtgactt caaaaatact gatcaggaca    2400 gataattta ttttaccttt tatattttct cacttccccc atttaaccaa aaagaaatcc    2460 cgttcccct cccccgttcc ttctgcttct ccctttatgc aaactgaaaa tggcaatgcc    2520
ttattattat agccataatg gtatagtgtt tgagttggct gtgtgttatg tgttttttc    2580 tttttttttc tttttaaat tatgaatatg tgtaaaatct gaagtaactt gctaacgtga    2640
atggtcatat aactttaaag atatatttat aattatttaa tgacatttgg acatttggaa    2700
catttcttag tgtaatgata tgttgacttc ggtctctaaa agtgtgcttc ttcttcaata    2760
ccaagtttct tcagtgggct agagccatat cggaaatatt gctaagcaat ctcaattcct    2820
tcaggcataa tgtgattttt ttttttttt gaagataact cccatctcca aatagtttag    2880
atgtagtttg ttttcacgat gtatgaagga gatgctctgt ttctttcttt caggcatttg    2940
attgcctctg acacagcttt gcctttaaa gcaataatta gggattaaaa taacaaaaac    3000
aaaacaaaag ccacctatag ccccttaaca cttaacgtgg cccctttact agcatgaaat    3060
gctggagaca tgtggtttcc taatttctcc atttgggg tggtgggagg ggggagggtg    3120
gccattatga ctcttatcat attaaaaagc caagcacaag tgattggttg aactgcagaa    3180
aagtgttctg tggtctctga gttgagcaaa actctaaatt gcaggcttcg tggttgaggg    3240
cctagtcagc tgaaagccac gcgtgtggta aaggctcagg catggcttgg agaacctagg    3300
aacacattag gagcctgcac ctaccagcct caccatacag ccattcaggg gaacccaaaa    3360
agtgccttac ccaaggaggg cccccagcag ctttccagga agtcgaatga agtcgctgtc    3420
ctcggggaac tggtcagctg aagtagcaac cggtagctga tgtcagtaga caacagaacc    3480 tgtgggacc tccaggaaac ctttgacatt ggaggctttc attaggcagg ccaacaaga    3540 gcagggaagg ccatgtaccc attggtatct gccattgtgt gtgagtttga gatccagccc    3600
tccttggagt atgtactgtg atcattcctg gtaccttagg gccaatccct aagtgtggct    3660
tcctaatcca ggccagggat cattcagtga taccaccagg ccaatcccag cattcctcct    3720
gcacaaagtg tttgtgtgtg gggggataga ttgggtggg gccaccttca tttgaatcct    3780
gagtcattct aagagttctg caagcttttg ccttcagcac cctataccc ctcgctctct    3840 gttccttctc aggttgacct ttgtcccaat gcgggacagt ccagaggcag atgggacct    3900 atgtgtgcct ccaacctgcg ttttcctcag aattcatcct gactccctct gacacagatt    3960
gagggggggg ggaagaaacc caacccgcac caaagcaaaa cactttgcct tctaaaggct    4020
```

```
gtgcaccaag tagacgcaga tggtcagccc acctttgtgt ttccttaaga tggaaattgt    4080
aactgatgct atttattgtt tgtgtgtggt agcttgaagc acaccacggt ccatgtgttt    4140
gtctgatacc tatttcagca gcatttacaa aagccagtgt ctggttacac ttttcagttt    4200
tcattaatca acatgaaaat gttaccattg gtgccagctg caccctattt aatttttta    4260 agggcactat atttgtacat ttcgtttta atgttaaagg gcttcttaaa gtttacagta    4320
cagttatcaa gggaatagag gggatgcatt agtgcctaaa tgttattcta gtggctgcag    4380
gcagcaaccc agaagcagtt ttgaaaacag gttgtttccc tctgtcctcc cttatttggg    4440
aaaattcaag tgctttcttc acctttcagg cacctcacgg tgactcccgt tacttagagc    4500
agtctgtcgt cgtcttcttc ttcttcctct tcctcttcct cttcctcttc ctcttcctct    4560
tcctcttcct cttcctcttc ctcttcttct tcttcttctt cttcttcttc ttcttcttct    4620
tcctcctagg gtttaaaatc cccttcctc ttcccttatc tcttaaactc ttcatttgca    4680
ctgggtcaca cgtatgattt gtggttttaa gaccaaagca atgtcttatt actcttctgg    4740
agccgtttat gtgtactaac caaccctttcc ctccacttcc ctgggtttag atgcacacgg    4800
ttctcaaagg agcacaaaca tggccagatt cacagtggga cccacacagc catgttaaaa    4860
aaaaaaacaa aaaaaaacct cttcacttgt ctgagaattt taacctgggc cccaattgct    4920
aacgggcacc atggcttggg tttcaggtta gggaacgttg cccagtgagt aacagaaaga    4980
cttaactgat ttaattagtt tgccctcatc cttcactcca agaccctaag aaaccgatca    5040
gagaaacatc tccacaccat tagaggttga aagggagga gccatgtggg ggttccctcc    5100
gctcggagga aaggcactga ctgacctagt tagagtggta gcagaagcac ccatggtatc    5160
tgagagagca ataaacaata aaagatgatc ctcccaagct tagaatttgt tgttcttaaa    5220
gaagacgatg catctaaaac aaagaatttt tttttctatg tgggaacttt cttcgttgtc    5280
tgtttacttc atgtttacaa ataattgttt gcttttaat gcagtacttt aaaaaatata    5340
tcagccaaaa ccataactta cagtaatttt tttaggtatt ctgaataaaa ttccatgtct    5400
tttgatatgt ctactgttct taggtttctg tgaacaaca acaacaacaa caacaaaatt    5460
gtagcatttt gtgtaaatac agctttcgtt cttattttt attttctga ttgctattgc    5520 ccaagatttg ctttctatgc acgtattgta caaattgtgc tttgtgccac aggtcatgat    5580
cgtggatgag tttactctga acttcaaagg gactatttgt attgtatgtt gcaactgtaa    5640
attgaattat ttggcatttc cccctctcat gattgtaata ttaatttgaa gtttgaattt    5700
aattttcaat aaaaaggctt ttttttttcct tttggttttg                         5740
```

<210> SEQ ID NO 37
<211> LENGTH: 5904
<212> TYPE: DNA
<213> ORGANISM: Mus musculus

<400> SEQUENCE: 37

```
atgcttcatt cgcctcacaa acaaccacag aaccacaagt gcggtgcaaa ctttctccag      60
gaagactgca agaaggctct ggcgtttaaa tggttaatct ctgcaggtca ctaccagcca     120
ccgagaccaa ccgagtcagt gagtgctcta accacagtcc atgcaggaat agtaggtcct     180
tcaaatattt gctcactccg ttttgttttg tttccttgct tttcacatgt taccagctac     240
ataatttctt gacagaaaaa aataaatata aagtctatgt actccaggca tactgtacaa     300
ctaaaacagg gactgggtat ggtttgtatt ttcagtttaa ggctgcaagc agtatttaca     360
acagagggca caagttctat ctggaaaaaa aaggagggac tatggcgtca aacagcctct     420
```

```
tcagcgcagt gacaccgtgt cagcaaagct tcttttggga tccgagcacc agccggcgct    480 tcagccccc  ctccagcagc ctgcagcccg gcaagatgag cgacgtgagc ccggtggtgg    540
ctgcgcagca gcagcaacag cagcagcagc agcagcaaca gcagcagcaa caacagcaac    600
agcaacaaca gcagcagcag cagcagcagc aggaggcggc cgcagcagca gcggcggcag    660
cggcggcggc agcagcggcg gcggccgcag tgccccgatt gaggccgccg cacgacaacc    720
gcaccatggt ggagatcatc gcggaccacc cggccgaact ggtccgcacc gacagtccca    780
acttcctgtg ctccgtgctg ccctcgcact ggcggtgcaa caagaccctg cccgtggcct    840
tcaaggttgt agccctcgga gaggtaccag atgggactgt ggttaccgtc atggccggga    900
atgatgagaa ctactccgcc gagctccgaa atgcctccgc tgttatgaaa aaccaagtag    960
ccaggttcaa cgatctgaga tttgtgggcc ggagcggacg aggcaagagt ttcaccttga    1020
ccataacagt cttcacaaat cctccccaag tggccactta ccacagagct attaaagtga    1080
cagtggacgg tccccgggaa ccaagaaggc acagacagaa gcttgatgac tctaaaccta    1140
gtttgttctc tgatcgcctc agtgatttag gcgcattcc  tcatcccagt atgagagtag    1200
gtgtcccgcc tcagaaccca cggccctccc tgaactctgc accaagtcct tttaatccac    1260
aaggacagag tcagattaca gatcccaggc aggcacagtc ttccccaccg tggtcctatg    1320
accagtctta cccctcctat ctgagccaga tgacatcccc atccatccac tccaccacgc    1380
cgctgtcttc cacacggggc accgggctac ctgccatcac tgacgtgccc aggcgtattt    1440
cagatgatga cactgccacc tctgacttct gcctctggcc ttcctctctc agtaagaaga    1500
gccaggcagg tgcttcagaa ctgggccctt tttcagaccc caggcagttc ccaagcattt    1560
catccctcac tgagagccgc ttctccaacc cacgaatgca ctaccagcc  acctttacct    1620 acaccccgcc agtcacgtca ggcatgtccc tcggcatgtc cgccaccact cactaccaca    1680
cgtacctgcc accaccctac cccggctctt cccaaagcca gagtggaccc ttccagacca    1740
gcagcactcc atatctctac tatggtactt cgtcagcatc ctatcagttc ccaatggtac    1800
ccgggggaga ccggtctcct tccaggatgg tcccaccatg caccaccacc tcgaatggca    1860
gcacgctatt aaatccaaat ttgcctaacc agaatgatgg tgttgacgct gacggaagcc    1920
acagcagttc cccaactgtt ttgaattcta gcggcagaat ggatgagtct gtttggcggc    1980
catattgaaa ttcgtcaacc atgcccagt  ggcatggggg ccacatcccg catgtgttaa    2040
tatatacata tataaagaga gtgcctatat atgtatattg attagctaac tagaagattt    2100
ctcattcaat ccctagtcat gatcttgcaa ccctaagagg gtgggggcag tcataactgg    2160
gtttcatatt gtttactatt taagatgtcc cctttaccaa ggaacaaacc gtcaaggtg     2220 ttgtctggtc tgttttcata agtgacctgt tcccacgccg gttcagagag gtggactctg    2280
ggtctgggag gaaggagaga cacttcctct ctgtgctttg aaaccacagc ctctgctgtg    2340
tggcagccgg tacactctgc agacccgctt acagagtcag atgtggtgca ctcagaaagg    2400
gacaagaggc agagtggctg cttctgtccg ctgccgtcca ctctgccgtc cacctgttcc    2460
aaagttttcc ttcagacttg ctgcaggtac tcatttgaac ttttgagttc acttttttt     2520 tttcctattc taagaaagtg acttcaaaaa tactgatcag gacagataat tttattttac    2580
cttttatatt ttctcacttc ccccattaa  ccaaaaagaa atcccgttcc cctcccccg     2640 ttccttctgc ttctcccttt atgcaaactg aaaatggcaa tgcctattta ttatagccat    2700
aatggtatag tgtttgagtt ggctgtgtgt tatgtgtttt tttctttttt ttcttttt      2760
```

```
aaattatgaa tatgtgtaaa atctgaagta acttgctaac gtgaatggtc atataacttt    2820
aaagatatat ttataattat ttaatgacat ttggacattt ggaacatttc ttagtgtaat    2880
gatatgttga cttcggtctc taaaagtgtg cttcttcttc aataccaagt ttcttcagtg    2940
ggctagagcc atatcggaaa tattgctaag caatctcaat tccttcaggc ataatgtgat    3000
tttttttttt ttttgaagat aactcccatc tccaaatagt ttagatgtag tttgttttca    3060
cgatgtatga aggagatgct ctgtttcttt ctttcaggca tttgattgcc tctgacacag    3120
ctttgccttt taaagcaata attagggatt aaaataacaa aaacaaaaca aaagccacct    3180
atagcccttt aacacttaac gtggcccctt tactagcatg aaatgctgga gacatgtggt    3240
ttcctaattt ctccattttg ggggtggtgg gagggggag ggtggccatt atgactctta    3300
tcatattaaa aagccaagca caagtgattg gttgaactgc agaaaagtgt tctgtggtct    3360
ctgagttgag caaaactcta aattgcaggc ttcgtggttg agggcctagt cagctgaaag    3420
ccacgcgtgt ggtaaaggct caggcatggc ttggagaacc taggaacaca ttaggagcct    3480
gcacctacca gcctcaccat acagccattc aggggaaccc aaaaagtgcc ttacccaagg    3540
agggccccca gcagctttcc aggaagtcga atgaagtcgc tgtcctcggg gaactggtca    3600
gctgaagtag caaccggtag ctgatgtcag tagacaacag aacctgtggg gacctccagg    3660
aaacctttga cattggaggc tttcattagg cagggccaac aagagcaggg aaggccatgt    3720
acccattggt atctgccatt gtgtgtgagt ttgagatcca gccctccttg gaggatgtac    3780
tgtgatcatt cctggtacct tagggccaat ccctaagtgt ggcttcctaa tccaggccag    3840
ggatcattca gtgataccac caggccaatc ccagcattcc tcctgcacaa agtgtttgtg    3900
tgtgggggga tagattgggg tggggccacc ttcatttgaa tcctgagtca ttctaagagt    3960
tctgcaagct tttgccttca gcaccctata cccctcgct ctctgttcct tctcaggttg    4020
acctttgtcc caatgcggga cagtccagag gcagatgggg acctatgtgt gcctccaacc    4080
tgcgttttcc tcagaattca tcctgactcc ctctgacaca gattgagggg gggggaaga    4140
aacccaaccc gcaccaaagc aaaacacttt gccttctaaa ggctgtgcac caagtagacg    4200
cagatggtca gcccaccttt gtgtttcctt aagatggaaa ttgtaactga tgctatttat    4260
tgtttgtgtg tggtagcttg aagcacacca cggtccatgt gtttgtctga tacctatttc    4320
agcagcattt acaaaagcca gtgtctggtt acacttttca gttttcatta atcaacatga    4380
aaatgttacc attggtgcca gctgcaccct atttaatttt tttaagggca ctatatttgt    4440
acatttcgtt tttaatgtta aagggcttct taaagtttac agtacagtta tcaagggaat    4500
agagggatg cattagtgcc taaatgttat tctagtggct gcaggcagca acccagaagc    4560
agttttgaaa acaggttgtt tccctctgtc ctcccttatt tgggaaaatt caagtgcttt    4620
cttcaccttt caggcacctc acggtgactc ccgttactta gagcagtctg tcgtcgtctt    4680
cttcttcttc ctcttcctct tcctcttcct cttcctcttc ctcttcctct tcctcttcct    4740
cttcctcttc ttcttcttct tcttcttctt cttcttcttc ttcttcctcc tagggtttaa    4800
aatccccctt cctctcccct tatctcttaa actcttcatt tgcactgggt cacacgtatg    4860
atttgtggtt ttaagaccaa agcaatgtct tattactctt ctggagccgt ttatgtgtac    4920
taaccaaccc ttccctccac ttccctgggt ttagatgcac acggttctca aaggagcaca    4980
aacatggcca gattcacagt gggacccaca cagccatgtt aaaaaaaaaa acaaaaaaaa    5040
acctcttcac ttgtctgaga attttaacct gggcccaat tgctaacggg caccatggct    5100
tgggtttcag gttagggaac gttgcccagt gagtaacaga aagacttaac tgatttaatt    5160
```

-continued

| | |
|---|---|
| agtttgccct catccttcac tccaagaccc taagaaaccg atcagagaaa catctccaca | 5220 |
| ccattagagg ttgagaaggg aggagccatg tgggggttcc ctccgctcgg aggaaaggca | 5280 |
| ctgactgacc tagttagagt ggtagcagaa gcacccatgg tatctgagag agcaataaac | 5340 |
| aataaaagat gatcctccca agcttagaat ttgttgttct taaagaagac gatgcatcta | 5400 |
| aaacaaagaa ttttttttc tatgtgggaa ctttcttcgt tgtctgttta cttcatgttt | 5460 |
| acaaataatt gtttgctttt taatgcagta ctttaaaaaa tatatcagcc aaaaccataa | 5520 |
| cttacagtaa ttttttttagg tattctgaat aaaattccat gtcttttgat atgtctactg | 5580 |
| ttcttaggtt tctgtggaac aacaacaaca acaacaacaa aattgtagca ttttgtgtaa | 5640 |
| atacagcttt cgttcttatt ttttatttt ctgattgcta ttgcccaaga tttgctttct | 5700 |
| atgcacgtat tgtacaaatt gtgctttgtg ccacaggtca tgatcgtgga tgagtttact | 5760 |
| ctgaacttca aagggactat ttgtattgta tgttgcaact gtaaattgaa ttatttggca | 5820 |
| tttccccctc tcatgattgt aatattaatt tgaagtttga atttaatttt caataaaaag | 5880 |
| gcttttttt tccttttggt tttg | 5904 |

<210> SEQ ID NO 38
<211> LENGTH: 5829
<212> TYPE: DNA
<213> ORGANISM: Mus musculus

<400> SEQUENCE: 38

| | |
|---|---|
| ggcggaggag gcggcgcggg caagcgacgg cgccgcgagc tgggcagccg cgctctgctt | 60 |
| ggcggtggcg gacagcgagg agccacacgc accgccgaga tggactgctg aacctgcggg | 120 |
| gctccactac cgtactggaa cccggagcgg ggcgccagcg cacccaggac acggtgcccc | 180 |
| aaggggcccc tactgcaagc tgttaacttc aagtcccttg cggcggctgg gccaaacacg | 240 |
| cccccgcgtc ccgctcgttg cagccaccgc cagggactcc caagcctccc ggtggagatc | 300 |
| cgcgcctctc gggtgtcccc acccgctacc ccgactctgt ccggtctcca gtcgccggcc | 360 |
| cccagcagac tccgcccggc acacggcttc ctcgaacttg atttctcacc tcctctgtcc | 420 |
| cgtcacctcc atcctctttc cgccccgtc tcgcctccac cccctcgatt tcctcctcct | 480 |
| cgccccccat ttccaccctc ctccccctcc cccggccact tcgctaactt gtggctgttg | 540 |
| tgatgcgtat tcctgtagat ccgagcacca gccggcgctt cagccccccc tccagcagcc | 600 |
| tgcagcccgg caagatgagc gacgtgagcc cggtggtggc tgcgcagcag cagcaacagc | 660 |
| agcagcagca gcagcaacag cagcagcaac aacagcaaca gcaacaacag cagcagcagc | 720 |
| agcagcagca ggaggcggcc gcagcagcag cggcggcagc ggcggcggca gcagcggcgg | 780 |
| cggccgcagt gccccgattg aggccgccgc acgacaaccg caccatggtg gagatcatcg | 840 |
| cggaccaccc ggccgaactg gtccgcaccg acagtcccaa cttcctgtgc tccgtgctgc | 900 |
| cctcgcactg gcggtgcaac aagaccctgc ccgtggcctt caaggttgta gccctcggag | 960 |
| aggtaccaga tgggactgtg ttaccgtca tggccgggaa tgatgagaac tactccgccg | 1020 |
| agctccgaaa tgcctccgct gttatgaaaa accaagtagc caggttcaac gatctgagat | 1080 |
| ttgtgggccg gagcggacga ggcaagagtt tcaccttgac cataacagtc ttcacaaatc | 1140 |
| ctccccaagt ggccacttac cacagagcta ttaaagtgac agtggacggt ccccgggaac | 1200 |
| caagaaatcc caggcaggca cagtcttccc caccgtggtc ctatgaccag tcttacccct | 1260 |
| cctatctgag ccagatgaca tccccatcca tccactccac cacgccgctg tcttccacac | 1320 |

```
ggggcaccgg gctacctgcc atcactgacg tgcccaggcg tatttcagat gatgacactg   1380
ccacctctga cttctgcctc tggccttcct ctctcagtaa gaagagccag gcaggtgctt   1440
cagaactggg ccctttttca gaccccaggc agttcccaag catttcatcc ctcactgaga   1500
gccgcttctc caacccacga atgcactacc cagccaccTt tacctacacc ccgccagtca   1560
cgtcaggcat gtccctcggc atgtccgcca ccactcacta ccacacgtac ctgccaccac   1620
cctaccccgg ctcttcccaa agccagagtg gaccct tcca gaccagcagc actccatatc   1680
tctactatgg tacttcgtca gcatcctatc agttcccaat ggtacccggg ggagaccggt   1740
ctccttccag gatggtccca ccatgcacca ccacctcgaa tggcagcacg ctattaaatc   1800
caaatttgcc taaccagaat gatggtgttg acgctgacgg aagccacagc agttccccaa   1860
ctgttttgaa ttctagcggc agaatggatg agtctgtttg gcggccatat tgaaattcgt   1920
caaccatggc ccagtggcat gggggccaca tcccgcatgt gttaatatat acatatataa   1980
agagagtgcc tatatatgta tattgattag ctaactagaa gatttctcat tcaatcccta   2040
gtcatgatct tgcaacccta agagggtggg ggcagtcata actgggtttc atattgttta   2100
ctatttaaga tgtccccttt accaaggaac aaaccgtcaa aggtgttgtc tggtctgttt   2160
tcataagtga cctgttccca cgccggttca gagaggtgga ctctgggtct gggaggaagg   2220
agagacactt cctctctgtg ctttgaaacc acagcctctg ctgtgtggca gccggtacac   2280
tctgcagacc cgcttacaga gtcagatgtg gtgcactcag aaagggacaa gaggcagagt   2340
ggctgcttct gtccgctgcc gtccactctg ccgtccacct gttccaaagt tttccttcag   2400
acttgctgca ggtactcatt tgaacttttg agttcacttt tttttttttcc tattctaaga   2460 aagtgacttc aaaaatactg atcaggacag ataatttat tttacctttt atattttctc   2520
acttccccca tttaaccaaa aagaaatccc gttccccctc ccccgttcct tctgcttctc   2580
cctttatgca aactgaaaat ggcaatgcct tattattata gccataatgg tatagtgttt   2640
gagttggctg tgtgttatgt gttttttttct ttttttttct tttttaaatt atgaatatgt   2700
gtaaaatctg aagtaacttg ctaacgtgaa tggtcatata actttaaaga tatatttata   2760
attatttaat gacatttgga catttggaac atttcttagt gtaatgatat gttgacttcg   2820
gtctctaaaa gtgtgcttct tcttcaatac caagtttctt cagtgggcta gagccatatc   2880
ggaaatattg ctaagcaatc tcaattcctt caggcataat gtgatttttt ttttttttg   2940 aagataactc ccatctccaa atagtttaga tgtagtttgt tttcacgatg tatgaaggag   3000
atgctctgtt tctttctttc aggcatttga ttgcctctga cacagctttg ccttttaaag   3060
caataattag ggattaaaat aacaaaaaca aaacaaaagc cacctatagc cctttaacac   3120
ttaacgtggc ccctttacta gcatgaaatg ctggagacat gtggtttcct aatttctcca   3180
ttttgggggt ggtgggaggg gggagggtgg ccattatgac tcttatcata ttaaaaagcc   3240
aagcacaagt gattggttga actgcagaaa agtgttctgt ggtctctgag ttgagcaaaa   3300
ctctaaattg caggcttcgt ggttgagggc ctagtcagct gaaagccacg cgtgtggtaa   3360
aggctcaggc atggcttgga gaacctagga acacattagg agcctgcacc taccagcctc   3420
accatacagc cattcagggg aacccaaaaa gtgccttacc caaggagggc ccccagcagc   3480
tttccaggaa gtcgaatgaa gtcgctgtcc tcggggaact ggtcagctga agtagcaacc   3540
ggtagctgat gtcagtagac aacagaacct gtgggacct ccaggaaacc tttgacattg   3600
gaggctttca ttaggcaggg ccaacaagag cagggaaggc catgtaccca ttggtatctg   3660
ccattgtgtg tgagtttgag atccagccct ccttggagga tgtactgtga tcattcctgg   3720
```

```
taccttaggg ccaatcccta agtgtggctt cctaatccag gccagggatc attcagtgat    3780
accaccaggc caatcccagc attcctcctg cacaaagtgt tgtgtgtgg ggggatagat    3840
tggggtgggg ccaccttcat ttgaatcctg agtcattcta agagttctgc aagcttttgc    3900
cttcagcacc ctataccccc tcgctctctg ttccttctca ggttgacctt tgtcccaatg    3960
cgggacagtc cagaggcaga tggggaccta tgtgtgcctc caacctgcgt tttcctcaga    4020
attcatcctg actccctctg acacagattg aggggggggg gaagaaaccc aacccgcacc    4080
aaagcaaaac actttgcctt ctaaaggctg tgcaccaagt agacgcagat ggtcagccca    4140
cctttgtgtt tccttaagat ggaaattgta actgatgcta tttattgttt gtgtgtggta    4200
gcttgaagca caccacggtc catgtgtttg tctgatacct atttcagcag catttacaaa    4260
agccagtgtc tggttacact tttcagtttt cattaatcaa catgaaaatg ttaccattgg    4320
tgccagctgc accctattta attttttaa gggcactata tttgtacatt tcgtttttaa    4380
tgttaaaggg cttcttaaag tttacagtac agttatcaag ggaatagagg ggatgcatta    4440
gtgcctaaat gttattctag tggctgcagg cagcaaccca gaagcagttt tgaaaacagg    4500
ttgtttccct ctgtcctccc ttatttggga aaattcaagt gctttcttca cctttcaggc    4560
acctcacggt gactcccgtt acttagagca gtctgtcgtc gtcttcttct tcttcctctt    4620
cctcttcctc ttcctcttcc tcttcctctt cctcttcctc ttcctcttcc tcttcttctt    4680
cttcttcttc ttcttcttct tcttcttctt cctcctaggg tttaaaatcc cccttcctct    4740
tcccttatct cttaaactct tcatttgcac tgggtcacac gtatgatttg tggttttaag    4800
accaaagcaa tgtcttatta ctcttctgga gccgtttatg tgtactaacc aacccttccc    4860
tccacttccc tgggtttaga tgcacacggt tctcaaagga gcacaaacat ggccagattc    4920
acagtgggac ccacacagcc atgttaaaaa aaaaaacaaa aaaaaacctc ttcacttgtc    4980
tgagaatttt aacctgggcc ccaattgcta acgggcacca tggcttgggt ttcaggttag    5040
ggaacgttgc ccagtgagta acagaaagac ttaactgatt taattagttt gccctcatcc    5100
ttcactccaa gaccctaaga aaccgatcag agaaacatct ccacaccatt agaggttgag    5160
aagggaggag ccatgtgggg gttccctccg ctcggaggaa aggcactgac tgacctagtt    5220
agagtggtag cagaagcacc catggtatct gagagagcaa taaacaataa aagatgatcc    5280
tcccaagctt agaatttgtt gttcttaaag aagacgatgc atctaaaaca aagaattttt    5340
ttttctatgt gggaactttc ttcgttgtct gtttacttca tgtttacaaa taattgtttg    5400
cttttaatg cagtacttta aaaatatat cagccaaaac cataacttac agtaattttt    5460
ttaggtattc tgaataaaat tccatgtctt ttgatatgtc tactgttctt aggtttctgt    5520
ggaacaacaa caacaacaac aacaaaattg tagcattttg tgtaaataca gctttcgttc    5580
ttatttttta ttttctgat tgctattgcc caagatttgc tttctatgca cgtattgtac    5640
aaattgtgct ttgtgccaca ggtcatgatc gtggatgagt ttactctgaa cttcaaaggg    5700
actatttgta ttgtatgttg caactgtaaa ttgaattatt tggcatttcc ccctctcatg    5760
attgtaatat taatttgaag tttgaattta attttcaata aaaaggcttt ttttttcctt    5820
ttggttttg                                                          5829
```

<210> SEQ ID NO 39
<211> LENGTH: 5724
<212> TYPE: DNA
<213> ORGANISM: Mus musculus

<400> SEQUENCE: 39

```
ggcggaggag gcggcgcggg caagcgacgg cgccgcgagc tgggcagccg cgctctgctt      60
ggcggtggcg gacagcgagg agccacacgc accgccgaga tggactgctg aacctgcggg     120
gctccactac cgtactggaa cccggagcgg ggcgccagcg cacccaggac acggtgcccc     180
aaggggcccc tactgcaagc tgttaacttc aagtcccttg cggcggctgg gccaaacacg     240
cccccgcgtc ccgctcgttg cagccaccgc cagggactcc caagcctccc ggtggagatc     300
cgcgcctctc gggtgtcccc acccgctacc ccgactctgt ccggtctcca gtcgccggcc     360
cccagcagac tccgcccggc acacggcttc ctcgaacttg atttctcacc tcctctgtcc     420
cgtcacctcc atcctctttc cgcccccgtc tcgcctccac ccctcgatt tcctcctcct      480
cgccccccat ttccaccctc ctcccctcc cccggccact tcgctaactt gtggctgttg     540
tgatgcgtat tcctgtagat ccgagcacca gccggcgctt cagccccccc tccagcagcc     600
tgcagcccgg caagatgagc gacgtgagcc cggtggtggc tgcgcagcag cagcaacagc     660
agcagcagca gcagcaacag cagcagcaac aacagcaaca gcaacaacag cagcagcagc     720
agcagcagca ggaggcggcc gcagcagcag cggcggcagc ggcggcggca gcagcggcgg     780
cggccgcagt gccccgattg aggccgccgc acgacaaccg caccatggtg agatcatcg      840
cggaccaccc ggccgaactg gtccgcaccg acagtcccaa cttcctgtgc tccgtgctgc     900
cctcgcactg gcggtgcaac aagacccctgc ccgtggcctt caaggttgta gccctcggag    960
aggtaccaga tgggactgtg gttaccgtca tggccgggaa tgatgagaac tactccgccg    1020
agctccgaaa tgcctccgct gttatgaaaa accaagtagc caggttcaac gatctgagat    1080
ttgtgggccg gagcggacga gatcccaggc aggcacagtc ttccccaccg tggtcctatg    1140
accagtctta cccctcctat ctgagccaga tgacatcccc atccatccac tccaccacgc    1200
cgctgtcttc cacacgggc accgggctac ctgccatcac tgacgtgccc aggcgtattt     1260
cagatgatga cactgccacc tctgacttct gcctctggcc ttcctctctc agtaagaaga    1320
gccaggcagg tgcttcagaa ctgggccctt tttcagaccc caggcagttc ccaagcattt    1380
catccctcac tgagagccgc ttctccaacc cacgaatgca ctaccagcc acctttacct     1440
acaccccgcc agtcacgtca ggcatgtccc tcggcatgtc cgccaccact cactaccaca    1500
cgtacctgcc accaccctac cccggctctt cccaaagcca gagtggaccc ttccagacca    1560
gcagcactcc atatctctac tatggtactt cgtcagcatc ctatcagttc ccaatggtac    1620
ccggggggaga ccggtctcct tccaggatgg tcccaccatg caccaccacc tcgaatggca    1680
gcacgctatt aaatccaaat ttgcctaacc agaatgatgg tgttgacgct gacggaagcc    1740
acagcagttc cccaactgtt ttgaattcta gcggcagaat ggatgagtct gtttggcggc    1800
catattgaaa ttcgtcaacc atggcccagt ggcatggggg ccacatcccg catgtgttaa    1860
tatatacata tataaagaga gtgcctatat atgtatattg attagctaac tagaagattt    1920
ctcattcaat ccctagtcat gatcttgcaa ccctaagagg gtggggggcag tcataactgg    1980
gtttcatatt gtttactatt taagatgtcc cctttaccaa ggaacaaacc gtcaaggtg      2040
ttgtctggtc tgttttcata agtgacctgt tcccacgccg gttcagagag gtggactctg    2100
ggtctgggag gaaggagaga cacttcctct ctgtgctttg aaaccacagc ctctgctgtg    2160
tggcagccgg tacactctgc agacccgctt acagagtcag atgtggtgca ctcagaaagg    2220
gacaagaggc agagtggctg cttctgtccg ctgccgtcca ctctgccgtc cacctgttcc    2280
aaagttttcc ttcagacttg ctgcaggtac tcatttgaac ttttgagttc acttttttt     2340
```

```
tttcctattc taagaaagtg acttcaaaaa tactgatcag gacagataat tttattttac    2400
cttttatatt ttctcacttc ccccatttaa ccaaaaagaa atcccgttcc ccctcccccg    2460
ttccttctgc ttctcccttt atgcaaactg aaaatggcaa tgccttatta ttatagccat    2520
aatggtatag tgtttgagtt ggctgtgtgt tatgtgtttt tttctttttt tttctttttt    2580
aaattatgaa tatgtgtaaa atctgaagta acttgctaac gtgaatggtc atataacttt    2640
aaagatatat ttataattat ttaatgacat ttggacatttt ggaacatttc ttagtgtaat    2700
gatatgttga cttcggtctc taaaagtgtg cttcttcttc aataccaagt ttcttcagtg    2760
ggctagagcc atatcggaaa tattgctaag caatctcaat tccttcaggc ataatgtgat    2820
tttttttttt ttttgaagat aactcccatc tccaaatagt ttagatgtag tttgttttca    2880
cgatgtatga aggagatgct ctgtttcttt ctttcaggca tttgattgcc tctgacacag    2940
ctttgccttt taaagcaata attagggatt aaaataacaa aaacaaaaca aaagccacct    3000 atagccctt aacacttaac gtggccccttt tactagcatg aaatgctgga gacatgtggt    3060
ttcctaattt ctccattttg ggggtggtgg gagggggag ggtggccatt atgactctta    3120
tcatattaaa aagccaagca caagtgattg gttgaactgc agaaaagtgt tctgtggtct    3180
ctgagttgag caaaactcta aattgcaggc ttcgtggttg agggcctagt cagctgaaag    3240
ccacgcgtgt ggtaaaggct caggcatggc ttggagaacc taggaacaca ttaggagcct    3300
gcacctacca gcctcaccat acagccattc aggggaaccc aaaagtgcc ttacccaagg    3360 agggccccca gcagctttcc aggaagtcga atgaagtcgc tgtcctcggg gaactggtca    3420
gctgaagtag caaccggtag ctgatgtcag tagacaacag aacctgtggg gacctccagg    3480
aaacctttga cattggaggc tttcattagg cagggccaac aagagcaggg aaggccatgt    3540
acccattggt atctgccatt gtgtgtgagt ttgagatcca gccctccttg gaggatgtac    3600
tgtgatcatt cctggtacct tagggccaat ccctaagtgt ggcttcctaa tccaggccag    3660
ggatcattca gtgataccac caggccaatc ccagcattcc tcctgcacaa agtgtttgtg    3720
tgtgggggga tagattgggg tggggccacc ttcatttgaa tcctgagtca ttctaagagt    3780
tctgcaagct tttgccttca gcaccctata cccctcgct ctctgttcct tctcaggttg    3840
acctttgtcc caatgcggga cagtccagag gcagatgggg acctatgtgt gcctccaacc    3900
tgcgttttcc tcagaattca tcctgactcc ctctgacaca gattgagggg gggggaaga    3960 aacccaaccc gcaccaaagc aaaacacttt gccttctaaa ggctgtgcac caagtagacg    4020
cagatggtca gcccaccttt gtgtttcctt aagatggaaa ttgtaactga tgctatttat    4080
tgtttgtgtg tggtagcttg aagcacacca cggtccatgt gtttgtctga tacctatttc    4140
agcagcattt acaaaagcca gtgtctggtt acactttca gttttcatta atcaacatga    4200
aaatgttacc attggtgcca gctgcaccct atttaatttt tttaagggca ctatatttgt    4260
acatttcgtt tttaatgtta aagggcttct taaagtttac agtacagtta tcaagggaat    4320 agagggatg cattagtgcc taaatgttat tctagtggct gcaggcagca acccagaagc    4380
agttttgaaa acaggttgtt tccctctgtc ctcccttatt tgggaaaatt caagtgcttt    4440 cttcacctttt caggcacctc acggtgactc ccgttactta gagcagtctg tcgtcgtctt    4500
cttcttcttc ctcttcctct tcctcttcct cttcctcttc ctcttcctct tcctcttcct    4560
cttcctcttc ttcttcttct tcttcttctt cttcttcttc ttcttcctcc tagggtttaa    4620 aatcccccttt cctcttccct tatctcttaa actcttcatt tgcactgggt cacacgtatg    4680
```

| | | | | | | |
|---|---|---|---|---|---|---|
| atttgtggtt | ttaagaccaa | agcaatgtct | tattactctt | ctggagccgt | ttatgtgtac | 4740 |
| taaccaaccc | ttccctccac | ttccctgggt | ttagatgcac | acggttctca | aaggagcaca | 4800 |
| aacatggcca | gattcacagt | gggacccaca | cagccatgtt | aaaaaaaaaa | acaaaaaaaa | 4860 |
| acctcttcac | ttgtctgaga | attttaacct | gggccccaat | tgctaacggg | caccatggct | 4920 |
| tgggtttcag | gttagggaac | gttgcccagt | gagtaacaga | aagacttaac | tgatttaatt | 4980 |
| agtttgccct | catccttcac | tccaagaccc | taagaaaccg | atcagagaaa | catctccaca | 5040 |
| ccattagagg | ttgagaaggg | aggagccatg | tggggttcc | ctccgctcgg | aggaaaggca | 5100 |
| ctgactgacc | tagttagagt | ggtagcagaa | gcacccatgg | tatctgagag | agcaataaac | 5160 |
| aataaaagat | gatcctccca | agcttagaat | ttgttgttct | taaagaagac | gatgcatcta | 5220 |
| aaacaaagaa | ttttttttc | tatgtgggaa | ctttcttcgt | tgtctgttta | cttcatgttt | 5280 |
| acaaataatt | gtttgctttt | taatgcagta | ctttaaaaaa | tatatcagcc | aaaaccataa | 5340 |
| cttacagtaa | ttttttagg | tattctgaat | aaaattccat | gtcttttgat | atgtctactg | 5400 |
| ttcttaggtt | tctgtggaac | aacaacaaca | acaacaacaa | aattgtagca | ttttgtgtaa | 5460 |
| atacagcttt | cgttcttatt | ttttatttt | ctgattgcta | ttgcccaaga | tttgctttct | 5520 |
| atgcacgtat | tgtacaaatt | gtgctttgtg | ccacaggtca | tgatcgtgga | tgagtttact | 5580 |
| ctgaacttca | aagggactat | ttgtattgta | tgttgcaact | gtaaattgaa | ttatttggca | 5640 |
| tttccccctc | tcatgattgt | aatattaatt | tgaagtttga | atttaatttt | caataaaaag | 5700 |
| gctttttttt | tccttttggt | tttg | | | | 5724 |